(12) United States Patent
Davies et al.

(10) Patent No.: US 8,222,371 B2
(45) Date of Patent: Jul. 17, 2012

(54) VWFA AND/OR ANT_IG DOMAIN CONTAINING PROTEINS

(75) Inventors: Mark Douglas Davies, London (GB);
David Michalovich, London (GB);
Melanie Yorke, Confignon (CH);
Christine Power, Thoiry (FR)

(73) Assignee: Ares Trading S.A., Aubonne (CH)

( * ) Notice: Subject to any disclaimer, the term of this patent is extended or adjusted under 35 U.S.C. 154(b) by 920 days.

(21) Appl. No.: 11/718,183

(22) PCT Filed: Oct. 28, 2005

(86) PCT No.: PCT/GB2005/004191
§ 371 (c)(1),
(2), (4) Date: Jul. 8, 2008

(87) PCT Pub. No.: WO2006/046072
PCT Pub. Date: May 4, 2006

(65) Prior Publication Data
US 2009/0104197 A1    Apr. 23, 2009

(30) Foreign Application Priority Data
Oct. 28, 2004 (GB) .................................. 0423974.5

(51) Int. Cl.
*A61K 38/16* (2006.01)
*A61K 35/00* (2006.01)
*C07K 14/00* (2006.01)

(52) U.S. Cl. ........................................ 530/350; 514/1.1

(58) Field of Classification Search .................... None
See application file for complete search history.

(56) References Cited

U.S. PATENT DOCUMENTS

2003/0144193 A1    7/2003    Rottman et al.
2008/0299042 A1*   12/2008   Bechtel et al. ................. 424/9.1

FOREIGN PATENT DOCUMENTS

| EP | 1 293 569       | 3/2003  |
|----|-----------------|---------|
| WO | WO 02/10217 A3  | 2/2002  |
| WO | WO 02/46228     | 6/2002  |
| WO | WO 03/033515 A1 | 4/2003  |
| WO | WO 2004/093804 A2 | 11/2004 |
| WO | WO 2005/108415  | 11/2005 |

OTHER PUBLICATIONS

Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
SEQ ID No. 1708 from US 2008/0299042 above. Published Dec. 4, 2008.*
Bradley, K. A. et al. "Anthrax toxin receptor proteins" *Biochemical Pharmacology*, Feb. 2003, pp. 309-314, vol. 65, No. 3.
Scobie, H. M. et al. "Human capillary morphogenesis protein 2 functions as an anthrax toxin receptor" *PNAS*, Apr. 29, 2003, pp. 5170-5174, vol. 100, No. 9.
Database Geneseq [Online], Database Accession No. ABM36159, Oct. 20, 2003, "Propionibacterium acnes predicted ORF-encoded polypeptide #835", XP002386360, pp. 1-2.
Database Geneseq [Online], Database Accession No. ADA53850, Nov. 20, 2003, "Human coding sequence, SEQ ID 1418", XP002386361, pp. 1-2.
Database EPO Proteins [Online], Database Accession No. AX393371, Mar. 22, 2002, "Sequence 301 from Patent WO0210217", XP00238406233, p. 1.
Deloukas, P. et al. "The DNA sequence and comparative analysis of human chromosome 10" *Nature*, May 27, 2004, pp. 375-381, vol. 429.
Okazaki, Y. et al. "Analysis of the mouse transcriptome based on functional annotation of 60,770 full-length cDNAs" *Nature*, Dec. 5, 2002, pp. 563-573, vol. 420.
Database GenBank [Online], Database Accession No. BAC36683, Dec. 5, 2002, pp. 1-4.
Database Swiss-Prot [Online], Database Accession No. A6NF34.2, May 27, 2004, pp. 1-3.
Transmittal letter from agent in a corresponding Israeli application, 2009, p. 1.
Lacy, D. B. et al. "Crystal structure of the von Willebrand factor A domain of human capillary morphogenesis protein 2: An anthrax toxin receptor" *PNAS*, Apr. 27, 2004, pp. 6367-6372, vol. 101, No. 17.
Database GenBank [Online], Database Accession No. AL705755, Oct. 16, 2008, pp. 1-2.
Database GenBank [Online], Database Accession No. AL450388, Jan. 13, 2009, pp. 1-43.

* cited by examiner

*Primary Examiner* — Julie Ha
(74) *Attorney, Agent, or Firm* — Saliwanchik, Lloyd & Eisenchenk

(57) ABSTRACT

Proteins (INSP141, INSP142, INSP143, and INSP144) identified as anthrax receptor-like proteins containing von Willebrand factor A (vWFA) and Anthrax receptor extracellular (ANT_IG) domains and the use of these proteins and nucleic acid sequences from the encoding genes in the diagnosis, prevention and treatment of disease are described.

8 Claims, 19 Drawing Sheets

Figure 1: Top 10 BLASTp results searching with INSP141 against the NCBI non-redundant database.

INSP141

```
Query= INSP141
        (306 letters)

Database: All non-redundant GenBank CDS
translations+PDB+SwissProt+PIR+PRF
           1,448,673 sequences; 466,090,050 total letters Searching..................................................done
```

|  | Score | E |
|---|---|---|
| Sequences producing significant alignments: | (bits) | Value |

```
ref|XP_113625.3| similar to hypothetical protein 4933430J11 [Hom...    407   e-113
ref|NP_766396.1| hypothetical protein 4933430J11 [Mus musculus] ...   284   1e-75
sp|Q9CZ52|ATR_MOUSE Anthrax toxin receptor precursor (Tumor endo...   225   8e-58
ref|XP_132709.1| RIKEN cDNA 2310008J16 [Mus musculus]                 225   8e-58
ref|NP_444262.1| tumor endothelial marker 8 isoform 2 precursor;...   223   4e-57
ref|NP_115584.1| tumor endothelial marker 8 isoform 1 precursor;...   223   4e-57
ref|NP_060623.2| tumor endothelial marker 8 isoform 3 precursor;...   223   4e-57
dbj|BAC03731.1| unnamed protein product [Homo sapiens]                193   3e-48
gb|AAP04016.1| capillary morphogenesis protein 2 [Homo sapiens]       193   3e-48
dbj|BAA91707.1| unnamed protein product [Homo sapiens]                172   8e-42

>ref|XP_113625.3| similar to hypothetical protein 4933430J11 [Homo sapiens]
         Length = 483
```

Figure 2: Top 10 BLASTp results searching with INSP142 against the NCBI non-redundant database

INSP142

```
Query= INSP142
       (352 letters)

Database: All non-redundant GenBank CDS
translations+PDB+SwissProt+PIR+PRF
       1,448,673 sequences; 466,090,050 total letters Searching..................................................done Score     E
Sequences producing significant alignments:                  (bits)  Value ref|XP_113625.3| similar to hypothetical protein 4933430J11 [Hom...    510   e-143
ref|NP_766396.1| hypothetical protein 4933430J11 [Mus musculus] ...    336   3e-91
sp|Q9CZ52|ATR_MOUSE Anthrax toxin receptor precursor (Tumor endo...    266   4e-70
ref|XP_132709.1| RIKEN cDNA 2310008J16 [Mus musculus]                  266   4e-70
ref|NP_444262.1| tumor endothelial marker 8 isoform 2 precursor;...    265   8e-70
ref|NP_115584.1| tumor endothelial marker 8 isoform 1 precursor;...    265   8e-70
ref|NP_060623.2| tumor endothelial marker 8 isoform 3 precursor;...    265   8e-70
dbj|BAC03731.1| unnamed protein product [Homo sapiens]                 234   2e-60
gb|AAP04016.1| capillary morphogenesis protein 2 [Homo sapiens]        234   2e-60
dbj|BAB28591.1| unnamed protein product [Mus musculus]                 199   6e-50

>ref|XP_113625.3| similar to hypothetical protein 4933430J11 [Homo sapiens]
         Length = 483
```

Figure 3: Top 10 BLASTp results searching with INSP143 against the NCBI non-redundant database

```
INSP143

Query= INSP143
        (608 letters)

Database: All non-redundant GenBank CDS
translations+PDB+SwissProt+PIR+PRF
        1,448,673 sequences; 466,090,050 total letters Searching..................................................done Score     E
Sequences producing significant alignments:                  (bits)  Value ref|XP_113625.3| similar to hypothetical protein 4933430J11 [Hom...   1003   0.0
ref|NP_766396.1| hypothetical protein 4933430J11 [Mus musculus] ...    514  e-144
sp|Q9CZ52|ATR_MOUSE Anthrax toxin receptor precursor (Tumor endo...    290  5e-77
ref|XP_132709.1| RIKEN cDNA 2310008J16 [Mus musculus]                  290  5e-77
ref|NP_115584.1| tumor endothelial marker 8 isoform 1 precursor;...    288  2e-76
ref|NP_444262.1| tumor endothelial marker 8 isoform 2 precursor;...    281  2e-74
gb|AAP04016.1| capillary morphogenesis protein 2 [Homo sapiens]        273  5e-72
dbj|BAC03731.1| unnamed protein product [Homo sapiens]                 270  4e-71
ref|NP_060623.2| tumor endothelial marker 8 isoform 3 precursor;...    266  8e-70
dbj|BAB28591.1| unnamed protein product [Mus musculus]                 223  7e-57

>ref|XP_113625.3| similar to hypothetical protein 4933430J11 [Homo sapiens]
        Length = 483
```

Figure 4: Top 10 BLASTp results searching with INSP144 against the NCBI non-redundant database

INSP144

```
Query= INSP144
       (631 letters)

Database: All non-redundant GenBank CDS
translations+PDB+SwissProt+PIR+PRF
          1,448,673 sequences; 466,090,050 total letters Searching..................................................done Score     E
Sequences producing significant alignments:                    (bits)  Value ref|XP_113625.3| similar to hypothetical protein 4933430J11 [Hom...   990   0.0
ref|NP_766396.1| hypothetical protein 4933430J11 [Mus musculus] ...   503   e-141
sp|Q9CZ52|ATR_MOUSE Anthrax toxin receptor precursor (Tumor endo...   290   5e-77
ref|XP_132709.1| RIKEN cDNA 2310008J16 [Mus musculus]                 290   5e-77
ref|NP_115584.1| tumor endothelial marker 8 isoform 1 precursor;...   288   3e-76
ref|NP_444262.1| tumor endothelial marker 8 isoform 2 precursor;...   281   2e-74
gb|AAP04016.1| capillary morphogenesis protein 2 [Homo sapiens]       273   5e-72
dbj|BAC03731.1| unnamed protein product [Homo sapiens]                270   4e-71
ref|NP_060623.2| tumor endothelial marker 8 isoform 3 precursor;...   266   8e-70
dbj|BAB28591.1| unnamed protein product [Mus musculus]                223   8e-57

>ref|XP_113625.3| similar to hypothetical protein 4933430J11 [Homo sapiens]
          Length = 483
```

Figure 5: Alignment of INSP141, INSP142, INSP143 and INSP144 coding exons.
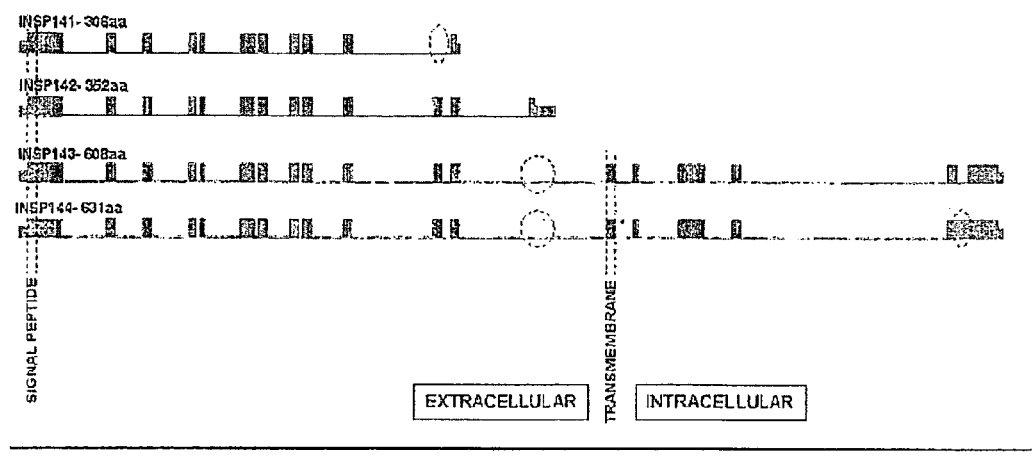

Figure 6: Alignment of the ORFs of INSP141, INSP142, INSP143, INSP144.

```
                              ┌─Signal peptide─────────────┐
INSP141         MGSHESLGPY FLVFLLLLLL PPPLFRAGSL RYHGPDWRIF HRLALGSRRA
CLONEDINSP141   MGSHESLGPY FLVFLLLLLL PPPLFRAGSL RYHGPDWRIF HRLALGSRRA
INSP142         MGSHESLGPY FLVFLLLLLL PPPLFRAGSL RYHGPDWRIF HRLALGSRRA
CLONEDINSP142   MGSHESLGPY FLVFLLLLLL PPPLFRAGSL RYHGPDWRIF HRLALGSRRA
INSP143         MGSHESLGPY FLVFLLLLLL PPPLFRAGSL RYHGPDWRIF HRLALGSRRA
CLONEDINSP143   MGSHESLGPY FLVFLLLLLL PPPLFRAGSL RYHGPDWRIF HRLALGSRRA
INSP144         MGSHESLGPY FLVFLLLLLL PPPLFRAGSL RYHGPDWRIF HRLALGSRRA INSP141         HHHHGPGWRQ HWRQGQAGHR CQGSFDLYFI LDKSGSVNNN WIDLYMWVEE
CLONEDINSP141   HHHHGPGWRQ HWRQGQAGHR CQGSFDLYFI LDKSGSVNNN WIDLYMWVEE
INSP142         HHHHGPGWRQ HWRQGQAGHR CQGSFDLYFI LDKSGSVNNN WIDLYMWVEE
CLONEDINSP142   HHHHGPGWRQ HWRQGQAGHR CQGSFDLYFI LDKSGSVNNN WIDLYMWVEE
INSP143         HHHHGPGWRQ HWRQGQAGHR CQGSFDLYFI LDKSGSVNNN WIDLYMWVEE
CLONEDINSP143   HHHHGPGWRQ HWRQGQAGHR CQGSFDLYFI LDKSGSVNNN WIDLYMWVEE
INSP144         HHHHGPGWRQ HWRQGQAGHR CQGSFDLYFI LDKSGSVNNN WIDLYMWVEE INSP141         TVARFQSPNI RMCFITYSTD GQTVLPLTSD KNRIKNGLDQ LQKIVPDGHT
CLONEDINSP141   TVARFQSPNI RMCFITYSTD GQTVLPLTSD KNRIKNGLDQ LQKIVPDGHT
INSP142         TVARFQSPNI RMCFITYSTD GQTVLPLTSD KNRIKNGLDQ LQKIVPDGHT
CLONEDINSP142   TVARFQSPNI RMCFITYSTD GQTVLPLTSD KNRIKNGLDQ LQKIVPDGHT
INSP143         TVARFQSPNI RMCFITYSTD GQTVLPLTSD KNRIKNGLDQ LQKIVPDGHT
CLONEDINSP143   TVARFQSPNI RMCFITYSTD GQTVLPLTSD KNRIKNGLDQ LQKIVPDGHT
INSP144         TVARFQSPNI RMCFITYSTD GQTVLPLTSD KNRIKNGLDQ LQKIVPDGHT INSP141         FMQAGFRKAI QQIESFNSGN KVPSMIIAMT DGELVAHAFQ DTLREAQKAR
CLONEDINSP141   FMQAGFRKAI QQIESFNSGN KVPSMIIAMT DGELVAHAFQ DTLREAQKAR
INSP142         FMQAGFRKAI QQIESFNSGN KVPSMIIAMT DGELVAHAFQ DTLREAQKAR
CLONEDINSP142   FMQAGFRKAI QQIESFNSGN KVPSMIIAMT DGELVAHAFQ DTLREAQKAR
INSP143         FMQAGFRKAI QQIESFNSGN KVPSMIIAMT DGELVAHAFQ DTLREAQKAR
CLONEDINSP143   FMQAGFRKAI QQIESFNSGN KVPSMIIAMT DGELVAHAFQ DTLREAQKAR
INSP144         FMQAGFRKAI QQIESFNSGN KVPSMIIAMT DGELVAHAFQ DTLREAQKAR INSP141         KLGANVYTLG VADYNLDQIT AIADSPGHVF AVENGFKALR STIDALTSKV
CLONEDINSP141   KLGANVYTLG VADYNLDQIT AIADSPGHVF AVENGFKALR STIDALTSKV
INSP142         KLGANVYTLG VADYNLDQIT AIADSPGHVF AVENGFKALR STIDALTSKV
CLONEDINSP142   KLGANVYTLG VADYNLDQIT AIADSPGHVF AVENGFKALR STIDALTSKV
INSP143         KLGANVYTLG VADYNLDQIT AIADSPGHVF AVENGFKALR STIDALTSKV
CLONEDINSP143   KLGANVYTLG VADYNLDQIT AIADSPGHVF AVENGFKALR STIDALTSKV
INSP144         KLGANVYTLG VADYNLDQIT AIADSPGHVF AVENGFKALR STIDALTSKV INSP141         CLDVTSVEPS SECVGEPYHV VIHGNGFQNL KKRDEVICRF IFNESTIIGS
CLONEDINSP141   CLDVTSVEPS SECVGEPYHV VIHGNGFQNL KKRDEVICRF IFNESTIIGS
INSP142         CLDVTSVEPS SECVGEPYHV VIHGNGFQNL KKRDEVICRF IFNESTIIDE
CLONEDINSP142   CLDVTSVEAS SECVGEPYHV VIHGNGFQNL KKRDEVICRF IFNESTIIDE
INSP143         CLDVTSVEPS SECVGEPYHV VIHGNGFQNL KKRDEVICRF IFNESTIIDE
CLONEDINSP143   CLDVTSVEPS SECVGEPYHV VIHGNGFQNL KKRDEVICRF IFNESTIIDE
INSP144         CLDVTSVEPS SECVGEPYHV VIHGNGFQNL KKRDEVICRF IFNESTIIDE INSP141         TLLKSA
CLONEDINSP141   TLLKSA
INSP142         KPTSIDNNSM NCPGPKLEKP GEEYSIEVSL NKGKTFFKSN VSITSTTCPS
CLONEDINSP142   KPTSIDNNSM NCPGPKLEKP GEEYSIEVSL NKGKTFFKSN VSITS.
INSP143         KPTSIDNNSM NCPGPKLEKP GEEYSIEVSL NKGKTFFKSN VSITSTTCGI
CLONEDINSP143   KPTSIDNNSM NCPGPKLEKP GEEYSIEVSL NKGKTFFKSN VSITSTTCGI
INSP144         KPTSIDNNSM NCPGPKLEKP GEEYSIEVSL NKGKTFFKSN VSITSTTCGI ┌────────────────────────────────────────┐
INSP142         LK
INSP143         FRNWLYFVPL LLLVPLLLCC VWRLCRKQTV KEPPPVQKPE KEPEQEKPPS
CLONEDINSP143   FR
INSP144         FRNWLYFVPL LLLVPLLLCC VWRLCRKQTV KEPPPVQKPE KEPEQEKPPS
                              └─Transmembrane domain──────┘

INSP143         PPPPPPPPPP PLPPPPPAPV NTCPTVIICC CGCQGVGGMR RIEGNLDTFC
INSP144         PPPPPPPPPP PLPPPPPAPV NTCPTVIICC CGCQGVGGMR RIEGNLDTFC
```

(Figure 6 Cont.)

```
INSP143        DLSHASCHQV PWMCCQSRDQ GRYLSLALAQ SQYAQAPCCP RICFPHSQEC
INSP144        DLSHASCHQV PWMCCQSRDQ GRYLSLALAQ SQYAQAPCCP RICFPHSQEC

INSP143        LSLPQAPCSP RMCLRHSREC LALKQARCSP NICLR----- ----------
INSP144        LSLPQAPCSP RMCLRHSREC LALKQARCSP NICLRHSQHS RECLARKQAP

INSP143        --------HS PEYFSQAQTL CNPKSCLQPS RECLPLTCSS RCRLPPARCL
INSP144        CSPRICLRHS PEYFSQAQTL CNPKSCLQPS RECLPLTCSS RCRLPPARCL

INSP143        RPPSRMLPLL SPLLRHTAEP PLSLPPSEPN F
INSP144        RPPSRMLPLL SPLLRHTAEP PLSLPPSEPN F
```

Figure 7: Nucleotide alignment of INSP141, INSP142, INSP143, INSP144
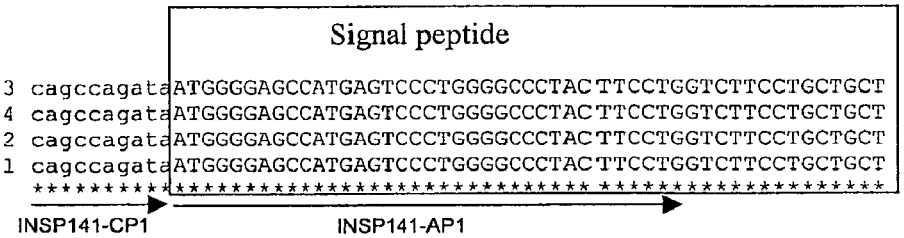

(Figure 7 Cont.)

```
INSP143    AAAGGCAATTCAACAGATCGAAAGTTTCAACTCCGGAAACAAGGTTCCCAGCATGATTAT
INSP144    AAAGGCAATTCAACAGATCGAAAGTTTCAACTCCGGAAACAAGGTTCCCAGCATGATTAT
INSP142    AAAGGCAATTCAACAGATCGAAAGTTTCAACTCCGGAAACAAGGTTCCCAGCATGATTAT
INSP141    AAAGGCAATTCAACAGATCGAAAGTTTCAACTCCGGAAACAAGGTTCCCAGCATGATTAT
           ************************************************************

INSP143    TGCTATGACTGATGGAGAACTGGTGGCACATGCATTTCAGGACACTCTCAGAGAAGCTCA
INSP144    TGCTATGACTGATGGAGAACTGGTGGCACATGCATTTCAGGACACTCTCAGAGAAGCTCA
INSP142    TGCTATGACTGATGGAGAACTGGTGGCACATGCATTTCAGGACACTCTCAGAGAAGCTCA
INSP141    TGCTATGACTGATGGAGAACTGGTGGCACATGCATTTCAGGACACTCTCAGAGAAGCTCA
           ************************************************************

INSP143    AAAGGCTCGGAAACTGGGGGCCAACGTTTACACCCTGGGTGTGGCTGATTATAATCTGGA
INSP144    AAAGGCTCGGAAACTGGGGGCCAACGTTTACACCCTGGGTGTGGCTGATTATAATCTGGA
INSP142    AAAGGCTCGGAAACTGGGGGCCAACGTTTACACCCTGGGTGTGGCTGATTATAATCTGGA
INSP141    AAAGGCTCGGAAACTGGGGGCCAACGTTTACACCCTGGGTGTGGCTGATTATAATCTGGA
           ************************************************************
                                                  INSP143-CP3
                                         ─────────────────────────▶
INSP143    CCAGATAACAGCAATTGCAGACAGCCCTGGCCACGTGTTTGCAGTGGAGAATGGCTTCAA
INSP144    CCAGATAACAGCAATTGCAGACAGCCCTGGCCACGTGTTTGCAGTGGAGAATGGCTTCAA
INSP142    CCAGATAACAGCAATTGCAGACAGCCCTGGCCACGTGTTTGCAGTGGAGAATGGCTTCAA
INSP141    CCAGATAACAGCAATTGCAGACAGCCCTGGCCACGTGTTTGCAGTGGAGAATGGCTTCAA
           ************************************************************

INSP143    GGCCCTGAGAAGCACCATTGATGCCCTCACGTCAAAGGTCTGTCTTGATGTGACATCGGT
INSP144    GGCCCTGAGAAGCACCATTGATGCCCTCACGTCAAAGGTCTGTCTTGATGTGACATCGGT
INSP142    GGCCCTGAGAAGCACCATTGATGCCCTCACGTCAAAGGTCTGTCTTGATGTGACATCGGT
INSP141    GGCCCTGAGAAGCACCATTGATGCCCTCACGTCAAAGGTCTGTCTTGATGTGACATCGGT
           ************************************************************

INSP143    GGAGCCTTCCTCTGAGTGTGTAGGAGAACCCTACCATGTGGTTATTCATGGAAATGGCTT
INSP144    GGAGCCTTCCTCTGAGTGTGTAGGAGAACCCTACCATGTGGTTATTCATGGAAATGGCTT
INSP142    GGAGCCTTCCTCTGAGTGTGTAGGAGAACCCTACCATGTGGTTATTCATGGAAATGGCTT
INSP141    GGAGCCTTCCTCTGAGTGTGTAGGAGAACCCTACCATGTGGTTATTCATGGAAATGGCTT
           ************************************************************

INSP143    TCAGAATCTAAAGAAACGGGATGAAGTTATTTGCAGATTTATCTTCAATGAAAGCACTAT
INSP144    TCAGAATCTAAAGAAACGGGATGAAGTTATTTGCAGATTTATCTTCAATGAAAGCACTAT
INSP142    TCAGAATCTAAAGAAACGGGATGAAGTTATTTGCAGATTTATCTTCAATGAAAGCACTAT
INSP141    TCAGAATCTAAAGAAACGGGATGAAGTTATTTGCAGATTTATCTTCAATGAAAGCACTAT
           ************************************************************
                                                       ◀─────────────
                                                          INSP141-AP2
INSP143    CATTGATGAAAAGCCAACCAGTATCGACAATAATTCCATGAATTGCCCTGGGCCAAAACT
INSP144    CATTGATGAAAAGCCAACCAGTATCGACAATAATTCCATGAATTGCCCTGGGCCAAAACT
INSP142    CATTGATGAAAAGCCAACCAGTATCGACAATAATTCCATGAATTGCCCTGGGCCAAAACT
INSP141    CATTG-------------------------------------------------------
           *****

INSP143    AGAAAAACCTGGAGAGGAGTACTCTATTGAAGTCAGCTTGAACAAAGGCAAAACATTCTT
INSP144    AGAAAAACCTGGAGAGGAGTACTCTATTGAAGTCAGCTTGAACAAAGGCAAAACATTCTT
INSP142    AGAAAAACCTGGAGAGGAGTACTCTATTGAAGTCAGCTTGAACAAAGGCAAAACATTCTT
INSP141    ---------------GGAGTACTCTATTGAAGTCAGCTtga
                          ****************************
                          ─────────────────────────────
                                  INSP141-AP2
             INSP143-AP1
           ◀──────────────
INSP143    CAAGAGCAATGTCAGCATCACCAGCACCACATGT---------------------------
INSP144    CAAGAGCAATGTCAGCATCACCAGCACCACATGT---------------------------
INSP142    CAAGAGCAATGTCAGCATCACCAGCACCACATGTCCTTCTCTTAAGtag
           *********************************
           ◀──────────────
             INSP141-CP2
```

(Figure 7 Cont.)

```
                 INSP143-AP1    | Transmembrane domain         INSP143-CP4 |
INSP143   ---GGCATTTTCCGC|AACTGGCTCTATTTTGTGCCACTCCTGCTGCTTGTGCCACTGCTG
INSP144   ---GGCATTTTCCGC|AACTGGCTCTATTTTGTGCCACTCCTGCTGCTTGTGCCACTGCTG
          ---************ ********************************************

|INSP143-CP4
INSP143   |CTGTGTTGTGTCTGGCGGCTGTGCCGCA|AGCAGACTGTCAAGGAGCCACCACCTGTGCAG
INSP144   |CTGTGTTGTGTCTGGCGGCTGTGCCGCA|AGCAGACTGTCAAGGAGCCACCACCTGTGCAG
           **************************** ********************************

INSP143   AAGCCAGAAAAGGAGCCAGAGCAGGAAAAACCACCATCACCACCACCACCGCCTCCGCCT
INSP144   AAGCCAGAAAAGGAGCCAGAGCAGGAAAAACCACCATCACCACCACCACCGCCTCCGCCT
          ************************************************************

INSP143   CCACCACCTCCACTCCCACCTCCGCCCCCAGCTCCTGTAAACACCTGCCCCACTGTGATT
INSP144   CCACCACCTCCACTCCCACCTCCGCCCCCAGCTCCTGTAAACACCTGCCCCACTGTGATT
          ************************************************************

INSP143   ATTTGTTGCTGTGGATGCCAAGGAGTGGGCGGGATGAGAAGGATAGAGGGCAATCTGGAT
INSP144   ATTTGTTGCTGTGGATGCCAAGGAGTGGGCGGGATGAGAAGGATAGAGGGCAATCTGGAT
          ************************************************************

INSP143   ACCTTTTGTGACCTCTCTCACGCAAGCTGCCACCAGGTGCCATGGATGTGTTGTCAGAGC
INSP144   ACCTTTTGTGACCTCTCTCACGCAAGCTGCCACCAGGTGCCATGGATGTGTTGTCAGAGC
          ************************************************************

INSP143   AGGGACCAGGGGAGGTACCTCAGCTTAGCCCTTGCACAGTCCCAATATGCACAGGCTCCC
INSP144   AGGGACCAGGGGAGGTACCTCAGCTTAGCCCTTGCACAGTCCCAATATGCACAGGCTCCC
          ************************************************************

INSP143   TGCTGCCCAAGGATCTGCTTTCCACACAGCCAGGAGTGCCTTTCCCTACCACAGGCTCCC
INSP144   TGCTGCCCAAGGATCTGCTTTCCACACAGCCAGGAGTGCCTTTCCCTACCACAGGCTCCC
          ************************************************************

INSP143   TGCAGCCCAAGGATGTGCCTGAGACACAGCCGGGAGTGCCTCGCCCTCAAACAGGCTCGC
INSP144   TGCAGCCCAAGGATGTGCCTGAGACACAGCCGGGAGTGCCTCGCCCTCAAACAGGCTCGC
          ************************************************************

INSP143   TGCAGCCCAAACAT---------------------------------------------
INSP144   TGCAGCCCAAACATCTGCCTGAGACACAGCCAACACAGCAGGGAGTGCCTTGCCGGCAAA
          **************

INSP143   ------------------------CTGCCTGAGACACAGCCCGGAGTACTTTTCCCAAGCA
INSP144   CAGGCTCCCTGCAGCCCAAGGATCTGCCTGAGACACAGCCCGGAGTACTTTTCCCAAGCA
                                  ****************************************

INSP143   CAGACTCTGTGCAACCCAAAGAGCTGCCTTCAACCCAGCCGGGAGTGCCTCCCCCTCACC
INSP144   CAGACTCTGTGCAACCCAAAGAGCTGCCTTCAACCCAGCCGGGAGTGCCTCCCCCTCACC
          ************************************************************

INSP143   TGCTCCTCCAGGTGCCGCCTCCCCCCAGCTAGGTGCTTGAGGCCTCCCTCCAGGATGCTG
INSP144   TGCTCCTCCAGGTGCCGCCTCCCCCCAGCTAGGTGCTTGAGGCCTCCCTCCAGGATGCTG
          ************************************************************

INSP143   CCGCTGCTGTCCCCACTGCTCAGGCACACGGCAGAACCCCCTTTGTCACTCCCCCCCTCA
INSP144   CCGCTGCTGTCCCCACTGCTCAGGCACACGGCAGAACCCCCTTTGTCACTCCCCCCCTCA
          ************************************************************

INSP143   GAGCCCAACTTCtaa
INSP144   GAGCCCAACTTCtaa
          ***************
```

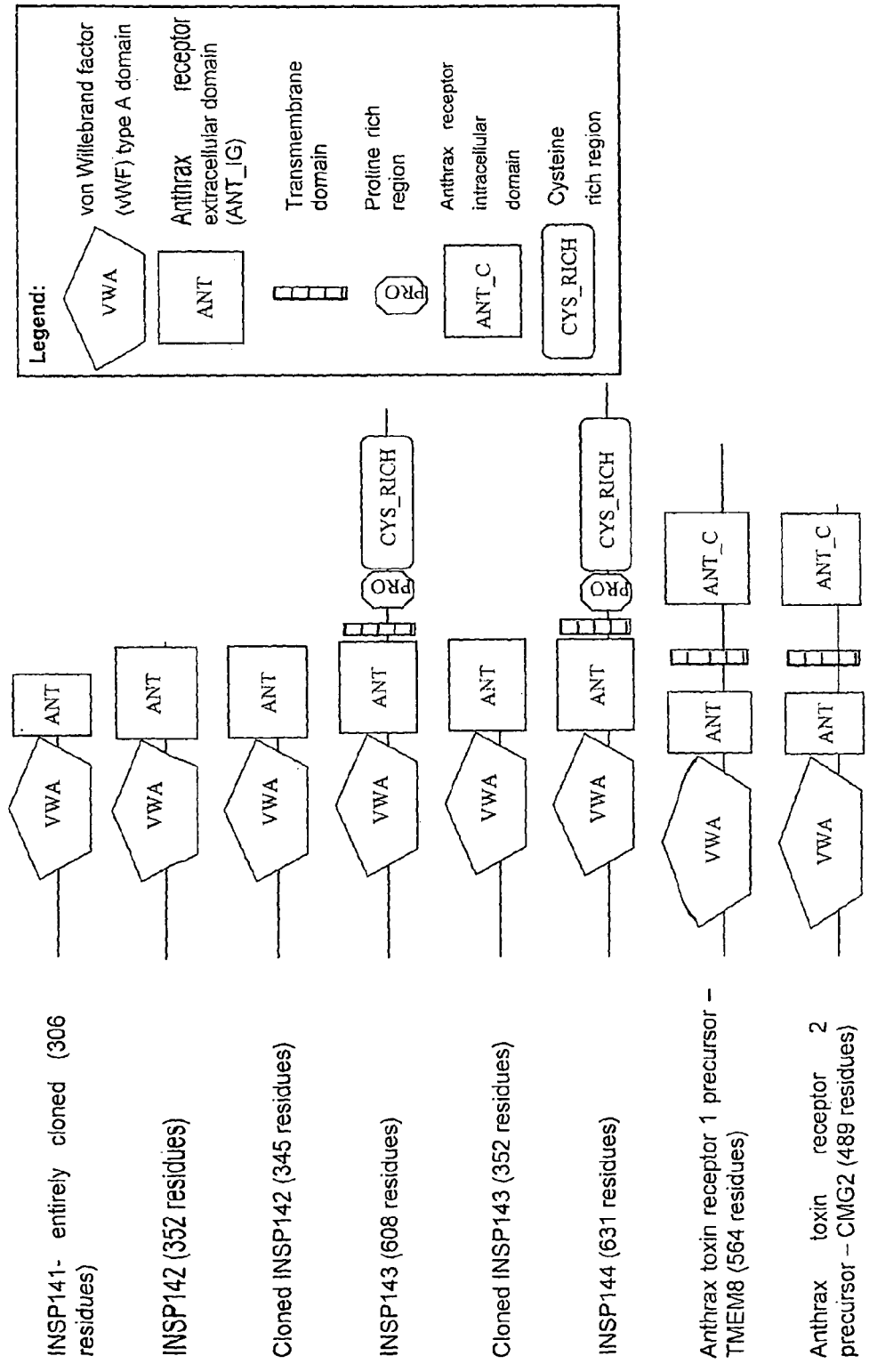
Figure 8: Schematic representation of predicted and cloned INSP141, INSP142, INSP143, INSP144, TMEM8 and CMG2.

Figure 9: Amino acid alignment of the extracellular vWFA and ANT_IG domains of INSP141, INSP142, INSP143, INSP144, TMEM8 and CMG2.

```
                                                         vWFA domain
ATR1_HUMAN       -----QGGRREDGGPACYGG FDLYFILDKSGSVLHHWNEIYYFVEQLAHKFISPQLRMSF
ATR2_HUMAN       ----------QEQPSCRRA  FDLYFVLDKSGSVANNWIEIYNFVQQLAERFVSPEMRLSF
INSP141          GPGWRQHWRQGQAGHRCQGS FDLYFILDKSGSVNNNWIDLYMWVEETVARFQSPNIRMCF
INSP142          GPGWRQHWRQGQAGHRCQGS FDLYFILDKSGSVNNNWIDLYMWVEETVARFQSPNIRMCF
INSP143          GPGWRQHWRQGQAGHRCQGS FDLYFILDKSGSVNNNWIDLYMWVEETVARFQSPNIRMCF
INSP144          GPGWRQHWRQGQAGHRCQGS FDLYFILDKSGSVNNNWIDLYMWVEETVARFQSPNIRMCF
                        :      *    .***:**** :  :* ::*  :*::  .:* **::*:.* vWFA domain
ATR1_HUMAN       IVFSTRGTTLMKLTEDREQIRQGLEELQKVLPGGD TYMHEGFERASEQIYYENRQGYRTA
ATR2_HUMAN       IVFSSQATIILPLTGDRGKISKGLEDLKRVSPVGE TYIHEGLKLANEQIQK-A-GGLKTS
INSP141          ITYSTDGQTVLPLTSDKNRIKNGLDQLQKIVPDGH HTFMQAGFRKAIQQIESFN-SGNKVP
INSP142          ITYSTDGQTVLPLTSDKNRIKNGLDQLQKIVPDGH HTFMQAGFRKAIQQIESFN-SGNKVP
INSP143          ITYSTDGQTVLPLTSDKNRIKNGLDQLQKIVPDGH HTFMQAGFRKAIQQIESFN-SGNKVP
INSP144          ITYSTDGQTVLPLTSDKNRIKNGLDQLQKIVPDGH HTFMQAGFRKAIQQIESFN-SGNKVP
                 *..:*:  .  ::  **  :* :**::*:::      *: *  *:   *    *  :..

vWFA domain
ATR1_HUMAN       SVIIALTDGELHEDLFFYSEREANRSRDLGAIVYCVGVKDFNETQLARIADSKDHVFPVN
ATR2_HUMAN       SIIIALTDGKLDGLVPSYAEKEAKISRSLGASVYCVGVLDFEQAQLERIADSKEQVFPVK
INSP141          SMIIAMTDGELVAHAFQDTLREAQKARKLGANVYTLGVADYNLDQITAIADSPGHVFAVE
INSP142          SMIIAMTDGELVAHAFQDTLREAQKARKLGANVYTLGVADYNLDQITAIADSPGHVFAVE
INSP143          SMIIAMTDGELVAHAFQDTLREAQKARKLGANVYTLGVADYNLDQITAIADSPGHVFAVE
INSP144          SMIIAMTDGELVAHAFQDTLREAQKARKLGANVYTLGVADYNLDQITAIADSPGHVFAVE
                 * :***:***:*        :  :**: *** ** :**  :  :**  :**** . :**.  :*:*.:

vWFA
ATR1_HUMAN       DGFQALQGIIHSI LKKSCIEILAAEPSTICAGES FQVVVRGNGFRHARNVDRVLCSFKIN
ATR2_HUMAN       GGFQALKGIINSI LAQSCTEILELQPSSVCVGEE FQIVLSGRGFMLGSRNGSVLCTYTVN
INSP141          NGFKALRSTIDAL TSKVCLDVTSVEPSSECVGEP YHVVIHGNGFQNLKKRDEVICRFIFN
INSP142          NGFKALRSTIDAL TSKVCLDVTSVEPSSECVGEP YHVVIHGNGFQNLKKRDEVICRFIFN
INSP143          NGFKALRSTIDAL TSKVCLDVTSVEPSSECVGEP YHVVIHGNGFQNLKKRDEVICRFIFN
INSP144          NGFKALRSTIDAL TSKVCLDVTSVEPSSECVGEP YHVVIHGNGFQNLKKRDEVICRFIFN
                 .**:**:. *.:    : *  :  .  :*:.*.**  :::: .:**  .  ::  :*  . *
                                                  ANT_IG domain ATR1_HUMAN       DSVTLNEKPFS
ATR2_HUMAN       ETYTTSVKPVS
INSP141          ESTIIGSTLLK
INSP142          ESTIIDEKPTS
INSP143          ESTIIDEKPTS
INSP144          ESTIIDEKPTS
                 ::   . .
                  ANT_IG
```

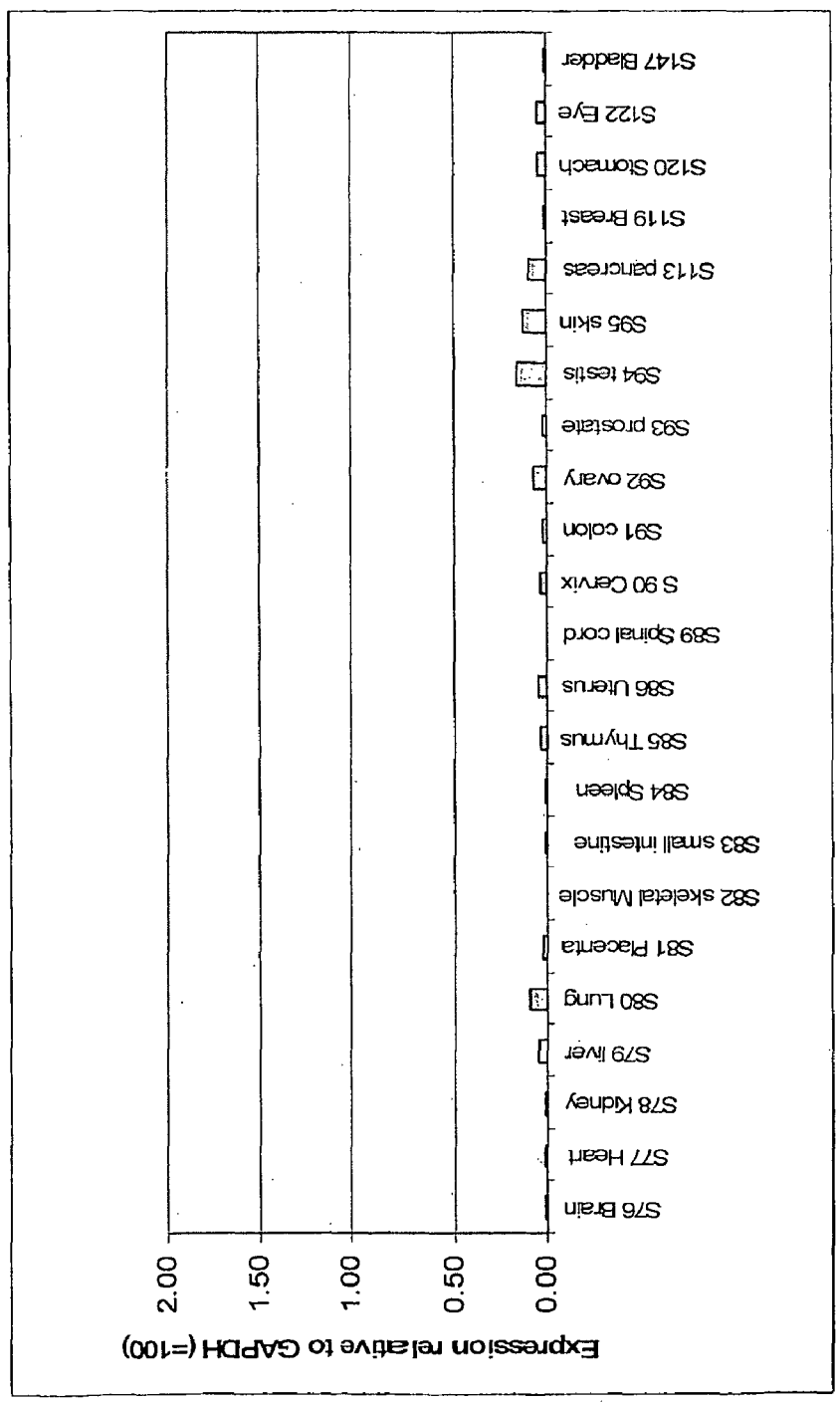
Figure 10: Expression of INSP142 in major human tissues as measured by RT-PCR (TaqMan).

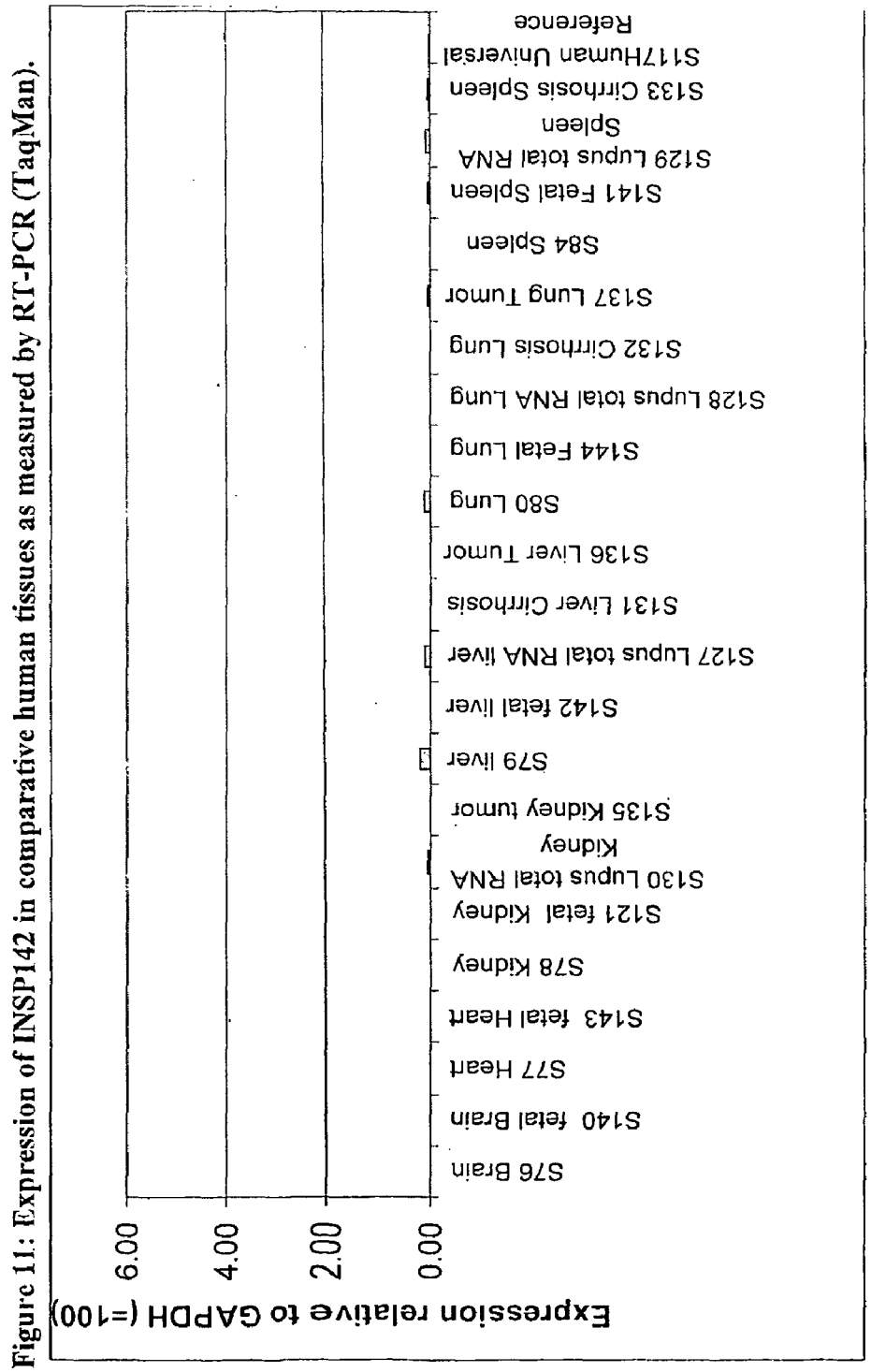
Figure 11: Expression of INSP142 in comparative human tissues as measured by RT-PCR (TaqMan).

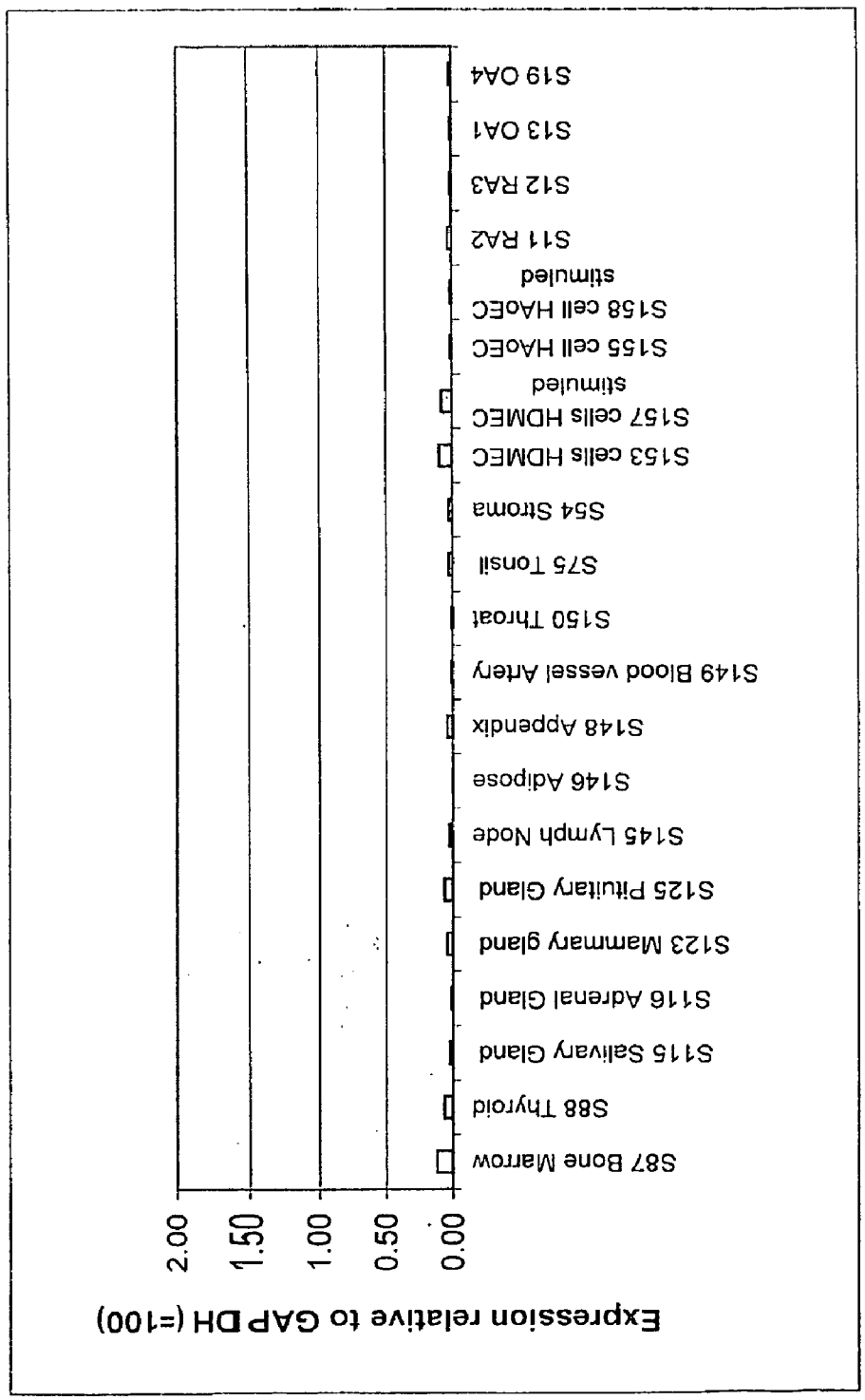
Figure 12: Expression of INSP142 in secretory and immune tissues as measured by RT-PCR (TaqMan).

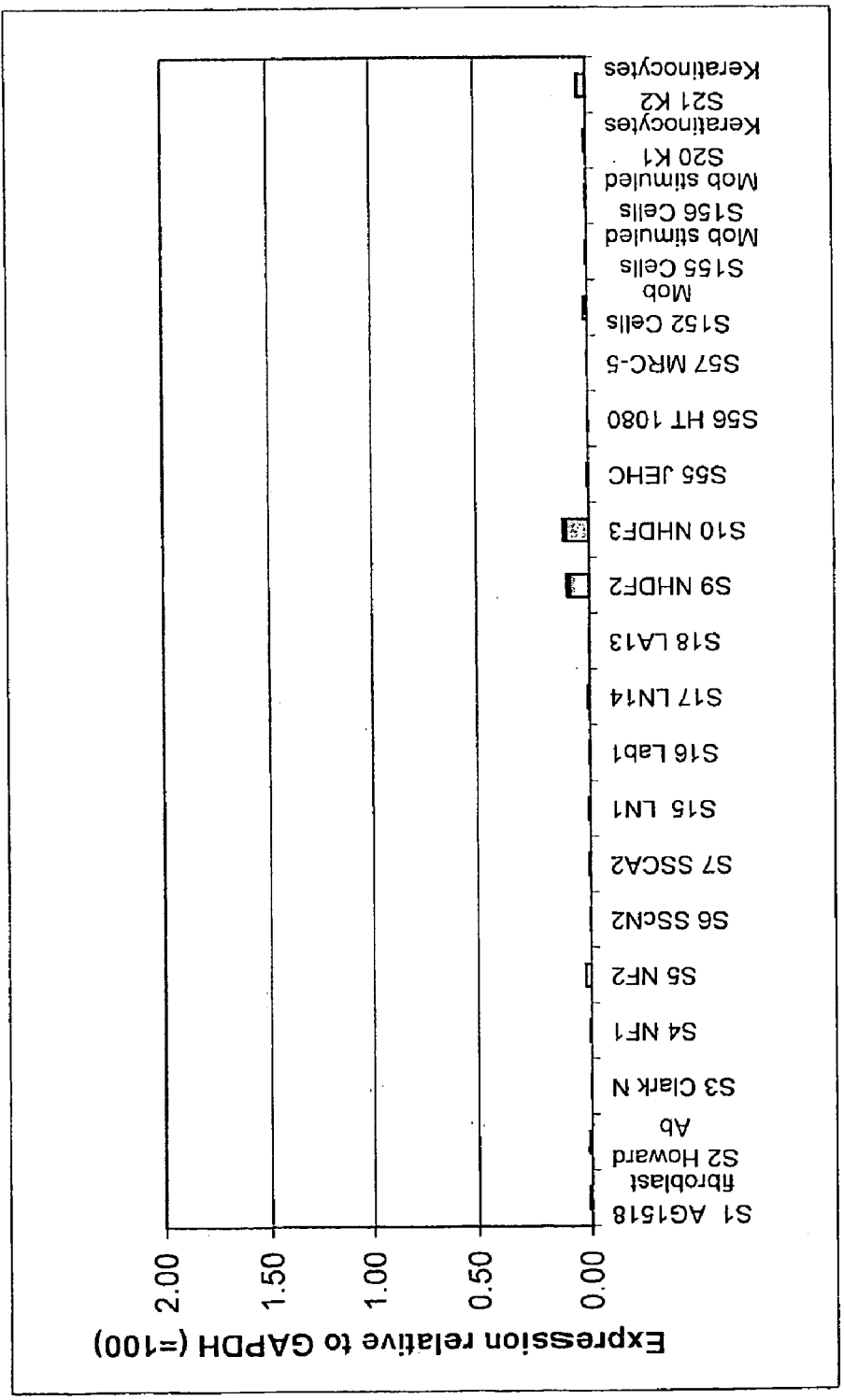
Figure 13: Expression of INSP142 in primary cells and cell lines as measured by RT-PCR (TaqMan).

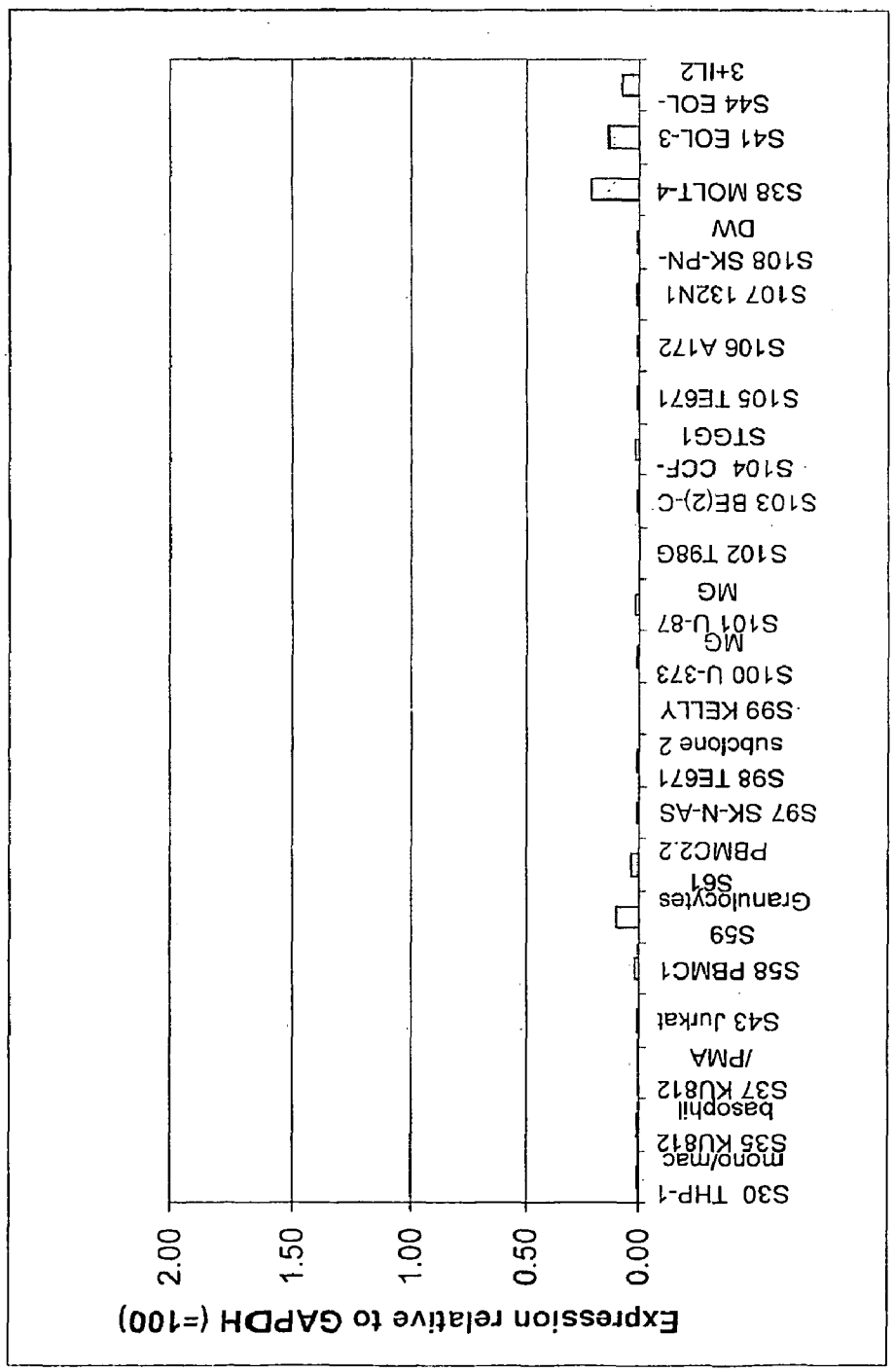
Figure 14: Expression of INSP142 in primary cells and cell lines of immune or CNS origin as measured by RT-PCR (TaqMan)

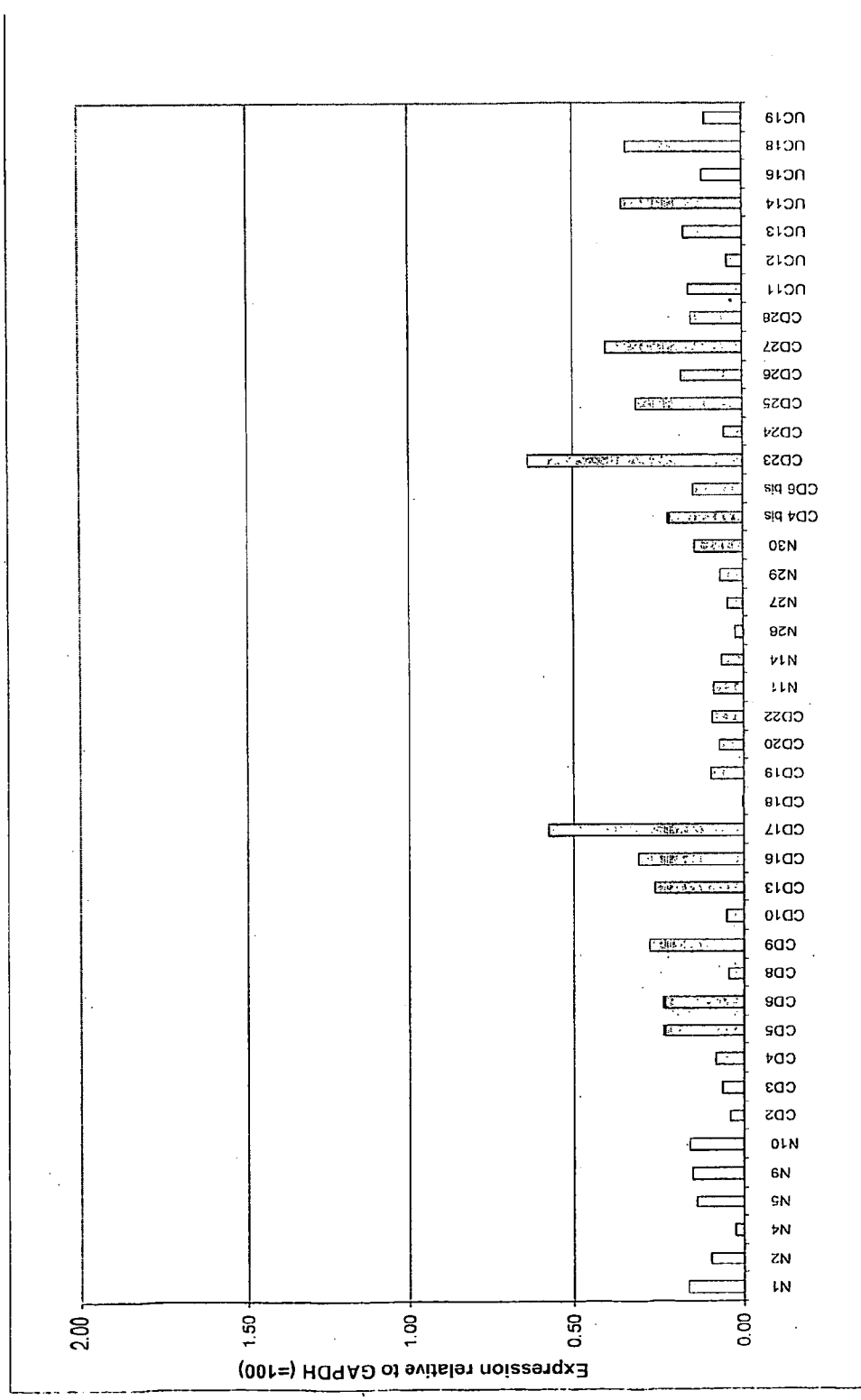
Figure 15: Expression of INSP142 in diseased colon and ileum biopsies as measured by RT-PCR (TaqMan)

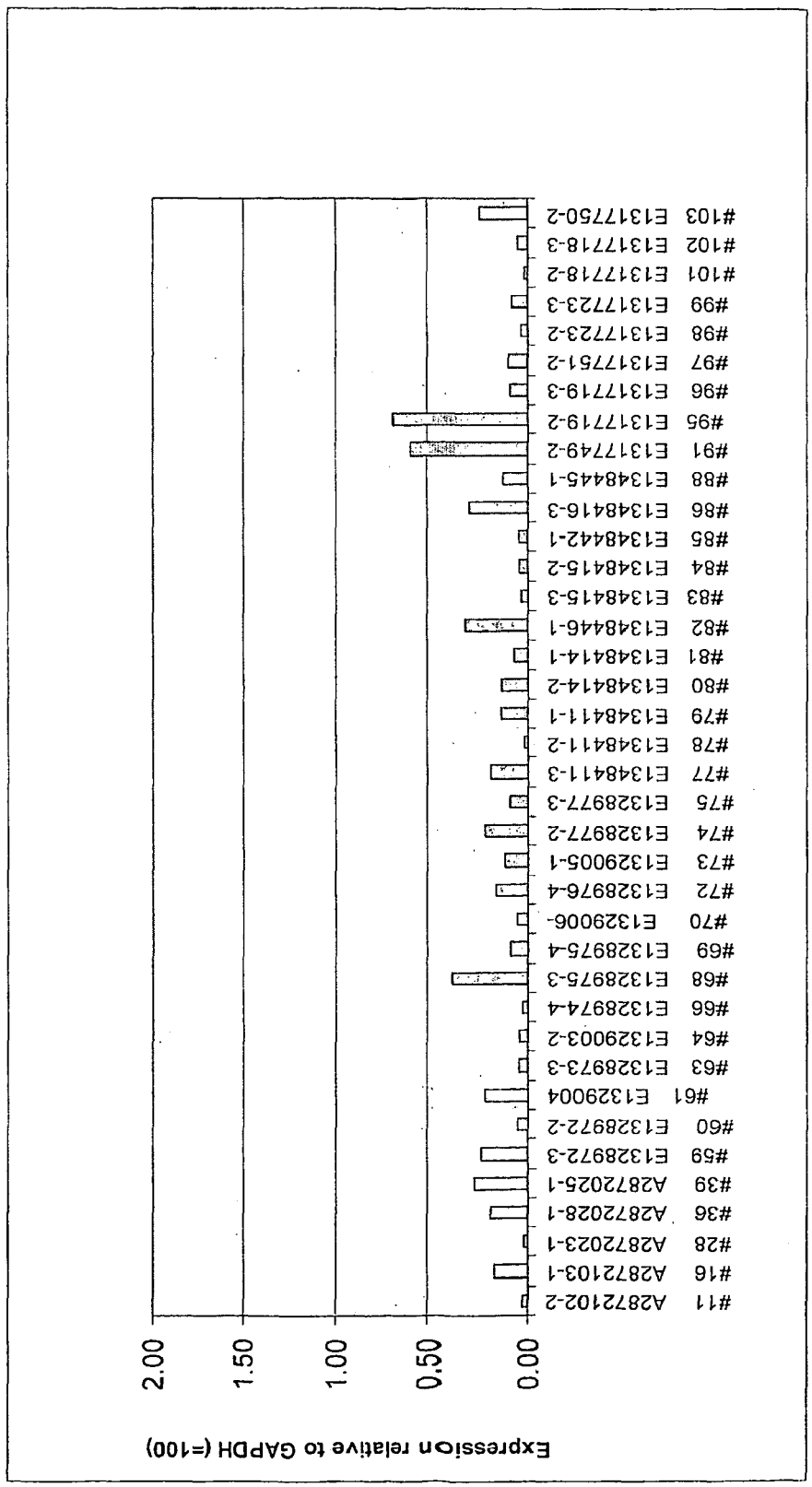
Figure 16: Expression of INSP142 in diseased skin biopsies from IL18BP clinical trial as measured by RT-PCR (TaqMan)

SEQUENCE LISTING

<160> NUMBER OF SEQ ID NOS: 169

<210> SEQ ID NO 1
<211> LENGTH: 248
<212> TYPE: DNA
<213> ORGANISM: Homo sapiens

<400> SEQUENCE: 1

```
atggggagcc atgagtccct ggggccctac ttcctggtct tcctgctgct gctgctgctt    60
cctccaccgc tttttagagc aggaagcctt cggtaccatg gacctgactg gagaatattt   120
caccgcctgg ccctgggctc aggagagcc caccaccacc atggcccagg atggaggcag   180
cactggcgcc aggggcaagc aggtcacaga tgccagggct catttgacct ctacttcatc   240
ttggacaa                                                             248
```

<210> SEQ ID NO 2
<211> LENGTH: 83
<212> TYPE: PRT
<213> ORGANISM: Homo sapiens

<400> SEQUENCE: 2

```
Met Gly Ser His Glu Ser Leu Gly Pro Tyr Phe Leu Val Phe Leu Leu
1               5                   10                  15

Leu Leu Leu Pro Pro Pro Leu Phe Arg Ala Gly Ser Leu Arg Tyr
            20                  25                  30

His Gly Pro Asp Trp Arg Ile Phe His Arg Leu Ala Leu Gly Ser Arg
        35                  40                  45

Arg Ala His His His Gly Pro Gly Trp Arg Gln His Trp Arg Gln
    50                  55                  60

Gly Gln Ala Gly His Arg Cys Gln Gly Ser Phe Asp Leu Tyr Phe Ile
65                  70                  75                  80

Leu Asp Lys
```

<210> SEQ ID NO 3
<211> LENGTH: 72
<212> TYPE: DNA
<213> ORGANISM: Homo sapiens

<400> SEQUENCE: 3

```
gtctggcagc gtgaacaata actggattga cctttatatg tgggtggagg aaacagtggc    60
gaggttccaa ag                                                        72
```

<210> SEQ ID NO 4
<211> LENGTH: 24
<212> TYPE: PRT
<213> ORGANISM: Homo sapiens

<400> SEQUENCE: 4

```
Ser Gly Ser Val Asn Asn Asn Trp Ile Asp Leu Tyr Met Trp Val Glu
1               5                   10                  15

Glu Thr Val Ala Arg Phe Gln Ser
            20
```

<210> SEQ ID NO 5
<211> LENGTH: 72
<212> TYPE: DNA
<213> ORGANISM: Homo sapiens

<400> SEQUENCE: 5

```
cccaaatatt cggatgtgct tcatcaccta ctccacagac ggccagactg tcttgccact    60
cacctcagac aa                                                       72
```

<210> SEQ ID NO 6
<211> LENGTH: 24
<212> TYPE: PRT
<213> ORGANISM: Homo sapiens

<400> SEQUENCE: 6

```
Pro Asn Ile Arg Met Cys Phe Ile Thr Tyr Ser Thr Asp Gly Gln Thr
1               5                   10                  15

Val Leu Pro Leu Thr Ser Asp Lys
            20
```

<210> SEQ ID NO 7
<211> LENGTH: 82
<212> TYPE: DNA
<213> ORGANISM: Homo sapiens

<400> SEQUENCE: 7

```
gaatagaata aaaaacggtc ttgaccaact tcagaaaatt gtgcctgacg gtcacacatt    60
catgcaggca ggatttagaa ag                                            82
```

<210> SEQ ID NO 8
<211> LENGTH: 27
<212> TYPE: PRT
<213> ORGANISM: Homo sapiens

<400> SEQUENCE: 8

```
Asn Arg Ile Lys Asn Gly Leu Asp Gln Leu Gln Lys Ile Val Pro Asp
1               5                   10                  15

Gly His Thr Phe Met Gln Ala Gly Phe Arg Lys
            20                  25
```

<210> SEQ ID NO 9
<211> LENGTH: 34
<212> TYPE: DNA
<213> ORGANISM: Homo sapiens

<400> SEQUENCE: 9

```
gcaattcaac agatcgaaag tttcaactcc ggaa                               34
```

<210> SEQ ID NO 10
<211> LENGTH: 12
<212> TYPE: PRT
<213> ORGANISM: Homo sapiens

<400> SEQUENCE: 10

```
Ala Ile Gln Gln Ile Glu Ser Phe Asn Ser Gly Asn
1               5                   10
```

<210> SEQ ID NO 11
<211> LENGTH: 77
<212> TYPE: DNA
<213> ORGANISM: Homo sapiens

<400> SEQUENCE: 11

```
acaaggttcc cagcatgatt attgctatga ctgatggaga actggtggca catgcatttc    60
aggacactct cagagaa                                                  77
```

<210> SEQ ID NO 12

```
<211> LENGTH: 25
<212> TYPE: PRT
<213> ORGANISM: Homo sapiens

<400> SEQUENCE: 12

Lys Val Pro Ser Met Ile Ile Ala Met Thr Asp Gly Glu Leu Val Ala
1               5                   10                  15

His Ala Phe Gln Asp Thr Leu Arg Glu
            20                  25

<210> SEQ ID NO 13
<211> LENGTH: 69
<212> TYPE: DNA
<213> ORGANISM: Homo sapiens

<400> SEQUENCE: 13
gctcaaaagg ctcggaaact gggggccaac gtttacaccc tgggtgtggc tgattataat      60
ctggaccag                                                              69

<210> SEQ ID NO 14
<211> LENGTH: 23
<212> TYPE: PRT
<213> ORGANISM: Homo sapiens

<400> SEQUENCE: 14

Ala Gln Lys Ala Arg Lys Leu Gly Ala Asn Val Tyr Thr Leu Gly Val
1               5                   10                  15

Ala Asp Tyr Asn Leu Asp Gln
            20

<210> SEQ ID NO 15
<211> LENGTH: 81
<212> TYPE: DNA
<213> ORGANISM: Homo sapiens

<400> SEQUENCE: 15
ataacagcaa ttgcagacag ccctggccac gtgtttgcag tggagaatgg cttcaaggcc      60
ctgagaagca ccattgatgc c                                                81

<210> SEQ ID NO 16
<211> LENGTH: 27
<212> TYPE: PRT
<213> ORGANISM: Homo sapiens

<400> SEQUENCE: 16

Ile Thr Ala Ile Ala Asp Ser Pro Gly His Val Phe Ala Val Glu Asn
1               5                   10                  15

Gly Phe Lys Ala Leu Arg Ser Thr Ile Asp Ala
            20                  25

<210> SEQ ID NO 17
<211> LENGTH: 61
<212> TYPE: DNA
<213> ORGANISM: Homo sapiens

<400> SEQUENCE: 17
ctcacgtcaa aggtctgtct tgatgtgaca tcggtggagc cttcctctga gtgtgtagga      60
g                                                                      61

<210> SEQ ID NO 18
<211> LENGTH: 21
<212> TYPE: PRT
```

<213> ORGANISM: Homo sapiens

<400> SEQUENCE: 18

Leu Thr Ser Lys Val Cys Leu Asp Val Thr Ser Val Glu Pro Ser Ser
1               5                   10                  15

Glu Cys Val Gly Glu
            20

<210> SEQ ID NO 19
<211> LENGTH: 99
<212> TYPE: DNA
<213> ORGANISM: Homo sapiens

<400> SEQUENCE: 19
aaccctacca tgtggttatt catggaaatg gctttcagaa tctaaagaaa cgggatgaag      60
ttatttgcag atttatcttc aatgaaagca ctatcattg                            99

<210> SEQ ID NO 20
<211> LENGTH: 33
<212> TYPE: PRT
<213> ORGANISM: Homo sapiens

<400> SEQUENCE: 20

Pro Tyr His Val Val Ile His Gly Asn Gly Phe Gln Asn Leu Lys Lys
1               5                   10                  15

Arg Asp Glu Val Ile Cys Arg Phe Ile Phe Asn Glu Ser Thr Ile Ile
            20                  25                  30

Gly

<210> SEQ ID NO 21
<211> LENGTH: 26
<212> TYPE: DNA
<213> ORGANISM: Homo sapiens

<400> SEQUENCE: 21
ggagtactct attgaagtca gcttga                                          26

<210> SEQ ID NO 22
<211> LENGTH: 7
<212> TYPE: PRT
<213> ORGANISM: Homo sapiens

<400> SEQUENCE: 22

Ser Thr Leu Leu Lys Ser Ala
1               5

<210> SEQ ID NO 23
<211> LENGTH: 921
<212> TYPE: DNA
<213> ORGANISM: Homo sapiens

<400> SEQUENCE: 23
atggggagcc atgagtccct ggggccctac ttcctggtct tcctgctgct gctgctgctt      60
cctccaccgc tttttagagc aggaagcctt cggtaccatg acctgactg agaatattt       120 caccgcctgg ccctgggctc caggagagcc accaccacc atgcccagg atggaggcag       180 cactggcgcc aggggcaagc aggtcacaga tgccagggc catttgacct ctacttcatc      240
ttggacaagt ctggcagcgt gaacaataac tggattgacc tttatatgtg ggtggaggaa      300
acagtggcga ggttccaaag cccaaatatt cggatgtgct catcaccta ctccacagac      360 ggccagactg tcttgccact cacctcagac aagaataaa taaaaaacgg tcttgaccaa      420

```
cttcagaaaa ttgtgcctga cggtcacaca ttcatgcagg caggatttag aaaggcaatt      480
caacagatcg aaagtttcaa ctccggaaac aaggttccca gcatgattat tgctatgact      540
gatggagaac tggtggcaca tgcatttcag acactctca gagaagctca aaaggctcgg       600
aaactggggg ccaacgttta caccctgggt gtggctgatt ataatctgga ccagataaca      660
gcaattgcag acagccctgg ccacgtgttt gcagtggaga atggcttcaa ggccctgaga      720
agcaccattg atgccctcac gtcaaaggtc tgtcttgatg tgacatcggt ggagccttcc      780
tctgagtgtg taggagaacc ctaccatgtg gttattcatg gaaatggctt tcagaatcta      840
aagaaacggg atgaagttat ttgcagattt atcttcaatg aaagcactat cattgggagt      900
actctattga agtcagcttg a                                                921
```

<210> SEQ ID NO 24
<211> LENGTH: 306
<212> TYPE: PRT
<213> ORGANISM: Homo sapiens

<400> SEQUENCE: 24

```
Met Gly Ser His Glu Ser Leu Gly Pro Tyr Phe Leu Val Phe Leu Leu
1               5                   10                  15

Leu Leu Leu Pro Pro Leu Phe Arg Ala Gly Ser Leu Arg Tyr
            20                  25                  30

His Gly Pro Asp Trp Arg Ile Phe His Arg Leu Ala Leu Gly Ser Arg
        35                  40                  45

Arg Ala His His His Gly Pro Gly Trp Arg Gln His Trp Arg Gln
    50                  55                  60

Gly Gln Ala Gly His Arg Cys Gln Gly Ser Phe Asp Leu Tyr Phe Ile
65                  70                  75                  80

Leu Asp Lys Ser Gly Ser Val Asn Asn Asn Trp Ile Asp Leu Tyr Met
                85                  90                  95

Trp Val Glu Glu Thr Val Ala Arg Phe Gln Ser Pro Asn Ile Arg Met
            100                 105                 110

Cys Phe Ile Thr Tyr Ser Thr Asp Gly Gln Thr Val Leu Pro Leu Thr
        115                 120                 125

Ser Asp Lys Asn Arg Ile Lys Asn Gly Leu Asp Gln Leu Gln Lys Ile
    130                 135                 140

Val Pro Asp Gly His Thr Phe Met Gln Ala Gly Phe Arg Lys Ala Ile
145                 150                 155                 160

Gln Gln Ile Glu Ser Phe Asn Ser Gly Asn Lys Val Pro Ser Met Ile
                165                 170                 175

Ile Ala Met Thr Asp Gly Glu Leu Val Ala His Ala Phe Gln Asp Thr
            180                 185                 190

Leu Arg Glu Ala Gln Lys Ala Arg Lys Leu Gly Ala Asn Val Tyr Thr
        195                 200                 205

Leu Gly Val Ala Asp Tyr Asn Leu Asp Gln Ile Thr Ala Ile Ala Asp
    210                 215                 220

Ser Pro Gly His Val Phe Ala Val Glu Asn Gly Phe Lys Ala Leu Arg
225                 230                 235                 240

Ser Thr Ile Asp Ala Leu Thr Ser Lys Val Cys Leu Asp Val Thr Ser
                245                 250                 255

Val Glu Pro Ser Ser Glu Cys Val Gly Glu Pro Tyr His Val Val Ile
            260                 265                 270

His Gly Asn Gly Phe Gln Asn Leu Lys Lys Arg Asp Glu Val Ile Cys
        275                 280                 285
```

Arg Phe Ile Phe Asn Glu Ser Thr Ile Ile Gly Ser Thr Leu Leu Lys
    290                 295                 300

Ser Ala
305

<210> SEQ ID NO 25
<211> LENGTH: 248
<212> TYPE: DNA
<213> ORGANISM: Homo sapiens

<400> SEQUENCE: 25
atggggagcc atgagtccct ggggccctac ttcctggtct tcctgctgct gctgctgctt    60
cctccaccgc tttttagagc aggaagcctt cggtaccatg gacctgactg gagaatattt   120
caccgcctgg ccctgggctc aggagagcc caccaccacc atggcccagg atggaggcag   180
cactggcgcc aggggcaagc aggtcacaga tgccagggct catttgacct ctacttcatc   240
ttggacaa                                                            248

<210> SEQ ID NO 26
<211> LENGTH: 83
<212> TYPE: PRT
<213> ORGANISM: Homo sapiens

<400> SEQUENCE: 26

Met Gly Ser His Glu Ser Leu Gly Pro Tyr Phe Leu Val Phe Leu Leu
1               5                   10                  15

Leu Leu Leu Pro Pro Leu Phe Arg Ala Gly Ser Leu Arg Tyr
            20                  25                  30

His Gly Pro Asp Trp Arg Ile Phe His Arg Leu Ala Leu Gly Ser Arg
        35                  40                  45

Arg Ala His His His His Gly Pro Gly Trp Arg Gln His Trp Arg Gln
    50                  55                  60

Gly Gln Ala Gly His Arg Cys Gln Gly Ser Phe Asp Leu Tyr Phe Ile
65                  70                  75                  80

Leu Asp Lys

<210> SEQ ID NO 27
<211> LENGTH: 72
<212> TYPE: DNA
<213> ORGANISM: Homo sapiens

<400> SEQUENCE: 27
gtctggcagc gtgaacaata actggattga cctttatatg tgggtggagg aaacagtggc    60
gaggttccaa ag                                                        72

<210> SEQ ID NO 28
<211> LENGTH: 24
<212> TYPE: PRT
<213> ORGANISM: Homo sapiens

<400> SEQUENCE: 28

Ser Gly Ser Val Asn Asn Asn Trp Ile Asp Leu Tyr Met Trp Val Glu
1               5                   10                  15

Glu Thr Val Ala Arg Phe Gln Ser
            20

<210> SEQ ID NO 29
<211> LENGTH: 72
<212> TYPE: DNA

<213> ORGANISM: Homo sapiens

<400> SEQUENCE: 29

```
cccaaatatt cggatgtgct tcatcaccta ctccacagac ggccagactg tcttgccact    60
cacctcagac aa                                                        72
```

<210> SEQ ID NO 30
<211> LENGTH: 24
<212> TYPE: PRT
<213> ORGANISM: Homo sapiens

<400> SEQUENCE: 30

```
Pro Asn Ile Arg Met Cys Phe Ile Thr Tyr Ser Thr Asp Gly Gln Thr
1               5                   10                  15
Val Leu Pro Leu Thr Ser Asp Lys
            20
```

<210> SEQ ID NO 31
<211> LENGTH: 82
<212> TYPE: DNA
<213> ORGANISM: Homo sapiens

<400> SEQUENCE: 31

```
gaatagaata aaaaacggtc ttgaccaact tcagaaaatt gtgcctgacg gtcacacatt    60
catgcaggca ggatttagaa ag                                             82
```

<210> SEQ ID NO 32
<211> LENGTH: 27
<212> TYPE: PRT
<213> ORGANISM: Homo sapiens

<400> SEQUENCE: 32

```
Asn Arg Ile Lys Asn Gly Leu Asp Gln Leu Gln Lys Ile Val Pro Asp
1               5                   10                  15
Gly His Thr Phe Met Gln Ala Gly Phe Arg Lys
            20                  25
```

<210> SEQ ID NO 33
<211> LENGTH: 34
<212> TYPE: DNA
<213> ORGANISM: Homo sapiens

<400> SEQUENCE: 33

```
gcaattcaac agatcgaaag tttcaactcc ggaa                                34
```

<210> SEQ ID NO 34
<211> LENGTH: 12
<212> TYPE: PRT
<213> ORGANISM: Homo sapiens

<400> SEQUENCE: 34

```
Ala Ile Gln Gln Ile Glu Ser Phe Asn Ser Gly Asn
1               5                   10
```

<210> SEQ ID NO 35
<211> LENGTH: 77
<212> TYPE: DNA
<213> ORGANISM: Homo sapiens

<400> SEQUENCE: 35

```
acaaggttcc cagcatgatt attgctatga ctgatggaga actggtggca catgcatttc    60
aggacactct cagagaa                                                   77
```

<210> SEQ ID NO 36
<211> LENGTH: 25
<212> TYPE: PRT
<213> ORGANISM: Homo sapiens

<400> SEQUENCE: 36

Lys Val Pro Ser Met Ile Ile Ala Met Thr Asp Gly Glu Leu Val Ala
1               5                   10                  15

His Ala Phe Gln Asp Thr Leu Arg Glu
            20                  25

<210> SEQ ID NO 37
<211> LENGTH: 69
<212> TYPE: DNA
<213> ORGANISM: Homo sapiens

<400> SEQUENCE: 37
gctcaaaagg ctcggaaact gggggccaac gtttacaccc tgggtgtggc tgattataat    60
ctggaccag                                                            69

<210> SEQ ID NO 38
<211> LENGTH: 23
<212> TYPE: PRT
<213> ORGANISM: Homo sapiens

<400> SEQUENCE: 38

Ala Gln Lys Ala Arg Lys Leu Gly Ala Asn Val Tyr Thr Leu Gly Val
1               5                   10                  15

Ala Asp Tyr Asn Leu Asp Gln
            20

<210> SEQ ID NO 39
<211> LENGTH: 81
<212> TYPE: DNA
<213> ORGANISM: Homo sapiens

<400> SEQUENCE: 39
ataacagcaa ttgcagacag ccctggccac gtgtttgcag tggagaatgg cttcaaggcc    60
ctgagaagca ccattgatgc c                                              81

<210> SEQ ID NO 40
<211> LENGTH: 27
<212> TYPE: PRT
<213> ORGANISM: Homo sapiens

<400> SEQUENCE: 40

Ile Thr Ala Ile Ala Asp Ser Pro Gly His Val Phe Ala Val Glu Asn
1               5                   10                  15

Gly Phe Lys Ala Leu Arg Ser Thr Ile Asp Ala
            20                  25

<210> SEQ ID NO 41
<211> LENGTH: 61
<212> TYPE: DNA
<213> ORGANISM: Homo sapiens

<400> SEQUENCE: 41
ctcacgtcaa aggtctgtct tgatgtgaca tcggtggagc cttcctctga gtgtgtagga    60
g                                                                    61

```
<210> SEQ ID NO 42
<211> LENGTH: 21
<212> TYPE: PRT
<213> ORGANISM: Homo sapiens

<400> SEQUENCE: 42

Leu Thr Ser Lys Val Cys Leu Asp Val Thr Ser Val Glu Pro Ser Ser
1               5                   10                  15

Glu Cys Val Gly Glu
            20

<210> SEQ ID NO 43
<211> LENGTH: 99
<212> TYPE: DNA
<213> ORGANISM: Homo sapiens

<400> SEQUENCE: 43
aaccctacca tgtggttatt catggaaatg gctttcagaa tctaaagaaa cgggatgaag     60
ttatttgcag atttatcttc aatgaaagca ctatcattg                           99

<210> SEQ ID NO 44
<211> LENGTH: 33
<212> TYPE: PRT
<213> ORGANISM: Homo sapiens

<400> SEQUENCE: 44

Pro Tyr His Val Val Ile His Gly Asn Gly Phe Gln Asn Leu Lys Lys
1               5                   10                  15

Arg Asp Glu Val Ile Cys Arg Phe Ile Phe Asn Glu Ser Thr Ile Ile
            20                  25                  30

Asp

<210> SEQ ID NO 45
<211> LENGTH: 70
<212> TYPE: DNA
<213> ORGANISM: Homo sapiens

<400> SEQUENCE: 45
atgaaaagcc aaccagtatc gacaataatt ccatgaattg ccctgggcca aaactagaaa     60
aacctggaga                                                           70

<210> SEQ ID NO 46
<211> LENGTH: 23
<212> TYPE: PRT
<213> ORGANISM: Homo sapiens

<400> SEQUENCE: 46

Glu Lys Pro Thr Ser Ile Asp Asn Asn Ser Met Asn Cys Pro Gly Pro
1               5                   10                  15

Lys Leu Glu Lys Pro Gly Glu
            20

<210> SEQ ID NO 47
<211> LENGTH: 79
<212> TYPE: DNA
<213> ORGANISM: Homo sapiens

<400> SEQUENCE: 47
ggagtactct attgaagtca gcttgaacaa aggcaaaaca ttcttcaaga gcaatgtcag     60
catcaccagc accacatgt                                                 79
```

<210> SEQ ID NO 48
<211> LENGTH: 26
<212> TYPE: PRT
<213> ORGANISM: Homo sapiens

<400> SEQUENCE: 48

Glu Tyr Ser Ile Glu Val Ser Leu Asn Lys Gly Lys Thr Phe Phe Lys
1               5                   10                  15

Ser Asn Val Ser Ile Thr Ser Thr Thr Cys
            20                  25

<210> SEQ ID NO 49
<211> LENGTH: 15
<212> TYPE: DNA
<213> ORGANISM: Homo sapiens

<400> SEQUENCE: 49
ccttctctta agtag                                                15

<210> SEQ ID NO 50
<211> LENGTH: 4
<212> TYPE: PRT
<213> ORGANISM: Homo sapiens

<400> SEQUENCE: 50

Pro Ser Leu Lys
1

<210> SEQ ID NO 51
<211> LENGTH: 1059
<212> TYPE: DNA
<213> ORGANISM: Homo sapiens

<400> SEQUENCE: 51

```
atgggagcc atgagtccct ggggccctac ttcctggtct tcctgctgct gctgctgctt     60
cctccaccgc ttttagagc aggaagcctt cggtaccatg acctgactg gagaatattt    120
caccgcctgg ccctgggctc aggagagcc accaccacc atgcccagg atggaggcag    180
cactggcgcc aggggcaagc aggtcacaga tgccagggct catttgacct ctacttcatc    240
ttggacaagt ctggcagcgt gaacaataac tggattgacc tttatatgtg ggtggaggaa    300
acagtggcga ggttccaaag cccaaatatt cggatgtgct tcatcaccta ctccacagac    360
ggccagactg tcttgccact cacctcagac aagaatagaa taaaaaacgg tcttgaccaa    420
cttcagaaaa ttgtgcctga cggtcacaca ttcatgcagg caggatttag aaaggcaatt    480
caacagatcg aaagtttcaa ctccggaaac aaggttccca gcatgattat tgctatgact    540
gatggagaac tggtggcaca tgcatttcag gacactctca gagaagctca aaaggctcgg    600
aaactggggg ccaacgttta caccctgggt gtggctgatt ataatctgga ccagataaca    660
gcaattgcag acagccctgg ccacgtgttt gcagtggaga atggcttcaa ggccctgaga    720
agcaccattg atgccctcac gtcaaaggtc tgtcttgatg tgacatcggt ggagccttcc    780
tctgagtgtg taggagaacc ctaccatgtg gttattcatg gaaatggctt tcagaatcta    840
aagaaacggg atgaagttat ttgcagattt atcttcaatg aaagcactat cattgatgaa    900
aagccaacca gtatcgacaa taattccatg aattgccctg gccaaaaact agaaaaacct    960
ggagaggagt actctattga agtcagcttg aacaaggca aacattctt caagagcaat   1020
gtcagcatca ccagcaccac atgtccttct cttaagtag                         1059
```

<210> SEQ ID NO 52

<211> LENGTH: 352
<212> TYPE: PRT
<213> ORGANISM: Homo sapiens

<400> SEQUENCE: 52

```
Met Gly Ser His Glu Ser Leu Gly Pro Tyr Phe Leu Val Phe Leu Leu
1               5                   10                  15

Leu Leu Leu Leu Pro Pro Leu Phe Arg Ala Gly Ser Leu Arg Tyr
            20                  25                  30

His Gly Pro Asp Trp Arg Ile Phe His Arg Leu Ala Leu Gly Ser Arg
        35                  40                  45

Arg Ala His His His Gly Pro Gly Trp Arg Gln His Trp Arg Gln
50                  55                  60

Gly Gln Ala Gly His Arg Cys Gln Gly Ser Phe Asp Leu Tyr Phe Ile
65                  70                  75                  80

Leu Asp Lys Ser Gly Ser Val Asn Asn Asn Trp Ile Asp Leu Tyr Met
                85                  90                  95

Trp Val Glu Glu Thr Val Ala Arg Phe Gln Ser Pro Asn Ile Arg Met
            100                 105                 110

Cys Phe Ile Thr Tyr Ser Thr Asp Gly Gln Thr Val Leu Pro Leu Thr
        115                 120                 125

Ser Asp Lys Asn Arg Ile Lys Asn Gly Leu Asp Gln Leu Gln Lys Ile
130                 135                 140

Val Pro Asp Gly His Thr Phe Met Gln Ala Gly Phe Arg Lys Ala Ile
145                 150                 155                 160

Gln Gln Ile Glu Ser Phe Asn Ser Gly Asn Lys Val Pro Ser Met Ile
                165                 170                 175

Ile Ala Met Thr Asp Gly Glu Leu Val Ala His Ala Phe Gln Asp Thr
            180                 185                 190

Leu Arg Glu Ala Gln Lys Ala Arg Lys Leu Gly Ala Asn Val Tyr Thr
        195                 200                 205

Leu Gly Val Ala Asp Tyr Asn Leu Asp Gln Ile Thr Ala Ile Ala Asp
    210                 215                 220

Ser Pro Gly His Val Phe Ala Val Glu Asn Gly Phe Lys Ala Leu Arg
225                 230                 235                 240

Ser Thr Ile Asp Ala Leu Thr Ser Lys Val Cys Leu Asp Val Thr Ser
                245                 250                 255

Val Glu Pro Ser Ser Glu Cys Val Gly Glu Pro Tyr His Val Val Ile
            260                 265                 270

His Gly Asn Gly Phe Gln Asn Leu Lys Lys Arg Asp Glu Val Ile Cys
        275                 280                 285

Arg Phe Ile Phe Asn Glu Ser Thr Ile Ile Asp Glu Lys Pro Thr Ser
    290                 295                 300

Ile Asp Asn Asn Ser Met Asn Cys Pro Gly Pro Lys Leu Glu Lys Pro
305                 310                 315                 320

Gly Glu Glu Tyr Ser Ile Glu Val Ser Leu Asn Lys Gly Lys Thr Phe
                325                 330                 335

Phe Lys Ser Asn Val Ser Ile Thr Ser Thr Thr Cys Pro Ser Leu Lys
            340                 345                 350
```

<210> SEQ ID NO 53
<211> LENGTH: 248
<212> TYPE: DNA
<213> ORGANISM: Homo sapiens

<400> SEQUENCE: 53

```
atggggagcc atgagtccct ggggccctac ttcctggtct tcctgctgct gctgctgctt    60
cctccaccgc ttttagagc aggaagcctt cggtaccatg gacctgactg agaatattt     120 caccgcctgg ccctgggctc aggagagcc accaccacc atggcccagg atggaggcag    180
cactggcgcc aggggcaagc aggtcacaga tgccagggct catttgacct ctacttcatc  240
ttggacaa                                                            248
```

<210> SEQ ID NO 54
<211> LENGTH: 83
<212> TYPE: PRT
<213> ORGANISM: Homo sapiens

<400> SEQUENCE: 54

Met Gly Ser His Glu Ser Leu Gly Pro Tyr Phe Leu Val Phe Leu Leu
1               5                   10                  15
Leu Leu Leu Pro Pro Pro Leu Phe Arg Ala Gly Ser Leu Arg Tyr
            20                  25                  30
His Gly Pro Asp Trp Arg Ile Phe His Arg Leu Ala Leu Gly Ser Arg
        35                  40                  45
Arg Ala His His His Gly Pro Gly Trp Arg Gln His Trp Arg Gln
    50                  55                  60
Gly Gln Ala Gly His Arg Cys Gln Gly Ser Phe Asp Leu Tyr Phe Ile
65                  70                  75                  80
Leu Asp Lys

<210> SEQ ID NO 55
<211> LENGTH: 72
<212> TYPE: DNA
<213> ORGANISM: Homo sapiens

<400> SEQUENCE: 55

```
gtctggcagc gtgaacaata actggattga cctttatatg tgggtggagg aaacagtggc    60
gaggttccaa ag                                                        72
```

<210> SEQ ID NO 56
<211> LENGTH: 24
<212> TYPE: PRT
<213> ORGANISM: Homo sapiens

<400> SEQUENCE: 56

Ser Gly Ser Val Asn Asn Asn Trp Ile Asp Leu Tyr Met Trp Val Glu
1               5                   10                  15
Glu Thr Val Ala Arg Phe Gln Ser
            20

<210> SEQ ID NO 57
<211> LENGTH: 72
<212> TYPE: DNA
<213> ORGANISM: Homo sapiens

<400> SEQUENCE: 57

```
cccaaatatt cggatgtgct tcatcaccta ctccacagac ggccagactg tcttgccact    60
cacctcagac aa                                                        72
```

<210> SEQ ID NO 58
<211> LENGTH: 24
<212> TYPE: PRT
<213> ORGANISM: Homo sapiens

<400> SEQUENCE: 58

```
Pro Asn Ile Arg Met Cys Phe Ile Thr Tyr Ser Thr Asp Gly Gln Thr
1               5                   10                  15

Val Leu Pro Leu Thr Ser Asp Lys
            20
```

<210> SEQ ID NO 59
<211> LENGTH: 82
<212> TYPE: DNA
<213> ORGANISM: Homo sapiens

<400> SEQUENCE: 59

```
gaatagaata aaaacggtc ttgaccaact tcagaaaatt gtgcctgacg gtcacacatt    60
catgcaggca ggatttagaa ag                                           82
```

<210> SEQ ID NO 60
<211> LENGTH: 27
<212> TYPE: PRT
<213> ORGANISM: Homo sapiens

<400> SEQUENCE: 60

```
Asn Arg Ile Lys Asn Gly Leu Asp Gln Leu Gln Lys Ile Val Pro Asp
1               5                   10                  15

Gly His Thr Phe Met Gln Ala Gly Phe Arg Lys
            20                  25
```

<210> SEQ ID NO 61
<211> LENGTH: 34
<212> TYPE: DNA
<213> ORGANISM: Homo sapiens

<400> SEQUENCE: 61

```
gcaattcaac agatcgaaag tttcaactcc ggaa                              34
```

<210> SEQ ID NO 62
<211> LENGTH: 12
<212> TYPE: PRT
<213> ORGANISM: Homo sapiens

<400> SEQUENCE: 62

```
Ala Ile Gln Gln Ile Glu Ser Phe Asn Ser Gly Asn
1               5                   10
```

<210> SEQ ID NO 63
<211> LENGTH: 77
<212> TYPE: DNA
<213> ORGANISM: Homo sapiens

<400> SEQUENCE: 63

```
acaaggttcc cagcatgatt attgctatga ctgatggaga actggtggca catgcatttc    60
aggacactct cagagaa                                                  77
```

<210> SEQ ID NO 64
<211> LENGTH: 25
<212> TYPE: PRT
<213> ORGANISM: Homo sapiens

<400> SEQUENCE: 64

```
Lys Val Pro Ser Met Ile Ile Ala Met Thr Asp Gly Glu Leu Val Ala
1               5                   10                  15

His Ala Phe Gln Asp Thr Leu Arg Glu
            20                  25
```

<210> SEQ ID NO 65
<211> LENGTH: 69
<212> TYPE: DNA
<213> ORGANISM: Homo sapiens

<400> SEQUENCE: 65
gctcaaaagg ctcggaaact gggggccaac gtttacaccc tgggtgtggc tgattataat     60
ctggaccag                                                             69

<210> SEQ ID NO 66
<211> LENGTH: 23
<212> TYPE: PRT
<213> ORGANISM: Homo sapiens

<400> SEQUENCE: 66

Ala Gln Lys Ala Arg Lys Leu Gly Ala Asn Val Tyr Thr Leu Gly Val
1               5                   10                  15

Ala Asp Tyr Asn Leu Asp Gln
            20

<210> SEQ ID NO 67
<211> LENGTH: 81
<212> TYPE: DNA
<213> ORGANISM: Homo sapiens

<400> SEQUENCE: 67
ataacagcaa ttgcagacag ccctggccac gtgtttgcag tggagaatgg cttcaaggcc     60
ctgagaagca ccattgatgc c                                               81

<210> SEQ ID NO 68
<211> LENGTH: 27
<212> TYPE: PRT
<213> ORGANISM: Homo sapiens

<400> SEQUENCE: 68

Ile Thr Ala Ile Ala Asp Ser Pro Gly His Val Phe Ala Val Glu Asn
1               5                   10                  15

Gly Phe Lys Ala Leu Arg Ser Thr Ile Asp Ala
            20                  25

<210> SEQ ID NO 69
<211> LENGTH: 61
<212> TYPE: DNA
<213> ORGANISM: Homo sapiens

<400> SEQUENCE: 69
ctcacgtcaa aggtctgtct tgatgtgaca tcggtggagc cttcctctga gtgtgtagga     60
g                                                                     61

<210> SEQ ID NO 70
<211> LENGTH: 21
<212> TYPE: PRT
<213> ORGANISM: Homo sapiens

<400> SEQUENCE: 70

Leu Thr Ser Lys Val Cys Leu Asp Val Thr Ser Val Glu Pro Ser Ser
1               5                   10                  15

Glu Cys Val Gly Glu
            20

<210> SEQ ID NO 71

```
<211> LENGTH: 99
<212> TYPE: DNA
<213> ORGANISM: Homo sapiens

<400> SEQUENCE: 71
aaccctacca tgtggttatt catggaaatg gctttcagaa tctaaagaaa cgggatgaag    60
ttatttgcag atttatcttc aatgaaagca ctatcattg                          99

<210> SEQ ID NO 72
<211> LENGTH: 33
<212> TYPE: PRT
<213> ORGANISM: Homo sapiens

<400> SEQUENCE: 72

Pro Tyr His Val Val Ile His Gly Asn Gly Phe Gln Asn Leu Lys Lys
1               5                   10                  15

Arg Asp Glu Val Ile Cys Arg Phe Ile Phe Asn Glu Ser Thr Ile Ile
            20                  25                  30

Asp

<210> SEQ ID NO 73
<211> LENGTH: 70
<212> TYPE: DNA
<213> ORGANISM: Homo sapiens

<400> SEQUENCE: 73
atgaaaagcc aaccagtatc gacaataatt ccatgaattg ccctgggcca aaactagaaa    60
aacctggaga                                                          70

<210> SEQ ID NO 74
<211> LENGTH: 23
<212> TYPE: PRT
<213> ORGANISM: Homo sapiens

<400> SEQUENCE: 74

Glu Lys Pro Thr Ser Ile Asp Asn Asn Ser Met Asn Cys Pro Gly Pro
1               5                   10                  15

Lys Leu Glu Lys Pro Gly Glu
            20

<210> SEQ ID NO 75
<211> LENGTH: 79
<212> TYPE: DNA
<213> ORGANISM: Homo sapiens

<400> SEQUENCE: 75
ggagtactct attgaagtca gcttgaacaa aggcaaaaca ttcttcaaga gcaatgtcag    60
catcaccagc accacatgt                                                79

<210> SEQ ID NO 76
<211> LENGTH: 26
<212> TYPE: PRT
<213> ORGANISM: Homo sapiens

<400> SEQUENCE: 76

Glu Tyr Ser Ile Glu Val Ser Leu Asn Lys Gly Lys Thr Phe Phe Lys
1               5                   10                  15

Ser Asn Val Ser Ile Thr Ser Thr Thr Cys
            20                  25

<210> SEQ ID NO 77
```

<211> LENGTH: 90
<212> TYPE: DNA
<213> ORGANISM: Homo sapiens

<400> SEQUENCE: 77 ggcatttttcc gcaactggct ctattttgtg ccactcctgc tgcttgtgcc actgctgctg    60
tgttgtgtct ggcggctgtg ccgcaagcag                                      90

<210> SEQ ID NO 78
<211> LENGTH: 30
<212> TYPE: PRT
<213> ORGANISM: Homo sapiens

<400> SEQUENCE: 78

Gly Ile Phe Arg Asn Trp Leu Tyr Phe Val Pro Leu Leu Leu Val
1               5                   10                  15

Pro Leu Leu Leu Cys Cys Val Trp Arg Leu Cys Arg Lys Gln
            20                  25                  30

<210> SEQ ID NO 79
<211> LENGTH: 39
<212> TYPE: DNA
<213> ORGANISM: Homo sapiens

<400> SEQUENCE: 79
actgtcaagg agccaccacc tgtgcagaag ccagaaaag                             39

<210> SEQ ID NO 80
<211> LENGTH: 13
<212> TYPE: PRT
<213> ORGANISM: Homo sapiens

<400> SEQUENCE: 80

Thr Val Lys Glu Pro Pro Pro Val Gln Lys Pro Glu Lys
1               5                   10

<210> SEQ ID NO 81
<211> LENGTH: 156
<212> TYPE: DNA
<213> ORGANISM: Homo sapiens

<400> SEQUENCE: 81
gagccagagc aggaaaaacc accatcacca ccaccaccgc ctccgcctcc accacctcca    60
ctcccacctc cgcccccagc tcctgtaaac acctgcccca ctgtgattat tgttgctgt    120 ggatgccaag gagtgggcgg gatgagaagg atagag                              156

<210> SEQ ID NO 82
<211> LENGTH: 52
<212> TYPE: PRT
<213> ORGANISM: Homo sapiens

<400> SEQUENCE: 82

Glu Pro Glu Gln Glu Lys Pro Pro Ser Pro Pro Pro Pro Pro Pro
1               5                   10                  15

Pro Pro Pro Pro Leu Pro Pro Pro Pro Ala Pro Val Asn Thr Cys
            20                  25                  30

Pro Thr Val Ile Ile Cys Cys Cys Gly Cys Gln Gly Val Gly Gly Met
            35                  40                  45

Arg Arg Ile Glu
        50

<210> SEQ ID NO 83
<211> LENGTH: 81
<212> TYPE: DNA
<213> ORGANISM: Homo sapiens

<400> SEQUENCE: 83
ggcaatctgg atacctttg tgacctctct cacgcaagct gccaccaggt gccatggatg     60
tgttgtcaga gcagggacca g                                              81

<210> SEQ ID NO 84
<211> LENGTH: 27
<212> TYPE: PRT
<213> ORGANISM: Homo sapiens

<400> SEQUENCE: 84

Gly Asn Leu Asp Thr Phe Cys Asp Leu Ser His Ala Ser Cys His Gln
1               5                  10                  15

Val Pro Trp Met Cys Cys Gln Ser Arg Asp Gln
            20                  25

<210> SEQ ID NO 85
<211> LENGTH: 140
<212> TYPE: DNA
<213> ORGANISM: Homo sapiens

<400> SEQUENCE: 85
gggaggtacc tcagcttagc ccttgcacag tcccaatatg cacaggctcc ctgctgccca     60
aggatctgct ttccacacag ccaggagtgc ctttccctac acaggctcc ctgcagccca    120 aggatgtgcc tgagacacag                                               140

<210> SEQ ID NO 86
<211> LENGTH: 47
<212> TYPE: PRT
<213> ORGANISM: Homo sapiens

<400> SEQUENCE: 86

Gly Arg Tyr Leu Ser Leu Ala Leu Ala Gln Ser Gln Tyr Ala Gln Ala
1               5                  10                  15

Pro Cys Cys Pro Arg Ile Cys Phe Pro His Ser Gln Glu Cys Leu Ser
            20                  25                  30

Leu Pro Gln Ala Pro Cys Ser Pro Arg Met Cys Leu Arg His Ser
        35                  40                  45

<210> SEQ ID NO 87
<211> LENGTH: 277
<212> TYPE: DNA
<213> ORGANISM: Homo sapiens

<400> SEQUENCE: 87
ccgggagtgc ctcgccctca acaggctcg ctgcagccca acatctgcc tgagacacag      60 cccggagtac tttccccaag cacagactct gtgcaaccca aagagctgcc ttcaacccag   120 ccggagtgc ctcccctca cctgctcctc caggtgccgc ctcccccag ctaggtgctt      180 gaggcctccc tccaggatgc tgccgctgct gtccccactg ctcaggcaca cggcagaacc   240
ccctttgtca ctcccccct cagagcccaa cttctaa                             277

<210> SEQ ID NO 88
<211> LENGTH: 91
<212> TYPE: PRT
<213> ORGANISM: Homo sapiens

<400> SEQUENCE: 88

| Arg | Glu | Cys | Leu | Ala | Leu | Lys | Gln | Ala | Arg | Cys | Ser | Pro | Asn | Ile | Cys |
|---|---|---|---|---|---|---|---|---|---|---|---|---|---|---|---|
| 1 | | | | 5 | | | | | 10 | | | | | 15 | |

| Leu | Arg | His | Ser | Pro | Glu | Tyr | Phe | Ser | Gln | Ala | Gln | Thr | Leu | Cys | Asn |
|---|---|---|---|---|---|---|---|---|---|---|---|---|---|---|---|
| | | | 20 | | | | | 25 | | | | | 30 | | |

| Pro | Lys | Ser | Cys | Leu | Gln | Pro | Ser | Arg | Glu | Cys | Leu | Pro | Leu | Thr | Cys |
|---|---|---|---|---|---|---|---|---|---|---|---|---|---|---|---|
| | | 35 | | | | | 40 | | | | | 45 | | | |

| Ser | Ser | Arg | Cys | Arg | Leu | Pro | Pro | Ala | Arg | Cys | Leu | Arg | Pro | Pro | Ser |
|---|---|---|---|---|---|---|---|---|---|---|---|---|---|---|---|
| | 50 | | | | | 55 | | | | | 60 | | | | |

| Arg | Met | Leu | Pro | Leu | Leu | Ser | Pro | Leu | Leu | Arg | His | Thr | Ala | Glu | Pro |
|---|---|---|---|---|---|---|---|---|---|---|---|---|---|---|---|
| 65 | | | | 70 | | | | | 75 | | | | | 80 | |

| Pro | Leu | Ser | Leu | Pro | Pro | Ser | Glu | Pro | Asn | Phe |
|---|---|---|---|---|---|---|---|---|---|---|
| | | | | 85 | | | | 90 | | |

<210> SEQ ID NO 89
<211> LENGTH: 1827
<212> TYPE: DNA
<213> ORGANISM: Homo sapiens

<400> SEQUENCE: 89

```
atggggagcc atgagtccct ggggccctac ttcctggtct tcctgctgct gctgctgctt    60
cctccaccgc tttttagagc aggaagcctt cggtaccatg gacctgactg gagaatattt   120
caccgcctgg ccctgggctc caggagagcc accaccacc atgcccagg atggaggcag    180
cactggcgcc aggggcaagc aggtcacaga tgccagggct catttgacct ctacttcatc   240
ttggacaagt ctggcagcgt gaacaataac tggattgacc tttatatgtg ggtggaggaa   300
acagtggcga ggttccaaag cccaaatatt cggatgtgct tcatcaccta ctccacagac   360
ggccagactg tcttgccact cacctcagac aagaatagaa taaaaaacgg tcttgaccaa   420
cttcagaaaa ttgtgcctga cggtcacaca ttcatgcagg caggatttag aaaggcaatt   480
caacagatcg aaagtttcaa ctccggaaac aaggttccca gcatgattat tgctatgact   540
gatggagaac tggtggcaca tgcatttcag gacactctca gagaagctca aaaggctcgg   600
aaactggggg ccaacgttta caccctgggt gtggctgatt ataatctgga ccagataaca   660
gcaattgcag acagccctgg ccacgtgttt gcagtggaga atggcttcaa ggccctgaga   720
agcaccattg atgccctcac gtcaaaggtc tgtcttgatg tgcatcggt ggagccttcc   780
tctgagtgtg taggagaacc ctaccatgtg ttattcatg gaaatggctt tcagaatcta   840
aagaaacggg atgaagttat ttgcagattt atcttcaatg aaagcactat cattgatgaa   900
aagccaacca gtatcgacaa taattccatg aattgccctg gccaaaaact agaaaaacct   960
ggagaggagt actctattga agtcagcttg aacaaaggca aaacattctt caagagcaat  1020
gtcagcatca ccagcaccac atgtggcatt ttccgcaact ggctctattt tgtgccactc  1080
ctgctgcttg tgccactgct gctgtgttgt gtctggcggc tgtgccgcaa gcagactgtc  1140
aaggagccac cacctgtgca gaagccagaa aaggagccag agcaggaaaa accaccatca  1200
ccaccaccac cgcctccgcc tccaccacct ccactcccac ctccgccccc agctcctgta  1260
aacacctgcc ccactgtgat tatttgttgc tgtggatgcc aaggagtggg cgggatgaga  1320
aggatagagg gcaatctgga tacctttgt gacctctctc acgcaagctg ccaccaggtg  1380
ccatggatgt gttgtcagag cagggaccag gggaggtacc tcagcttagc ccttgcacag  1440
tcccaatatg cacaggctcc ctgctgccca aggatctgct ttccacacag ccaggagtgc  1500
cttttccctac cacaggctcc ctgcagccca aggatgtgcc tgacacacag ccgggagtgc  1560
```

```
ctcgccctca aacaggctcg ctgcagccca acatctgcc tgagacacag cccggagtac    1620
ttttcccaag cacagactct gtgcaaccca agagctgcc ttcaacccag ccgggagtgc    1680 ctcccccctca cctgctcctc caggtgccgc ctccccccag ctaggtgctt gaggcctccc    1740
tccaggatgc tgccgctgct gtccccactg ctcaggcaca cggcagaacc ccctttgtca    1800
ctccccccct cagagcccaa cttctaa                                        1827

<210> SEQ ID NO 90
<211> LENGTH: 608
<212> TYPE: PRT
<213> ORGANISM: Homo sapiens

<400> SEQUENCE: 90

Met Gly Ser His Glu Ser Leu Gly Pro Tyr Phe Leu Val Phe Leu Leu
1               5                   10                  15

Leu Leu Leu Pro Pro Pro Leu Phe Arg Ala Gly Ser Leu Arg Tyr
            20                  25                  30

His Gly Pro Asp Trp Arg Ile Phe His Arg Leu Ala Leu Gly Ser Arg
        35                  40                  45

Arg Ala His His His Gly Pro Gly Trp Arg Gln His Trp Arg Gln
50                  55                  60

Gly Gln Ala Gly His Arg Cys Gln Gly Ser Phe Asp Leu Tyr Phe Ile
65                  70                  75                  80

Leu Asp Lys Ser Gly Ser Val Asn Asn Asn Trp Ile Asp Leu Tyr Met
                85                  90                  95

Trp Val Glu Glu Thr Val Ala Arg Phe Gln Ser Pro Asn Ile Arg Met
            100                 105                 110

Cys Phe Ile Thr Tyr Ser Thr Asp Gly Gln Thr Val Leu Pro Leu Thr
        115                 120                 125

Ser Asp Lys Asn Arg Ile Lys Asn Gly Leu Asp Gln Leu Gln Lys Ile
    130                 135                 140

Val Pro Asp Gly His Thr Phe Met Gln Ala Gly Phe Arg Lys Ala Ile
145                 150                 155                 160

Gln Gln Ile Glu Ser Phe Asn Ser Gly Asn Lys Val Pro Ser Met Ile
                165                 170                 175

Ile Ala Met Thr Asp Gly Glu Leu Val Ala His Ala Phe Gln Asp Thr
            180                 185                 190

Leu Arg Glu Ala Gln Lys Ala Arg Lys Leu Gly Ala Asn Val Tyr Thr
        195                 200                 205

Leu Gly Val Ala Asp Tyr Asn Leu Asp Gln Ile Thr Ala Ile Ala Asp
    210                 215                 220

Ser Pro Gly His Val Phe Ala Val Glu Asn Gly Phe Lys Ala Leu Arg
225                 230                 235                 240

Ser Thr Ile Asp Ala Leu Thr Ser Lys Val Cys Leu Asp Val Thr Ser
                245                 250                 255

Val Glu Pro Ser Ser Glu Cys Val Gly Glu Pro Tyr His Val Val Ile
            260                 265                 270

His Gly Asn Gly Phe Gln Asn Leu Lys Lys Arg Asp Glu Val Ile Cys
        275                 280                 285

Arg Phe Ile Phe Asn Glu Ser Thr Ile Ile Asp Glu Lys Pro Thr Ser
    290                 295                 300

Ile Asp Asn Asn Ser Met Asn Cys Pro Gly Pro Lys Leu Glu Lys Pro
305                 310                 315                 320

Gly Glu Glu Tyr Ser Ile Glu Val Ser Leu Asn Lys Gly Lys Thr Phe
                325                 330                 335
```

Phe Lys Ser Asn Val Ser Ile Thr Ser Thr Thr Cys Gly Ile Phe Arg
            340                 345                 350

Asn Trp Leu Tyr Phe Val Pro Leu Leu Leu Val Pro Leu Leu Leu
            355                 360                 365

Cys Cys Val Trp Arg Leu Cys Arg Lys Gln Thr Val Lys Glu Pro Pro
            370                 375                 380

Pro Val Gln Lys Pro Glu Lys Glu Pro Gln Glu Lys Pro Pro Ser
385                 390                 395                 400

Pro Pro Pro Pro Pro Pro Pro Pro Pro Leu Pro Pro Pro Pro
                    405                 410                 415

Pro Ala Pro Val Asn Thr Cys Pro Thr Val Ile Ile Cys Cys Cys Gly
                    420                 425                 430

Cys Gln Gly Val Gly Gly Met Arg Arg Ile Glu Gly Asn Leu Asp Thr
            435                 440                 445

Phe Cys Asp Leu Ser His Ala Ser Cys His Gln Val Pro Trp Met Cys
            450                 455                 460

Cys Gln Ser Arg Asp Gln Gly Arg Tyr Leu Ser Leu Ala Leu Ala Gln
465                 470                 475                 480

Ser Gln Tyr Ala Gln Ala Pro Cys Cys Pro Arg Ile Cys Phe Pro His
                    485                 490                 495

Ser Gln Glu Cys Leu Ser Leu Pro Gln Ala Pro Cys Ser Pro Arg Met
            500                 505                 510

Cys Leu Arg His Ser Arg Glu Cys Leu Ala Leu Lys Gln Ala Arg Cys
            515                 520                 525

Ser Pro Asn Ile Cys Leu Arg His Ser Pro Glu Tyr Phe Ser Gln Ala
            530                 535                 540

Gln Thr Leu Cys Asn Pro Lys Ser Cys Leu Gln Pro Ser Arg Glu Cys
545                 550                 555                 560

Leu Pro Leu Thr Cys Ser Ser Arg Cys Arg Leu Pro Ala Arg Cys
                    565                 570                 575

Leu Arg Pro Pro Ser Arg Met Leu Pro Leu Ser Pro Leu Leu Arg
            580                 585                 590

His Thr Ala Glu Pro Pro Leu Ser Leu Pro Pro Ser Glu Pro Asn Phe
            595                 600                 605

<210> SEQ ID NO 91
<211> LENGTH: 248
<212> TYPE: DNA
<213> ORGANISM: Homo sapiens

<400> SEQUENCE: 91
atggggagcc atgagtccct ggggccctac ttcctggtct cctgctgctg ctgctgctt      60 cctccaccgc tttttagagc aggaagcctt cggtaccatg acctgactg gagaatattt     120 caccgcctgg ccctgggctc caggagagcc accaccacc atgcccagg atggaggcag      180 cactggcgcc aggggcaagc aggtcacaga tgccagggct catttgacct ctacttcatc    240
ttggacaa                                                             248

<210> SEQ ID NO 92
<211> LENGTH: 83
<212> TYPE: PRT
<213> ORGANISM: Homo sapiens

<400> SEQUENCE: 92

Met Gly Ser His Glu Ser Leu Gly Pro Tyr Phe Leu Val Phe Leu Leu
1               5                   10                  15

Leu Leu Leu Leu Pro Pro Pro Leu Phe Arg Ala Gly Ser Leu Arg Tyr
            20                  25                  30

His Gly Pro Asp Trp Arg Ile Phe His Arg Leu Ala Leu Gly Ser Arg
        35                  40                  45

Arg Ala His His His Gly Pro Gly Trp Arg Gln His Trp Arg Gln
50                  55                  60

Gly Gln Ala Gly His Arg Cys Gln Gly Ser Phe Asp Leu Tyr Phe Ile
65                  70                  75                  80

Leu Asp Lys

<210> SEQ ID NO 93
<211> LENGTH: 72
<212> TYPE: DNA
<213> ORGANISM: Homo sapiens

<400> SEQUENCE: 93
gtctggcagc gtgaacaata actggattga cctttatatg tgggtggagg aaacagtggc    60
gaggttccaa ag                                                       72

<210> SEQ ID NO 94
<211> LENGTH: 24
<212> TYPE: PRT
<213> ORGANISM: Homo sapiens

<400> SEQUENCE: 94

Ser Gly Ser Val Asn Asn Asn Trp Ile Asp Leu Tyr Met Trp Val Glu
1               5                   10                  15

Glu Thr Val Ala Arg Phe Gln Ser
            20

<210> SEQ ID NO 95
<211> LENGTH: 72
<212> TYPE: DNA
<213> ORGANISM: Homo sapiens

<400> SEQUENCE: 95
cccaaatatt cggatgtgct tcatcaccta ctccacagac ggccagactg tcttgccact    60
cacctcagac aa                                                       72

<210> SEQ ID NO 96
<211> LENGTH: 24
<212> TYPE: PRT
<213> ORGANISM: Homo sapiens

<400> SEQUENCE: 96

Pro Asn Ile Arg Met Cys Phe Ile Thr Tyr Ser Thr Asp Gly Gln Thr
1               5                   10                  15

Val Leu Pro Leu Thr Ser Asp Lys
            20

<210> SEQ ID NO 97
<211> LENGTH: 82
<212> TYPE: DNA
<213> ORGANISM: Homo sapiens

<400> SEQUENCE: 97
gaatagaata aaaaacggtc ttgaccaact tcagaaaatt gtgcctgacg gtcacacatt    60
catgcaggca ggatttagaa ag                                            82

```
<210> SEQ ID NO 98
<211> LENGTH: 27
<212> TYPE: PRT
<213> ORGANISM: Homo sapiens

<400> SEQUENCE: 98

Asn Arg Ile Lys Asn Gly Leu Asp Gln Leu Gln Lys Ile Val Pro Asp
1               5                   10                  15

Gly His Thr Phe Met Gln Ala Gly Phe Arg Lys
            20                  25

<210> SEQ ID NO 99
<211> LENGTH: 34
<212> TYPE: DNA
<213> ORGANISM: Homo sapiens

<400> SEQUENCE: 99
gcaattcaac agatcgaaag tttcaactcc ggaa                               34

<210> SEQ ID NO 100
<211> LENGTH: 12
<212> TYPE: PRT
<213> ORGANISM: Homo sapiens

<400> SEQUENCE: 100

Ala Ile Gln Gln Ile Glu Ser Phe Asn Ser Gly Asn
1               5                   10

<210> SEQ ID NO 101
<211> LENGTH: 77
<212> TYPE: DNA
<213> ORGANISM: Homo sapiens

<400> SEQUENCE: 101
acaaggttcc cagcatgatt attgctatga ctgatggaga actggtggca catgcatttc    60
aggacactct cagagaa                                                  77

<210> SEQ ID NO 102
<211> LENGTH: 25
<212> TYPE: PRT
<213> ORGANISM: Homo sapiens

<400> SEQUENCE: 102

Lys Val Pro Ser Met Ile Ile Ala Met Thr Asp Gly Glu Leu Val Ala
1               5                   10                  15

His Ala Phe Gln Asp Thr Leu Arg Glu
            20                  25

<210> SEQ ID NO 103
<211> LENGTH: 69
<212> TYPE: DNA
<213> ORGANISM: Homo sapiens

<400> SEQUENCE: 103
gctcaaaagg ctcggaaact gggggccaac gtttacaccc tgggtgtggc tgattataat    60
ctggaccag                                                           69

<210> SEQ ID NO 104
<211> LENGTH: 23
<212> TYPE: PRT
<213> ORGANISM: Homo sapiens

<400> SEQUENCE: 104
```

Ala Gln Lys Ala Arg Lys Leu Gly Ala Asn Val Tyr Thr Leu Gly Val
1               5                   10                  15

Ala Asp Tyr Asn Leu Asp Gln
            20

<210> SEQ ID NO 105
<211> LENGTH: 81
<212> TYPE: DNA
<213> ORGANISM: Homo sapiens

<400> SEQUENCE: 105
ataacagcaa ttgcagacag ccctggccac gtgtttgcag tggagaatgg cttcaaggcc    60
ctgagaagca ccattgatgc c                                             81

<210> SEQ ID NO 106
<211> LENGTH: 27
<212> TYPE: PRT
<213> ORGANISM: Homo sapiens

<400> SEQUENCE: 106

Ile Thr Ala Ile Ala Asp Ser Pro Gly His Val Phe Ala Val Glu Asn
1               5                   10                  15

Gly Phe Lys Ala Leu Arg Ser Thr Ile Asp Ala
            20                  25

<210> SEQ ID NO 107
<211> LENGTH: 61
<212> TYPE: DNA
<213> ORGANISM: Homo sapiens

<400> SEQUENCE: 107
ctcacgtcaa aggtctgtct tgatgtgaca tcggtggagc cttcctctga gtgtgtagga    60
g                                                                   61

<210> SEQ ID NO 108
<211> LENGTH: 21
<212> TYPE: PRT
<213> ORGANISM: Homo sapiens

<400> SEQUENCE: 108

Leu Thr Ser Lys Val Cys Leu Asp Val Thr Ser Val Glu Pro Ser Ser
1               5                   10                  15

Glu Cys Val Gly Glu
            20

<210> SEQ ID NO 109
<211> LENGTH: 99
<212> TYPE: DNA
<213> ORGANISM: Homo sapiens

<400> SEQUENCE: 109
aaccctacca tgtggttatt catggaaatg gctttcagaa tctaaagaaa cgggatgaag    60
ttatttgcag atttatcttc aatgaaagca ctatcattg                          99

<210> SEQ ID NO 110
<211> LENGTH: 33
<212> TYPE: PRT
<213> ORGANISM: Homo sapiens

<400> SEQUENCE: 110

Pro Tyr His Val Val Ile His Gly Asn Gly Phe Gln Asn Leu Lys Lys
1               5                   10                  15

-continued

Arg Asp Glu Val Ile Cys Arg Phe Ile Phe Asn Glu Ser Thr Ile Ile
            20                  25                  30
Asp

<210> SEQ ID NO 111
<211> LENGTH: 70
<212> TYPE: DNA
<213> ORGANISM: Homo sapiens

<400> SEQUENCE: 111
atgaaaagcc aaccagtatc gacaataatt ccatgaattg ccctgggcca aaactagaaa      60
aacctggaga                                                             70

<210> SEQ ID NO 112
<211> LENGTH: 23
<212> TYPE: PRT
<213> ORGANISM: Homo sapiens

<400> SEQUENCE: 112

Glu Lys Pro Thr Ser Ile Asp Asn Asn Ser Met Asn Cys Pro Gly Pro
1               5                   10                  15

Lys Leu Glu Lys Pro Gly Glu
            20

<210> SEQ ID NO 113
<211> LENGTH: 79
<212> TYPE: DNA
<213> ORGANISM: Homo sapiens

<400> SEQUENCE: 113
ggagtactct attgaagtca gcttgaacaa aggcaaaaca ttcttcaaga gcaatgtcag      60
catcaccagc accacatgt                                                   79

<210> SEQ ID NO 114
<211> LENGTH: 26
<212> TYPE: PRT
<213> ORGANISM: Homo sapiens

<400> SEQUENCE: 114

Glu Tyr Ser Ile Glu Val Ser Leu Asn Lys Gly Lys Thr Phe Phe Lys
1               5                   10                  15

Ser Asn Val Ser Ile Thr Ser Thr Thr Cys
            20                  25

<210> SEQ ID NO 115
<211> LENGTH: 90
<212> TYPE: DNA
<213> ORGANISM: Homo sapiens

<400> SEQUENCE: 115
ggcattttcc gcaactggct ctattttgtg ccactcctgc tgcttgtgcc actgctgctg      60
tgttgtgtct ggcggctgtg ccgcaagcag                                       90

<210> SEQ ID NO 116
<211> LENGTH: 30
<212> TYPE: PRT
<213> ORGANISM: Homo sapiens

<400> SEQUENCE: 116

Gly Ile Phe Arg Asn Trp Leu Tyr Phe Val Pro Leu Leu Leu Leu Val
1               5                   10                  15

Pro Leu Leu Leu Cys Cys Val Trp Arg Leu Cys Arg Lys Gln
         20              25              30

<210> SEQ ID NO 117
<211> LENGTH: 39
<212> TYPE: DNA
<213> ORGANISM: Homo sapiens

<400> SEQUENCE: 117
actgtcaagg agccaccacc tgtgcagaag ccagaaaag                              39

<210> SEQ ID NO 118
<211> LENGTH: 13
<212> TYPE: PRT
<213> ORGANISM: Homo sapiens

<400> SEQUENCE: 118

Thr Val Lys Glu Pro Pro Val Gln Lys Pro Glu Lys
1               5                   10

<210> SEQ ID NO 119
<211> LENGTH: 156
<212> TYPE: DNA
<213> ORGANISM: Homo sapiens

<400> SEQUENCE: 119
gagccagagc aggaaaaacc accatcacca ccaccaccgc ctccgcctcc accacctcca       60
ctcccacctc cgcccccagc tcctgtaaac acctgcccca ctgtgattat ttgttgctgt      120
ggatgccaag gagtgggcgg gatgagaagg atagag                                156

<210> SEQ ID NO 120
<211> LENGTH: 52
<212> TYPE: PRT
<213> ORGANISM: Homo sapiens

<400> SEQUENCE: 120

Glu Pro Glu Gln Glu Lys Pro Pro Ser Pro Pro Pro Pro Pro Pro Pro
1               5                   10                  15

Pro Pro Pro Pro Leu Pro Pro Pro Pro Ala Pro Val Asn Thr Cys
            20                  25                  30

Pro Thr Val Ile Ile Cys Cys Cys Gly Cys Gln Gly Val Gly Gly Met
        35                  40                  45

Arg Arg Ile Glu
    50

<210> SEQ ID NO 121
<211> LENGTH: 81
<212> TYPE: DNA
<213> ORGANISM: Homo sapiens

<400> SEQUENCE: 121
ggcaatctgg ataccttttg tgacctctct cacgcaagct gccaccaggt gccatggatg       60
tgttgtcaga gcagggacca g                                                 81

<210> SEQ ID NO 122
<211> LENGTH: 27
<212> TYPE: PRT
<213> ORGANISM: Homo sapiens

<400> SEQUENCE: 122

Gly Asn Leu Asp Thr Phe Cys Asp Leu Ser His Ala Ser Cys His Gln

```
                1               5              10              15

Val Pro Trp Met Cys Cys Gln Ser Arg Asp Gln
             20                  25
```

<210> SEQ ID NO 123
<211> LENGTH: 486
<212> TYPE: DNA
<213> ORGANISM: Homo sapiens

<400> SEQUENCE: 123

```
gggaggtacc tcagcttagc ccttgcacag tcccaatatg cacaggctcc ctgctgccca    60
aggatctgct ttccacacag ccaggagtgc ctttccctac acaggctcc  ctgcagccca   120
aggatgtgcc tgagacacag ccgggagtgc ctcgccctca acaggctcg  ctgcagccca   180
aacatctgcc tgagacacag ccaacacagc agggagtgcc ttgcccgcaa acaggctccc   240
tgcagcccaa ggatctgcct gagacacagc ccggagtact tttcccaagc acagactctg   300
tgcaacccaa agagctgcct tcaacccagc cgggagtgcc tccccctcac ctgctcctcc   360
aggtgccgcc tcccccagc taggtgcttg aggcctccct ccaggatgct gccgctgctg    420
tccccactgc tcaggcacac ggcagaaccc cctttgtcac tccccccctc agagcccaac   480
ttctaa                                                              486
```

<210> SEQ ID NO 124
<211> LENGTH: 161
<212> TYPE: PRT
<213> ORGANISM: Homo sapiens

<400> SEQUENCE: 124

```
Gly Arg Tyr Leu Ser Leu Ala Leu Ala Gln Ser Gln Tyr Ala Gln Ala
1               5                  10                  15

Pro Cys Cys Pro Arg Ile Cys Phe Pro His Ser Gln Glu Cys Leu Ser
            20                  25                  30

Leu Pro Gln Ala Pro Cys Ser Pro Arg Met Cys Leu Arg His Ser Arg
        35                  40                  45

Glu Cys Leu Ala Leu Lys Gln Ala Arg Cys Ser Pro Asn Ile Cys Leu
    50                  55                  60

Arg His Ser Gln His Ser Arg Glu Cys Leu Ala Arg Lys Gln Ala Pro
65                  70                  75                  80

Cys Ser Pro Arg Ile Cys Leu Arg His Ser Pro Glu Tyr Phe Ser Gln
                85                  90                  95

Ala Gln Thr Leu Cys Asn Pro Lys Ser Cys Leu Gln Pro Ser Arg Glu
            100                 105                 110

Cys Leu Pro Leu Thr Cys Ser Ser Arg Cys Arg Leu Pro Pro Ala Arg
        115                 120                 125

Cys Leu Arg Pro Pro Ser Arg Met Leu Pro Leu Leu Ser Pro Leu Leu
    130                 135                 140

Arg His Thr Ala Glu Pro Pro Leu Ser Leu Pro Pro Ser Glu Pro Asn
145                 150                 155                 160

Phe
```

<210> SEQ ID NO 125
<211> LENGTH: 1896
<212> TYPE: DNA
<213> ORGANISM: Homo sapiens

<400> SEQUENCE: 125

```
atggggagcc atgagtccct ggggccctac ttcctggtct tcctgctgct gctgctgctt    60
```

```
cctccaccgc tttttagagc aggaagcctt cggtaccatg gacctgactg gagaatattt      120
caccgcctgg ccctgggctc caggagagcc caccaccacc atggcccagg atggaggcag      180
cactggcgcc aggggcaagc aggtcacaga tgccagggct catttgacct ctacttcatc      240
ttggacaagt ctggcagcgt gaacaataac tggattgacc tttatatgtg ggtggaggaa      300
acagtggcga ggttccaaag cccaaatatt cggatgtgct catcaccta ctccacagac       360
ggccagactg tcttgccact cacctcagac aagaatagaa taaaaacgg tcttgaccaa       420
cttcagaaaa ttgtgcctga cggtcacaca ttcatgcagg caggatttag aaaggcaatt     480
caacagatcg aaagtttcaa ctccggaaac aaggttccca gcatgattat tgctatgact     540
gatggagaac tggtggcaca tgcatttcag gacactctca gagaagctca aaaggctcgg    600
aaactggggg ccaacgttta caccctgggt gtggctgatt ataatctgga ccagataaca    660
gcaattgcag acagccctgg ccacgtgttt gcagtggaga atggcttcaa ggccctgaga    720
agcaccattg atgccctcac gtcaaggtc tgtcttgatg tgcatcggt ggagccttcc      780
tctgagtgtg taggagaacc ctaccatgtg gttattcatg gaatggctt tcagaatcta    840
aagaaacggg atgaagttat tgcagattt atcttcaatg aaagcactat cattgatgaa   900
aagccaacca gtatcgacaa taattccatg aattgccctg gccaaaaact agaaaaacct    960
ggagaggagt actctattga agtcagcttg aacaaaggca aaacattctt caagagcaat   1020
gtcagcatca ccagcaccac atgtggcatt ttccgcaact ggctctattt tgtgccactc   1080
ctgctgcttg tgccactgct gctgtgttgt gtctggcggc tgtgccgcaa gcagactgtc  1140
aaggagccac cacctgtgca gaagccagaa aaggagccag agcaggaaaa accaccatca   1200
ccaccaccac cgcctccgcc tccaccacct ccactcccac ctccgccccc agctcctgta    1260
aacacctgcc ccactgtgat tatttgttgc tgtggatgcc aaggagtggg cgggatgaga  1320
aggatagagg gcaatctgga taccttttgt gacctctctc acgcaagctg ccaccaggtg  1380
ccatggatgt gttgtcagag cagggaccag gggaggtacc tcagcttagc ccttgcacag  1440
tcccaatatg cacaggctcc ctgctgccca aggatctgct ttccacacag ccaggagtgc  1500
cttttcctac acaggctcc ctgcagccca aggatgtgcc tgagacacag ccgggagtgc  1560
ctcgccctca aacaggctcg ctgcagccca acatctgcc tgagacacag ccaacacagc  1620
agggagtgcc ttgcccgcaa acaggctccc tgcagcccaa ggatctgcct gagacacagc  1680
ccggagtact tttcccaagc acagactctg tgcaacccaa agagctgcct tcaacccagc  1740
cgggagtgcc tcccctcac ctgctcctcc aggtgccgcc tccccccagc taggtgcttg   1800
aggcctccct ccaggatgct gccgctgctg tccccactgc tcaggcacac ggcagaaccc   1860
cctttgtcac tccccccctc agagcccaac ttctaa                              1896
```

<210> SEQ ID NO 126
<211> LENGTH: 631
<212> TYPE: PRT
<213> ORGANISM: Homo sapiens

<400> SEQUENCE: 126

Met Gly Ser His Glu Ser Leu Gly Pro Tyr Phe Leu Val Phe Leu Leu
1               5                   10                  15

Leu Leu Leu Leu Pro Pro Pro Leu Phe Arg Ala Gly Ser Leu Arg Tyr
            20                  25                  30

His Gly Pro Asp Trp Arg Ile Phe His Arg Leu Ala Leu Gly Ser Arg
        35                  40                  45

-continued

Arg Ala His His His Gly Pro Gly Trp Arg Gln His Trp Arg Gln
 50                  55                  60

Gly Gln Ala Gly His Arg Cys Gln Gly Ser Phe Asp Leu Tyr Phe Ile
 65                  70                  75                  80

Leu Asp Lys Ser Gly Ser Val Asn Asn Asn Trp Ile Asp Leu Tyr Met
                 85                  90                  95

Trp Val Glu Glu Thr Val Ala Arg Phe Gln Ser Pro Asn Ile Arg Met
             100                 105                 110

Cys Phe Ile Thr Tyr Ser Thr Asp Gly Gln Thr Val Leu Pro Leu Thr
         115                 120                 125

Ser Asp Lys Asn Arg Ile Lys Asn Gly Leu Asp Gln Leu Gln Lys Ile
130                 135                 140

Val Pro Asp Gly His Thr Phe Met Gln Ala Gly Phe Arg Lys Ala Ile
145                 150                 155                 160

Gln Gln Ile Glu Ser Phe Asn Ser Gly Asn Lys Val Pro Ser Met Ile
                165                 170                 175

Ile Ala Met Thr Asp Gly Glu Leu Val Ala His Ala Phe Gln Asp Thr
            180                 185                 190

Leu Arg Glu Ala Gln Lys Ala Arg Lys Leu Gly Ala Asn Val Tyr Thr
        195                 200                 205

Leu Gly Val Ala Asp Tyr Asn Leu Asp Gln Ile Thr Ala Ile Ala Asp
    210                 215                 220

Ser Pro Gly His Val Phe Ala Val Glu Asn Gly Phe Lys Ala Leu Arg
225                 230                 235                 240

Ser Thr Ile Asp Ala Leu Thr Ser Lys Val Cys Leu Asp Val Thr Ser
                245                 250                 255

Val Glu Pro Ser Ser Glu Cys Val Gly Glu Pro Tyr His Val Val Ile
            260                 265                 270

His Gly Asn Gly Phe Gln Asn Leu Lys Lys Arg Asp Glu Val Ile Cys
        275                 280                 285

Arg Phe Ile Phe Asn Glu Ser Thr Ile Ile Asp Glu Lys Pro Thr Ser
    290                 295                 300

Ile Asp Asn Asn Ser Met Asn Cys Pro Gly Pro Lys Leu Glu Lys Pro
305                 310                 315                 320

Gly Glu Glu Tyr Ser Ile Glu Val Ser Leu Asn Lys Gly Lys Thr Phe
                325                 330                 335

Phe Lys Ser Asn Val Ser Ile Thr Ser Thr Thr Cys Gly Ile Phe Arg
            340                 345                 350

Asn Trp Leu Tyr Phe Val Pro Leu Leu Leu Val Pro Leu Leu Leu
        355                 360                 365

Cys Cys Val Trp Arg Leu Cys Arg Lys Gln Thr Val Lys Glu Pro Pro
    370                 375                 380

Pro Val Gln Lys Pro Glu Lys Glu Pro Glu Gln Glu Lys Pro Pro Ser
385                 390                 395                 400

Pro Pro Pro Pro Pro Pro Pro Pro Pro Leu Pro Pro Pro Pro
                405                 410                 415

Pro Ala Pro Val Asn Thr Cys Pro Thr Val Ile Cys Cys Cys Gly
                420                 425                 430

Cys Gln Gly Val Gly Gly Met Arg Arg Ile Glu Gly Asn Leu Asp Thr
        435                 440                 445

Phe Cys Asp Leu Ser His Ala Ser Cys His Gln Val Pro Trp Met Cys
    450                 455                 460

Cys Gln Ser Arg Asp Gln Gly Arg Tyr Leu Ser Leu Ala Leu Ala Gln
465                 470                 475                 480

Ser Gln Tyr Ala Gln Ala Pro Cys Cys Pro Arg Ile Cys Phe Pro His
            485                 490                 495

Ser Gln Glu Cys Leu Ser Leu Pro Gln Ala Pro Cys Ser Pro Arg Met
        500                 505                 510

Cys Leu Arg His Ser Arg Glu Cys Leu Ala Leu Lys Gln Ala Arg Cys
            515                 520                 525

Ser Pro Asn Ile Cys Leu Arg His Ser Gln His Ser Arg Glu Cys Leu
        530                 535                 540

Ala Arg Lys Gln Ala Pro Cys Ser Pro Arg Ile Cys Leu Arg His Ser
545                 550                 555                 560

Pro Glu Tyr Phe Ser Gln Ala Gln Thr Leu Cys Asn Pro Lys Ser Cys
                565                 570                 575

Leu Gln Pro Ser Arg Glu Cys Leu Pro Leu Thr Cys Ser Ser Arg Cys
            580                 585                 590

Arg Leu Pro Pro Ala Arg Cys Leu Arg Pro Pro Ser Arg Met Leu Pro
            595                 600                 605

Leu Leu Ser Pro Leu Leu Arg His Thr Ala Glu Pro Pro Leu Ser Leu
    610                 615                 620

Pro Pro Ser Glu Pro Asn Phe
625                 630

<210> SEQ ID NO 127
<211> LENGTH: 918
<212> TYPE: DNA
<213> ORGANISM: Homo sapiens

<400> SEQUENCE: 127
atggggagcc atgagtccct ggggccctac ttcctggtct cctgctgct gctgctgctt      60 cctccaccgc ttttagagc aggaagcctt cggtaccatg acctgactg agaatattt      120 caccgcctgg ccctgggctc caggagagcc accaccacc atgcccagg atggaggcag      180 cactggcgcc aggggcaagc aggtcacaga tgccagggct catttgacct ctacttcatc      240
ttggacaagt ctggcagcgt gaacaataac tggattgacc tttatatgtg ggtggaggaa      300
acagtggcga ggttccaaag cccaaatatt cggatgtgct catcaccta ctccacagac      360 ggccagactg tcttgccact cacctcagac aagaatagaa taaaaaacgg tcttgaccaa      420
cttcagaaaa ttgtgcctga cggtcacaca ttcatgcagg caggatttag aaaggcaatt      480
caacagatcg aaagtttcaa ctccggaaac aaggttccca gcatgattat tgctatgact      540
gatggagaac tggtggcaca tgcatttcag gacactctca gagaagctca aaaggctcgg      600
aaactggggg ccaacgttta caccctgggt gtggctgatt ataatctgga ccagataaca      660
gcaattgcag acagccctgg ccacgtgttt gcagtggaga atggcttcaa ggccctgaga      720
agcaccattg atgccctcac gtcaaaggtc tgtcttgatg tgacatcggt ggagccttcc      780
tctgagtgtg taggagaacc ctaccatgtg ttattcatg gaaatggctt tcagaatcta      840
aagaaacggg atgaagttat ttgcagattt atcttcaatg aaagcactat cattgggagt      900
actctattga agtcagct                                                   918

<210> SEQ ID NO 128
<211> LENGTH: 306
<212> TYPE: PRT
<213> ORGANISM: Homo sapiens

<400> SEQUENCE: 128

Met Gly Ser His Glu Ser Leu Gly Pro Tyr Phe Leu Val Phe Leu Leu

```
        1               5                  10                 15
Leu Leu Leu Leu Pro Pro Pro Leu Phe Arg Ala Gly Ser Leu Arg Tyr
                20                  25                  30

His Gly Pro Asp Trp Arg Ile Phe His Arg Leu Ala Leu Gly Ser Arg
            35                  40                  45

Arg Ala His His His His Gly Pro Gly Trp Arg Gln His Trp Arg Gln
        50                  55                  60

Gly Gln Ala Gly His Arg Cys Gln Gly Ser Phe Asp Leu Tyr Phe Ile
65                  70                  75                  80

Leu Asp Lys Ser Gly Ser Val Asn Asn Asn Trp Ile Asp Leu Tyr Met
                85                  90                  95

Trp Val Glu Glu Thr Val Ala Arg Phe Gln Ser Pro Asn Ile Arg Met
                100                 105                 110

Cys Phe Ile Thr Tyr Ser Thr Asp Gly Gln Thr Val Leu Pro Leu Thr
            115                 120                 125

Ser Asp Lys Asn Arg Ile Lys Asn Gly Leu Asp Gln Leu Gln Lys Ile
        130                 135                 140

Val Pro Asp Gly His Thr Phe Met Gln Ala Gly Phe Arg Lys Ala Ile
145                 150                 155                 160

Gln Gln Ile Glu Ser Phe Asn Ser Gly Asn Lys Val Pro Ser Met Ile
                165                 170                 175

Ile Ala Met Thr Asp Gly Glu Leu Val Ala His Ala Phe Gln Asp Thr
            180                 185                 190

Leu Arg Glu Ala Gln Lys Ala Arg Lys Leu Gly Ala Asn Val Tyr Thr
        195                 200                 205

Leu Gly Val Ala Asp Tyr Asn Leu Asp Gln Ile Thr Ala Ile Ala Asp
210                 215                 220

Ser Pro Gly His Val Phe Ala Val Glu Asn Gly Phe Lys Ala Leu Arg
225                 230                 235                 240

Ser Thr Ile Asp Ala Leu Thr Ser Lys Val Cys Leu Asp Val Thr Ser
            245                 250                 255

Val Glu Pro Ser Ser Glu Cys Val Gly Glu Pro Tyr His Val Val Ile
        260                 265                 270

His Gly Asn Gly Phe Gln Asn Leu Lys Lys Arg Asp Glu Val Ile Cys
        275                 280                 285

Arg Phe Ile Phe Asn Glu Ser Thr Ile Ile Gly Ser Thr Leu Leu Lys
        290                 295                 300

Ser Ala
305
```

<210> SEQ ID NO 129
<211> LENGTH: 936
<212> TYPE: DNA
<213> ORGANISM: Artificial Sequence
<220> FEATURE:
<223> OTHER INFORMATION: cloned histidine tag INSP141

<400> SEQUENCE: 129

```
atgggagcc atgagtccct ggggccctac ttcctggtct tcctgctgct gctgctgctt    60
cctccaccgc tttttagagc aggaagcctt cggtaccatg gacctgactg gagaatattt   120
caccgcctgg ccctgggctc aggagagcc accaccacc atggcccagg atggaggcag    180
cactggcgcc aggggcaagc aggtcacaga tgccagggct catttgacct ctacttcatc   240
ttggacaagt ctggcagcgt gaacaataac tggattgacc tttatatgtg ggtgaggaa    300 acagtggcga ggttccaaag cccaaatatt cggatgtgct tcatcaccta ctccacagac   360
```

```
ggccagactg tcttgccact cacctcagac aagaatagaa taaaaaacgg tcttgaccaa      420
cttcagaaaa ttgtgcctga cggtcacaca ttcatgcagg caggatttag aaaggcaatt      480
caacagatcg aaagtttcaa ctccggaaac aaggttccca gcatgattat tgctatgact      540
gatggagaac tggtggcaca tgcatttcag gacactctca gagaagctca aaaggctcgg      600
aaactggggg ccaacgttta caccctgggt gtggctgatt ataatctgga ccagataaca      660
gcaattgcag acagccctgg ccacgtgttt gcagtggaga atggcttcaa ggccctgaga      720
agcaccattg atgccctcac gtcaaaggtc tgtcttgatg tgacatcggt ggagccttcc      780
tctgagtgtg taggagaacc ctaccatgtg gttattcatg gaaatggctt tcagaatcta      840
aagaaacggg atgaagttat ttgcagattt atcttcaatg aaagcactat cattgggagt      900
actctattga agtcagctca ccatcaccat caccat                               936

<210> SEQ ID NO 130
<211> LENGTH: 312
<212> TYPE: PRT
<213> ORGANISM: Artificial Sequence
<220> FEATURE:
<223> OTHER INFORMATION: cloned histidine tag INSP141

<400> SEQUENCE: 130

Met Gly Ser His Glu Ser Leu Gly Pro Tyr Phe Leu Val Phe Leu Leu
1               5                   10                  15

Leu Leu Leu Pro Pro Pro Leu Phe Arg Ala Gly Ser Leu Arg Tyr
            20                  25                  30

His Gly Pro Asp Trp Arg Ile Phe His Arg Leu Ala Leu Gly Ser Arg
        35                  40                  45

Arg Ala His His His His Gly Pro Gly Trp Arg Gln His Trp Arg Gln
    50                  55                  60

Gly Gln Ala Gly His Arg Cys Gln Gly Ser Phe Asp Leu Tyr Phe Ile
65                  70                  75                  80

Leu Asp Lys Ser Gly Ser Val Asn Asn Asn Trp Ile Asp Leu Tyr Met
                85                  90                  95

Trp Val Glu Glu Thr Val Ala Arg Phe Gln Ser Pro Asn Ile Arg Met
            100                 105                 110

Cys Phe Ile Thr Tyr Ser Thr Asp Gly Gln Thr Val Leu Pro Leu Thr
        115                 120                 125

Ser Asp Lys Asn Arg Ile Lys Asn Gly Leu Asp Gln Leu Gln Lys Ile
    130                 135                 140

Val Pro Asp Gly His Thr Phe Met Gln Ala Gly Phe Arg Lys Ala Ile
145                 150                 155                 160

Gln Gln Ile Glu Ser Phe Asn Ser Gly Asn Lys Val Pro Ser Met Ile
                165                 170                 175

Ile Ala Met Thr Asp Gly Glu Leu Val Ala His Ala Phe Gln Asp Thr
            180                 185                 190

Leu Arg Glu Ala Gln Lys Ala Arg Lys Leu Gly Ala Asn Val Tyr Thr
        195                 200                 205

Leu Gly Val Ala Asp Tyr Asn Leu Asp Gln Ile Thr Ala Ile Ala Asp
    210                 215                 220

Ser Pro Gly His Val Phe Ala Val Glu Asn Gly Phe Lys Ala Leu Arg
225                 230                 235                 240

Ser Thr Ile Asp Ala Leu Thr Ser Lys Val Cys Leu Asp Val Thr Ser
                245                 250                 255

Val Glu Pro Ser Ser Glu Cys Val Gly Glu Pro Tyr His Val Val Ile
```

```
              260                 265                 270
His Gly Asn Gly Phe Gln Asn Leu Lys Lys Arg Asp Glu Val Ile Cys
            275                 280                 285

Arg Phe Ile Phe Asn Glu Ser Thr Ile Ile Gly Ser Thr Leu Leu Lys
            290                 295                 300

Ser Ala His His His His His His
305                 310

<210> SEQ ID NO 131
<211> LENGTH: 837
<212> TYPE: DNA
<213> ORGANISM: Homo sapiens

<400> SEQUENCE: 131
ggaagccttc ggtaccatgg acctgactgg agaatatttc accgcctggc cctgggctcc     60
aggagagccc accaccacca tgcccaggga tggaggcagc actggcgcca ggggcaagca    120
ggtcacagat gccagggctc atttgacctc tacttcatct tggacaagtc tggcagcgtg    180
aacaataact ggattgacct ttatatgtgg gtggaggaaa cagtggcgag gttccaaagc    240
ccaaatattc ggatgtgctt catcacctac tccacagacg ccagactgt cttgccactc     300
acctcagaca agaatagaat aaaaaacggt cttgaccaac ttcagaaaat tgtgcctgac    360
ggtcacacat tcatgcaggc aggatttaga aaggcaattc aacagatcga agtttcaac     420
tccggaaaca aggttcccag catgattatt gctatgactg atggagaact ggtggcacat    480
gcatttcagg acactctcag agaagctcaa aaggctcgga actgggggc caacgtttac     540
accctgggtg tggctgatta atctggac cagataacag caattgcaga cagccctggc     600
cacgtgtttg cagtggagaa tggcttcaag gccctgagaa gcaccattga tgccctcacg    660
tcaaaggtct gtcttgatgt gacatcggtg gagccttcct ctgagtgtgt aggagaaccc    720
taccatgtgg ttattcatgg aaatggcttt cagaatctaa agaaacggga tgaagttatt    780
tgcagattta tcttcaatga aagcactatc attgggagta ctctattgaa gtcagct     837

<210> SEQ ID NO 132
<211> LENGTH: 279
<212> TYPE: PRT
<213> ORGANISM: Homo sapiens

<400> SEQUENCE: 132

Gly Ser Leu Arg Tyr His Gly Pro Asp Trp Arg Ile Phe His Arg Leu
1               5                  10                  15

Ala Leu Gly Ser Arg Arg Ala His His His Gly Pro Gly Trp Arg
            20                  25                  30

Gln His Trp Arg Gln Gly Gln Ala Gly His Arg Cys Gly Ser Phe
        35                  40                  45

Asp Leu Tyr Phe Ile Leu Asp Lys Ser Gly Ser Val Asn Asn Asn Trp
50                  55                  60

Ile Asp Leu Tyr Met Trp Val Glu Glu Thr Val Ala Arg Phe Gln Ser
65                  70                  75                  80

Pro Asn Ile Arg Met Cys Phe Ile Thr Tyr Ser Thr Asp Gly Gln Thr
            85                  90                  95

Val Leu Pro Leu Thr Ser Asp Lys Asn Arg Ile Lys Asn Gly Leu Asp
            100                 105                 110

Gln Leu Gln Lys Ile Val Pro Asp Gly His Thr Phe Met Gln Ala Gly
        115                 120                 125

Phe Arg Lys Ala Ile Gln Gln Ile Glu Ser Phe Asn Ser Gly Asn Lys
```

```
            130                 135                 140
Val Pro Ser Met Ile Ile Ala Met Thr Asp Gly Glu Leu Val Ala His
145                 150                 155                 160

Ala Phe Gln Asp Thr Leu Arg Glu Ala Gln Lys Ala Arg Lys Leu Gly
            165                 170                 175

Ala Asn Val Tyr Thr Leu Gly Val Ala Asp Tyr Asn Leu Asp Gln Ile
            180                 185                 190

Thr Ala Ile Ala Asp Ser Pro Gly His Val Phe Ala Val Glu Asn Gly
            195                 200                 205

Phe Lys Ala Leu Arg Ser Thr Ile Asp Ala Leu Thr Ser Lys Val Cys
210                 215                 220

Leu Asp Val Thr Ser Val Glu Pro Ser Ser Glu Cys Val Gly Glu Pro
225                 230                 235                 240

Tyr His Val Val Ile His Gly Asn Gly Phe Gln Asn Leu Lys Lys Arg
            245                 250                 255

Asp Glu Val Ile Cys Arg Phe Ile Phe Asn Glu Ser Thr Ile Ile Gly
            260                 265                 270

Ser Thr Leu Leu Lys Ser Ala
            275
```

<210> SEQ ID NO 133
<211> LENGTH: 855
<212> TYPE: DNA
<213> ORGANISM: Artificial Sequence
<220> FEATURE:
<223> OTHER INFORMATION: cloned mature histidine tag INSP141

<400> SEQUENCE: 133

```
ggaagccttc ggtaccatgg acctgactgg agaatatttc accgcctggc cctgggctcc    60
aggagagccc accaccacca tgcccagga tggaggcagc actggcgcca ggggcaagca   120
ggtcacagat gccagggctc atttgacctc tacttcatct ggacaagtc tggcagcgtg   180
aacaataact ggattgacct ttatatgtgg gtggaggaaa cagtggcgag gttccaaagc   240
ccaaatattc ggatgtgctt catcacctac tccacagacg ccagactgt cttgccactc   300
acctcagaca gaatagaat aaaaaacggt cttgaccaac ttcagaaaat gtgcctgac   360
ggtcacacat tcatgcaggc aggatttaga aaggcaattc aacagatcga agtttcaac   420
tccggaaaca aggttccag catgattatt gctatgactg atggagaact ggtggcacat   480
gcatttcagg acactctcag agaagctcaa aaggctcgga actgggggc caacgttac   540
accctgggtg tggctgatta taatctggac cagataacag caattgcaga cagccctggc   600
cacgtgtttg cagtggagaa tggcttcaag gccctgagaa gcaccattga tgccctcacg   660
tcaaaggtct gtcttgatgt gacatcggtg gagccttcct ctgagtgtgt aggagaaccc   720
taccatgtgg ttattcatgg aaatggctt cagaatctaa agaaacggga tgaagttatt   780
tgcagattta tcttcaatga agcactatc attgggagta ctctattgaa gtcagctcac   840
catcaccatc accat                                                   855
```

<210> SEQ ID NO 134
<211> LENGTH: 285
<212> TYPE: PRT
<213> ORGANISM: Artificial Sequence
<220> FEATURE:
<223> OTHER INFORMATION: cloned mature histidine tag INSP141

<400> SEQUENCE: 134

Gly Ser Leu Arg Tyr His Gly Pro Asp Trp Arg Ile Phe His Arg Leu

```
              1               5              10              15
        Ala Leu Gly Ser Arg Arg Ala His His His Gly Pro Gly Trp Arg
                         20                  25                  30

Gln His Trp Arg Gln Gly Gln Ala Gly His Arg Cys Gln Gly Ser Phe
                     35                  40                  45

Asp Leu Tyr Phe Ile Leu Asp Lys Ser Gly Ser Val Asn Asn Asn Trp
         50                  55                  60

Ile Asp Leu Tyr Met Trp Val Glu Glu Thr Val Ala Arg Phe Gln Ser
         65                  70                  75                  80

Pro Asn Ile Arg Met Cys Phe Ile Thr Tyr Ser Thr Asp Gly Gln Thr
                         85                  90                  95

Val Leu Pro Leu Thr Ser Asp Lys Asn Arg Ile Lys Asn Gly Leu Asp
                    100                 105                 110

Gln Leu Gln Lys Ile Val Pro Asp Gly His Thr Phe Met Gln Ala Gly
                    115                 120                 125

Phe Arg Lys Ala Ile Gln Gln Ile Glu Ser Phe Asn Ser Gly Asn Lys
                130                 135                 140

Val Pro Ser Met Ile Ile Ala Met Thr Asp Gly Glu Leu Val Ala His
        145                 150                 155                 160

Ala Phe Gln Asp Thr Leu Arg Glu Ala Gln Lys Ala Arg Lys Leu Gly
                        165                 170                 175

Ala Asn Val Tyr Thr Leu Gly Val Ala Asp Tyr Asn Leu Asp Gln Ile
                    180                 185                 190

Thr Ala Ile Ala Asp Ser Pro Gly His Val Phe Ala Val Glu Asn Gly
                    195                 200                 205

Phe Lys Ala Leu Arg Ser Thr Ile Asp Ala Leu Thr Ser Lys Val Cys
                210                 215                 220

Leu Asp Val Thr Ser Val Glu Pro Ser Ser Glu Cys Val Gly Glu Pro
        225                 230                 235                 240

Tyr His Val Val Ile His Gly Asn Gly Phe Gln Asn Leu Lys Lys Arg
                        245                 250                 255

Asp Glu Val Ile Cys Arg Phe Ile Phe Asn Glu Ser Thr Ile Ile Gly
                    260                 265                 270

Ser Thr Leu Leu Lys Ser Ala His His His His His His
                    275                 280                 285

<210> SEQ ID NO 135
<211> LENGTH: 1035
<212> TYPE: DNA
<213> ORGANISM: Homo sapiens

<400> SEQUENCE: 135
atggggagcc atgagtccct ggggccctac ttcctggtct cctgctgct  gctgctgctt     60 cctccaccgc tttttagagc aggaagcctt cggtaccatg gacctgactg gagaatattt    120
caccgcctgg ccctgggctc aggagagcc  accaccacc  atggcccagg atggaggcag    180
cactggcgcc aggggcaagc aggtcacaga tgccagggct catttgacct ctacttcatc    240
ttggacaagt ctggcagcgt gaacaataac tggattgacc tttatatgtg ggtggaggaa    300
acagtggcga ggttccaaag cccaaatatt cggatgtgct tcatcaccta ctccacagac    360
ggccagactg tcttgccact cacctcagac aagaatagaa taaaaaacgg tcttgaccaa    420
cttcagaaaa ttgtgcctga cggtcacaca ttcatgcagg caggatttag aaaggcaatt    480
caacagatcg aaagtttcaa ctccggaaac aaggttccca gcatgattat tgctatgact    540
gatggagaac tggtggcaca tgcatttcag gacactctca gagaagctca aaaggctcgg    600
```

```
aaactggggg ccaacgttta cccctgggt gtggctgatt ataatctgga ccagataaca    660
gcaattgcag acagccctgg ccacgtgttt gcagtggaga atggcttcaa ggccctgaga    720
agcaccattg atgccctcac gtcaaaggtc tgtcttgatg tgacatcggt ggaggcttcc    780
tctgagtgtg taggagaacc ctaccatgtg gttattcatg gaaatggctt tcagaatcta    840
aagaaacggg atgaagttat ttgcagattt atcttcaatg aaagcactat cattgatgaa    900
aagccaacca gtatcgacaa taattccatg aattgccctg gccaaaact agaaaaacct    960 ggagaggagt actctattga agtcagcttg aacaaaggca aacattctt caagagcaat    1020 gtcagcatca ccagc                                                    1035
```

<210> SEQ ID NO 136
<211> LENGTH: 345
<212> TYPE: PRT
<213> ORGANISM: Homo sapiens

<400> SEQUENCE: 136

```
Met Gly Ser His Glu Ser Leu Gly Pro Tyr Phe Leu Val Phe Leu Leu
1               5                   10                  15

Leu Leu Leu Leu Pro Pro Pro Leu Phe Arg Ala Gly Ser Leu Arg Tyr
                20                  25                  30

His Gly Pro Asp Trp Arg Ile Phe His Arg Leu Ala Leu Gly Ser Arg
            35                  40                  45

Arg Ala His His His Gly Pro Gly Trp Arg Gln His Trp Arg Gln
    50                  55                  60

Gly Gln Ala Gly His Arg Cys Gln Gly Ser Phe Asp Leu Tyr Phe Ile
65                  70                  75                  80

Leu Asp Lys Ser Gly Ser Val Asn Asn Asn Trp Ile Asp Leu Tyr Met
                85                  90                  95

Trp Val Glu Glu Thr Val Ala Arg Phe Gln Ser Pro Asn Ile Arg Met
            100                 105                 110

Cys Phe Ile Thr Tyr Ser Thr Asp Gly Gln Thr Val Leu Pro Leu Thr
        115                 120                 125

Ser Asp Lys Asn Arg Ile Lys Asn Gly Leu Asp Gln Leu Gln Lys Ile
    130                 135                 140

Val Pro Asp Gly His Thr Phe Met Gln Ala Gly Phe Arg Lys Ala Ile
145                 150                 155                 160

Gln Gln Ile Glu Ser Phe Asn Ser Gly Asn Lys Val Pro Ser Met Ile
                165                 170                 175

Ile Ala Met Thr Asp Gly Glu Leu Val Ala His Ala Phe Gln Asp Thr
            180                 185                 190

Leu Arg Glu Ala Gln Lys Ala Arg Lys Leu Gly Ala Asn Val Tyr Thr
        195                 200                 205

Leu Gly Val Ala Asp Tyr Asn Leu Asp Gln Ile Thr Ala Ile Ala Asp
    210                 215                 220

Ser Pro Gly His Val Phe Ala Val Glu Asn Gly Phe Lys Ala Leu Arg
225                 230                 235                 240

Ser Thr Ile Asp Ala Leu Thr Ser Lys Val Cys Leu Asp Val Thr Ser
                245                 250                 255

Val Glu Ala Ser Ser Glu Cys Val Gly Glu Pro Tyr His Val Val Ile
            260                 265                 270

His Gly Asn Gly Phe Gln Asn Leu Lys Lys Arg Asp Glu Val Ile Cys
        275                 280                 285

Arg Phe Ile Phe Asn Glu Ser Thr Ile Ile Asp Glu Lys Pro Thr Ser
```

```
              290                 295                 300
Ile Asp Asn Asn Ser Met Asn Cys Pro Gly Pro Lys Leu Glu Lys Pro
305                 310                 315                 320

Gly Glu Glu Tyr Ser Ile Glu Val Ser Leu Asn Lys Gly Lys Thr Phe
                325                 330                 335

Phe Lys Ser Asn Val Ser Ile Thr Ser
                340                 345

<210> SEQ ID NO 137
<211> LENGTH: 1056
<212> TYPE: DNA
<213> ORGANISM: Homo sapiens

<400> SEQUENCE: 137
atggggagcc atgagtccct ggggccctac ttcctggtct tcctgctgct gctgctgctt      60
cctccaccgc tttttagagc aggaagcctt cggtaccatg gacctgactg gagaatattt     120
caccgcctgg ccctgggctc caggagagcc accaccacc atgcccagg atggaggcag       180 cactggcgcc aggggcaagc aggtcacaga tgccagggct catttgacct ctacttcatc     240
ttggacaagt ctggcagcgt gaacaataac tggattgacc tttatatgtg ggtggaggaa     300
acagtggcga ggttccaaag cccaaatatt cggatgtgct catcaccta ctccacagac      360 ggccagactg tcttgccact cacctcagac aagaatagaa taaaaaacgg tcttgaccaa     420
cttcagaaaa ttgtgcctga cggtcacaca ttcatgcagg caggatttag aaaggcaatt     480
caacagatcg aaagtttcaa ctccggaaac aaggttccca gcatgattat tgctatgact     540
gatggagaac tggtggcaca tgcatttcag gacactctca gagaagctca aaaggctcgg     600
aaactggggg ccaacgttta caccctgggt gtggctgatt ataatctgga ccagataaca     660
gcaattgcag acagccctgg ccacgtgttt gcagtggaga tggcttcaa ggccctgaga      720 agcaccattg atgccctcac gtcaaaggtc tgtcttgatg tgacatcggt ggagccttcc     780
tctgagtgtg taggagaacc ctaccatgtg gttattcatg gaaatggctt tcagaatcta     840
aagaaacggg atgaagttat ttgcagattt atcttcaatg aaagcactat cattgatgaa     900
aagccaacca gtatcgacaa taattccatg aattgccctg gccaaaact agaaaaacct     960 ggagaggagt actctattga agtcagcttg aacaaaggca aacattctt caagagcaat    1020 gtcagcatca ccagcaccac atgtggcatt ttccgc                              1056

<210> SEQ ID NO 138
<211> LENGTH: 352
<212> TYPE: PRT
<213> ORGANISM: Homo sapiens

<400> SEQUENCE: 138

Met Gly Ser His Glu Ser Leu Gly Pro Tyr Phe Leu Val Phe Leu Leu
1               5                   10                  15

Leu Leu Leu Pro Pro Pro Leu Phe Arg Ala Gly Ser Leu Arg Tyr
                20                  25                  30

His Gly Pro Asp Trp Arg Ile Phe His Arg Leu Ala Leu Gly Ser Arg
                35                  40                  45

Arg Ala His His His Gly Pro Gly Trp Gln His Trp Arg Gln
        50                  55                  60

Gly Gln Ala Gly His Arg Cys Gln Gly Ser Phe Asp Leu Tyr Phe Ile
65                  70                  75                  80

Leu Asp Lys Ser Gly Ser Val Asn Asn Asn Trp Ile Asp Leu Tyr Met
                85                  90                  95
```

| | | | | | | | | | | | | |
|---|---|---|---|---|---|---|---|---|---|---|---|---|
|Trp|Val|Glu|Glu|Thr|Val|Ala|Arg|Phe|Gln|Ser|Pro|Asn|Ile|Arg|Met|
| | | |100| | | | |105| | | | |110| | |

Trp Val Glu Glu Thr Val Ala Arg Phe Gln Ser Pro Asn Ile Arg Met
                100                 105                 110

Cys Phe Ile Thr Tyr Ser Thr Asp Gly Gln Thr Val Leu Pro Leu Thr
            115                 120                 125

Ser Asp Lys Asn Arg Ile Lys Asn Gly Leu Asp Gln Leu Gln Lys Ile
130                 135                 140

Val Pro Asp Gly His Thr Phe Met Gln Ala Gly Phe Arg Lys Ala Ile
145                 150                 155                 160

Gln Gln Ile Glu Ser Phe Asn Ser Gly Asn Lys Val Pro Ser Met Ile
                165                 170                 175

Ile Ala Met Thr Asp Gly Glu Leu Val Ala His Ala Phe Gln Asp Thr
            180                 185                 190

Leu Arg Glu Ala Gln Lys Ala Arg Lys Leu Gly Ala Asn Val Tyr Thr
        195                 200                 205

Leu Gly Val Ala Asp Tyr Asn Leu Asp Gln Ile Thr Ala Ile Ala Asp
    210                 215                 220

Ser Pro Gly His Val Phe Ala Val Glu Asn Gly Phe Lys Ala Leu Arg
225                 230                 235                 240

Ser Thr Ile Asp Ala Leu Thr Ser Lys Val Cys Leu Asp Val Thr Ser
                245                 250                 255

Val Glu Pro Ser Ser Glu Cys Val Gly Glu Pro Tyr His Val Val Ile
            260                 265                 270

His Gly Asn Gly Phe Gln Asn Leu Lys Lys Arg Asp Glu Val Ile Cys
        275                 280                 285

Arg Phe Ile Phe Asn Glu Ser Thr Ile Ile Asp Glu Lys Pro Thr Ser
    290                 295                 300

Ile Asp Asn Asn Ser Met Asn Cys Pro Gly Pro Lys Leu Glu Lys Pro
305                 310                 315                 320

Gly Glu Glu Tyr Ser Ile Glu Val Ser Leu Asn Lys Gly Lys Thr Phe
                325                 330                 335

Phe Lys Ser Asn Val Ser Ile Thr Ser Thr Thr Cys Gly Ile Phe Arg
            340                 345                 350

<210> SEQ ID NO 139
<211> LENGTH: 1074
<212> TYPE: DNA
<213> ORGANISM: Artificial Sequence
<220> FEATURE:
<223> OTHER INFORMATION: cloned histidine tag INSP143

<400> SEQUENCE: 139

```
atggggagcc atgagtccct ggggccctac ttcctggtct tcctgctgct gctgctgctt      60
cctccaccgc tttttagagc aggaagcctt cggtaccatg acctgactg gagaatattt      120
caccgcctgg ccctgggctc aggagagcc accaccacc atggcccagg atggaggcag      180
cactggcgcc aggggcaagc aggtcacaga tgccagggct catttgacct ctacttcatc      240
ttggacaagt ctggcagcgt gaacaataac tggattgacc tttatatgtg ggtggaggaa      300
acagtggcga ggttccaaag cccaaatatt cggatgtgct catcaccta ctccacagac      360
ggccagactg tcttgccact cacctcagac aagaatagaa taaaaaacgg tcttgaccaa      420
cttcagaaaa ttgtgcctga cggtcacaca ttcatgcagg caggatttag aaaggcaatt      480
caacagatcg aaagtttcaa ctccggaaac aaggttccca gcatgattat tgctatgact      540
gatggagaac tggtggcaca tgcatttcag gacactctca gagaagctca aaaggctcgg      600
aaactggggg ccaacgttta caccctgggt gtggctgatt ataatctgga ccagataaca      660
```

```
gcaattgcag acagccctgg ccacgtgttt gcagtggaga atggcttcaa ggccctgaga      720
agcaccattg atgccctcac gtcaaaggtc tgtcttgatg tgacatcggt ggagccttcc      780
tctgagtgtg taggagaacc ctaccatgtg gttattcatg gaaatggctt tcagaatcta      840
aagaaacggg atgaagttat ttgcagattt atcttcaatg aaagcactat cattgatgaa      900
aagccaacca gtatcgacaa taattccatg aattgccctg gccaaaact agaaaaaccct      960 ggagaggagt actctattga agtcagcttg aacaaaggca aaacattctt caagagcaat     1020
gtcagcatca ccagcaccac atgtggcatt ttccgccacc atcaccatca ccat           1074
```

<210> SEQ ID NO 140
<211> LENGTH: 358
<212> TYPE: PRT
<213> ORGANISM: Artificial Sequence
<220> FEATURE:
<223> OTHER INFORMATION: cloned histidine tag INSP143

<400> SEQUENCE: 140

```
Met Gly Ser His Glu Ser Leu Gly Pro Tyr Phe Leu Val Phe Leu Leu
1               5                   10                  15

Leu Leu Leu Leu Pro Pro Pro Leu Phe Arg Ala Gly Ser Leu Arg Tyr
                20                  25                  30

His Gly Pro Asp Trp Arg Ile Phe His Arg Leu Ala Leu Gly Ser Arg
            35                  40                  45

Arg Ala His His His Gly Pro Gly Trp Arg Gln His Trp Arg Gln
50                  55                  60

Gly Gln Ala Gly His Arg Cys Gln Gly Ser Phe Asp Leu Tyr Phe Ile
65                  70                  75                  80

Leu Asp Lys Ser Gly Ser Val Asn Asn Asn Trp Ile Asp Leu Tyr Met
                85                  90                  95

Trp Val Glu Glu Thr Val Ala Arg Phe Gln Ser Pro Asn Ile Arg Met
            100                 105                 110

Cys Phe Ile Thr Tyr Ser Thr Asp Gly Gln Thr Val Leu Pro Leu Thr
        115                 120                 125

Ser Asp Lys Asn Arg Ile Lys Asn Gly Leu Asp Gln Leu Gln Lys Ile
    130                 135                 140

Val Pro Asp Gly His Thr Phe Met Gln Ala Gly Phe Arg Lys Ala Ile
145                 150                 155                 160

Gln Gln Ile Glu Ser Phe Asn Ser Gly Asn Lys Val Pro Ser Met Ile
                165                 170                 175

Ile Ala Met Thr Asp Gly Glu Leu Val Ala His Ala Phe Gln Asp Thr
            180                 185                 190

Leu Arg Glu Ala Gln Lys Ala Arg Lys Leu Gly Ala Asn Val Tyr Thr
        195                 200                 205

Leu Gly Val Ala Asp Tyr Asn Leu Asp Gln Ile Thr Ala Ile Ala Asp
    210                 215                 220

Ser Pro Gly His Val Phe Ala Val Glu Asn Gly Phe Lys Ala Leu Arg
225                 230                 235                 240

Ser Thr Ile Asp Ala Leu Thr Ser Lys Val Cys Leu Asp Val Thr Ser
                245                 250                 255

Val Glu Pro Ser Ser Glu Cys Val Gly Glu Pro Tyr His Val Val Ile
            260                 265                 270

His Gly Asn Gly Phe Gln Asn Leu Lys Lys Arg Asp Glu Val Ile Cys
        275                 280                 285

Arg Phe Ile Phe Asn Glu Ser Thr Ile Ile Asp Glu Lys Pro Thr Ser
```

```
                290              295              300
Ile Asp Asn Asn Ser Met Asn Cys Pro Gly Pro Lys Leu Glu Lys Pro
305                 310              315                 320

Gly Glu Glu Tyr Ser Ile Glu Val Ser Leu Asn Lys Gly Lys Thr Phe
            325              330              335

Phe Lys Ser Asn Val Ser Ile Thr Ser Thr Thr Cys Gly Ile Phe Arg
            340              345              350

His His His His His His
        355

<210> SEQ ID NO 141
<211> LENGTH: 975
<212> TYPE: DNA
<213> ORGANISM: Homo sapiens

<400> SEQUENCE: 141
ggaagccttc ggtaccatgg acctgactgg agaatatttc accgcctggc cctgggctcc      60
aggagagccc accaccacca tgcccaggat tggaggcagc actggcgcca ggggcaagca     120
ggtcacagat gccagggctc atttgacctc tacttcatct tggacaagtc tggcagcgtg     180
aacaataact ggattgacct ttatatgtgg gtggaggaaa cagtggcgag gttccaaagc     240
ccaaatattc ggatgtgctt catcacctac tccacagacg ccagactgt cttgccactc     300 acctcagaca gaatagaat aaaaaacggt cttgaccaac ttcagaaaat tgtgcctgac     360
ggtcacacat tcatgcaggc aggatttaga aaggcaattc aacagatcga agtttcaac     420 tccgaaaaca aggttcccag catgattatt gctatgactg atggagaact ggtggcacat     480
gcatttcagg acactctcag agaagctcaa aaggctcgga actgggggc caacgtttac     540 accctgggtg tggctgatta taatctggac cagataacag caattgcaga cagccctggc     600
cacgtgtttg cagtggagaa tggcttcaag ccctgagaa gcaccattga tgccctcacg     660
tcaaaggtct gtcttgatgt gacatcggtg gagccttcct ctgagtgtgt aggagaaccc     720
taccatgtgg ttattcatgg aaatggcttt cagaatctaa agaaacggga tgaagttatt     780
tgcagattta tcttcaatga aagcactatc attgatgaaa agccaaccag tatcgacaat     840
aattccatga attgccctgg gccaaaacta gaaaaacctg gagaggagta ctctattgaa     900
gtcagcttga caaaggcaa aacattcttc aagagcaatg tcagcatcac cagcaccaca     960
tgtggcattt tccgc                                                      975

<210> SEQ ID NO 142
<211> LENGTH: 325
<212> TYPE: PRT
<213> ORGANISM: Homo sapiens

<400> SEQUENCE: 142

Gly Ser Leu Arg Tyr His Gly Pro Asp Trp Arg Ile Phe His Arg Leu
1               5                   10                  15

Ala Leu Gly Ser Arg Arg Ala His His His Gly Pro Gly Trp Arg
            20                  25                  30

Gln His Trp Arg Gln Gly Gln Ala Gly His Arg Cys Gln Gly Ser Phe
        35                  40                  45

Asp Leu Tyr Phe Ile Leu Asp Lys Ser Gly Ser Val Asn Asn Asn Trp
    50                  55                  60

Ile Asp Leu Tyr Met Trp Val Glu Glu Thr Val Ala Arg Phe Gln Ser
65                  70                  75                  80

Pro Asn Ile Arg Met Cys Phe Ile Thr Tyr Ser Thr Asp Gly Gln Thr
```

```
                    85                  90                  95
Val Leu Pro Leu Thr Ser Asp Lys Asn Arg Ile Lys Asn Gly Leu Asp
            100                 105                 110

Gln Leu Gln Lys Ile Val Pro Asp Gly His Thr Phe Met Gln Ala Gly
        115                 120                 125

Phe Arg Lys Ala Ile Gln Gln Ile Glu Ser Phe Asn Ser Gly Asn Lys
    130                 135                 140

Val Pro Ser Met Ile Ile Ala Met Thr Asp Gly Glu Leu Val Ala His
145                 150                 155                 160

Ala Phe Gln Asp Thr Leu Arg Glu Ala Gln Lys Ala Arg Lys Leu Gly
                165                 170                 175

Ala Asn Val Tyr Thr Leu Gly Val Ala Asp Tyr Asn Leu Asp Gln Ile
            180                 185                 190

Thr Ala Ile Ala Asp Ser Pro Gly His Val Phe Ala Val Glu Asn Gly
        195                 200                 205

Phe Lys Ala Leu Arg Ser Thr Ile Asp Ala Leu Thr Ser Lys Val Cys
    210                 215                 220

Leu Asp Val Thr Ser Val Glu Pro Ser Ser Glu Cys Val Gly Glu Pro
225                 230                 235                 240

Tyr His Val Val Ile His Gly Asn Gly Phe Gln Asn Leu Lys Lys Arg
                245                 250                 255

Asp Glu Val Ile Cys Arg Phe Ile Phe Asn Glu Ser Thr Ile Ile Asp
            260                 265                 270

Glu Lys Pro Thr Ser Ile Asp Asn Asn Ser Met Asn Cys Pro Gly Pro
        275                 280                 285

Lys Leu Glu Lys Pro Gly Glu Glu Tyr Ser Ile Glu Val Ser Leu Asn
    290                 295                 300

Lys Gly Lys Thr Phe Phe Lys Ser Asn Val Ser Ile Thr Ser Thr Thr
305                 310                 315                 320

Cys Gly Ile Phe Arg
                325

<210> SEQ ID NO 143
<211> LENGTH: 993
<212> TYPE: DNA
<213> ORGANISM: Artificial Sequence
<220> FEATURE:
<223> OTHER INFORMATION: cloned mature histidine tag INSP143

<400> SEQUENCE: 143
ggaagccttc ggtaccatgg acctgactgg agaatatttc accgcctggc cctgggctcc      60
aggagagccc accaccacca tgcccaggat tggaggcagc actggcgcca ggggcaagca     120
ggtcacagat gccagggctc atttgacctc tacttcatct tggacaagtc tggcagcgtg     180
aacaataact ggattgacct ttatatgtgg gtggaggaaa cagtggcgag gttccaaagc     240
ccaaatattc ggatgtgctt catcacctac tccacagacg ccagactgt cttgccactc      300 acctcagaca agaatagaat aaaaaacggt cttgaccaac ttcagaaaat tgtgcctgac     360
ggtcacacat tcatgcaggc aggatttaga aaggcaattc aacagatcga aagtttcaac     420
tccggaaaca aggttcccag catgattatt gctatgactg atggagaact ggtggcacat     480
gcatttcagg acactctcag agaagctcaa aaggctcgga actggggc caacgtttac       540 accctgggtg tggctgatta taatctggac cagataacag caattgcaga cagccctggc     600
cacgtgtttg cagtggagaa tggcttcaag gccctgagaa gcaccattga tgccctcacg     660
tcaaaggtct gtcttgatgt gacatcggtg gagccttcct ctgagtgtgt aggagaaccc     720
```

```
taccatgtgg ttattcatgg aaatggcttt cagaatctaa agaaacggga tgaagttatt    780
tgcagattta tcttcaatga aagcactatc attgatgaaa agccaaccag tatcgacaat    840
aattccatga attgccctgg gccaaaacta gaaaaacctg agaggagta ctctattgaa     900 gtcagcttga acaaaggcaa acattcttc aagagcaatg tcagcatcac cagcaccaca    960
tgtggcattt tccgccacca tcaccatcac cat                                  993
```

```
<210> SEQ ID NO 144
<211> LENGTH: 331
<212> TYPE: PRT
<213> ORGANISM: Artificial Sequence
<220> FEATURE:
<223> OTHER INFORMATION: cloned mature histidine tag INSP143

<400> SEQUENCE: 144
```

```
Gly Ser Leu Arg Tyr His Gly Pro Asp Trp Arg Ile Phe His Arg Leu
1               5                   10                  15

Ala Leu Gly Ser Arg Arg Ala His His His Gly Pro Gly Trp Arg
            20                  25                  30

Gln His Trp Arg Gln Gly Gln Ala Gly His Arg Cys Gln Gly Ser Phe
        35                  40                  45

Asp Leu Tyr Phe Ile Leu Asp Lys Ser Gly Ser Val Asn Asn Asn Trp
    50                  55                  60

Ile Asp Leu Tyr Met Trp Val Glu Glu Thr Val Ala Arg Phe Gln Ser
65                  70                  75                  80

Pro Asn Ile Arg Met Cys Phe Ile Thr Tyr Ser Thr Asp Gly Gln Thr
                85                  90                  95

Val Leu Pro Leu Thr Ser Asp Lys Asn Arg Ile Lys Asn Gly Leu Asp
            100                 105                 110

Gln Leu Gln Lys Ile Val Pro Asp Gly His Thr Phe Met Gln Ala Gly
        115                 120                 125

Phe Arg Lys Ala Ile Gln Gln Ile Glu Ser Phe Asn Ser Gly Asn Lys
    130                 135                 140

Val Pro Ser Met Ile Ile Ala Met Thr Asp Gly Glu Leu Val Ala His
145                 150                 155                 160

Ala Phe Gln Asp Thr Leu Arg Glu Ala Gln Lys Ala Arg Lys Leu Gly
                165                 170                 175

Ala Asn Val Tyr Thr Leu Gly Val Ala Asp Tyr Asn Leu Asp Gln Ile
            180                 185                 190

Thr Ala Ile Ala Asp Ser Pro Gly His Val Phe Ala Val Glu Asn Gly
        195                 200                 205

Phe Lys Ala Leu Arg Ser Thr Ile Asp Ala Leu Thr Ser Lys Val Cys
    210                 215                 220

Leu Asp Val Thr Ser Val Glu Pro Ser Glu Cys Val Gly Glu Pro
225                 230                 235                 240

Tyr His Val Val Ile His Gly Asn Gly Phe Gln Asn Leu Lys Lys Arg
                245                 250                 255

Asp Glu Val Ile Cys Arg Phe Ile Phe Asn Glu Ser Thr Ile Ile Asp
            260                 265                 270

Glu Lys Pro Thr Ser Ile Asp Asn Asn Ser Met Asn Cys Pro Gly Pro
        275                 280                 285

Lys Leu Glu Lys Pro Gly Glu Glu Tyr Ser Ile Glu Val Ser Leu Asn
    290                 295                 300

Lys Gly Lys Thr Phe Phe Lys Ser Asn Val Ser Ile Thr Ser Thr Thr
305                 310                 315                 320
```

Cys Gly Ile Phe Arg His His His His His His
                325                 330

<210> SEQ ID NO 145
<211> LENGTH: 516
<212> TYPE: DNA
<213> ORGANISM: Homo sapiens

<400> SEQUENCE: 145
tttgacctct acttcatctt ggacaagtct ggcagcgtga acaataactg gattgacctt      60
tatatgtggg tggaggaaac agtggcgagg ttccaaagcc caaatattcg gatgtgcttc     120
atcacctact ccacagacgg ccagactgtc ttgccactca cctcagacaa gaatagaata     180
aaaaacggtc ttgaccaact tcagaaaatt gtgcctgacg gtcacacatt catgcaggca     240
ggatttagaa aggcaattca acagatcgaa agtttcaact ccggaaacaa ggttcccagc     300
atgattattg ctatgactga tggagaactg gtggcacatg catttcagga cactctcaga     360
gaagctcaaa aggctcggaa actgggggcc aacgtttaca ccctgggtgt ggctgattat     420
aatctggacc agataacagc aattgcagac agccctggcc acgtgtttgc agtggagaat     480
ggcttcaagg ccctgagaag caccattgat gccctc                               516

<210> SEQ ID NO 146
<211> LENGTH: 172
<212> TYPE: PRT
<213> ORGANISM: Homo sapiens

<400> SEQUENCE: 146

Phe Asp Leu Tyr Phe Ile Leu Asp Lys Ser Gly Ser Val Asn Asn Asn
1               5                   10                  15

Trp Ile Asp Leu Tyr Met Trp Val Glu Glu Thr Val Ala Arg Phe Gln
            20                  25                  30

Ser Pro Asn Ile Arg Met Cys Phe Ile Thr Tyr Ser Thr Asp Gly Gln
        35                  40                  45

Thr Val Leu Pro Leu Thr Ser Asp Lys Asn Arg Ile Lys Asn Gly Leu
    50                  55                  60

Asp Gln Leu Gln Lys Ile Val Pro Asp Gly His Thr Phe Met Gln Ala
65                  70                  75                  80

Gly Phe Arg Lys Ala Ile Gln Gln Ile Glu Ser Phe Asn Ser Gly Asn
                85                  90                  95

Lys Val Pro Ser Met Ile Ile Ala Met Thr Asp Gly Glu Leu Val Ala
            100                 105                 110

His Ala Phe Gln Asp Thr Leu Arg Glu Ala Gln Lys Ala Arg Lys Leu
        115                 120                 125

Gly Ala Asn Val Tyr Thr Leu Gly Val Ala Asp Tyr Asn Leu Asp Gln
    130                 135                 140

Ile Thr Ala Ile Ala Asp Ser Pro Gly His Val Phe Ala Val Glu Asn
145                 150                 155                 160

Gly Phe Lys Ala Leu Arg Ser Thr Ile Asp Ala Leu
                165                 170

<210> SEQ ID NO 147
<211> LENGTH: 174
<212> TYPE: DNA
<213> ORGANISM: Homo sapiens

<400> SEQUENCE: 147
acgtcaaagg tctgtcttga tgtgacatcg gtggagcctt cctctgagtg tgtaggagaa      60

```
ccctaccatg tggttattca tggaaatggc tttcagaatc taaagaaacg ggatgaagtt      120
atttgcagat ttatcttcaa tgaaagcact atcattggga gtactctatt gaag            174
```

<210> SEQ ID NO 148
<211> LENGTH: 58
<212> TYPE: PRT
<213> ORGANISM: Homo sapiens

<400> SEQUENCE: 148

```
Thr Ser Lys Val Cys Leu Asp Val Thr Ser Val Glu Pro Ser Ser Glu
1               5                   10                  15

Cys Val Gly Glu Pro Tyr His Val Val Ile His Gly Asn Gly Phe Gln
                20                  25                  30

Asn Leu Lys Lys Arg Asp Glu Val Ile Cys Arg Phe Ile Phe Asn Glu
            35                  40                  45

Ser Thr Ile Ile Gly Ser Thr Leu Leu Lys
        50                  55
```

<210> SEQ ID NO 149
<211> LENGTH: 174
<212> TYPE: DNA
<213> ORGANISM: Homo sapiens

<400> SEQUENCE: 149

```
acgtcaaagg tctgtcttga tgtgacatcg gtggagcctt cctctgagtg tgtaggagaa      60
ccctaccatg tggttattca tggaaatggc tttcagaatc taaagaaacg ggatgaagtt      120
atttgcagat ttatcttcaa tgaaagcact atcattgatg aaaagccaac cagt            174
```

<210> SEQ ID NO 150
<211> LENGTH: 58
<212> TYPE: PRT
<213> ORGANISM: Homo sapiens

<400> SEQUENCE: 150

```
Thr Ser Lys Val Cys Leu Asp Val Thr Ser Val Glu Pro Ser Ser Glu
1               5                   10                  15

Cys Val Gly Glu Pro Tyr His Val Val Ile His Gly Asn Gly Phe Gln
                20                  25                  30

Asn Leu Lys Lys Arg Asp Glu Val Ile Cys Arg Phe Ile Phe Asn Glu
            35                  40                  45

Ser Thr Ile Ile Asp Glu Lys Pro Thr Ser
        50                  55
```

<210> SEQ ID NO 151
<211> LENGTH: 13
<212> TYPE: PRT
<213> ORGANISM: Artificial Sequence
<220> FEATURE:
<223> OTHER INFORMATION: Fusion protein linker sequence

<400> SEQUENCE: 151

```
Glu Phe Gly Ala Gly Leu Val Leu Gly Gly Gln Phe Met
1               5                   10
```

<210> SEQ ID NO 152
<211> LENGTH: 27
<212> TYPE: PRT
<213> ORGANISM: Homo sapiens

<400> SEQUENCE: 152

```
Met Gly Ser His Glu Ser Leu Gly Pro Tyr Phe Leu Val Phe Leu Leu
1               5                   10                  15

Leu Leu Leu Leu Pro Pro Pro Leu Phe Arg Ala
            20                  25
```

<210> SEQ ID NO 153
<211> LENGTH: 20
<212> TYPE: DNA
<213> ORGANISM: Artificial Sequence
<220> FEATURE:
<223> OTHER INFORMATION: Primer INSP141-CP1

<400> SEQUENCE: 153
gtcacaggga cagccagata                                              20

<210> SEQ ID NO 154
<211> LENGTH: 20
<212> TYPE: DNA
<213> ORGANISM: Artificial Sequence
<220> FEATURE:
<223> OTHER INFORMATION: Primer INSP141-CP2

<400> SEQUENCE: 154
gctggtgatg ctgacattgc                                              20

<210> SEQ ID NO 155
<211> LENGTH: 36
<212> TYPE: DNA
<213> ORGANISM: Artificial Sequence
<220> FEATURE:
<223> OTHER INFORMATION: Primer INSP141-AP1

<400> SEQUENCE: 155
atggggagcc atgagtccct ggggccctac ttcctg                            36

<210> SEQ ID NO 156
<211> LENGTH: 47
<212> TYPE: DNA
<213> ORGANISM: Artificial Sequence
<220> FEATURE:
<223> OTHER INFORMATION: Primer INSP141-AP2

<400> SEQUENCE: 156
agctgacttc aatagagtac tcccaatgat agtgctttca ttgaaga                47

<210> SEQ ID NO 157
<211> LENGTH: 46
<212> TYPE: DNA
<213> ORGANISM: Artificial Sequence
<220> FEATURE:
<223> OTHER INFORMATION: Primer INSP143-AP1

<400> SEQUENCE: 157
gcggaaaatg ccacatgtgg tgctggtgat gctgacattg ctcttg                 46

<210> SEQ ID NO 158
<211> LENGTH: 18
<212> TYPE: DNA
<213> ORGANISM: Artificial Sequence
<220> FEATURE:
<223> OTHER INFORMATION: Primer 21M13

<400> SEQUENCE: 158
tgtaaaacga cggccagt                                                18

<210> SEQ ID NO 159

```
<211> LENGTH: 18
<212> TYPE: DNA
<213> ORGANISM: Artificial Sequence
<220> FEATURE:
<223> OTHER INFORMATION: Primer M13REV

<400> SEQUENCE: 159
caggaaacag ctatgacc                                                 18

<210> SEQ ID NO 160
<211> LENGTH: 19
<212> TYPE: DNA
<213> ORGANISM: Artificial Sequence
<220> FEATURE:
<223> OTHER INFORMATION: Primer T7

<400> SEQUENCE: 160
taatacgact cactatagg                                                19

<210> SEQ ID NO 161
<211> LENGTH: 18
<212> TYPE: DNA
<213> ORGANISM: Artificial Sequence
<220> FEATURE:
<223> OTHER INFORMATION: Primer T3

<400> SEQUENCE: 161
attaaccctc actaaagg                                                 18

<210> SEQ ID NO 162
<211> LENGTH: 21
<212> TYPE: DNA
<213> ORGANISM: Artificial Sequence
<220> FEATURE:
<223> OTHER INFORMATION: Primer INSP142-936F

<400> SEQUENCE: 162
ccctgggcca aaactagaaa a                                             21

<210> SEQ ID NO 163
<211> LENGTH: 22
<212> TYPE: DNA
<213> ORGANISM: Artificial Sequence
<220> FEATURE:
<223> OTHER INFORMATION: Primer INSP142-1044R

<400> SEQUENCE: 163
aagagaagga catgtggtgc tg                                            22

<210> SEQ ID NO 164
<211> LENGTH: 18
<212> TYPE: DNA
<213> ORGANISM: Artificial Sequence
<220> FEATURE:
<223> OTHER INFORMATION: Primer hGAPDH-F

<400> SEQUENCE: 164
ccacccatgg caaattcc                                                 18

<210> SEQ ID NO 165
<211> LENGTH: 22
<212> TYPE: DNA
<213> ORGANISM: Artificial Sequence
<220> FEATURE:
<223> OTHER INFORMATION: Primer hGAPDH-R

<400> SEQUENCE: 165
```

```
gatgggattt ccattgatga ca                                              22
```

<210> SEQ ID NO 166
<211> LENGTH: 21
<212> TYPE: DNA
<213> ORGANISM: Artificial Sequence
<220> FEATURE:
<223> OTHER INFORMATION: Primer Intron-hGAPDH-F

<400> SEQUENCE: 166

```
cctagtccca gggctttgat t                                               21
```

<210> SEQ ID NO 167
<211> LENGTH: 21
<212> TYPE: DNA
<213> ORGANISM: Artificial Sequence
<220> FEATURE:
<223> OTHER INFORMATION: Primer Intron-hGAPDH-R

<400> SEQUENCE: 167

```
ctgtgctccc actcctgatt t                                               21
```

<210> SEQ ID NO 168
<211> LENGTH: 500
<212> TYPE: PRT
<213> ORGANISM: Homo sapiens

<400> SEQUENCE: 168

```
Met Gly Ser His Glu Ser Leu Gly Pro Tyr Phe Leu Val Phe Leu Leu
1               5                   10                  15

Leu Leu Leu Leu Pro Pro Pro Leu Phe Arg Ala Gly Ser Leu Arg Tyr
            20                  25                  30

His Gly Pro Asp Trp Arg Ile Phe His Arg Leu Ala Leu Gly Ser Arg
        35                  40                  45

Arg Ala His His His His Gly Pro Gly Trp Arg Gln His Trp Arg Gln
    50                  55                  60

Gly Gln Ala Gly His Arg Cys Gln Gly Ser Phe Asp Leu Tyr Phe Ile
65                  70                  75                  80

Leu Asp Lys Ser Gly Ser Val Asn Asn Asn Trp Ile Asp Leu Tyr Met
                85                  90                  95

Trp Val Glu Glu Thr Val Ala Arg Phe Gln Ser Pro Asn Ile Arg Met
            100                 105                 110

Cys Phe Ile Thr Tyr Ser Thr Asp Gly Gln Thr Val Leu Pro Leu Thr
        115                 120                 125

Ser Asp Lys Asn Arg Ile Lys Asn Gly Leu Asp Gln Leu Gln Lys Ile
    130                 135                 140

Val Pro Asp Gly His Thr Phe Met Gln Ala Gly Phe Arg Lys Ala Ile
145                 150                 155                 160

Gln Gln Ile Glu Ser Phe Asn Ser Gly Asn Lys Val Pro Ser Met Ile
                165                 170                 175

Ile Ala Met Thr Asp Gly Glu Leu Val Ala His Ala Phe Gln Asp Thr
            180                 185                 190

Leu Arg Glu Ala Gln Lys Ala Arg Lys Leu Gly Ala Asn Val Tyr Thr
        195                 200                 205

Leu Gly Val Ala Asp Tyr Asn Leu Asp Gln Ile Thr Ala Ile Ala Asp
    210                 215                 220

Ser Pro Gly His Val Phe Ala Val Glu Asn Gly Phe Lys Ala Leu Arg
225                 230                 235                 240

Ser Thr Ile Asp Ala Leu Thr Ser Lys Val Cys Leu Asp Val Thr Ser
```

```
                    245                 250                 255
Val Glu Pro Ser Ser Glu Cys Val Gly Glu Pro Tyr His Val Ile
        260                 265                 270

His Gly Asn Gly Phe Gln Asn Leu Lys Lys Arg Asp Glu Val Ile Cys
    275                 280                 285

Arg Phe Ile Phe Asn Glu Ser Thr Ile Ile Asp Glu Lys Pro Thr Ser
    290                 295                 300

Ile Asp Asn Asn Ser Met Asn Cys Pro Gly Pro Lys Leu Glu Lys Pro
305                 310                 315                 320

Gly Glu Glu Tyr Ser Ile Glu Val Ser Leu Asn Lys Gly Lys Thr Phe
                325                 330                 335

Phe Lys Ser Asn Val Ser Ile Thr Ser Thr Thr Cys Val Ser Thr Ser
            340                 345                 350

Met Gly Leu Gln Thr Cys Met Arg Thr Val Gln Ser Leu Cys Thr Arg
        355                 360                 365

Arg Ser Thr Glu Lys Ala Asp Arg Ser Gln Ala Val Pro Glu Ser Ser
    370                 375                 380

Val Cys Ser Arg His Leu Arg Leu Leu Gln Pro Gly Phe Trp Met Val
385                 390                 395                 400

Gln Ala Pro Glu Met Ser Leu Ser Ala Pro Ser Pro Ser Pro Val Val
                405                 410                 415

Cys Pro Leu Leu Leu Lys Gly Arg Leu Ser Gly Thr Arg Thr Arg
            420                 425                 430

Ala Gln Leu Gln Glu Ala Pro Gly Asn Gly Asp Ala Val Pro Gln Gly
        435                 440                 445

Ile Phe Arg Asn Trp Leu Tyr Phe Val Pro Leu Leu Leu Val Pro
    450                 455                 460

Leu Leu Leu Cys Cys Val Trp Arg Leu Cys Arg Lys Gln Ala Ser Ala
465                 470                 475                 480

Pro Cys Pro Pro Ser Ser Gly Ala Gln Ala Gln Ala His Pro Leu Arg
                485                 490                 495

Asp Ser Asn Met
            500

<210> SEQ ID NO 169
<211> LENGTH: 641
<212> TYPE: PRT
<213> ORGANISM: Unknown
<220> FEATURE:
<223> OTHER INFORMATION: IPI00480015.1

<400> SEQUENCE: 169

Met Gly Ser His Glu Ser Leu Gly Pro Tyr Phe Leu Val Phe Leu Leu
1               5                   10                  15

Leu Leu Leu Pro Pro Pro Leu Phe Arg Ala Gly Ser Leu Arg Tyr
            20                  25                  30

His Gly Pro Asp Trp Arg Ile Phe His Arg Leu Ala Leu Gly Ser Arg
        35                  40                  45

Arg Ala His His His Gly Pro Gly Trp Arg Gln His Trp Arg Gln
    50                  55                  60

Gly Gln Ala Gly His Arg Cys Gln Gly Ser Phe Asp Leu Tyr Phe Ile
65                  70                  75                  80

Leu Asp Lys Ser Gly Ser Val Asn Asn Asn Trp Ile Asp Leu Tyr Met
                85                  90                  95

Trp Val Glu Glu Thr Val Ala Arg Phe Gln Ser Pro Asn Ile Arg Met
            100                 105                 110
```

```
Cys Phe Ile Thr Tyr Ser Thr Asp Gly Gln Thr Val Leu Pro Leu Thr
            115                 120                 125

Ser Asp Lys Asn Arg Ile Lys Asn Gly Leu Asp Gln Leu Gln Lys Ile
130                 135                 140

Val Pro Asp Gly His Thr Phe Met Gln Ala Gly Phe Arg Lys Ala Ile
145                 150                 155                 160

Gln Gln Ile Glu Ser Phe Asn Ser Gly Asn Lys Val Pro Ser Met Ile
                165                 170                 175

Ile Ala Met Thr Asp Gly Glu Leu Val Ala His Ala Phe Gln Asp Thr
            180                 185                 190

Leu Arg Glu Ala Gln Lys Ala Arg Lys Leu Gly Ala Asn Val Tyr Thr
            195                 200                 205

Leu Gly Val Ala Asp Tyr Asn Leu Asp Gln Val Ile Pro Ser Ser Pro
        210                 215                 220

Gly His Val Phe Ala Val Glu Asn Gly Phe Lys Ala Leu Arg Ser Thr
225                 230                 235                 240

Ile Asp Ala Leu Thr Ser Lys Val Cys Leu Asp Val Thr Ser Val Glu
                245                 250                 255

Pro Ser Ser Glu Cys Val Gly Glu Pro Tyr His Val Val Ile His Gly
                260                 265                 270

Asn Gly Phe Gln Asn Leu Lys Lys Arg Asp Glu Val Ile Cys Arg Phe
            275                 280                 285

Ile Phe Asn Glu Ser Thr Ile Ile Asp Glu Lys Pro Thr Ser Ile Asp
        290                 295                 300

Asn Asn Ser Met Asn Cys Pro Gly Pro Lys Leu Glu Lys Pro Gly Glu
305                 310                 315                 320

Glu Tyr Ser Ile Glu Val Ser Leu Asn Lys Gly Lys Thr Phe Phe Lys
                325                 330                 335

Ser Asn Val Ser Ile Thr Ser Thr Thr Cys Arg Pro Arg Pro Arg Ser
            340                 345                 350

Tyr Gly Ala Leu Phe Leu His Gln Gly Ile Phe Arg Asn Trp Leu Tyr
        355                 360                 365

Phe Val Pro Leu Leu Leu Leu Val Pro Leu Leu Leu Cys Cys Val Trp
370                 375                 380

Arg Leu Cys Arg Lys Gln Ala Ser Ala Pro Cys Pro Pro Ser Ser Gly
385                 390                 395                 400

Ala Gln Ala Gln Ala His Pro Leu Arg Asp Ser Asn Met Arg Arg Ser
                405                 410                 415

Leu Pro Gly Thr Ser Ser Gln Ala Gln Gly Gln Ser Asp Thr Pro
            420                 425                 430     Pro

Lys Ala Val Leu Cys Pro Gly Ala Pro Gly Gln Gly Pro Ser Cys Val
            435                 440                 445

Gln Gly Gln Gly Arg Ala Arg Pro Pro Ser Ser Leu Ser Pro Val
450                 455                 460

Asn Thr Cys Pro Thr Val Ile Ile Cys Cys Gly Cys Gln Gly Val
465                 470                 475             480

Gly Gly Met Arg Arg Ile Glu Gly Asn Leu Asp Thr Phe Cys Asp Leu
            485                 490                 495

Ser His Ala Ser Cys His Gln Val Pro Trp Met Cys Cys Gln Ser Arg
                500                 505                 510

Asp Gln Gly Arg Tyr Leu Ser Leu Ala Leu Ala Gln Ser Gln Tyr Ala
            515                 520                 525

Gln Ala Pro Cys Cys Pro Arg Ile Cys Phe Pro His Ser Gln Glu Cys
```

-continued

```
              530                 535                 540
Leu Ser Leu Pro Gln Ala Pro Cys Ser Pro Arg Met Cys Leu Arg His
545                 550                 555                 560

Ser Arg Glu Glu Cys Leu Ala Arg Lys Gln Ala Pro Cys Ser Pro Arg
                565                 570                 575

Ile Cys Leu Arg His Ser Pro Glu Tyr Phe Ser Gln Ala Gln Thr Leu
                580                 585                 590

Cys Asn Pro Lys Ser Cys Leu Gln Pro Ser Arg Glu Cys Leu Pro Leu
                595                 600                 605

Thr Cys Ser Ser Arg Cys Arg Leu Pro Pro Ala Arg Cys Leu Arg Pro
        610                 615                 620

Pro Ser Arg Met Leu Pro Leu Leu Ser Pro Leu Leu Arg His Thr Ala
625                 630                 635                 640

Glu
```

VWFA AND/OR ANT_IG DOMAIN CONTAINING PROTEINS

CROSS-REFERENCE TO RELATED APPLICATION

This application is the National Stage of International Application Number PCT/GB2005/004191, filed Oct. 28, 2005, which is hereby incorporated by reference herein in its entirety, including any figures, tables, nucleic acid sequences, amino acid sequences, or drawings.

This invention relates to novel proteins (herein termed INSP141, INSP142, INSP143, and INSP144), herein identified as anthrax receptor-like proteins containing von Willebrand factor A (vWFA) and Anthrax receptor extracellular (ANT_IG) domains and to the use of these proteins and nucleic acid sequences from the encoding genes in the diagnosis, prevention and treatment of disease.

All publications, patents and patent applications cited herein are incorporated in full by reference.

BACKGROUND

The process of drug discovery is presently undergoing a fundamental revolution as the era of functional genomics comes of age. The term "functional genomics" applies to an approach utilising bioinformatics tools to ascribe function to protein sequences of interest. Such tools are becoming increasingly necessary as the speed of generation of sequence data is rapidly outpacing the ability of research laboratories to assign functions to these protein sequences.

As bioinformatics tools increase in potency and in accuracy, these tools are rapidly replacing the conventional techniques of biochemical characterisation. Indeed, the advanced bioinformatics tools used in identifying the present invention are now capable of outputting results in which a high degree of confidence can be placed.

Various institutions and commercial organisations are examining sequence data as they become available and significant discoveries are being made on an on-going basis. However, there remains a continuing need to identify and characterise further genes and the polypeptides that they encode, as targets for research and for drug discovery.

Introduction

Anthrax Toxin Receptor

Anthrax is primarily a disease of domesticated and wild animals, particularly herbivorous animals; such as cattle, sheep, horses, mules, and goats. Humans become infected incidentally when brought into contact with diseased animals, which includes their flesh, bones, hides, hair and excrement.

One component of the anthrax toxin has a lethal mode of the action that is not understood at this time. Death is apparently due to oxygen depletion, secondary shock, increased vascular permeability, respiratory failure and cardiac failure. Death from anthrax in humans or animals frequently occurs suddenly and unexpectedly. The level of the lethal toxin in the circulation increases rapidly quite late in the disease, and it closely parallels the concentration of organisms in the blood.

The tripartite toxin Anthrax toxin is produced by *Bacillus anthracis*, the causative agent of anthrax. It helps the bacterium evade the immune system and can kill the host during a systemic infection. The toxin consists of three proteins: protective antigen (PA) (a single receptor-binding moiety) and two enzymatic moieties, called edema factor (EF) and lethal factor (LF). Once these proteins are released from the bacteria as nontoxic molecules, they move to the surface of mammalian cells and assemble into toxic, cell-bound complexes (Mourez M. et al., *Nat. Biotechnol.* 2001, 19, 958-961).

Two components of the toxin enzymatically modify substrates within the cytosol of mammalian cells: edema factor (EF) is an adenylate cyclase that impairs host defenses through a variety of mechanisms including suppressing neutrophil function and impairing host resistance. Lethal factor (LF) is a zinc-dependent protease that cleaves mitogen-activated protein kinase and causes lysis of macrophages. Protective antigen (PA), the third component, binds to a cellular receptor and mediates delivery of the enzymatic components to the cytosol (Leppla S H. Anthrax toxin, In Aktories K, Just I, editors. Handbook of experimental pharmacology. Berlin: Springer; 2000, pp. 447-72).

The anthrax toxin receptor (ATR) is encoded by the tumor endothelial marker 8 (TEM8) gene. The anthrax toxin exploits the protein product of the TEM8 gene in order to carry out the first stages of intoxication. The true physiological functions of the ATR is not known, however it has been shown that the TEM8 gene is up regulated in colorectal cancer (St Croix B. et al (2000) Science August 18; 289(5482):1197-1202). TEM8 transcription is also upregulated during angiogenesis. Studies on the mouse tumor endothelial marker 8 (mTEM8) gene, suggests the mTEM8 may be involved in neovascularization (Carson-Walter E. et al. (2001) Cancer Res. September 15; 61(18):6649-55).

The human capillary morphogenesis protein 2 (CMG2) has a similar domain organization to ATR and both sequences share 40% sequence identity over their full length. It has been shown experimentally CMG2 can bind the PA subunits of the anthrax toxin, suggesting CMG2 may be exploited in a similar way to ATR (Scobie H. M. et al (2003) Proc Natl Acad Sci USA. April 29; 100(9):5170-4). The true physiological functions of CMG2 are not known, however it has been shown that a recombinant form of CMG2 is able to bind collagen type IV and laminin (Bell S. et al. (2001) J Cell Sci. August; 114(Pt 15):2755-73).

The anthrax receptor extracellular domain (ANT_IG) is found in the putatively extracellular N-terminal half of the anthrax receptor. Another anthrax receptor domain is found in the intracellular part and is referred to as ANT_C. It is probably part of the Ig superfamily and most closely related to the IPT/TIG domain. The IPT/TIG family consists of a domain that has an immunoglobulin like fold. These domains are found in cell surface receptors such as Met and Ron as well as in intracellular transcription factors where it is involved in DNA binding. The Ron tyrosine kinase receptor shares with the members of its subfamily (Met and Sea) a unique functional feature: the control of cell dissociation, motility, and invasion of extracellular matrices (scattering).

One notable feature of ATR is an extracellular von Willebrand factor A (vWFA) domain, also known as an integrin (I) domain. The vWFA domain is found in many large extracellular proteins. Examples of such proteins include complement proteins factor B (FB), C2, CR3 and CR4, the integrins and collagen types VI, VII, XII XIV (Perkins S J et al, (1994) J Mol Biol. April 22; 238(1):104-19) and anthrax toxin receptors (Bradley K. et al (2003) Biochem Pharmacol. February 1; 65(3):309-14). Functions associated with vWFA domain containing proteins include acting as components of the extracellular matrix, hemostasis, cellular adhesion, and immune defense mechanisms (Colombatti A. et al (1993) Matrix. July; 13(4):297-306).

The vWFA domain found in the integrin class of proteins is referred to as an integrin 1 domain (Roland A et al. (2003) J. Biol. Chem. April 25; 278 (17) 15035-15039). It has been shown that the PA subunit of anthrax toxin binds directly to the ATR vWFA domain in a manner that appears to mimic the binding of integrins to their natural substrate. A soluble form of this domain has been shown to act as an effective extracellular anthrax antitoxin in cell culture (Bradley K. et al (2003) Biochem Pharmacol. February 1; 65(3):309-14).

A motif common to most vWFA domain containing proteins is the Metal Ion-Dependent Adhesion Site (MIDAS). The MIDAS motif is involved in cation (eg. $Mg^{2+}$, $Mn^{2+}$, $Zn^{2+}$ and $Ca^{2+}$) coordination and is made up of five residues, Asp-x-Ser-x-Ser, Thr and Asp (Scobie H. M. et al (2003) Proc Natl Acad Sci USA. April 29; 100(9):5170-4). A MIDAS motif located within the extracellular vWFA domain of ATR/TEM8 chelates a divalent cation that is critical for PA binding.

It has been shown that the soluble vWFA domain of ATR (sATR) functions to block anthrax intoxication of Chinese Hamster Ovary (CHO) cells in culture (Bradley et al. Nature 2001; 414:225-9; see also WO 04/052277 and WO 02/46228).

Bradley et al. also reviewed the implication of ATR/TEM8/CMG2 in cancer, notably in tumor endothelium, colorectal cancer, bladder cancer, esophageal cancer, lung cancer and melanoma (Bradley et al. Biochemical Pharmacology 2003. Vol. 65. pp. 309-314).

Antisense nucleic acids towards ATR/TEM8 have been suggested to treat anthrax infection as well as cancer (WO 04/013313 and WO 04/052277).

It has been suggested that ATR/TEM8/CMG2 has a natural role in angiogenesis (see Nanda and St. Croix for a review, Current Opinion in Oncology 2004. Vol. 16. pp. 44-49). The extracellular domain of TEM8 was shown to bind to the α3 subunit of collagen VI through the COOH-terminal C5 domain (Nanda et al. Cancer Research 2004. Vol. 64. pp. 817-820). PA might compete with collagen subunits for ATR binding. Nanda et al. suggest that the TEM8/C5 interaction may play an important role in tumor angiogenesis.

Mutations within the CMG2 gene (specifically in the vWFA domain) cause two allelic disorders, juvenile hyaline fibromatosis (JFH) and infantile systemic hyalinosis (ISH; Lacy et al. PNAS 2004. Vol. 101. No. 17. pp. 6367-6372).

In addition, missense mutations within the vWFA domains of various proteins lead to human diseases. Mutation of the Von Willebrand factor precursor (vWF) is associated with the von Willebrand disease (OMIM Acc. No. 193400). Mutation of the Collagen alpha 3 (VI) chain precursor is associated with Bethlem myopathy (OMIM Acc. Nos. 120250 and 158810). Mutation of the Collagen alpha 1 (VII) chain precursor (Long-chain collagen) (LC collagen) is associated with Epidermolysis bullosa dystrophica (dominant, OMIM Acc. No. 120120; recessive, OMIM Acc. No. 131750; pretibial, dominant and recessive OMIM Acc. No. 226600 and OMIM Acc. No. 131850).

Certain proteins that contain one or more copies of the type A domain take part in host defense mechanisms, such as immune response and inflammation (see, for example, Celikel et al., Nature Structural Biology 5: 189 (1998)).

WO 92/17192 discloses a therapeutic composition which is effective in treating or inhibiting thrombosis comprising a monomeric polypeptide patterned on a fragment of wild type mature von Willebrand factor (vWF) subunit. WO 04/062551 relates to polypeptides comprising at least one single domain antibody directed against vWF, vWF A1 domain, A1 domain of activated vWF, vWF A3 domain, gbIb and/or collagen, homologues and/or functional portions of the polypeptides, for the diagnosis and/or treatment for conditions which require a modulation of platelet-mediated aggregation.

Increasing knowledge of the vWFA domain and ANT_IG domain containing proteins, particularly ATR-like proteins, is therefore of extreme importance in increasing the understanding of the underlying pathways that lead to the disease states and associated disease states mentioned above, and in developing more effective gene and/or drug therapies to treat these disorders.

THE INVENTION

The invention is based on the discovery that the proteins referred to herein as INSP141, INSP142, INSP143 and INSP144 are splice variants of the same sequence, all of which share homology with the anthrax toxin receptor. In particular, the invention is based on the surprising findings that polypeptides of the present invention, preferably INSP142, show unexpected restricted expression in colon and ileum IBD biopsy samples as well as in psoriasis skin biopsies. Expression results from Taqman analysis gives a specific pattern of expression that implicates INSP142 in inflammatory bowel diseases, skin diseases and inflammation.

These surprising properties characterize the polypeptides of the present invention and their encoding polynucleotides and make them suitable for the preparation of a drug or pharmaceutical composition.

INSP141, INSP142, INSP143 and INSP144 are all predicted to contain a von Willebrand factor A (vWFA) domain and an anthrax receptor extracellular (ANT_IG) domain. These two extracellular domains confer receptor binding properties of anthrax toxin receptor (ATR)-like proteins. FIGS. 8 and 9 show the conserved features of the INSP141, INSP142, INSP143 and INSP144 proteins with ATR-like proteins at the structural and amino acid levels. The vWFA domain is identical in INSP141, INSP142, INSP143 and INSP144. The ANT_IG domain in the INSP141 protein is slightly different to the ANT_IG domain in INSP142, INSP143 and INSP144.

INSP141 and INSP142 are predicted to be secreted proteins, which do not contain transmembrane regions.

INSP143 and INSP144 are predicted to contain a signal peptide and a transmembrane region. For both INSP143 and INSP144 the N-terminal is predicted to be extracellular and the C-terminal intracellular.

In one embodiment of the first aspect of the invention, there is provided a polypeptide which:
(i) comprises the amino acid sequence as recited in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:128, SEQ ID NO:130, SEQ ID NO:132, SEQ ID NO:134, SEQ ID NO:146 and/or SEQ ID NO:148;
(ii) is a fragment thereof which functions as a vWFA and/or ANT_IG domain containing protein, preferably as an ATR-like protein, or has an antigenic determinant in common with the polypeptides of (i); or
(iii) is a functional equivalent of (i) or (ii).

Preferably, the polypeptide according to this first aspect of the invention:
(i) comprises the amino acid sequence as recited in SEQ ID NO:24, SEQ ID NO:128 and/or SEQ ID NO:132;
(ii) is a fragment thereof which functions as a vWFA and/or ANT_IG domain containing protein, preferably as an ATR-like protein, or has an antigenic determinant in common with the polypeptides of (i); or
(iii) is a functional equivalent of (i) or (ii).

A polypeptide according to this aspect of the invention may consist of any one of the sequences recited above as SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:128, SEQ ID NO:130, SEQ ID NO:132, SEQ ID NO:134, SEQ ID NO:128, SEQ ID NO:130, SEQ ID NO:132, SEQ ID NO:134, SEQ ID NO:146 and/or SEQ ID NO:148.

The polypeptides of the first aspect of the invention may further comprise a histidine tag. Preferably the histidine tag is found at the C-terminal of the polypeptide. Preferably the histidine tag comprises 1-10 histidine residues (e.g. 1, 2, 3, 4, 5, 6, 7, 8, 9 or 10 residues). More preferably the histidine tag comprises 6 histidine residues.

The polypeptide having the sequence recited in SEQ ID NO:2 is referred to hereafter as the "INSP141 exon 1 polypeptide". The polypeptide having the sequence recited in SEQ ID NO:4 is referred to hereafter as the "INSP141 exon 2 polypeptide". The polypeptide having the sequence recited in SEQ ID NO:6 is referred to hereafter as the "INSP141 exon 3 polypeptide". The polypeptide having the sequence recited in SEQ ID NO:8 is referred to hereafter as the "INSP141 exon 4 polypeptide". The polypeptide having the sequence recited in SEQ ID NO:10 is referred to hereafter as the "INSP141 exon 5 polypeptide". The polypeptide having the sequence recited in SEQ ID NO:12 is referred to hereafter as the "INSP141 exon 6 polypeptide". The polypeptide having the sequence recited in SEQ ID NO:14 is referred to hereafter as the "INSP141 exon 7 polypeptide". The polypeptide having the sequence recited in SEQ ID NO:16 is referred to hereafter as the "INSP141 exon 8 polypeptide". The polypeptide having the sequence recited in SEQ ID NO:18 is referred to hereafter as the "INSP141 exon 9 polypeptide". The polypeptide having the sequence recited in SEQ ID NO:20 is referred to hereafter as the "INSP141 exon 10 polypeptide". The polypeptide having the sequence recited in SEQ ID NO:22 is referred to hereafter as the "INSP141 exon 11 polypeptide". The polypeptide having the sequence recited in SEQ ID NO:24 is referred to hereafter as the "INSP141 polypeptide". The polypeptide having the sequence recited in SEQ ID NO:128 is referred to hereafter as the "cloned INSP141 polypeptide". The polypeptide having the sequence recited in SEQ ID NO:130 is referred to hereafter as the "cloned histidine tag INSP141 polypeptide". The polypeptide having the sequence recited in SEQ ID NO:132 is referred to hereafter as the "cloned mature INSP141 polypeptide". The polypeptide having the sequence recited in SEQ ID NO:134 is referred to hereafter as the "cloned mature histidine tag INSP141 polypeptide". The polypeptide having the sequence recited in SEQ ID NO: 146 is referred to hereafter as the "vWFA domain peptide sequence-INSP141-INSP142-INSP143-INSP144". The polypeptide having the sequence recited in SEQ ID NO:148 is referred to hereafter as the "ANT_IG domain peptide sequence-INSP141".

The term "INSP141 polypeptides" as used herein includes polypeptides comprising the INSP141 exon 1 polypeptide, the INSP141 exon 2 polypeptide, the INSP141 exon 3 polypeptide, the INSP141 exon 4 polypeptide, the INSP141 exon 5 polypeptide, the INSP141 exon 6 polypeptide, the INSP141 exon 7 polypeptide, the INSP141 exon 8 polypeptide, the INSP141 exon 9 polypeptide, the INSP141 exon 10 polypeptide, the INSP141 exon 11 polypeptide, the INSP141 polypeptide, the cloned INSP141 polypeptide, the cloned histidine tag INSP141 polypeptide, the cloned mature INSP141 polypeptide and the cloned mature histidine tag INSP141 polypeptide, the vWFA domain peptide sequence—INSP141-INSP142-INSP143-INSP144 and the ANT_IG domain peptide sequence—INSP141.

Preferably, a polypeptide according to this aspect of the invention functions as a vWFA and/or ANT_IG domain containing protein, preferably as an ATR-like protein. By "functions as an vWFA and/or ANT_IG domain containing protein" we refer to polypeptides that comprise amino acid sequence or structural features that can be identified as conserved features, by e.g. conventional bioinformatic tools, within the polypeptides of the vWFA and/or ANT_IG domain containing protein families, such that the polypeptide's interaction with ligand or receptor is not substantially affected detrimentally in comparison to the function of the full length wild type polypeptide. For example, the ANT_IG domain is defined by a specific signature (HMMER build information) in Protein Families Database of Alignments and HMMs (PFAM, The Pfam Protein Families Database. Alex et al. Nucleic Acids Research 2004. Database Issue 32:D138-D141). Determination of functionality should not be restricted to a particular bioinformatic tool such as PFAM, as other tools have their own particular signatures to detect conserved domains or motifs. In addition, conserved residues within the ANT_TG domain and the vWFA domain, that are likely to be critical residues for proper functioning, are indicated in FIG. 9 (e.g. 13 identical residues are present in the ANT_IG domain in all the family members). Moreover, the man of art, starting from the alignment shown in FIG. 9, could build specific signatures for both the vWFA domain and/or ANT_IG domain using conventional tools (e.g. Psi-blast).

By "functions as an ATR-like protein", we refer to polypeptides contain both the vWFA and ANT_IG domains and which have similar properties to an ATR protein. For example, the polypeptides of the invention are preferably capable of binding to a toxin, more particularly to a bacterial toxin, and/or are capable to prevent and/or treat cancer.

In a second embodiment of the first aspect of the invention, there is provided a polypeptide, which:
(i) comprises the amino acid sequence as recited in SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52; SEQ ID NO:136, SEQ ID NO:146 and/or SEQ ID NO:150;
(ii) is a fragment thereof which functions as an vWFA and/or ANT_IG domain containing protein, preferable as an ATR-like protein, or has an antigenic determinant in common with the polypeptides of (i); or
(iii) is a functional equivalent of (i) or (ii).

Preferably, the polypeptide according to this first aspect of the invention:
(i) comprises the amino acid sequence as recited in SEQ ID NO:52 and/or SEQ ID NO:136;
(ii) is a fragment thereof which functions as an vWFA and/or ANT_IG domain containing protein, preferably as an ATR-like protein, or has an antigenic determinant in common with the polypeptides of (i); or
(iii) is a functional equivalent of (i) or (ii).

A polypeptide according to this aspect of the invention may consist of any one of the sequences recited above as SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:136, SEQ ID NO:146 and/or SEQ ID NO:150.

The polypeptide having the sequence recited in SEQ ID NO:26 is referred to hereafter as the "INSP142 exon 1 polypeptide". The polypeptide having the sequence recited in SEQ ID NO:28 is referred to hereafter as the "INSP142 exon 2 polypeptide". The polypeptide having the sequence recited in SEQ ID NO:30 is referred to hereafter as the "INSP142 exon 3 polypeptide". The polypeptide having the sequence recited in SEQ ID NO:32 is referred to hereafter as the "INSP142 exon 4 polypeptide". The polypeptide having the sequence recited in SEQ ID NO:34 is referred to hereafter as the "INSP142 exon 5 polypeptide". The polypeptide having the sequence recited in SEQ ID NO:36 is referred to hereafter as the "INSP142 exon 6 polypeptide". The polypeptide having the sequence recited in SEQ ID NO:38 is referred to hereafter as the "INSP142 exon 7 polypeptide". The polypeptide having the sequence recited in SEQ ID NO:40 is referred to hereafter as the "INSP142 exon 8 polypeptide". The polypeptide having the sequence recited in SEQ ID NO:42 is referred to hereafter as the "INSP142 exon 9 polypeptide". The polypeptide having the sequence recited in SEQ ID NO:44 is referred to hereafter as the "INSP142 exon 10 polypeptide". The polypeptide having the sequence recited in SEQ ID NO:46 is referred to hereafter as the "INSP142 exon 11 polypeptide". The polypeptide having the sequence recited in SEQ ID NO:48 is referred to hereafter as the "INSP142 exon 12 polypeptide". The polypeptide having the sequence recited in SEQ ID NO:50 is referred to hereafter as the "INSP142 exon 13 polypeptide. The polypeptide having the sequence recited in SEQ ID NO:52 is referred to hereafter as the "INSP142 polypeptide". The polypeptide having the sequence recited in SEQ ID NO:136 is referred to hereafter as the "cloned INSP142 polypeptide". The polypeptide having the sequence recited in SEQ ID NO:146 is referred to hereafter as the "vWFA domain peptide sequence-INSP141-INSP142-INSP143-INSP144". The polypeptide having the sequence recited in SEQ ID NO:150 is referred to hereafter as the "ANT_IG domain peptide sequence-INSP142-INSP143-INSP144".

The term "INSP142 polypeptides" as used herein includes polypeptides comprising the INSP142 exon 1 polypeptide, the INSP142 exon 2 polypeptide, the INSP142 exon 3 polypeptide, the INSP142 exon 4 polypeptide, the INSP142 exon 5 polypeptide, the INSP142 exon 6 polypeptide, the INSP142 exon 7 polypeptide, the INSP142 exon 8 polypeptide, the INSP142 exon 9 polypeptide, the INSP142 exon 10 polypeptide, the INSP142 exon 11 polypeptide, the INSP142 exon 12 polypeptide, the INSP142 exon 13 polypeptide, the INSP142 polypeptide, the cloned INSP142 polypeptide, the vWFA domain peptide sequence-INSP141-INSP142-INSP143-INSP144 and the ANT_IG domain peptide sequence-INSP142-INSP143-INSP144".

Preferably, a polypeptide according to this aspect of the invention functions as a vWFA and/or ANT_IG domain containing protein, preferably as an ATR-like protein.

In a third embodiment of the first aspect of the invention, there is provided a polypeptide, which:
(i) comprises the amino acid sequence as recited in SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:138, SEQ ID NO:140, SEQ ID NO:142, SEQ ID NO:144, SEQ ID NO:146 and/or SEQ ID NO:150;
(ii) is a fragment thereof which functions as an vWFA and/or ANT_IG domain containing protein, preferably as an ATR-like protein, or has an antigenic determinant in common with the polypeptides of (i); or
(iii) is a functional equivalent of (i) or (ii).

Preferably, the polypeptide according to this first aspect of the invention:

(i) comprises the amino acid sequence as recited in SEQ ID NO:90, SEQ ID NO:138 and/or SEQ ID NO:141;
(ii) is a fragment thereof which functions as an vWFA and/or ANT_IG domain containing protein, preferably as an ATR-like protein, or has an antigenic determinant in common with the polypeptides of (i); or
(iii) is a functional equivalent of (i) or (ii).

A polypeptide according to this aspect of the invention may consist of any one of the sequences recited above as SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID 1 NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:138, SEQ ID NO:140, SEQ ID NO:142, SEQ ID NO:144, SEQ ID NO:146 and/or SEQ ID NO:150.

The polypeptide having the sequence recited in SEQ ID NO:54 is referred to hereafter as the "INSP143 exon 1 polypeptide". The polypeptide having the sequence recited in SEQ ID NO:56 is referred to hereafter as the "INSP143 exon 2 polypeptide". The polypeptide having the sequence recited in SEQ ID NO:58 is referred to hereafter as the "INSP143 exon 3 polypeptide". The polypeptide having the sequence recited in SEQ ID NO:60 is referred to hereafter as the "INSP143 exon 4 polypeptide". The polypeptide having the sequence recited in SEQ ID NO:62 is referred to hereafter as the "INSP143 exon 5 polypeptide". The polypeptide having the sequence recited in SEQ ID NO:64 is referred to hereafter as the "INSP143 exon 6 polypeptide". The polypeptide having the sequence recited in SEQ ID NO:66 is referred to hereafter as the "INSP143 exon 7 polypeptide". The polypeptide having the sequence recited in SEQ ID NO:68 is referred to hereafter as the "INSP143 exon 8 polypeptide". The polypeptide having the sequence recited in SEQ ID NO:70 is referred to hereafter as the "INSP143 exon 9 polypeptide". The polypeptide having the sequence recited in SEQ ID NO:72 is referred to hereafter as the "INSP143 exon 10 polypeptide". The polypeptide having the sequence recited in SEQ ID NO:74 is referred to hereafter as the "INSP143 exon 11 polypeptide". The polypeptide having the sequence recited in SEQ ID NO:76 is referred to hereafter as the "INSP143 exon 12 polypeptide". The polypeptide having the sequence recited in SEQ ID NO:78 is referred to hereafter as the "INSP143 exon 13 polypeptide". The polypeptide having the sequence recited in SEQ ID NO:80 is referred to hereafter as the "INSP143 exon 14 polypeptide". The polypeptide having the sequence recited in SEQ ID NO:82 is referred to hereafter as the "INSP143 exon 15 polypeptide". The polypeptide having the sequence recited in SEQ ID NO:84 is referred to hereafter as the "INSP143 exon 16 polypeptide". The polypeptide having the sequence recited in SEQ ID NO:86 is referred to hereafter as the "INSP143 exon 17 polypeptide". The polypeptide having the sequence recited in SEQ ID NO:88 is referred to hereafter as the "INSP143 exon 18 polypeptide". The polypeptide having the sequence recited in SEQ ID NO:90 is referred to hereafter as the "INSP143 polypeptide". The polypeptide having the sequence recited in SEQ ID NO:138 is referred to hereafter as the "cloned INSP143 polypeptide". The polypeptide having the sequence recited in SEQ ID NO:140 is referred to hereafter as the "cloned histidine tag INSP143 polypeptide". The polypeptide having the sequence recited in SEQ ID NO:142 is referred to hereafter as the "cloned mature INSP143 polypeptide". The polypeptide having the sequence recited in SEQ ID NO:144 is referred to hereafter as the "cloned mature histidine tag INSP143 polypeptide". The polypeptide having the sequence recited in SEQ ID NO:146 is referred to hereafter as the "vWFA domain peptide sequence-INSP141-INSP142-INSP143-INSP144". The polypeptide having the sequence recited in SEQ ID NO:150 is referred to hereafter as the "ANT_IG domain peptide sequence-INSP142-INSP143-INSP144".

The term "INSP143 polypeptides" as used herein includes polypeptides comprising the INSP143 exon 1 polypeptide, the INSP143 exon 2 polypeptide, the INSP143 exon 3 polypeptide, the INSP143 exon 4 polypeptide, the INSP143 exon 5 polypeptide, the INSP143 exon 6 polypeptide, the INSP143 exon 7 polypeptide, the INSP143 exon 8 polypeptide, the INSP143 exon 9 polypeptide, the INSP143 exon 10 polypeptide, the INSP143 exon 11 polypeptide, the INSP143 exon 12 polypeptide, the INSP143 exon 13 polypeptide, the INSP143 exon 14 polypeptide, the INSP143 exon 15 polypeptide, the INSP143 exon 16 polypeptide, the INSP143 exon 17 polypeptide, the INSP143 exon 18 polypeptide, the INSP143 polypeptide, the cloned INSP143 polypeptide, the cloned histidine tag INSP143 polypeptide, the cloned mature INSP143 polypeptide, the cloned mature histidine tag INSP143 polypeptide, the vWFA domain peptide sequence-INSP141-INSP142-INSP143-INSP144 and the ANT_IG domain peptide sequence-INSP142-INSP143-INSP144.

Preferably, a polypeptide according to this aspect of the invention functions as an vWFA and/or ANT_TG domain containing protein, preferably as an ATR-like protein.

In a fourth embodiment of the first aspect of the invention, there is provided a polypeptide, which polypeptide:
(i) comprises the amino acid sequence as recited in SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:146 and/or SEQ ID NO:150;
(ii) is a fragment thereof which functions as a vWFA and/or ANT_IG domain containing protein, preferably as an ATR-like protein, or has an antigenic determinant in common with the polypeptides of (i); or
(iii) is a functional equivalent of (i) or (ii).

Preferably, the polypeptide according to this first aspect of the invention:
(i) comprises the amino acid sequence as recited in SEQ ID NO:126;
(ii) is a fragment thereof which functions as an vWFA and/or ANT_IG domain containing protein, preferably as an ATR-like protein, or has an antigenic determinant in common with the polypeptides of (i); or
(iii) is a functional equivalent of (i) or (ii).

A polypeptide according to this aspect of the invention may consist of any one of the sequences recited above as SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:11)$_8$, SEQ ID NO:110, SEQ ID NO:112, SEQ ID NO:114, SEQ ID NO:116, SEQ ID NO:118, SEQ D) NO:120, SEQ ID NO:122, SEQ ID NO:124, SEQ ID NO:126, SEQ ID NO:146 and/or SEQ ID NO:150.

The polypeptide having the sequence recited in SEQ ID NO:92 is referred to hereafter as the "INSP144 exon 1 polypeptide". The polypeptide having the sequence recited in SEQ ID NO:94 is referred to hereafter as the "INSP144 exon 2 polypeptide". The polypeptide having the sequence recited in SEQ ID NO:96 is referred to hereafter as the "INSP144 exon 3 polypeptide". The polypeptide having the sequence recited in SEQ ID NO:98 is; referred to hereafter as the "INSP144 exon 4 polypeptide". The polypeptide having the sequence recited in SEQ ID NO:100 is referred to hereafter as the "INSP144 exon 5 polypeptide". The polypeptide having the sequence recited in SEQ ID NO:102 is referred to hereafter as the "INSP144 exon 6 polypeptide". The polypeptide having the sequence recited in SEQ ID NO:104 is referred to hereafter as the "INSP144 exon 7 polypeptide". The polypeptide having the sequence recited in SEQ ID NO:106 is referred to hereafter as the "INSP144 exon 8 polypeptide". The polypeptide having the sequence recited in SEA ID NO:108 is referred to hereafter as the "INSP144 exon 9 polypeptide". The polypeptide having the sequence recited in SEQ ID NO:110 is referred to hereafter as the "INSP144 exon 10 polypeptide". The polypeptide having the sequence recited in SEQ ID NO:112 is referred to hereafter as the "INSP144 exon 11 polypeptide". The polypeptide having the sequence recited in SEQ ID NO:114 is referred to hereafter as the "INSP144 exon 12 polypeptide". The polypeptide having the sequence recited in SEQ ID NO:116 is referred to hereafter as the "INSP144 exon 13 polypeptide". The polypeptide having the sequence recited in SEQ ID NO:118 is referred to hereafter as the "INSP144 exon 14 polypeptide". The polypeptide having the sequence recited in SEQ ID NO:120 is referred to hereafter as the "INSP144 exon 15 polypeptide". The polypeptide having the sequence recited in SEQ ID NO:122 is referred to hereafter as the "INSP144 exon 16 polypeptide". The polypeptide having the sequence recited in SEQ ID NO:124 is referred to hereafter as the "INSP144 exon 17 polypeptide". The polypeptide having the sequence recited in SEQ ID NO:126 is referred to hereafter as the "INSP144 polypeptide". The polypeptide having the sequence recited in SEQ ID NO:146 is referred to hereafter as the "vWFA domain peptide sequence—INSP141-INSP142-INSP143-INSP144". The polypeptide having the sequence recited in SEQ ID NO:150 is referred to hereafter as the "ANT_IG domain peptide sequence—INSP142-INSP143-INSP144".

The term "INSP144 polypeptides" as used herein includes polypeptides comprising the INSP144 exon 1 polypeptide, the INSP144 exon 2 polypeptide, the INSP144 exon 3 polypeptide, the INSP144 exon 4 polypeptide, the INSP144 exon 5 polypeptide, the INSP144 exon 6 polypeptide, the INSP144 exon 7 polypeptide, the INSP144 exon g polypeptide, the INSP144 exon 9 polypeptide, the INSP144 exon 10 polypeptide, the INSP144 exon 11 polypeptide, the INSP144 exon 12 polypeptide, the INSP144 exon 13 polypeptide, the INSP144 exon 14 polypeptide, the INSP144 exon 15 polypeptide, the INSP144 exon 16 polypeptide, the INSP144 exon 17 polypeptide, the INSP144 polypeptide, the vWFA domain peptide sequence-INSP141-INSP142-INSP143-INSP144 and the ANT_IG domain peptide sequence-INSP142-INSP143-INSP144.

Preferably, the "vWFA and/or ANT_IG domain containing protein" may be a molecule containing a vWFA and/or ANT_IG domain detected with an e-value lower than 0.1, 0.01, 0.001, 0.0001, 0.0002, 0.00001, 0.000001 or 0.0000001.

Preferably, a polypeptide according to this aspect of the invention functions as an vWFA and/or ANT_IG domain containing protein, preferably as an ATR-like protein.

Preferably, the activity of a polypeptide of the present invention can be confirmed in at least one of the following assays:
a) in the mouse model of inflammatory bowel disease induced by dextran sulphate sodium (DSS) as described in Okayasu et al. (A novel method in the induction of reliable experimental acute and chronic ulcerative colitis in mice. Gastroenterology 1990. Vol. 98, pp. 694-702), or b) in the in vitro and in vivo assays as well as animal models of inflammatory bowel diseases as reviewed by Borm and Gouma (Drug Discovery Today: Disease Models; Vol. 1, No. 4, 2004, pp. 437-443), or c) in models of cancer as reviewed by Kamb and Lassota (Drug Discovery Today: Disease Models; Vol. 1, No. 1, 2004, pp. 31-36) or in models of skin cancers as reviewed by Odashiro et al. (Drug Discovery Today: Disease Models 2005; In Press), d) in models of contact dermatitis or atopic eczema as reviewed by Gutermuth et al. (Drug Discovery Today: Disease Models 2005, in press), or e) in the modulation of the proliferation or the survival of normal and cancerous cells, or f) in the assays as described in Example 9, or g) in the modulation of angiogenesis or neovascularization, or h) in the blockage of bacterial intoxification, for example anthrax intoxification, or i) in its capacity to bind to a toxin, e.g. a bacterial toxin.

An "antigenic determinant" of the present invention may be a part of a polypeptide of the present invention, which binds to an antibody-combining site or to a T-cell receptor (TCR). Alternatively, an "antigenic determinant" may be a site on the surface of a polypeptide of the present invention to which a single antibody molecule binds. Generally an antigen has several or many different antigenic determinants and reacts with antibodies of many different specificities. Preferably, the antibody is immunospecific to a polypeptide of the invention. Preferably, the antibody is immunospecific to a polypeptide of the invention, which is not part of a fusion protein. Preferably, the antibody is immunospecific to INSP141, INSP142, INSP143 or INSP144 or a fragment thereof. Antigenic determinants usually consist of chemically active surface groupings of molecules, such as amino acids or sugar side chains, and can have specific three dimensional structural characteristics, as well as specific charge characteristics. Preferably, the "antigenic determinant" refers to a particular chemical group on a polypeptide of the present invention that is antigenic, i.e. that elicit a specific immune response.

The polypeptides ADU02541 (SEQ ID NO: 168) and IPI00480015.1/ENSP00000346942 (SEQ ID NO: 169), and their encoding nucleic acid sequences are specifically excluded from the scope of this invention.

In a second aspect, the invention provides a purified nucleic acid molecule which encodes a polypeptide of the first aspect of the invention.

The term "purified nucleic acid molecule" preferably refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "purified nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use. In a preferred embodiment, genomic DNA are specifically excluded from the scope of the invention. Preferably, genomic DNA larger than 10 kbp (kilo base pairs), 50 kbp, 100 kbp, 150 kbp, 200 kbp, 250 kbp or 300 kbp are specifically excluded from the scope of the invention. Preferably, the "purified nucleic acid molecule" consists of cDNA only.

Preferably, the purified nucleic acid molecule comprises the nucleic acid sequence as recited in SEQ ID NO:1 (encoding the INSP141 exon 1 polypeptide), SEQ ID NO:3 (encoding the INSP141 exon 2 polypeptide), SEQ ID NO:5 (encoding the INSP141 exon 3 polypeptide), SEQ ID NO:7 (encoding the INSP141 exon 4 polypeptide), SEQ ID NO:9 (encoding the INSP141 exon 5 polypeptide), SEQ ID NO:11 (encoding the INSP141 exon 6 polypeptide), SEQ ID NO:13 (encoding the INSP141 exon 7 polypeptide), SEQ ID NO:15 (encoding the INSP141 exon 8 polypeptide), SEQ ID NO:17 (encoding the INSP141 exon 9 polypeptide), SEQ ID NO:19 (encoding the INSP141 exon 10 polypeptide), SEQ ID NO:21 (encoding the INSP141 exon 11 polypeptide), SEQ ID NO:23 (encoding the INSP141 polypeptide), SEQ ID NO:25 (encoding the INSP142 exon 1 polypeptide), SEQ ID NO:27 (encoding the INSP142 exon 2 polypeptide), SEQ ID NO:29 (encoding the INSP142 exon 3 polypeptide), SEQ ID NO:31 (encoding the INSP142 exon 4 polypeptide), SEQ ID NO:33 (encoding the INSP142 exon 5 polypeptide), SEQ ID NO:35 (encoding the INSP142 exon 6 polypeptide), SEQ ID NO:37 (encoding the INSP142 exon 7 polypeptide), SEQ ID NO:39 (encoding the INSP142 exon 8 polypeptide), SEQ ID NO:41 (encoding the INSP142 exon 9 polypeptide), SEQ ID NO:43 (encoding the INSP142 exon 10 polypeptide), SEQ ID NO:45 (encoding the INSP142 exon 11 polypeptide), SEQ ID NO:47 (encoding the INSP142 exon 12 polypeptide), SEQ ID NO:49 (encoding the INSP142 exon 13 polypeptide), SEQ ID NO:51 (encoding the INSP142 polypeptide), SEQ ID NO:53 (encoding the INSP143 exon 1 polypeptide), SEQ ID NO:55 (encoding the INSP143 exon 2 polypeptide), SEQ ID NO:57 (encoding the INSP143 exon 3 polypeptide), SEQ ID NO:59 (encoding the INSP143 exon 4 polypeptide), SEQ ID NO:61 (encoding the INSP143 exon 5 polypeptide), SEQ ID NO:63 (encoding the INSP143 exon 6 polypeptide), SEQ ID NO:65 (encoding the INSP143 exon 7 polypeptide), SEQ ID NO:67 (encoding the INSP143 exon 8 polypeptide), SEQ ID NO:69 (encoding the INSP143 exon 9 polypeptide), SEQ ID NO:71 (encoding the INSP143 exon 10 polypeptide), SEQ ID NO:73 (encoding the INSP143 exon 11 polypeptide), SEQ ID NO:75 (encoding the INSP143 exon 12 polypeptide), SEQ ID NO:77 (encoding the INSP143 exon 13 polypeptide), SEQ ID NO:79 (encoding the INSP143 exon 14 polypeptide), SEQ ID NO:81 (encoding the INSP143 exon 15 polypeptide), SEQ ID NO:83 (encoding the INSP143 exon 16 polypeptide), SEQ ID NO:85 (encoding the INSP143 exon 17 polypeptide), SEQ ID NO:87 (encoding the INSP143 exon 18 polypeptide), SEQ ID NO:89 (encoding the INSP143 polypeptide), SEQ ID NO:91 (encoding the INSP144 exon 1 polypeptide), SEQ ID NO:93 (encoding the INSP144 exon 2 polypeptide), SEQ ID NO:95 (encoding the INSP144 exon 3 polypeptide), SEQ ID NO:97 (encoding the INSP144 exon 4 polypeptide), SEQ ID NO:99 (encoding the INSP144 exon 5 polypeptide), SEQ ID NO:101 (encoding the INSP144 exon 6 polypeptide), SEQ ID NO:103 (encoding the INSP144 exon 7 polypeptide), SEQ ID NO:105 (encoding the INSP144 exon 8 polypeptide), SEQ ID NO:107 (encoding the INSP144 exon 9 polypeptide), SEQ ID NO:109 (encoding the INSP144 exon 10 polypeptide), SEQ ID NO:111 (encoding the INSP144 exon 11 polypeptide), SEQ ID NO:113 (encoding the INSP144 exon 12 polypeptide), SEQ ID NO:115 (encoding the INSP144 exon 13 polypeptide), SEQ ID NO:117 (encoding the INSP144 exon 14 polypeptide), SEQ ID NO:119 (encoding the INSP144 exon 15 polypeptide), SEQ ID NO:121 (encoding the INSP144 exon 16 polypeptide), SEQ ID NO:123 (encoding the INSP144 exon 17 polypeptide), SEQ ID NO:125 (encoding the INSP144 polypeptide), SEQ ID NO:127 (encoding the cloned INSP141 polypeptide), SEQ ID NO:129 (encoding the cloned histidine tag INSP141 polypeptide), SEQ ID NO:131 (encoding the cloned mature INSP141 polypeptide), SEQ ID NO:133 (encoding the cloned mature histidine tag INSP141 polypeptide), SEQ ID NO:135 (encoding the cloned INSP142 polypeptide), SEQ ID NO:137 (encoding the cloned INSP143 polypeptide), SEQ ID NO:139 (encoding the cloned histidine tag INSP143 polypeptide), SEQ ID NO:141 (encoding the cloned mature INSP143 polypeptide), SEQ ID NO:143 (encoding the cloned mature histidine tag INSP143 polypeptide), SEQ ID NO:145 (encoding the vWFA domain peptide sequence—INSP141-INSP142-INSP143-INSP144), SEQ ID NO:147 (encoding the ANT_IG domain peptide sequence-INSP141), SEQ ID NO:149 (encoding the ANT_IG domain peptide sequence-INSP142-INSP143-INSP144) or is a redundant equivalent or fragment of any one of these sequences.

The invention further provides that the purified nucleic acid molecule consists of any one of the above recited nucleic acid sequences.

In a third aspect, the invention provides a purified nucleic acid molecule which hybridizes under high stringency conditions with a nucleic acid molecule of the second aspect of the invention. High stringency hybridisation conditions are defined as overnight incubation at 42° C. in a solution comprising 50% formamide, 5×SSC (150 mM NaCl, 15 mM trisodium citrate), 50 mM sodium phosphate (pH7.6), 5×Denhardts solution, 10% dextran sulphate, and 20 microgram/ml denatured, sheared salmon sperm DNA, followed by washing the filters in 0.1×SSC at approximately 65° C.

In a fourth aspect, the invention provides a vector, such as an expression vector, that contains a nucleic acid molecule of the second or third aspect of the invention.

In a fifth aspect, the invention provides a host cell transformed with a vector of the fourth aspect of the invention.

In a sixth aspect, the invention provides a ligand which binds specifically to the vWFA and/or ANT_TG domain containing proteins of the first aspect of the invention. Preferably the ligand inhibits the function of the vWFA and/or ANT_IG domain containing proteins of the first aspect of the invention. Ligands to a polypeptide according to the invention may come in various forms, including natural or modified substrates, enzymes, receptors, small organic molecules such as small natural or synthetic organic molecules of up to 2000 Da, preferably 800 Da or less, peptidomimetics, inorganic molecules, peptides, polypeptides, antibodies, structural or functional mimetics of the aforementioned. The vWFA and/or ANT_IG domain containing proteins of the invention may bind to bacterial toxins e.g. anthrax toxins, *Clostridium botulinum* C2 toxin. The invention further provides a polypeptide according to the first aspect of the invention complexed with a bacterial toxin.

In a seventh aspect, the invention provides a compound that is effective to alter the expression of a natural gene which encodes a polypeptide of the first aspect of the invention or to regulate the activity of a polypeptide of the first aspect of the invention.

Such compounds may be identified using the assays and screening methods disclosed herein.

A compound of the seventh aspect of the invention may either increase (agonise) or decrease (antagonise) the level of expression of the gene or the activity of the polypeptide.

Importantly, the identification of the function of the INSP141, INSP142, INSP143 and INSP144 exon polypeptides and the INSP141, INSP142, INSP143 and INSP144 polypeptides allows for the design of screening methods capable of identifying compounds that are effective in the treatment and/or diagnosis of disease. Ligands and compounds according to the sixth and seventh aspects of the invention may be identified using such methods. These methods are included as aspects of the present invention.

Another aspect of this invention resides in the use of an INSP141, INSP142, INSP143 or INSP144 gene or polypeptide as a target for the screening of candidate drug modulators, particularly candidate drugs active against vWFA and/or ANT_IG domain containing protein related disorders.

A further aspect of this invention resides in methods of screening of compounds for therapy of vWFA and/or ANT_IG domain containing protein related disorders, comprising determining the ability of a compound to bind to an INSP141, INSP142, INSP143 or INSP144 gene or polypeptide, or a fragment thereof.

A further aspect of this invention resides in methods of screening of compounds for therapy of vWFA and/or ANT_IG domain containing protein related disorders, comprising testing for modulation of the activity of an INSP141, INSP142, INSP143 or INSP144 gene or polypeptide, or a fragment thereof.

In an eighth aspect, the invention provides a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, for use in therapy or diagnosis of diseases in which vWFA and/or ANT_IG domain containing proteins, preferably ATR-like proteins, are implicated.

The polypeptides of the invention or fragments thereof (e.g. fragments containing the Willebrand factor (vWF) type A domain (VWA) and/or the ANT_IG domain) are preferably used in the diagnosis and/or treatment of diseases for which other Anthrax toxin receptor-like proteins (e.g. TEM8 or CMG2) demonstrate therapeutic activity.

In particular, the polypeptides of the invention may be used to block bacterial toxins. The soluble vWFA domain (through the MIDAS motif, critical residues are indicated in FIG. 9) or/and the soluble ANT_IG domain of the polypeptides of the invention May be used to block bacterial toxins (e.g. anthrax toxins, *Clostridium botulinum* C2 toxin) and thus prevent or treat bacterial infections.

The soluble vWFA domain and/or ANT_IG domain of the polypeptides of the invention may be anchored by a lipid tail, e.g. a glycosylphosphatidylinositol (GPI tail), which will act as a receptor for the PA subunit of the bacterial toxin to be blocked. Liu and Heppla. The Journal of Biological Chemistry 2003. Vol. 278, No. 7, pp. 5227-5234 disclose linking the TEM8 extracellular domain to the GPI-anchoring sequence uPAR.

The polypeptides of the invention, particularly the soluble vWFA domain (through the MIDAS motif, critical residues are indicated in FIG. 9), or/and the ANT_IG domain of the polypeptides of the invention may also be useful in the treatment of cancer.

Antagonists of the polypeptides of the invention, particularly the membrane-bound isoforms INSP143 and INSP144 may also be used against bacterial toxins and in the treatment of cancer. Preferably, such antagonists are monoclonal antibodies or antisense nucleic acids. Preferably, the antagonists target the vWFA domain, more particularly the MIDAS motif, and/or the ANT_IG domain.

Further diseases that may be treated include cell proliferative disorders, including neoplasm, melanoma, lung, colorectal, breast, pancreas, head and neck and other solid tumours; myeloproliferative disorders, such as leukemia, non-Hodgkin lymphoma, leukopenia, thrombocytopenia, angiogenesis disorder, Kaposis' sarcoma; autoimmune/inflammatory disorders, including allergy, inflammatory bowel disease, arthritis, psoriasis and respiratory tract inflammation, asthma, and organ transplant rejection; cardiovascular disorders, including hypertension, oedema, angina, atherosclerosis, thrombosis, sepsis, shock, reperfusion injury, and ischemia; neurological disorders including central nervous system disease, Alzheimer's disease, brain injury, amyotrophic lateral sclerosis, and pain; developmental disorders; metabolic disorders, including diabetes mellitus, osteoporosis, and obesity, AIDS and renal disease; infections including viral infection, bacterial infection, fungal infection and parasitic infection and other pathological conditions. Preferably, the disease is one in which vWFA and/or ANT_IG domain containing proteins, preferably ATR-like proteins, are implicated. Examples of diseases in which vWFA and/or ANT_IG domain containing proteins are implicated include; bacterial infections, bacterial intoxications, anthrax, blockage of toxins (e.g. bacterial toxins), cancer, tumour endothelium, colorectal cancer, bladder cancer, oesophageal cancer, lung cancer, melanoma, juvenile hyaline fibromatosis (JFH), infantile systemic hyalinosis (ISH), von Willebrand disease, Bethlem myopathy, epidemolysis bullosa dystrophica, thrombosis, modulation of platelet-mediated aggregation, autoimmune diseases and inflammation. These molecules may also be used in the manufacture of a medicament for the treatment of such diseases. These molecules may also be used in contraception or for the treatment of reproductive disorders including infertility.

Expression results obtained by the inventors and described herein show unexpected restricted expression of INSP42 in colon and ileum IBD biopsy samples and psoriasis skin biopsies. This specific pattern of expression leads to the conclusion of the involvement of INSP142 in inflammatory bowel diseases, skin diseases or inflammation.

These surprising properties characterizing the polynucleotides or the corresponding polypeptides of the present invention make them particularly suitable for the preparation of a drug or pharmaceutical composition.

Particularly preferred diseases are inflammatory bowel diseases, toxin-related disease, cancer, skin diseases, inflammation, Crohn's disease, ulcerative colitis, psoriasis, contact dermatitis, atopic eczema, cancer from blood and lymphatic systems, skin cancers, cancer of digestive systems, cancers of urinary systems, breast cancer, ovarian cancer, gynaecological cancers, choriocarcinoma, lung cancer, brain tumors, bone tumors, carcinoid tumor, colorectal cancer, nasopharyngeal cancer, retroperitoneal sarcomas, soft tissue tumors, thyroid cancer, cancer of the testis or liver cancer. Preferably the toxin-related disease is selected from a bacterial toxin-related disease, anthrax or *clostridium botulinum* C2 toxin-related disease. Preferably, the inflammatory disease is selected among Crohn's disease or ulcerative colitis. Preferably, the skin disease is psoriasis. Preferably, "cancer" is selected among cancer from blood and lymphatic systems, skin cancers, cancer of digestive systems, cancers of urinary systems, breast cancer, ovarian cancer, gynaecological cancers, choriocarcinoma, lung cancer, brain tumors, bone tumors, carcinoid tumor, nasopharyngeal cancer, retroperitoneal sarcomas, soft tissue tumors, thyroid cancer, cancer of the testis or liver cancer.

Preferably, the inflammatory disease is selected among Crohn's disease or ulcerative colitis.

Preferably, the skin disease is psoriasis, contact dermatitis or atopic eczema.

These moieties of the first, second, third, fourth, fifth, sixth or seventh aspects of the invention may also be used in the manufacture of a medicament for the treatment of such diseases.

In a ninth aspect, the invention provides a method of diagnosing a disease in a patient, comprising assessing the level of expression of a natural gene encoding a polypeptide of the first aspect of the invention or the activity of a polypeptide of the first aspect of the invention in tissue from said patient and comparing said level of expression or activity to a control level, wherein a level that is different to said control level is indicative of disease. Such a method will preferably be carried out in vitro. Similar methods may be used for monitoring the therapeutic treatment of disease in a patients wherein altering the level of expression or activity of a polypeptide or nucleic acid molecule over the period of time towards a control level is indicative of regression of disease.

A preferred method for detecting polypeptides of the first aspect of the invention comprises the steps of: (a) contacting a ligand, such as an antibody, of the sixth aspect of the invention with a biological sample under conditions suitable for the formation of a ligand-polypeptide complex; and (b) detecting said complex.

A number of different such methods according to the ninth aspect of the invention exist, as the skilled reader will be aware, such as methods of nucleic acid hybridization with short probes, point mutation analysis, polymerase chain reaction (PCR) amplification and methods using antibodies to detect aberrant protein levels. Similar methods may be used on a short or long term basis to allow therapeutic treatment of a disease to be monitored in a patient. The invention also provides kits that are useful in these methods for diagnosing disease.

Preferably, the disease diagnosed by a method of the ninth aspect of the invention is a disease in which vWFA and/or ANT_IG domain containing proteins, preferably ATR-like proteins, are implicated, as described above.

In a tenth aspect, the invention provides for the use of a polypeptide of the first aspect of the invention as an vWFA and/or ANT_IG domain containing protein, preferably as an ATR-like protein. Suitable uses of the polypeptides of the invention as vWFA and/or ANT_IG domain containing proteins, preferably as ATR-like proteins, include use as a regulator of cellular growth, metabolism or differentiation, use as part of a receptor/ligand pair and use as a diagnostic marker for a physiological or pathological conditions selected from the list given above. Further suitable uses include use in screening methods to identify ligands and other agonist or antagonist molecules that are useful in therapy and diagnosis of diseases and conditions in which this category of protein is implicated.

In an eleventh aspect, the invention provides a pharmaceutical composition comprising a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, in conjunction with a pharmaceutically-acceptable carrier.

In a twelfth aspect, the present invention provides a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, for use in the manufacture of a medicament for the diagnosis or treatment of a disease, such as, but not limited to, cell proliferative disorders, including neoplasm, melanoma, lung, colorectal, breast, pancreas, head and neck and other solid tumours; myeloproliferative disorders, such as leukemia, non-Hodgkin lymphoma, leukopenia, thrombocytopenia, angiogenesis disorder, Kaposis' sarcoma; autoimmune/inflammatory disorders, including allergy, inflammatory bowel disease, arthritis, psoriasis and respiratory tract inflammation, asthma, and organ transplant rejection; cardiovascular disorders, including hypertension, oedema, angina, atherosclerosis, thrombosis, sepsis, shock, reperfusion injury, and ischemia; neurological disorders including central nervous system disease, Alzheimer's disease, brain injury, amyotrophic lateral sclerosis, and pain; developmental disorders; metabolic disorders including diabetes mellitus, osteoporosis, and obesity, AIDS and renal disease; infections including viral infection, bacterial infection, fungal infection and parasitic infection and other pathological conditions. Preferably, the disease is one in which vWFA and/or ANT_TG domain containing proteins, preferably ATR-like proteins, are implicated. Examples of diseases in which vWFA and/or ANT_IG domain containing proteins are implicated include; bacterial infections, bacterial intoxications, anthrax, blockage of toxins (e.g. bacterial toxins), cancer, tumour endothelium, colorectal cancer, bladder cancer, oesophageal cancer, lung cancer, melanoma, juvenile hyaline fibromatosis (JFH), infantile systemic hyalinosis (ISH), von Willebrand disease, Bethlem myopathy, epidemolysis bullosa dystrophica, thrombosis, modulation of platelet-mediated aggregation, autoimmune diseases and inflammation.

In a thirteenth aspect, the invention provides a method of treating a disease in a patient comprising administering to the patient a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention.

For diseases in which the expression of a natural gene encoding a polypeptide of the first aspect of the invention, or in which the activity of a polypeptide of the first aspect of the invention, is lower in a diseased patient when compared to the level of expression or activity in a healthy patient, the polypeptide, nucleic acid molecule, ligand or compound administered to the patient should be an agonist. Conversely, for diseases in which the expression of the natural gene or activity of the polypeptide is higher in a diseased patient when compared to the level of expression or activity in a healthy patient, the polypeptide, nucleic acid molecule, ligand or compound administered to the patient should be an antagonist. Examples of such antagonists include antisense nucleic acid molecules, ribozymes and ligands, such as antibodies.

The INSP141, INSP142, INSP143 and INSP144 polypeptides are vWFA and/or ANTACID domain containing proteins and thus have roles in many disease states. Antagonists of the INSP141, INSP142, INSP143 and INSP144 polypeptides are of particular interest as they provide a way of modulating these disease states.

In a fourteenth aspect, the invention provides transgenic or knockout non-human animals that have been transformed to express higher, lower or absent levels of a polypeptide of the first aspect of the invention. Such transgenic animals are very useful models for the study of disease and may also be used in screening regimes for the identification of compounds that are effective in the treatment or diagnosis of such a disease.

As used herein, "functional equivalent" refers to a protein or nucleic acid molecule that possesses functional or structural characteristics that are substantially similar to a polypeptide or nucleic acid molecule of the present invention. A functional equivalent of a protein may contain modifications depending on the necessity of such modifications for the performance of a specific, function. The term "functional equivalent" is intended to include the fragments, mutants, hybrids, variants, analogs, or chemical derivatives of a molecule.

Preferably, the "functional equivalent" may be a protein or nucleic acid molecule that exhibits any one or more of the functional activities of the polypeptides of the present invention.

Preferably, the "functional equivalent" may be a protein or nucleic acid molecule that displays substantially similar activity compared with INSP141, INSP142, INSP143 or INSP144 or fragments thereof in a suitable assay for the measurement of biological activity or function. Preferably, the "functional equivalent" may be a protein or nucleic acid molecule that displays identical or higher activity compared with INSP141, INSP142, INSP143 or INSP144 or fragments thereof in a suitable assay for the measurement of biological activity or function. Preferably, the "functional equivalent" may be a protein or nucleic acid molecule that displays 50%, 60%, 70%, 80%, 90%, 95%, 98%, 99%, 100% or more activity compared with INSP141, INSP142, INSP143 or INSP144 or fragments thereof in a suitable assay for the measurement of biological activity or function.

Preferably, the "functional equivalent" may be a protein or polypeptide capable of exhibiting a substantially similar in vivo or in vitro activity as the polypeptides of the invention. Preferably, the "functional equivalent" may be a protein or polypeptide capable of interacting with other cellular or extracellular molecules in a manner substantially similar to the way in which the corresponding portion of the polypeptides of the invention would. For example, a "functional equivalent" would be able, in an immunoassay, to diminish the binding of an antibody to the corresponding peptide (i.e., the peptide the amino acid sequence of which was modified to achieve the "functional equivalent") of the polypeptide of the invention, or to the polypeptide of the invention itself, where the antibody was raised against the corresponding peptide of the polypeptide of the invention. An equimolar concentration of the functional equivalent will diminish the aforesaid binding of the corresponding peptide by at least about 5%, preferably between about 5% and 10%, more preferably between about 10% and 25%, even more preferably between about 25% and 50%, and most preferably between about 40% and 50%.

For example, functional equivalents can be fully functional or can lack function in one or more activities. Thus, in the present invention, variations can affect the function, for example, of the activities of the polypeptide that reflect its possession of a vWFA and/or ANT_IG domain.

A summary of standard techniques and procedures which may be employed in order to utilise the invention is given below. It will be understood that this invention is not limited to the particular methodology, protocols, cell lines, vectors and reagents described. It is also to be understood that the terminology used herein is for the purpose of describing particular embodiments only and it is not intended that this terminology should limit the scope of the present invention. The extent of the invention is limited only by the terms of the appended claims.

Standard abbreviations for nucleotides and amino acids are used in this specification.

The practice of the present invention will employ, unless otherwise indicated, conventional techniques of molecular biology, microbiology, recombinant DNA technology and immunology, which are within the skill of those working in the art.

Such techniques are explained fully in the literature. Examples of particularly suitable texts for consultation include the following: Sambrook Molecular Cloning; A Laboratory Manual, Second Edition (1989); DNA Cloning, Volumes I and II (D. N Glover ed. 1985); Oligonucleotide Synthesis (M. J. Gait ed. 1984); Nucleic Acid Hybridization (B. D. Hames & S. J. Higgins eds. 1984); Transcription and Translation (B. D. Hames & S. J. Higgins eds. 1984); Animal Cell Culture (R. I. Freshney ed. 1986); Immobilized Cells and Enzymes (IRL Press, 1986); B. Perbal, A Practical Guide to Molecular Cloning (1984); the Methods in Enzymology series (Academic Press, Inc.), especially volumes 154 & 155; Gene Transfer Vectors for Mammalian Cells (J. H. Miller and M. P. Calos eds. 1987, Cold Spring Harbor Laboratory); Immunochemical Methods in Cell and Molecular Biology (Mayer and Walker, eds. 1987, Academic Press, London); Scopes, (1987) Protein Purification: Principles and Practice, Second Edition (Springer Verlag, N.Y.); and Handbook of Experimental Immunology, Volumes I-IV (D. M. Weir and C. C. Blackwell eds. 1986).

As used herein, the term "polypeptide" includes any peptide or protein comprising two or more amino acids joined to each other by peptide bonds or modified peptide bonds, i.e. peptide isosteres. This term refers both to short chains (peptides and oligopeptides) and to longer chains (proteins).

The polypeptide of the present invention may be in the form of a mature protein or may be a pre-, pro- or preproprotein that can be activated by cleavage of the pre-, pro- or prepro-portion to produce an active mature polypeptide. In such polypeptides, the pre-, pro- or prepro-sequence may be a leader or secretory sequence or may be a sequence that is employed for purification of the mature polypeptide sequence.

The polypeptide of the first aspect of the invention may form part of a fusion protein. For example, it is often advantageous to include one or more additional amino acid sequences which may contain secretory or leader sequences, pro-sequences, sequences which aid in purification, or sequences that confer higher protein stability, for example during recombinant production. Alternatively or additionally, the mature polypeptide may be fused with another compound, such as a compound to increase the half-life of the polypeptide (for example, polyethylene glycol).

In a further preferred embodiment, a polypeptide of the invention, that may comprise a sequence having at least 85% of homology with INSP141, INSP142, INSP143 or INSP144, is a fusion protein.

These fusion proteins can be obtained by cloning a polynucleotide encoding a polypeptide comprising a sequence having at least 85% of homology with INSP141, INSP142, INSP143 or INSP144 in frame to the coding sequences for a heterologous protein sequence.

The term "heterologous", when used herein, is intended to designate any polypeptide other than a human INSP141, INSP142, INSP143 or INSP144 polypeptide. Examples of heterologous sequences, that can be comprised in the fusion proteins either at the N- or C-terminus, include: extracellular domains of membrane-bound protein, immunoglobulin constant regions (Fc regions), multimerization domains, domains of extracellular proteins; signal sequences, export sequences, and sequences allowing purification by affinity chromatography.

Many of these heterologous sequences are commercially available in expression plasmids since these sequences are commonly included in fusion proteins in order to provide additional properties without significantly impairing the specific biological activity of the protein fused to them (Terpe K, 2003, Appl Microbiol Biotechnol, 60:523-33). Examples of such additional properties are a longer lasting half-life in body fluids, the extracellular localization, or an easier purification procedure as allowed by the a stretch of Histidines forming the so-called "histidine tag" (Gentz et al. 1989, Proc Natl Acad Sci USA, 86:821-4) or by the "HA" tag, an epitope derived from the influenza hemagglutinin protein (Wilson et al. 1994, Cell, 37:767-78). If needed, the heterologous sequence can be eliminated by a proteolytic cleavage, for example by inserting a proteolytic cleavage site between the protein and the heterologous sequence, and exposing the purified fusion protein to the appropriate protease. These features are of particular importance for the fusion proteins since they facilitate their production and use in the preparation of pharmaceutical compositions. For example, the INSP141, INSP142, INSP143 or INSP144 polypeptide may be purified by means of a hexa-histidine peptide fused at the C-terminus of INSP141, INSP142, INSP143 or INSP144. When the fusion protein comprises an immunoglobulin region, the fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met (SEQ ID NO: 151) introduced between the sequence of the substances of the invention and the immunoglobulin sequence. The resulting fusion protein has improved properties, such as an extended residence time in body fluids (i.e. an increased half-life), increased specific activity, increased expression level, or the purification of the fusion protein is facilitated.

In a preferred embodiment, the protein is fused to the constant region of an Ig molecule. Preferably, it is fused to heavy chain regions, like the CH2 and CH3 domains of human IgG1, for example. Other isoforms of Ig molecules are also suitable for the generation of fusion proteins according to the present invention, such as isoforms IgG2 or IgG4, or other Ig classes, like IgM or IgA, for example. Fusion proteins may be monomeric or multimeric, hetero- or homomultimeric.

INSP141, INSP142 or the extracellular portions of INSP143 or INSP144 are useful on their own, as a component of fusion proteins such as Fc fusions, and/or in combination with another agent.

In a further preferred embodiment, the functional derivative comprises at least one moiety attached to one or more functional groups, which occur as one or more side chains on the amino acid residues. Preferably, the moiety is a polyethylene (PEG) moiety. PEGylation may be carried out by known methods, such as the ones described in WO99/55377, for example.

Polypeptides may contain amino acids other than the 20 gene-encoded amino acids, modified either by natural processes, such as by post-translational processing or by chemical modification techniques which are well known in the art. Among the known modifications which may commonly be present in polypeptides of the present invention are glycosylation, lipid attachment, sulphation, gamma-carboxylation, for instance of glutamic acid residues, hydroxylation and ADP-ribosylation. Other potential modifications include acetylation, acylation, amidation, covalent attachment of flavin, covalent attachment of a haeme moiety, covalent attachment of a nucleotide or nucleotide derivative, covalent attachment of a lipid derivative, covalent attachment of phosphatidylinositol, cross-linking, cyclization, disulphide bond formation, demethylation, formation of covalent cross-links, formation of cysteine, formation of pyroglutamate, formylation, GPI anchor formation, iodination, methylation, myristoylation, oxidation, proteolytic processing, phosphorylation, prenylation, racemization, selenoylation, transfer-RNA mediated addition of amino acids to proteins such as arginylation, and ubiquitination.

Modifications can occur anywhere in a polypeptide, including the peptide backbone, the amino acid side-chains and the amino or carboxyl termini. In fact, blockage of the amino or carboxyl terminus in a polypeptide, or both, by a covalent modification is common in naturally-occurring and synthetic polypeptides and such modifications may be present in polypeptides of the present invention.

The modifications that occur in a polypeptide often will be a function of how the polypeptide is made. For polypeptides that are made recombinantly, the nature and extent of the modifications in large part will be determined by the post-translational modification capacity of the particular host cell and the modification signals that are present in the amino acid sequence of the polypeptide in question. For instance, glycosylation patterns vary between different types of host cell.

The polypeptides of the present invention can be prepared in any suitable manner. Such polypeptides include isolated naturally-occurring polypeptides (for example purified from cell culture), recombinantly-produced polypeptides (including fusion proteins), synthetically-produced polypeptides or polypeptides that are produced by a combination of these methods.

The functionally-equivalent polypeptides of the first aspect of the invention may be polypeptides that are homologous to the INSP141, INSP142, INSP143 and INSP144 exon polypeptides and the INSP141, INSP142, INSP143 and INSP144 polypeptides. Two polypeptides are said to be "homologous", as the term is used herein, if the sequence of one of the polypeptides has a high enough degree of identity or similarity to the sequence of the other polypeptide. "Identity" indicates that at any particular position in the aligned sequences, the amino acid residue is identical between the sequences. "Similarity" indicates that, at any particular position in the aligned sequences, the amino acid residue is of a similar type between the sequences. Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

Homologous polypeptides therefore include natural biological variants (for example, allelic variants or geographical variations within the species from which the polypeptides are derived) and mutants (such as mutants containing amino acid substitutions, insertions or deletions) of the INSP141, INSP142, INSP143 and INSP144 exon polypeptides and the INSP141, INSP142, INSP143 and INSP144 polypeptides. Such mutants may include polypeptides in which one or more of the amino acid residues are substituted with a conserved or non-conserved amino acid residue (preferably a conserved amino acid residue) and such substituted amino acid residue may or may not be one encoded by the genetic code. Typical such substitutions are among Ala, Val, Leu and Ile; among Ser and Thr; among the acidic residues Asp and Glu; among Asn and Gln; among the basic residues Lys and Arg; or among the aromatic residues Phe and Tyr. Particularly preferred are variants in which several, i.e. between 5 and 10, 1 and 5, 1 and 3, 1 and 2 or just 1 amino acids are substituted, deleted or added in any combination. Especially preferred are silent substitutions, additions and deletions, which do not alter the properties and activities of the protein. Also especially preferred in this regard are conservative substitutions. Such mutants also include polypeptides in which one or more of the amino acid residues includes a substituent group.

In accordance with the present invention, any substitution should be preferably a "conservative" or "safe" substitution, which is commonly defined a substitution introducing an amino acids having sufficiently similar chemical properties (e.g. a basic, positively charged amino acid should be replaced by another basic, positively charged amino acid), in order to preserve the structure and the biological function of the molecule.

The literature provide many models on which the selection of conservative amino acids substitutions can be performed on the basis of statistical and physico-chemical studies on the sequence and/or the structure of proteins (Rogov S I and Nekrasov A N, 2001). Protein design experiments have shown that the use of specific subsets of amino acids can produce foldable and active proteins, helping in the classification of amino acid "synonymous" substitutions which can be more easily accommodated in protein structure, and which can be used to detect functional and structural homologs and paralogs (Murphy L R et al., 2000). The groups of synonymous amino acids and the groups of more preferred synonymous amino acids are shown in Table 1.

Specific, non-conservative mutations can be also introduced in the polypeptides of the invention with different purposes. Mutations reducing the affinity of the vWFA and/or ANT_IG domain containing protein may increase its ability to be reused and recycled, potentially increasing its therapeutic potency (Robinson C R, 2002). Immunogenic epitopes eventually present in the polypeptides of the invention can be exploited for developing vaccines (Stevanovic S, 2002), or eliminated by modifying their sequence following known methods for selecting mutations for increasing protein stability, and correcting them (van den Burg B and Eijsink V, 2002; WO 02/05146, WO 00/34317, WO 98/52976).

Preferred alternative, synonymous groups for amino acids derivatives included in peptide mimetics are those defined in Table 2. A non-exhaustive list of amino acid derivatives also include aminoisobutyric acid (Aib), hydroxyproline (Hyp), 1,2,3,4-tetrahydro-isoquinoline-3-COOH, indoline-2-carboxylic acid, 4-difluoro-proline, L-thiazolidine-4-carboxylic acid, L-homoproline, 3,4-dehydro-proline, 3,4-dihydroxy-phenylalanine, cyclohexyl-glycine, and phenylglycine.

By "amino acid derivative" is intended an amino acid or amino acid-like chemical entity other than one of the 20 genetically encoded naturally occurring amino acids. In particular, the amino acid derivative may contain substituted or non-substituted, linear, branched, or cyclic alkyl moieties, and may include one or more heteroatoms. The amino acid derivatives can be made de novo or obtained from commercial sources (Calbiochem-Novabiochem AG, Switzerland; Bachem, USA).

Various methodologies for incorporating unnatural amino acids derivatives into proteins, using both in vitro and in vivo translation systems, to probe and/or improve protein structure and function are disclosed in the literature (Dougherty D A, 2000). Techniques for the synthesis and the development of peptide mimetics, as well as non-peptide mimetics, are also well known in the art (Golebiowski A et al., 2001; Hruby V J and Balse P M, 2000; Sawyer T K, in "Structure Based Drug Design", edited by Veerapandian P, Marcel Dekker Inc., pg. 557-663, 1997).

Typically, greater than 30% identity between two polypeptides is considered to be an indication of functional equivalence. Preferably, functionally equivalent polypeptides of the first aspect of the invention have a degree of sequence identity with INSP141, INSP142, INSP143 and INSP144 exon polypeptides and the INSP141, INSP142, INSP143 and INSP144 polypeptides, or with active fragments thereof, of greater than 80%. More preferred polypeptides have degrees of identity of greater than 85%, 90%, 95%, 98%, or 99%, respectively.

The functionally-equivalent polypeptides of the first aspect of the invention may also be polypeptides which have been identified using one or more techniques of structural alignment. For example, the Inpharmatica Genome Threader technology that forms one aspect of the search tools used to generate the Biopendium™ search database may be used (see PCT application WO 01/69507) to identify polypeptides of presently-unknown function which, while having low sequence identity as compared to INSP141, INSP142, INSP143 and INSP144 exon polypeptides and the INSP141, INSP142, INSP143 and INSP144 polypeptides, are predicted to be vWFA and/or ANT_IG domain containing proteins, by virtue of sharing significant structural homology with the INSP141, INSP142, INSP143 and INSP144 exon polypeptides and the INSP141, INSP142, INSP143 and INSP144 polypeptides sequence. By "significant structural homology" is meant that the Inpharmatica Genome Threader predicts two proteins to share structural homology with a certainty of 10% and above.

The polypeptides of the first aspect of the invention also include fragments of the INSP141, INSP142, INSP143 and INSP144 exon polypeptides and the INSP141, INSP142, INSP143 and INSP144 polypeptides and fragments of the functional equivalents of the INSP141, INSP142, INSP143 and INSP144 exon polypeptides and the INSP141, INSP142, INSP143 and INSP144 polypeptides, provided that those fragments are vWFA and/or ANT_IG domain containing proteins or have an antigenic determinant in common with vWFA and/or ANT_IG domain containing proteins.

As used herein, the term "fragment" refers to a polypeptide having an amino acid sequence that is the same as part, but not all, of the amino acid sequence of the INSP141, INSP142, INSP143 and INSP144 exon polypeptides and the INSP141, INSP142, INSP143 and INSP144 polypeptides or one of their functional equivalents. The fragments should comprise at least n consecutive amino acids from the sequence and, depending on the particular sequence, n preferably is 7 or more (for example, 8, 10, 12, 14, 16, 18, 20 or more). Small fragments may form an antigenic determinant.

Nucleic acids according to the invention are preferably 10-2000 nucleotides in length, preferably 100-1750 nucleotides, preferably 500-1500, preferably 600-1200, preferably 750-1000 nucleotides in length. Polypeptides according to the invention are preferably 10-700 amino acids in length, preferably 50-600, preferably 100-500, preferably 200-400, preferably 300-375 amino acids in length.

Fragments of the full length INSP141, INSP142, INSP143 and INSP144 exon polypeptides and the INSP141, INSP142, INSP143 and INSP144 polypeptides may consist of combinations of 2, 3, 4, 5, 6, 7, 8, 9, 10, 11, 12, 13, 14, 15, 16 or 17 of neighbouring exon sequences in the INSP141, INSP142, INSP143 and INSP144 polypeptides, respectively.

Such fragments may be "free-standing", i.e. not part of or fused to other amino acids or polypeptides, or they may be comprised within a larger polypeptide of which they form a part or region. When comprised within a larger polypeptide, the fragment of the invention most preferably forms a single continuous region. For instance, certain preferred embodiments relate to a fragment having a pre- and/or pro-polypeptide region fused to the amino terminus of the fragment and/or an additional region fused to the carboxyl terminus of the fragment. However, several fragments may be comprised within a single larger polypeptide.

The polypeptides of the present invention or their immunogenic fragments (comprising at least one antigenic determinant) can be used to generate ligands, such as polyclonal or monoclonal antibodies, that are immunospecific for the polypeptides. Such antibodies may be employed to isolate or to identify clones expressing the polypeptides of the invention or to purify the polypeptides by affinity chromatography. The antibodies may also be employed as diagnostic or therapeutic aids, amongst other applications, as will be apparent to the skilled reader.

The term "immunospecific" means that the antibodies have substantially greater affinity for the polypeptides of the invention than their affinity for other related polypeptides in the prior art. As used herein, the term "antibody" refers to intact molecules as well as to fragments thereof, such as Fab, F(ab')2 and Fv, which are capable of binding to the antigenic determinant in question. Such antibodies thus bind to the polypeptides of the first aspect of the invention.

By "substantially greater affinity" we mean that there is a measurable increase in the affinity for a polypeptide of the invention as compared with the affinity for known vWFA and/or ANT_IG domain containing proteins, preferably ATR-like proteins.

Preferably, the affinity is at least 1.5-fold, 2-fold, 5-fold 10-fold, 100-fold, $10^3$-fold, $10^4$-fold, $10^5$-fold, $10^6$-fold or greater for a polypeptide of the invention than for known vWFA and/or ANT_IG-domain containing proteins.

Preferably, there is a measurable increase in the affinity for a polypeptide of the invention as compared with known vWFA and/or ANT_IG domain containing proteins.

If polyclonal antibodies are desired, a selected mammal, such as a mouse, rabbit, goat or horse, may be immunised with a polypeptide of the first aspect of the invention. The polypeptide used to immunise the animal can be derived by recombinant DNA technology or can be synthesized chemically. If desired, the polypeptide can be conjugated to a carrier protein. Commonly used carriers to which the polypeptides may be chemically coupled include bovine serum albumin, thyroglobulin and keyhole limpet haemocyanin. The coupled polypeptide is then used to immunise the animal. Serum from the immunised animal is collected and treated according to known procedures, for example by immunoaffinity chromatography.

Monoclonal antibodies to the polypeptides of the first aspect of the invention can also be readily produced by one skilled in the art. The general methodology for making monoclonal antibodies using hybridoma technology is well known (see, for example, Kohler, G. and Milstein, C., Nature 256: 495-497 (1975); Kozbor et al., Immunology Today 4: 72 (1983); Cole et al., 77-96 in Monoclonal Antibodies and Cancer Therapy, Alan R. Liss, Inc. (1985).

Panels of monoclonal antibodies produced against the polypeptides of the first aspect of the invention can be screened for various properties, i.e., for isotype, epitope, affinity, etc. Monoclonal antibodies are particularly useful in purification of the individual polypeptides against which they are directed. Alternatively, genes encoding the monoclonal antibodies of interest may be isolated from hybridomas, for instance by PCR techniques known in the art, and cloned and expressed in appropriate vectors.

Chimeric antibodies, in which non-human variable regions are joined or fused to human constant regions (see, for example, Liu et al., Proc. Natl. Acad. Sci. USA, 84, 3439 (1987)), may also be of use.

The antibody may be modified to make it less immunogenic in an individual, for example by humanisation (see Jones et al., Nature, 321,522 (1986); Verhoeyen et al., science, 239, 1534 (1988); Kabat et al., J. Immunol., 147, 1709 (1991); Queen et al., Proc. Natl Acad. Sci. USA, 86, 10029 (1989); Gorman et al., Proc. Natl. Acad. Sci. USA, 88, 34181 (1991); and Hodgson et al., Bio/Technology, 9, 421 (1991)). The term "humanised antibody", as used herein, refers to antibody molecules in which the CDR amino acids and selected other amino acids in the variable domains of the heavy and/or light chains of a non-human donor antibody have been substituted in place of the equivalent amino acids in a human antibody. The humanised antibody thus closely resembles a human antibody but has the binding ability of the donor antibody.

In a further alternative, the antibody may be a "bispecific" antibody, that is, an antibody having two different antigen binding domains, each domain being directed against a different epitope.

Phage display technology may be utilised to select genes which encode antibodies with binding activities towards the polypeptides of the invention either from repertoires of PCR amplified V-genes of lymphocytes from humans screened for possessing the relevant antibodies, or from naive libraries (McCafferty, J. et al., (1990), Nature 348, 552-554; Marks, J. et al., (1992) Biotechnology 10, 779-783). The affinity of these antibodies can also be improved by chain shuffling (Clackson, T. et al., (1991) Nature 352, 624-628).

Antibodies generated by the above techniques, whether polyclonal or monoclonal, have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme.

Preferred nucleic acid molecules of the second and third aspects of the invention are those which encode a polypeptide sequence as recited in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:04, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134; SEQ TD NO:136, SEQ ID NO:138, SEQ ID NO:140, SEQ ID NO:142, SEQ ID NO:144, SEQ ID NO:146, SEQ ID NO:148 and SEQ ID NO:150 and functionally equivalent polypeptides. These nucleic acid molecules may be used in the methods and applications described herein. The nucleic acid molecules of the invention preferably comprise at least n consecutive nucleotides from the sequences disclosed herein where, depending on the particular sequence, n is 10 or more (for example, 12, 14, 15, 18, 20, 25, 30, 35, 40 or more).

The nucleic acid molecules of the invention also include sequences that are complementary to nucleic acid molecules described above (for example, for antisense or probing purposes).

Nucleic acid molecules of the present invention may be in the form of RNA, such as mRNA, or in the form of DNA, including, for instance cDNA, synthetic DNA or genomic DNA. Such nucleic acid molecules may be obtained by cloning, by chemical synthetic techniques or by a combination thereof. The nucleic acid molecules can be prepared, for example, by chemical synthesis using techniques such as solid phase phosphoramidite chemical synthesis, from genomic or cDNA libraries or by separation from an organism. RNA molecules may generally be generated by the in vitro or in vivo transcription of DNA sequences.

The nucleic acid molecules may be double-stranded or single-stranded. Single-stranded DNA may be the coding strand, also known as the sense strand, or it may be the non-coding strand, also referred to as the anti-sense strand.

The term "nucleic acid molecule" also includes analogues of DNA and RNA, such as those containing modified backbones, and peptide nucleic acids (PNA). The term "PNA", as used herein, refers to an antisense molecule or an anti-gene agent which comprises an oligonucleotide of at least five nucleotides in length linked to a peptide backbone of amino acid residues, which preferably ends in lysine. The terminal lysine confers solubility to the composition. PNAs may be pegylated to extend their lifespan in a cell, where they preferentially bind complementary single stranded DNA and RNA and stop transcript elongation (Nielsen, P. E. et al. (1993) Anticancer Drug Des. 8:53-63).

A nucleic acid molecule which encodes a polypeptide of this invention may be identical to the coding sequence of one or more of the nucleic acid molecules disclosed herein.

These molecules also may have a different sequence which, as a result of the degeneracy of the genetic code, encodes a polypeptide SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:1100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134; SEQ ID NO:136, SEQ ID NO:138, SEQ ID NO:140, SEQ ID NO:142, SEQ ID NO:144, SEQ ID NO:146, SEQ ID NO:148 and SEQ ID NO:150. Such nucleic acid molecules may include, but are not limited to, the coding sequence for the mature polypeptide by itself; the coding sequence for the mature polypeptide and additional coding sequences, such as those encoding a leader or secretory sequence, such as a pro-, pre- or prepro-polypeptide sequence; the coding sequence of the mature polypeptide, with or without the aforementioned additional coding sequences, together with further additional, non-coding sequences, including non-coding 5' and 3' sequences, such as the transcribed, non-translated sequences that play a role in transcription (including termination signals), ribosome binding and mRNA stability. The nucleic acid molecules may also include additional sequences which encode additional amino acids, such as those which provide additional functionalities.

The nucleic acid molecules of the second and third aspects of the invention may also encode the fragments or the functional equivalents of the polypeptides and fragments of the first aspect of the invention. Such a nucleic acid molecule may be a naturally-occurring variant such as a naturally-occurring allelic variant, or the molecule may be a variant that is not known to occur naturally. Such non-naturally occurring variants of the nucleic acid molecule may be made by mutagenesis techniques, including those applied to nucleic acid molecules, cells or organisms.

Among variants in this regard are variants that differ from the aforementioned nucleic acid molecules by nucleotide substitutions, deletions or insertions. The substitutions, deletions or insertions may involve one or more nucleotides. The variants may be altered in coding or non-coding regions or both. Alterations in the coding regions may produce conservative or non-conservative amino acid substitutions, deletions or insertions.

The nucleic acid molecules of the invention can also be engineered, using methods generally known in the art, for a variety of reasons, including modifying the cloning, processing, and/or expression of the gene product (the polypeptide). DNA shuffling by random fragmentation and PCR reassembly of gene fragments and synthetic oligonucleotides are included as techniques which may be used to engineer the nucleotide sequences. Site-directed mutagenesis may be used to insert new restriction sites, alter glycosylation patterns, change codon preference, produce splice variants, introduce mutations and so forth.

Nucleic acid molecules which encode a polypeptide of the first aspect of the invention may be ligated to a heterologous sequence so that the combined nucleic acid molecule encodes a fusion protein. Such combined nucleic acid molecules are included within the second or third aspects of the invention. For example, to screen peptide libraries for inhibitors of the activity of the polypeptide, it may be useful to express, using such a combined nucleic acid molecule, a fusion protein that can be recognised by a commercially-available antibody. A fusion protein may also be engineered to contain a cleavage site located between the sequence of the polypeptide of the invention and the sequence of a heterologous protein so that the polypeptide may be cleaved and purified away from the heterologous protein.

The nucleic acid molecules of the invention also include antisense molecules that are partially complementary to nucleic acid molecules encoding polypeptides of the present invention and that therefore hybridize to the encoding nucleic acid molecules (hybridization). Such antisense molecules, such as oligonucleotides, can be designed to recognise, specifically bind to and prevent transcription of a target nucleic acid encoding a polypeptide of the invention, as will be known by those of ordinary skill in the art (see, for example, Cohen, J. S., Trends in Pharm. Sci., 10, 435 (1989), Okano, J. Neurochem. 56, 560 (1991); O'Connor, J. Neurochem 56, 560 (1991); Lee et al., Nucleic Acids Res 6, 3073 (1979); Cooney et al., Science 241, 456 (1988); Dervan et al., Science 251, 1360 (1991).

The term "hybridization" as used here refers to the association of two nucleic acid molecules with one another by hydrogen bonding. Typically, one molecule will be fixed to a solid support and the other will be free in solution. Then, the two molecules may be placed in contact with one another under conditions that favour hydrogen bonding. Factors (that affect this bonding include: the type and volume of solvent; reaction temperature; time of hybridization; agitation; agents to block the non-specific attachment of the liquid phase molecule to the solid support (Denhardt's reagent or BLOTTO); the concentration of the molecules; use of compounds to increase the rate of association of molecules (dextran sulphate or polyethylene glycol); and the stringency of the washing conditions following hybridization (see Sambrook et al. [supra]).

The inhibition of hybridization of a completely complementary molecule to a target molecule may be examined using a hybridization assay, as known in the art (see, for example, Sambrook et al. [supra]). A substantially homologous molecule will then compete for and inhibit the binding of a completely homologous molecule to the target molecule under various conditions of stringency, as taught in Wahl, G. M. and S. L. Berger (1987; Methods Enzymol. 152:399-407) and Kimmel, A. R. (1987; Methods Enzymol. 152:507-511).

"Stringency" refers to conditions in a hybridization reaction that favour the association of very similar molecules over association of molecules that differ. High stringency hybridisation conditions are defined as overnight incubation at 42° C. in a solution comprising 50% formamide, 5×SSC (150 mM NaCl, 15 mM trisodium citrate), 50 mM sodium phosphate (pH7.6), 5×Denhardts solution, 10% dextran sulphate, and 20 microgram/ml denatured, sheared salmon sperm DNA, followed by washing the filters in 0.1×SSC at approximately 65° C. Low stringency conditions involve the hybridisation reaction being carried out at 35° C. (see Sambrook et al. [supra]). Preferably, the conditions used for hybridization are those of high stringency.

Preferred embodiments of this aspect of the invention are nucleic acid molecules that are at least 70% identical over their entire length to a nucleic acid molecule encoding the INSP141, INSP142, INSP143 and INSP144 exon polypeptides and the INSP141, INSP142, INSP143 and INSP144 polypeptides and nucleic acid molecules that are substantially complementary to such nucleic acid molecules. Preferably, a nucleic acid molecule according to this aspect of the invention comprises a region that is at least 80% identical over its entire length to such coding sequences, or is a nucleic acid molecule that is complementary thereto. In this regard, nucleic acid molecules at least 90%, preferably at least 95%, more preferably at least 98%, 99% or more identical over their entire length to the same are particularly preferred. Preferred embodiments in this respect are nucleic acid molecules that encode polypeptides which retain substantially the same biological function or activity as the INSP141, INSP142, INSP143 and INSP144 exon polypeptides and the INSP141, INSP142, INSP143 and INSP144 polypeptides.

The invention also provides a process for detecting a nucleic acid molecule of the invention, comprising the steps of: (a) contacting a nucleic probe according to the invention pith a biological sample wider hybridizing conditions to form duplexes; and (b) detecting any such duplexes that are formed.

As discussed additionally below in connection with assays that may be utilised according to the invention, a nucleic acid molecule as described above may be used as a hybridization probe for RNA, cDNA or genomic DNA, in order to isolate full-length cDNAs and genomic clones encoding the INSP141, 142, 143 or 144 polypeptides and to isolate cDNA and genomic clones of homologous or orthologous genes that have a high sequence similarity to the gene encoding this polypeptide.

In this regard, the following techniques, among others known in the art, may be utilised and are discussed below for purposes of illustration. Methods for DNA sequencing and analysis are well known and are generally available in the art and may, indeed, be used to practice many of the embodiments of the invention discussed herein. Such methods may employ such enzymes as the Klenow fragment of DNA polymerase I, Sequenase (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL, (Gaithersburg, Md.). Preferably, the sequencing process may be automated using machines such as the Hamilton Micro Lab 2200 (Hamilton, Reno, Nev.), the Peltier Thermal Cycler (PTC200; MJ Research, Watertown, Mass.) and the ABI Catalyst and 373 and 377 DNA Sequencers (Perkin Elmer).

One method for isolating a nucleic acid molecule encoding a polypeptide with an equivalent function to that of the INSP141, 142, 143 or 144 polypeptides is to probe a genomic or cDNA library with a natural or artificially-designed probe using standard procedures that are recognised in the art (see, for example, "Current Protocols in Molecular Biology", Ausubel et al. (eds). Greene Publishing Association and John Wiley Interscience, New York, 1989, 1992). Probes comprising at least 15, preferably at least 30, and more preferably at least 50, contiguous bases that correspond to, or are complementary to, nucleic acid sequences from the appropriate encoding gene (SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147 and/or SEQ ID NO:149 are particularly useful probes. Such probes may be labelled with an analytically-detectable reagent to facilitate their identification. Useful reagents include, but are not limited to, radioisotopes, fluorescent dyes and enzymes that are capable of catalysing the formation of a detectable product. Using these probes, the ordinarily skilled artisan will be capable of isolating complementary copies of genomic DNA, cDNA or RNA polynucleotides encoding proteins of interest from human, mammalian or other animal sources and screening such sources for related sequences, for example, for additional members of the family, type and/or subtype.

In many cases, isolated cDNA sequences will be incomplete, in that the region encoding the polypeptide will be cut short, normally at the 5' end. Several methods are available to obtain full length cDNAs, or to extend short cDNAs. Such sequences may be extended utilising a partial nucleotide sequence and employing various methods known in the art to detect upstream sequences such as promoters and regulatory elements. For example, one method which may be employed is based on the method of Rapid Amplification of cDNA Ends (RACE; see, for example, Frohman et al., PNAS USA 85, 8998-9002, 1988). Recent modifications of this technique, exemplified by the MARATHON technology (Clontech Laboratories Inc.), for example, have significantly simplified the search for longer cDNAs. A slightly different technique, termed "restriction-site" PCR, uses universal primers to retrieve unknown nucleic acid sequence adjacent a known locus (Sarkar, G. (1993) PCR Methods Applic. 2:318-322). Inverse PCR may also be used to amplify or to extend sequences using divergent primers based on a known region (Triglia, T. et al. (1988) Nucleic Acids Res. 16:8186). Another method which may be used is capture PCR which involves PCR amplification of DNA fragments adjacent a known sequence in human and yeast artificial chromosome DNA (Lagerstrom, M. et al. (1991) PCR Methods Applic., 1, 111-119). Another method which may be used to retrieve unknown sequences is that of Parker, J. D. et al. (1991); Nucleic Acids Res. 19:3055-3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences that contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

In one embodiment of the invention, the nucleic acid molecules of the present invention may be used for chromosome localisation. In this technique, a nucleic acid molecule is specifically targeted to, and can hybridize with, a particular location on an individual human chromosome. The mapping of relevant sequences to chromosomes according to the present invention is an important step in the confirmatory correlation of those sequences with the gene-associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationships between genes and diseases that have been mapped to the same chromosomal region are then identified through linkage analysis (coinheritance of physically adjacent genes). This provides valuable information to investigators searching for disease genes using positional cloning or other gene discovery techniques. Once the disease or syndrome has been crudely localised by genetic linkage to a particular genomic region, any sequences mapping to that area may represent associated or regulatory genes for further investigation. The nucleic acid molecule may also be used to detect differences in the chromosomal location due to translocation, inversion, etc. among normal, carrier, or affected individuals.

The nucleic acid molecules of the present invention are also valuable for tissue localisation. Such techniques allow the determination of expression patterns of the polypeptide in tissues by detection of the mRNAs that encode them. These techniques include in situ hybridization techniques and nucleotide amplification techniques, such as PCR. Results from these studies provide an indication of the normal functions of the polypeptide in the organism. In addition, comparative studies of the normal expression pattern of mRNAs with that of mRNAs encoded by a mutant gene provide valuable insights into the role of mutant polypeptides in disease. Such inappropriate expression may be of a temporal, spatial or quantitative nature.

Gene silencing approaches may also be undertaken to down-regulate endogenous expression of a gene encoding a polypeptide of the invention. RNA interference (RNAi) (Elbashir, S M et al., Nature 2001, 411, 494-498) is one method of sequence specific post-transcriptional gene silencing that may be employed. Short dsRNA oligonucleotides are synthesised in vitro and introduced into a cell. The sequence specific binding of these dsRNA oligonucleotides triggers the degradation of target mRNA, reducing or ablating target protein expression.

Efficacy of the gene silencing approaches assessed above may be assessed through the measurement of polypeptide expression (for example, by Western blotting), and at the RNA level using TaqMan-based methodologies.

The vectors of the present invention comprise nucleic acid molecules of the invention and may be cloning or expression vectors. The host cells of the invention, which may be transformed, transfected or transduced with the vectors of the invention may be prokaryotic or eukaryotic.

The polypeptides of the invention may be prepared in recombinant form by expression of their encoding nucleic acid molecules in vectors contained within a host cell. Such expression methods are well known to those of skill in the art and many are described in detail by Sambrook et al. (supra) and Fernandez & Hoeffler (1998, eds. "Gene expression systems. Using nature for the art of expression". Academic Press, San Diego, London, Boston, New York, Sydney, Tokyo, Toronto).

Generally, any system or vector that is suitable to maintain, propagate or express nucleic acid molecules to produce a polypeptide in the required host may be used. The appropriate nucleotide sequence may be inserted into an expression system by any of a variety of well-known and routine techniques, such as, for example, those described in Sambrook et al., (supra). Generally, the encoding gene can be placed under the control of a control element such as a promoter, ribosome binding site (for bacterial expression) and, optionally, an operator, so that the DNA sequence encoding the desired polypeptide is transcribed into RNA in the transformed host cell.

Examples of suitable expression systems include, for example, chromosomal, episomal and virus-derived systems, including, for example, vectors derived from: bacterial plasmids, bacteriophage, transposons, yeast episomes, insertion elements, yeast chromosomal elements, viruses such as baculoviruses, papova viruses such as SV40, vaccinia viruses, adenoviruses, fowl pox viruses, pseudorabies viruses and retroviruses, or combinations thereof, such as those derived from plasmid and bacteriophage genetic elements, including cosmids and phagemids. Human artificial chromosomes (HACs) may also be employed to deliver larger fragments of DNA than can be contained and expressed in a plasmid. The vectors pCR4-TOPO-INSP142, pCR4-TOPO-INSP141, pCR4-TOPO-INSP143-EC, pDEST12.2_INSP141-6HIS-V1, pEAK12d_INSP141-6HIS-V1, pENTR_INSP141-6HIS-V1, pEAK12d_INSP143-EC-6HIS-V1, pDEST12d_INSP143-EC-6HIS-V1, pDONR-Zeo_INSP143-EC-6HIS-V1 and pEAK12d-INSP142-6HIS are preferred examples of suitable vectors for use in accordance with the aspects of this invention relating to INSP141, INSP142, INSP143 and INSP144.

Particularly suitable expression systems include microorganisms such as bacteria transformed with recombinant bacteriophage, plasmid or cosmid DNA expression vectors; yeast transformed with yeast expression vectors; insect cell systems infected with virus expression vectors (for example, baculovirus); plant cell systems transformed with virus expression vectors (for example, cauliflower mosaic virus, CaMV; tobacco mosaic virus, TMV) or with bacterial expression vectors (for example, Ti or pBR322 plasmids); or animal cell systems. Cell-free translation systems can also be employed to produce the polypeptides of the invention.

Introduction of nucleic acid molecules encoding a polypeptide of the present invention into host cells can be effected by methods described in many standard laboratory manuals, such as Davis et al., Basic Methods in Molecular Biology (1986) and Sambrook et al., (supra). Particularly suitable methods include calcium phosphate transfection, DEAE-dextran mediated transfection, transfection, microinjection, cationic lipid-mediated transfection, electroporation, transduction, scrape loading, ballistic introduction or infection (see Sambrook et al., 1989 [supra]; Ausubel et al., 1991 [supra]; Spector, Goldman & Leinwald, 1998). In eukaryotic cells, expression systems may either be transient (for example, episomal) or permanent (chromosomal integration) according to the needs of the system.

The encoding nucleic acid molecule may or may not include a sequence encoding a control sequence, such as a signal peptide or leader sequence, as desired, for example, for secretion of the translated polypeptide into the lumen of the endoplasmic reticulum, into the periplasmic space or into the extracellular environment. These signals may be endogenous to the polypeptide or they may be heterologous signals. Leader sequences can be removed by the bacterial host in post-translational processing.

In addition to control sequences, it may be desirable to add regulatory sequences that allow for regulation of the expression of the polypeptide relative to the growth of the host cell. Examples of regulatory sequences are those which cause the expression of a gene to be increased or decreased in response to a chemical or physical stimulus, including the presence of a regulatory compound or to various temperature or metabolic conditions. Regulatory sequences are those non-translated regions of the vector, such as enhancers, promoters and 5' and 3' untranslated regions. These interact with host cellular proteins to carry out transcription and translation. Such regulatory sequences may vary in their strength and specificity. Depending on the vector system and host utilised, any number of suitable transcription and translation elements, including constitutive and inducible promoters, may be used. For example, when cloning in bacterial systems, inducible promoters such as the hybrid lacZ promoter of the Bluescript phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (for example, heat shock, RUBISCO and storage protein genes) or from plant viruses (for example, viral promoters or leader sequences) may be cloned into the vector. In mammalian cell systems, promoters from mammalian genes or from mammalian viruses are preferable. If it is necessary to generate a cell line that contains multiple copies of the sequence, vectors based on SV40 or EBV may be used with an appropriate selectable marker.

An expression vector is constructed so that the particular nucleic acid coding sequence is located in the vector with the appropriate regulatory sequences, the positioning and orientation of the coding sequence with respect to the regulatory sequences being such that the coding sequence is transcribed under the "control" of the regulatory sequences, i.e., RNA polymerase which binds to the DNA molecule at the control sequences transcribes the coding sequence. In some cases it may be necessary to modify the sequence so that it may be attached to the control sequences with the appropriate orientation; i.e., to maintain the reading frame.

The control sequences and other regulatory sequences may be ligated to the nucleic acid coding sequence prior to insertion into a vector. Alternatively, the coding sequence can be cloned directly into an expression vector that already contains the control sequences and an appropriate restriction site.

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Bowes melanoma and human hepatocellular carcinoma (for example Hep G2) cells and a number of other cell lines.

In the baculovirus system, the materials for baculovirus/insect cell expression systems are commercially available in kit form from, inter alia, Invitrogen, San Diego Calif. (the "MaxBac" kit). These techniques are generally known to those skilled in the art and are described fully in Summers and Smith, Texas Agricultural Experiment Station Bulletin No. 1555 (1987). Particularly suitable host cells for use in this system include insect cells such as *Drosophila* S2 and *Spodoptera* Sf9 cells.

There are many plant cell culture and whole plant genetic expression systems known in the art. Examples of suitable plant cellular genetic expression systems include those described in U.S. Pat. Nos. 5,693,506; 5,659,122; and U.S. Pat. No. 5,608,143. Additional examples of genetic expression in plant cell culture has been described by Zenk, Phytochemistry 30, 3861-3863 (1991).

In particular, all plants from which protoplasts can be isolated and cultured to give whole regenerated plants can be utilised, so that whole plants are recovered which contain the transferred gene. Practically all plants can be regenerated from cultured cells or tissues, including but not limited to all major species of sugar cane, sugar beet, cotton, fruit and other trees, legumes and vegetables.

Examples of particularly preferred bacterial host cells include *streptococci, staphylococci, E. coli, Streptomyces* and *Bacillus subtilis* cells.

Examples of particularly suitable host cells for fungal expression include yeast cells (for example, *S. cerevisiae*) and *Aspergillus* cells.

Any number of selection systems are known in the art that may be used to recover transformed cell lines. Examples include the herpes simplex virus thymidine kinase (Wigler, M. et al. (1977) Cell 11:223-32) and adenine phosphoribosyltransferase (Lowy, I. et al. (1980) Cell 22:817-23) genes that can be employed in tk⁻ or aprt⁺ cells, respectively.

Also, antimetabolite, antibiotic or herbicide resistance can be used as the basis for selection; for example, dihydrofolate reductase (DHFR) that confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al. (1981) J. Mol. Biol. 150:1-14) and als or pat, which confer resistance to chlorsulfuron and phosphinotricin acetyltransferase, respectively. Additional selectable genes have been described, examples of which will be clear to those of skill in the art.

Although the presence or absence of marker gene expression suggests that the gene of interest is also present, its presence and expression may need to be confirmed. For example, if the relevant sequence is inserted within a marker gene sequence, transformed cells containing the appropriate sequences can be identified by the absence of marker gene function. Alternatively, a marker gene can be placed in tandem with a sequence encoding a polypeptide of the invention under the control of a single promoter. Expression of the marker gene in response to induction or selection usually indicates expression of the tandem gene as well.

Alternatively, host cells that contain a nucleic acid sequence encoding a polypeptide of the invention and which express said polypeptide may be identified by a variety of procedures known to those of skill in the art. These procedures include, but are not limited to, DNA-DNA or DNA-RNA hybridizations and protein bioassays, for example, fluorescence activated cell sorting (FACS) or immunoassay techniques (such as the enzyme-linked immunosorbent assay [ELISA] and radioimmunoassay [RIA]), that include membrane, solution, or chip based technologies for the detection and/or quantification of nucleic acid or protein (see Hampton, R. et al. (1990) Serological Methods, a Laboratory Manual, APS Press, St Paul, Minn.) and Maddox, D. E. et al. (1983) J. Exp. Med, 158, 1211-1216).

A wide variety of labels and conjugation techniques are known by those skilled in the art and may be used in various nucleic acid and amino acid assays. Means for producing labelled hybridization or PCR probes for detecting sequences related to nucleic acid molecules encoding polypeptides of the present invention include oligolabelling, nick translation, end-labelling or PCR amplification using a labelled polynucleotide. Alternatively, the sequences encoding the polypeptide of the invention may be cloned into a vector for the production of an mRNA probe. Such vectors are known in the art, are commercially available, and may be used to synthesise RNA probes in vitro by addition of an appropriate RNA polymerase such as T7, T3 or SP6 and labelled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio)).

Suitable reporter molecules or labels, which may be used for ease of detection, include radionuclides, enzymes and fluorescent, chemiluminescent or chromogenic agents as well as substrates, cofactors, inhibitors, magnetic particles, and the like.

Nucleic acid molecules according to the present invention may also be used to create transgenic animals, particularly rodent animals. Such transgenic animals form a further aspect of the present invention. This may be done locally by modification of somatic cells, or by germ line therapy to incorporate heritable modifications. Such transgenic animals may be particularly useful in the generation of animal models for drug molecules effective as modulators of the polypeptides of the present invention.

The polypeptide can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography is particularly useful for purification. Well known techniques for refolding proteins may be employed to regenerate an active conformation when the polypeptide is denatured during isolation and or purification.

Specialised vector constructions may also be used to facilitate purification of proteins, as desired, by joining sequences encoding the polypeptides of the invention to a nucleotide sequence encoding a polypeptide domain that will facilitate purification of soluble proteins. Examples of such purification-facilitating domains include metal chelating peptizes such as histidine-tryptophan modules that allow purification on immobilised metals, protein A domains that allow purification on immobilised immunoglobulin, and the domain utilised in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and the polypeptide of the invention may be used to facilitate purification. One such expression vector provides for expression of a fusion protein containing the polypeptide of the invention fused to several histidine residues preceding a thioredoxin or an enterokinase cleavage site. The histidine residues facilitate purification by IMAC (immobilised metal ion affinity chromatography as described in Porath, J. et al. (1992), Prot. Exp. Purif. 3: 263-281) while the thioredoxin or enterokinase cleavage site provides a means for purifying the polypeptide from the fusion protein. A discussion of vectors which contain fusion proteins is provided in Kroll, D. J. et al. (1993; DNA Cell Biol. 12:441-453).

If the polypeptide is to be expressed for use in screening assays, generally it is preferred that it be produced at the surface of the host cell in which it is expressed. In this event, the host cells may be harvested prior to use in the screening assay, for example using techniques such as fluorescence activated cell sorting (FACS) or immunoaffinity techniques. If the polypeptide is secreted into the medium, the medium can be recovered in order to recover and purify the expressed polypeptide. If polypeptide is produced intracellularly, the cells must first be lysed before the polypeptide is recovered.

The polypeptide of the invention can be used to screen libraries of compounds in any of a variety of drug screening techniques. Such compounds may activate (agonise) or inhibit (antagonise) the level of expression of the gene or the activity of the polypeptide of the invention and form a further aspect of the present invention. Preferred compounds are effective to alter the expression of a natural gene which encodes a polypeptide of the first aspect of the invention or to regulate the activity of a polypeptide of the first aspect of the invention.

Agonist or antagonist compounds may be isolated from, for example, cells, cell-free preparations, chemical libraries or natural product mixtures. These agonists or antagonists may be natural or modified substrates, ligands, enzymes, receptors or structural or functional mimetics. For a suitable review of such screening techniques, see Coligan et al., Current Protocols in Immunology 1(2):Chapter 5 (1991).

Compounds that are most likely to be good antagonists are molecules that bind to the polypeptide of the invention without inducing the biological effects of the polypeptide upon binding to it. Potential antagonists include small organic molecules, peptides, polypeptides and antibodies that bind to the polypeptide of the invention and thereby inhibit or extinguish its activity. In this fashion, binding of the polypeptide to normal cellular binding molecules may be inhibited, such that the normal biological activity of the polypeptide is prevented.

The polypeptide of the invention that is employed in such a screening technique may be free in solution, affixed to a solid support, borne on a cell surface or located intracellularly. In general, such screening procedures may involve using appropriate cells or cell membranes that express the polypeptide that are contacted with a test compound to observe binding, or stimulation or inhibition of a functional response. The functional response of the cells contacted with the test compound is then compared with control cells that were not contacted with the test compound. Such an assay may assess whether the test compound results in a signal generated by activation of the polypeptide, using an appropriate detection system. Inhibitors of activation are generally assayed in the presence of a known agonist and the effect on activation by the agonist in the presence of the test compound is observed.

Methods for generating detectable signals in the types of assays described herein will be known to those of skill in the art. A particular example is cotransfecting a construct expressing a polypeptide according to the invention, or a fragment such as the LBD, in fusion with the GAL4 DNA binding domain, into a cell together with a reporter plasmid, an example of which is pFR-Luc (Stratagene Europe, Amsterdam, The Netherlands). This particular plasmid contains a synthetic promoter with five tandem repeats of GAL4 binding sites that control the expression of the luciferase gene. When a potential ligand is added to the cells, it will bind the GAL4-polypeptide fusion and induce transcription of the luciferase gene. The level of the luciferase expression can be monitored by its activity using a luminescence reader (see, for example, Lehman et al. JBC 270, 12953, 1995; Pawar et al. JBC, 277, 39243, 2002).

A further preferred method for identifying an agonist or antagonist of a polypeptide of the invention comprises:
(a) contacting a labelled or unlabeled compound with the polypeptide immobilized on any solid support (for example beads, plates, matrix support, chip) and detection of the compound by measuring the label or the presence of the compound itself, or
(b) contacting a cell expressing on the surface thereof the polypeptide, by means of artificially anchoring it to the cell membrane, or by constructing a chimeric receptor being associated with a second component capable of providing a detectable signal in response to the binding of a compound to the polypeptide, with a compound to be screened under conditions to permit binding to the polypeptide; and
(c) determining whether the compound binds to and activates or inhibits the polypeptide by comparing the level of a signal generated from the interaction of the compound with the polypeptide with the level of a signal in the absence of the compound.

For example, a method such as FRET detection of a ligand bound to the polypeptide in the presence of peptide co-activators (Norris et al., Science 285, 744, 1999) might be used.

In further preferred embodiments, the general methods that are described above may further comprise conducting the identification of agonist or antagonist in the presence of labelled or unlabelled ligand for the polypeptide.

In another embodiment of the method for identifying agonist or antagonist of a polypeptide of the present invention comprises:
determining the inhibition of binding of a ligand to the polypeptide of the invention on any solid or cellular surface thereof, in the presence of a candidate compound under conditions to permit binding to the polypeptide, and determining the amount of ligand bound to the polypeptide. A compound capable of causing reduction of binding of a ligand is considered to be a competitor which may act as an agonist or antagonist. Preferably the ligand is labelled.

More particularly, a method of screening for a polypeptide antagonist or agonist compound comprises the steps of:
(a) incubating a labelled ligand with a polypeptide according to the invention on any solid support or the cell surface, or a cell membrane containing a polypeptide of the invention.
(b) measuring the amount of labelled ligand bound to the polypeptide on the solid support, whole cell or the cell membrane;
(c) adding a candidate compound to a mixture of labelled ligand and immobilized polypeptide on the solid support, the whole cell or the cell membrane of step (a) and allowing the mixture to attain equilibrium;
(d) measuring the amount of labelled ligand bound to the immobilized polypeptide or the whole cell or the cell membrane after step (c); and
(e) comparing the difference in the labelled ligand bound in step (b) and (d), such that the compound which causes the reduction in binding in step (d) is considered to be an agonist or antagonist.

The polypeptides may be found to modulate a variety of physiological and pathological processes in a dose-dependent manner in the above-described assays. Thus, the "functional equivalents" of the polypeptides of the invention include polypeptides that exhibit any of the same modulatory activities in the above-described assays in a dose-dependent manner. Although the degree of dose-dependent activity need not be identical to that of the polypeptides of the invention, preferably the "functional equivalents" will exhibit substantially similar dose-dependence in a given activity assay compared to the polypeptides of the invention.

The INSP141, INSP142, INSP143 and INSP144 exon polypeptides and the INSP141, INSP142, INSP143 and INSP144 polypeptides of the present invention may modulate cellular growth and differentiation. Thus, the biological activity of the INSP141, INSP142, INSP143 and INSP144 exon polypeptides and the INSP141, INSP142, INSP143 and INSP144 polypeptides can be examined in systems that allow the study of cellular growth and differentiation such as in vitro tissue culture. Stimulation or inhibition of cellular proliferation may be measured by a variety of assays.

For example, for observing cell growth inhibition, one can use a solid or liquid medium. In a solid medium, cells undergoing growth inhibition can easily be selected from the subject cell group by comparing the sizes of colonies formed. In a liquid medium, growth inhibition can be screened by measuring culture medium turbidity or incorporation of labelled thymidine in DNA. Typically, the incorporation of a nucleoside analog into newly synthesised DNA may be employed to measure proliferation (i.e., active cell growth) in a population of cells. For example, bromodeoxyuridine (BrdU) can be employed as a DNA labelling reagent and anti-BrdU mouse monoclonal antibodies can be employed as a detection reagent. This antibody binds only to cells containing DNA which has incorporated bromodeoxyuridine. A number of detection methods may be used in conjunction with this assay including immunofluorescence, immunohistochemical, ELISA, and calorimetric methods. Kits that include bromodeoxyuridine (BrdU) and anti-BrdU mouse monoclonal antibody are commercially available from Boehringer Mannheim (Indianapolis, Ind.).

The effect of the INSP141, INSP142, INSP143 and INSP144 exon polypeptides and the INSP141, INSP142, INSP143 and INSP144 polypeptides upon cellular differentiation can be measured by contacting stem cells or embryonic cells with various amounts of the polypeptides and observing the effect upon differentiation of the stem cells or embryonic cells. Tissue-specific antibodies and microscopy may be used to identify the resulting cells.

The INSP141, INSP142, INSP143 and INSP144 exon polypeptides and the INSP141, INSP142, INSP143 and INSP144 polypeptides may also be found to modulate immune and/or nervous system cell proliferation and differentiation in a dose-dependent manner in the above-described assays. Thus, the "functional equivalents" of the INSP141, INSP142, INSP143 and INSP144 exon polypeptides and the INSP141, INSP142, INSP143 and INSP144 polypeptides include polypeptides that exhibit any of the same growth and differentiation regulating activities in the above-described assays in a dose-dependent manner. Although the degree of dose-dependent activity need not be identical to that of the INSP141, INSP142, INSP143 and INSP144 exon polypeptides and the INSP141, INSP142, INSP143 and INSP144 polypeptides, preferably the "functional equivalents" will exhibit substantially similar dose-dependence in a given activity assay compared to the INSP141, INSP142, INSP143 and INSP144 exon polypeptides and the INSP141, INSP142, INSP143 and INSP144 polypeptides.

In certain of the embodiments described above, simple binding assays may be used, in which the adherence of a test compound to a surface bearing the polypeptide is detected by means of a label directly or indirectly associated with the test compound or in an assay involving competition with a labelled competitor. In another embodiment, competitive drug screening assays may be used, in which neutralising antibodies that are capable of binding the polypeptide specifically compete with a test compound for binding. In this manner, the antibodies can be used to detect the presence of any test compound that possesses specific binding affinity for the polypeptide.

Assays may also be designed to detect the effect of added test compounds on the production of mRNA encoding the polypeptide in cells. For example, an ELISA may be constructed that measures secreted or cell-associated levels of polypeptide using monoclonal or polyclonal antibodies by standard methods known in the art, and this can be used to search for compounds that may inhibit or enhance the production of the poly-peptide from suitably manipulated cells or tissues. The formation of binding complexes between the polypeptide and the compound being tested may then be measured.

Another technique for drug screening which may be used provides for high throughput screening of compounds having suitable binding affinity to the polypeptide of interest (see International patent application WO84/03564). In this method, large numbers of different small test compounds are synthesised on a solid substrate, which may then be reacted with the polypeptide of the invention and washed. One way of immobilising the polypeptide is to use non-neutralising antibodies. Bound polypeptide may then be detected using methods that are well known in the art. Purified polypeptide can also be coated directly onto plates for use in the aforementioned drug screening techniques.

Assay methods that are also included within the terms of the present invention are those that involve the use of the genes and polypeptides of the invention in overexpression or ablation assays. Such assays involve the manipulation of levels of these genes/polypeptides in cells and assessment of the impact of this manipulation event on the physiology of the manipulated cells. For example, such experiments reveal details of signalling and metabolic pathways in which the particular genes/polypeptides are implicated, generate information regarding the identities of polypeptides with which the studied polypeptides interact and provide clues as to methods by which related genes and proteins are regulated Another technique for drug screening which may be used provides for high throughput screening of compounds having suitable binding affinity to the polypeptide of interest (see International patent application WO84/03564). In this method, large numbers of different small test compounds are synthesised on a solid substrate, which may then be reacted with the polypeptide of the invention and washed. One way of immobilising the polypeptide is to use non-neutralising antibodies. Bound polypeptide may then be detected using methods that are well known in the art. Purified polypeptide can also be coated directly onto plates for use in the aforementioned drug screening techniques.

Examples of suitable assays for the identification of agonists or antagonists of the polypeptides of the invention are described in Rosen et al., Curr. Opin. Drug Discov. Devel. 2003 6(2):224-30.

The polypeptide of the invention may be used to identify membrane-bound or soluble receptors, through standard receptor binding techniques that are known in the art, such as ligand binding and crosslinking assays in which the polypeptide is labelled with a radioactive isotope, is chemically modified, or is fused to a peptide sequence that facilitates its detection or purification, and incubated with a source of the putative receptor (for example, a composition of cells, cell membranes, cell supernatants, tissue extracts, or bodily fluids). The efficacy of binding may be measured using biophysical techniques such as surface plasmon resonance and spectroscopy. Binding assays may be used for the purification and cloning of the receptor, but may also identify agonists and antagonists of the polypeptide, that compete with the binding of the polypeptide to its receptor. Standard methods for conducting screening assays are well understood in the art.

In another embodiment, this invention relates to the use of a INSP141, INSP142, INSP143 or INSP144 polypeptide or fragment thereof, whereby the fragment is preferably a INSP141, INSP142, INSP143 or INSP144 gene-specific fragment, for isolating or generating an agonist or stimulator of the INSP141, INSP142, INSP143 or INSP144 polypeptide for the treatment of an immune related disorder, wherein said agonist or stimulator is selected from the group consisting of:

1. a specific antibody or fragment thereof including: a) a chimeric, b) a humanized or c) a fully human antibody, as well as;
2. a bispecific or multispecific antibody,
3. a single chain (e.g. scFv) or
4. single domain-antibody, or
5. a peptide- or non-peptide mimetic derived from said antibodies or
6. an antibody-mimetic such as a) an anticalin or b) a fibronectin-based binding molecule (e.g. trinectin or adnectin).

The generation of peptide- or non-peptide mimetics from antibodies is known in the art (Saragovi et al., 1991 and Saragovi et al., 1992).

Anticalins are also known in the art (Vogt et al., 2004). Fibronectin-based binding molecules are described in U.S. Pat. No. 6,818,418 and WO2004029224.

Furthermore, the test compound may be of various origin, nature and composition, such as any small molecule, nucleic acid, lipid, peptide, polypeptide including an antibody such as a chimeric, humanized or fully human antibody or an antibody fragment, peptide- or non-peptide mimetic derived therefrom as well as a bispecific or multispecific antibody, a single chain (e.g. scFv) or single domain antibody or an antibody-mimetic such as an anticalin or fibronectin-based binding molecule (e.g. trinectin or adnectin), etc., in isolated form or in mixture or combinations.

The invention also includes a screening kit useful in the methods for identifying agonists, antagonists, ligands, receptors, substrates, enzymes, that are described above.

The invention includes the agonists, antagonists, ligands, receptors, substrates and enzymes, and other compounds which modulate the activity or antigenicity of the polypeptide of the invention discovered by the methods that are described above.

As mentioned above, it is envisaged that the various moieties of the invention (i.e. the polypeptides of the first aspect of the invention, a nucleic acid molecule of the second or third aspect of the invention, a vector of the fourth aspect of the invention, a host cell of the fifth aspect of the invention, a ligand of the sixth aspect of the invention, a compound of the seventh aspect of the invention) may be useful in the therapy or diagnosis of diseases. To assess the utility of the moieties of the invention for treating or diagnosing a disease one or more of the following assays may be carried out. Note that although some of the following assays refer to the test compound as being a protein/polypeptide, a person skilled in the art will readily be able to adapt the following assays so that the other moieties of the invention may also be used as the "test compound".

The invention also provides pharmaceutical compositions comprising a polypeptide, nucleic acid, ligand or compound of the invention in combination with a suitable pharmaceutical carrier. These compositions may be suitable as therapeutic or diagnostic reagents, as vaccines, or as other immunogenic compositions, as outlined in detail below.

According to the terminology used herein, a composition containing a polypeptide, nucleic acid, ligand or compound [X] is "substantially free of" impurities [herein, Y] when at least 85% by weight of the total X+Y in the composition is X. Preferably, X comprises at least about 90% by weight of the total of X+Y in the composition, more preferably at least about 95%, 98% or even 99% by weight.

The pharmaceutical compositions should preferably comprise a therapeutically effective amount of the polypeptide, nucleic acid molecule, ligand, or compound of the invention. The term "therapeutically effective amount" as used herein refers to an amount of a therapeutic agent needed to treat, ameliorate, or prevent a targeted disease or condition, or to exhibit a detectable therapeutic or preventative effect. For any compound, the therapeutically effective dose can be estimated initially either in cell culture assays, for example, of neoplastic cells, or in animal models, usually mice, rabbits, dogs, or pigs. The animal model may also be used to determine the appropriate concentration range and route of administration. Such information can then be used to determine useful doses and routes for administration in humans.

The precise effective amount for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. Generally, an effective dose will be from 0.01 mg/kg to 50 mg/kg, preferably 0.05 mg/kg to 10 mg/kg. Compositions may be administered individually to a patient or may be administered in combination with other agents, drugs or hormones.

A pharmaceutical composition may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity. Suitable carriers may be large, slowly metabolised macromolecules such as proteins, polysaccharides, polylactic acids, polyglycolic acids, polymeric amino acids, amino acid copolymers and inactive virus particles.

Pharmaceutically acceptable salts can be used therein, for example, mineral acid salts such as hydrochlorides, hydrobromides, phosphates, sulphates, and the like; and the salts of organic acids such as acetates, propionates, malonates, benzoates, and the like. A thorough discussion of pharmaceutically acceptable carriers is available in Remington's Pharmaceutical Sciences (Mack Pub. Co., N.J. 1991).

Pharmaceutically acceptable carriers in therapeutic compositions may additionally Contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The pharmaceutical compositions utilised in this invention may be administered by any number of routes including, but not limited to, oral, intravenous, intramuscular, intra-arterial, intramedullary, intrathecal, intraventricular, transdermal or transcutaneous applications (for example, see WO98/20734), subcutaneous, intraperitoneal, intranasal, enteral, topical, sublingual, intravaginal or rectal means. Gene guns or hyposprays may also be used to administer the pharmaceutical compositions of the invention. Typically, the therapeutic compositions may be prepared as injectables, either as liquid solutions or suspensions; solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

If the activity of the polypeptide of the invention is in excess in a particular disease state, several approaches are available. One approach comprises administering to a subject an inhibitor compound (antagonist) as described above, along with a pharmaceutically acceptable carrier in an amount effective to inhibit the function of the polypeptide, such as by blocking the binding of ligands, substrates, enzymes, receptors, or by inhibiting a second signal, and thereby alleviating the abnormal condition. Preferably, such antagonists are antibodies. Most preferably, such antibodies are chimeric and/or humanised to minimise their immunogenicity, as described previously.

In another approach, soluble forms of the polypeptide that retain binding affinity for the ligand, substrate, enzyme, receptor, in question, may be administered. Typically, the polypeptide may be administered in the form of fragments that retain the relevant portions.

In an alternative approach, expression of the gene encoding the polypeptide can be inhibited using expression blocking techniques, such as the use of antisense nucleic acid molecules (as described above), either internally generated or separately administered. Modifications of gene expression can be obtained by designing complementary sequences or antisense molecules (DNA, RNA, or PNA) to the control, 5' or regulatory regions (signal sequence, promoters, enhancers and introns) of the gene encoding the polypeptide. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, Molecular and Immunologic Approaches, Futura Publishing Co., Mt. Kisco, N.Y.). The complementary sequence or antisense molecule may also be designed to block translation of mRNA by preventing the transcript from binding to ribosomes. Such oligonucleotides may be administered or may be generated in situ from expression in vivo.

In addition, expression of the polypeptide of the invention may be prevented by using ribozymes specific to its encoding mRNA sequence. Ribozymes are catalytically active RNAs that can be natural or synthetic (see for example Usman, N, et al., Curr. Opin. Struct. Biol (1996) 6(4), 527-33). Synthetic ribozymes can be designed to specifically cleave mRNAs at selected positions thereby preventing translation of the mRNAs into functional polypeptide. Ribozymes may be synthesised with a natural ribose phosphate backbone and natural bases, as normally found in RNA molecules. Alternatively the ribozymes may be synthesised with non-natural backbones, for example, 2'-O-methyl RNA, to provide protection from ribonuclease degradation and may contain modified bases.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of non-traditional bases such as inosine, queosine and butosine, as well as acetyl-, methyl-, thio- and similarly modified forms of adenine, cytidine, guanine, thymine and uridine which are not as easily recognised by endogenous endonucleases.

For treating abnormal conditions related to an under-expression of the polypeptide of the invention and its activity, several approaches are also available. One approach comprises administering to a subject a therapeutically effective amount of a compound that activates the polypeptide, i.e., an agonist as described above, to alleviate the abnormal condition. Alternatively, a therapeutic amount of the polypeptide in combination with a suitable pharmaceutical carrier may be administered to restore the relevant physiological balance of polypeptide.

Gene therapy may be employed to effect the endogenous production of the polypeptide by the relevant cells in the subject. Gene therapy is used to treat permanently the inappropriate production of the polypeptide by replacing a defective gene with a corrected therapeutic gene.

Gene therapy of the present invention can occur in vivo or ex vivo. Ex vivo gene therapy requires the isolation and purification of patient cells, the introduction of a therapeutic gene and introduction of the genetically altered cells back into the patient. In contrast, in vivo gene therapy does not require isolation and purification of a patient's cells.

The therapeutic gene is typically "packaged" for administration to a patient. Gene delivery vehicles may be non-viral, such as liposomes, or replication-deficient viruses, such as adenovirus as described by Berkner, K. L., in Curr. Top. Microbiol. Immunol., 158, 39-66 (1992) or adeno-associated virus (AAV) vectors as described by Muzyczka, N., in Curr. Top. Microbiol. Immunol., 158, 97-129 (1992) and U.S. Pat. No. 5,252,479. For example, a nucleic acid molecule encoding a polypeptide of the invention may be engineered for expression in a replication-defective retroviral vector. This expression construct may then be isolated and introduced into a packaging cell transduced with a retroviral plasmid vector containing RNA encoding the polypeptide, such that the packaging cell now produces infectious viral particles containing the gene of interest. These be administered to a subject for engineering cells in vivo and expression of the polypeptide in vivo (see Chapter 20, Gene Therapy and other Molecular Genetic-based Therapeutic Approaches, (and references cited therein) in Human Molecular Genetics (1996), T Strachan and A P Read, BIOS Scientific Publishers Ltd).

Another approach is the administration of "naked DNA" in which the therapeutic gene is directly injected into the bloodstream or muscle tissue.

In situations in which the polypeptides or nucleic acid molecules of the invention are disease-causing agents, the invention provides that they can be used in vaccines to raise antibodies against the disease causing agent.

Vaccines according to the invention may either be prophylactic (i.e. to prevent infection) or therapeutic (i.e. to treat disease after infection). Such vaccines comprise immunising antigen(s), immunogen(s), polypeptide(s), protein(s) or nucleic acid, usually in combination with pharmaceutically-acceptable carriers as described above, which include any carrier that does not itself induce the production of antibodies harmful to the individual receiving the composition. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, and other pathogens.

Since polypeptides may be broken down in the stomach, vaccines comprising polypeptides are preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation isotonic with the blood of the recipient, and aqueous and non-aqueous sterile suspensions which may include suspending agents or thickening agents.

The vaccine formulations of the invention may be presented in unit-dose or multi-dose containers. For example, sealed ampoules and vials and may be stored in a freeze-dried condition requiring only the addition of the sterile liquid carrier immediately prior to use. The dosage will depend on the specific activity of the vaccine and can be readily determined by routine experimentation.

Genetic delivery of antibodies that bind to polypeptides according to the invention may also be effected, for example, as described in International patent application WO98/55607. The technology referred to as jet injection (see, for example, See Worldwide Website: powderject.com) may also be useful in the formulation of vaccine compositions.

A number of suitable methods for vaccination and vaccine delivery systems are described in International patent application WO00/29428.

This invention also relates to the use of nucleic acid molecules according to the present invention as diagnostic reagents. Detection of a mutated form of the gene characterised by the nucleic acid molecules of the invention which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acid molecules for diagnosis may be obtained from a subject's cells, such as from blood, urine, saliva, tissue biopsy or autopsy material. The genomic DNA may be used directly for detection or may be amplified enzymatically by using PCR, ligase chairs reaction (LCR), strand displacement amplification (SDA), or other amplification techniques (see Saiki et al., Nature, 324, 163-166 (1986); Bej, et al., Crit. Rev. Biochem Molec. Biol., 26, 301-334 (1991); Birkenmeyer et al., J. Virol. Meth., 35, 117-126 (1991); Van Brunt, J., Bio/Technology, 8, 291-294 (1990)) prior to analysis.

In one embodiment, this aspect of the invention provides a method of diagnosing a disease in a patient, comprising assessing the level of expression of a natural gene encoding a polypeptide according to the invention and comparing said level of expression to a control level, wherein a level that is different to said control level is indicative of disease. The method may comprise the steps of:

a) contacting a sample of tissue from the patient with a nucleic acid probe under stringent conditions that allow the formation of a hybrid complex between a nucleic acid molecule of the invention and the probe;

b) contacting a control sample with said probe under the same conditions used in step a);

c) and detecting the presence of hybrid complexes in said samples;

wherein detection of levels of the hybrid complex in the patient sample that differ from levels of the hybrid complex in the control sample is indicative of disease.

A further aspect of the invention comprises a diagnostic method comprising the steps of:

a) obtaining a tissue sample from a patient being tested for disease;

b) isolating a nucleic acid molecule according to the invention from said tissue sample; and c) diagnosing the patient for disease by detecting the presence of a mutation in the nucleic acid molecule which is associated with disease.

To aid the detection of nucleic acid molecules in the above-described methods, an amplification step, for example using PCR, may be included.

A further aspect of the invention comprises a diagnostic method comprising the steps of:
a) obtaining a tissue sample from a patient being tested for disease;
b) isolating a nucleic acid molecule according to the invention from said tissue sample; and
c) diagnosing the patient for disease by detecting the presence of a mutation in the nucleic acid molecule which is associated with disease.

To aid the detection of nucleic acid molecules in the above-described methods, an amplification step, for example using PCR, may be included. Suitable probes are discussed in some detail above.

Deletions and insertions can be detected by a change in the size of the amplified product in comparison to the normal genotype. Point mutations can be identified by hybridizing amplified DNA to labelled RNA of the invention or alternatively, labelled antisense DNA sequences of the invention. Perfectly-matched sequences can be distinguished from mismatched duplexes by RNase digestion or by assessing differences in melting temperatures. The presence or absence of the mutation in the patient may be detected by contacting DNA with a nucleic acid probe that hybridises to the DNA tinder stringent conditions to form a hybrid double-stranded molecule, the hybrid double-stranded molecule having an unhybridised portion of the nucleic acid probe strand at any portion corresponding to a mutation associated with disease; and detecting the presence or absence of an unhybridised portion of the probe strand as an indication of the presence or absence of a disease-associated mutation in the corresponding portion of the DNA strand.

Such diagnostics are particularly useful for prenatal and even neonatal testing.

Point mutations and other sequence differences between the reference gene and "mutant" genes can be identified by other well-known techniques, such as direct DNA sequencing or single-strand conformational polymorphism, (see Orita et al., Genomics, 5, 874-879 (1989)). For example, a sequencing primer may be used with double-stranded PCR product or a single-stranded template molecule generated by a modified PCR. The sequence determination is performed by conventional procedures with radiolabelled nucleotides or by automatic sequencing procedures with fluorescent-tags. Cloned DNA segments may also be used as probes to detect specific DNA segments. The sensitivity of this method is greatly enhanced when combined with PCR. Further, point mutations and other sequence variations, such as polymorphisms, can be detected as described above, for example, through the use of allele-specific oligonucleotides for PCR amplification of sequences that differ by single nucleotides.

DNA sequence differences may also be detected by alterations in the electrophoretic mobility of DNA fragments in gels, with or without denaturing agents, or by direct DNA sequencing (for example, Myers et al., Science (1985) 230: 1242). Sequence changes at specific locations may also be revealed by nuclease protection assays, such as RNase and S1 protection or the chemical cleavage method (see Cotton et al., Proc. Natl. Acad. Sci. USA (1985) 85: 4397-4401).

In addition to conventional gel electrophoresis and DNA sequencing, mutations such as microdeletions, aneuploidies, translocations, inversions, can also be detected by in situ analysis (see, for example, Keller et al., DNA Probes, 2nd Ed., Stockton Press, New York, N.Y., USA (1993)), that is, DNA or RNA sequences in cells can be analysed for mutations without need for their isolation and/or immobilisation onto a membrane. Fluorescence in situ hybridization (FISH) is presently the most commonly applied method and numerous reviews of FISH have appeared (see, for example, Trachuck et al., Science, 250, 559-562 (1990), and Trask et al., Trends, Genet., 7, 149-154 (1991)).

In another embodiment of the invention, an array of oligonucleotide probes comprising a nucleic acid molecule according to the invention can be constructed to conduct efficient screening of genetic variants, mutations and polymorphisms. Array technology methods are well known and have general applicability and can be used to address a variety of questions in molecular genetics including gene expression, genetic linkage, and genetic variability (see for example: M. Chee et al., Science (1996), Vol 274, pp 610-613).

In one embodiment, the array is prepared and used according to the methods described in PCT application WO95/11995 (Chee et al); Lockhart, D. J. et al. (1996) Nat. Biotech. 1.4: 1675-1680); and Schena, M. et al. (1996) Proc. Natl. Acad. Sci. 93: 10614-10619). Oligonucleotide pairs may range from two to over one million. The oligomers are synthesized at designated areas on a substrate using a light-directed chemical process. The substrate may be paper, nylon or other type of membrane, filter, chip, glass slide or any other suitable solid support. In another aspect, an oligonucleotide may be synthesized on the surface of the substrate by using a chemical coupling procedure and an ink jut application apparatus, as described in PCT application WO95/25116 (Baldeschweiler et al.). In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blat or dot blot apparatus), materials (any suitable solid support), and machines (including robotic instruments), and may contain 8, 24, 96, 384, 1536 or 6144 oligonucleotides, or any other number between two and over one million which lends itself to the efficient use of commercially-available instrumentation.

In addition to the methods discussed above, diseases may be diagnosed by methods comprising determining, from a sample derived from a subject, an abnormally decreased (r increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods.

Assay techniques that can be used to determine levels of a polypeptide of the present invention in a sample derived from a host are well-known to those of skill in the art and are discussed in some detail above (including radioimmunoassays, competitive-binding assays, Western Blot analysis and ELISA assays). This aspect of the invention provides a diagnostic method which comprises the steps of: (a) contacting a ligand as described above with a biological sample under conditions suitable for the formation of a ligand-polypeptide complex; and (b) detecting said complex.

Protocols such as ELISA, RIA, and FACS for measuring polypeptide levels may additionally provide a basis for diagnosing altered or abnormal levels of polypeptide expression. Normal or standard values for polypeptide expression are established by combining body fluids or cell extracts taken from normal mammalian subjects, preferably humans, with antibody to the polypeptide under conditions suitable for complex formation The amount of standard complex formation may be quantified by various methods, such as 4 by photometric means.

Antibodies which specifically bind to a polypeptide of the invention may be used for the diagnosis of conditions or diseases characterised by expression of the polypeptide, or in assays to monitor patients being treated with the polypeptides, nucleic acid molecules, ligands and other compounds of the invention. Antibodies useful for diagnostic purposes may be prepared in the same manner as those described above for therapeutics. Diagnostic assays for the polypeptide include methods that utilise the antibody and a label to detect the polypeptide in human body fluids or extracts of cells or tissues. The antibodies may be used with or without modification, and may be labelled by joining them, either covalently or non-covalently, With a reporter molecule. A wide variety of reporter molecules known in the art may be used, several of which are described above.

Quantities of polypeptide expressed in subject, control and disease samples from biopsied tissues are compared with the standard values. Deviation between standard and subject values establishes the parameters for diagnosing disease. Diagnostic assays may be used to distinguish between absence, presence, and excess expression of polypeptide and to monitor regulation of polypeptide levels during therapeutic intervention. Such assays may also be used to evaluate the efficacy of a particular therapeutic treatment regimen in animal studies, in clinical trials or in monitoring the treatment of an individual patient.

A diagnostic kit of the present invention may comprise:
(a) a nucleic acid molecule of the present invention;
(b) a polypeptide of the present invention; or
(c) a ligand of the present invention.

In one aspect of the invention, a diagnostic kit may comprise a first container containing a nucleic acid probe that hybridises under stringent conditions with a nucleic acid molecule according to the invention; a second container containing primers useful for amplifying the nucleic acid molecule; and instructions for using the probe and primers for facilitating the diagnosis of disease. The kit may further comprise a third container holding an agent for digesting unhybridised RNA.

In an alternative aspect of the invention, a diagnostic kit may comprise an array of nucleic acid molecules, at least one of which may be a nucleic acid molecule according to the invention.

To detect polypeptide according to the invention, a diagnostic kit may comprise one or more antibodies that bind to a polypeptide according to the invention; and a reagent useful for the detection of a binding reaction between the antibody and the polypeptide.

Such kits will be of use in diagnosing a disease or susceptibility to disease in which I-domain containing proteins are implicated. Such diseases may include cell proliferative disorders, including neoplasm, melanoma, lung, colorectal, breast, pancreas, head and neck and other solid tumours; myeloproliferative disorders, such as leukemia, non-Hodgkin lymphoma, leukopenia, thrombocytopenia, angiogenesis disorder, Kaposis' sarcoma; autoimmune/inflammatory disorders, including allergy, inflammatory bowel disease, arthritis, psoriasis and respiratory tract inflammation, asthma, and organ transplant rejection; cardiovascular disorders, including hypertension, oedema, angina, atherosclerosis, thrombosis, sepsis, shock, reperfusion injury, and ischemia; neurological disorders including central nervous system disease, Alzheimer's disease, brain injury, amyotrophic lateral sclerosis, and pain; developmental disorders; metabolic disorders including diabetes mellitus, osteoporosis, and obesity, AIDS and renal disease; infections including viral infection, bacterial infection, fungal infection and parasitic infection and other pathological conditions. Preferably, the diseases are those in which vWFA and/or ANT_IG domain containing proteins are implicated. Examples of diseases in which vWFA and/or ANT_IG domain containing proteins are implicated include; bacterial infections, bacterial intoxications, anthrax, blockage of toxins (e.g. bacterial toxins), cancer, tumour endothelium, colorectal cancer, bladder cancer, oesophageal cancer, lung cancer, melanoma, juvenile hyaline fibromatosis (JFH), infantile systemic hyalinosis (ISH), von Willebrand disease, Bethlem myopathy, epidemolysis bullosa dystrophica, thrombosis, modulation of platelet-mediated aggregation, autoimmune diseases and inflammation. Such kits may also be used for the detection of reproductive disorders including infertility.

Various aspects and embodiments of the present invention will now be described in more detail by way of example, with particular reference to the INSP141, INSP142, INSP143 and INSP144 exon polypeptides and the INSP141, INSP142, INSP143 and INSP144 polypeptides.

It will be appreciated that modification of detail may be made without departing from the scope of the invention.

BRIEF DESCRIPTION OF THE FIGURES

FIG. 1: Top ten results from BLAST against NCBI non-redundant database using SEQ ID NO:24 (INSP141 full protein sequence).

FIG. 2: Alignment generated by BLAST between SEQ ID NO:52 (INSP142 full protein sequence) and the top five hits, FIG. 3: Top ten results from BLAST against NCBI non-redundant database using SEQ ID NO:90 (INSP143 full protein sequence).

FIG. 4: Top ten results from BLAST against NCBI non-redundant database using SEQ ID NO:126 (INSP143 full protein sequence).

FIG. 5: Alignment of INSP141, INSP142, INSP143 and INSP144 coding exons.

FIG. 6: Alignment of the ORFs of INSP141 (SEQ ID NO: 24), clonedINSP141 (SEQ ID NO: 128), INSP142 (SEQ ID NO: 52), clonedINSP142 (SEQ ID NO: 136), INSP143 (SEQ ID NO: 90), clonedINSP143 (SEQ ID NO: 138), INSP144 (SEQ ID NO: 126). P259A in INSP142 is indicated by shading.

FIG. 7: Nucleotide alignment of INSP141 (SEQ ID NO: 24), INSP142 (SEQ ID NO: 52), INSP143 (SEQ ID NO: 90), INSP144 (SEQ ID NO: 126). Upper case denotes coding sequence. Lower case denotes untranslated regions.

FIG. 8: Schematic representation of predicted and cloned INSP141, INSP142, INSP143, INSP144, TMEM8 and CMG2.

FIG. 9: Amino acid alignment of the extracellular vWFA and ANT_IG domains of INSP141 (SEQ ID NO: 24), INSP142 (SEQ ID NO: 52), INSP143 (SEQ ID NO: 90), INSP144 (SEQ ID NO: 126), TMEM8 and CMG2. Identical residues are indicated by an asterisk. Secondary structure assignments can be deduced from Lacy et al. PNAS. VOL. 101. No. 17. pp. 6367-6372. The five MIDAS motif residues of each protein are indicated by shading. ATR1_HUMAN: NCBI Acc. No. q9h6x2. ATR2_HUMAN: NCBI Acc. No. P58335.

FIG. 10: Expression of INSP142 in major human tissues as measured by RT-PCR (TaqMan).

FIG. 11: Expression of INSP142 in comparative human tissues as measured by RT-PCR (TaqMan).

FIG. 12: Expression of INSP142 in secretory and immune tissues as measured by RT-PCR (TaqMan).

FIG. 13: Expression of INSP142 in primary cells and cell lines as measured by RT-PCR (TaqMan).

FIG. 14: Expression of INSP142 in primary cells and cell lines of immune or CNS origin as measured by RT-PCR (TaqMan).

FIG. 15: Expression of INSP142 in diseased colon and ileum biopsies as measured by RT-PCR (TaqMan).

FIG. 16: Expression of INSP142 in diseased skin biopsies from IL18BP clinical trial as measured by RT-PCR (TaqMan).

TABLE 1

| Amino Acid | Synonymous Groups | More Preferred Synonymous Groups |
| --- | --- | --- |
| Ser | Gly, Ala, Ser, Thr, Pro | Thr, Ser |
| Arg | Asn, Lys, Gln, Arg, His | Arg, Lys, His |
| Leu | Phe, Ile, Val, Leu, Met | Ile, Val, Leu, Met |
| Pro | Gly, Ala, Ser, Thr, Pro | Pro |
| Thr | Gly, Ala, Ser, Thr, Pro | Thr, Ser |
| Ala | Gly, Thr, Pro, Ala, Ser | Gly, Ala |
| Val | Met, Phe, Ile, Leu, Val | Met, Ile, Val, Leu |
| Gly | Ala, Thr, Pro, Ser, Gly | Gly, Ala |
| Ile | Phe, Ile, Val, Leu, Met | Ile, Val, Leu, Met |
| Phe | Trp, Phe, Tyr | Tyr, Phe |
| Tyr | Trp, Phe, Tyr | Phe, Tyr |
| Cys | Ser, Thr, Cys | Cys |
| His | Asn, Lys, Gln, Arg, His | Arg, Lys, His |
| Gln | Glu, Asn, Asp, Gln | Asn, Gln |
| Asn | Glu, Asn, Asp, Gln | Asn, Gln |
| Lys | Asn, Lys, Gln, Arg, His | Arg, Lys, His |
| Asp | Glu, Asn, Asp, Gln | Asp, Glu |
| Glu | Glu, Asn, Asp, Gln | Asp, Glu |
| Met | Phe, Ile, Val, Leu, Met | Ile, Val, Leu, Met |
| Trp | Trp, Phe, Tyr | Trp |

TABLE 2

| Amino Acid | Synonymous Groups |
| --- | --- |
| Ser | D-Ser, Thr, D-Thr, allo-Thr, Met, D-Met, Met(O), D-Met(O), L-Cys, D-Cys |
| Arg | D-Arg, Lys, D-Lys, homo-Arg, D-homo-Arg, Met, Ile, D-.Met, D-Ile, Orn, D-Orn |
| Leu | D-Leu, Val, D-Val, AdaA, AdaG, Leu, D-Leu, Met, D-Met |
| Pro | D-Pro, L-I-thioazolidine-4-carboxylic acid, D-or L-1-oxazolidine-4-carboxylic acid |
| Thr | D-Thr, Ser, D-Ser, allo-Thr, Met, D-Met, Met(O), D-Met(O), Val, D-Val |
| Ala | D-Ala, Gly, Aib, B-Ala, Acp, L-Cys, D-Cys |
| Val | D-Val, Leu, D-Leu, Ile, D-Ile, Met, D-Met, AdaA, AdaG |
| Gly | Ala, D-Ala, Pro, D-Pro, Aib, .beta.-Ala, Acp |
| Ile | D-Ile, Val, D-Val, AdaA, AdaG, Leu, D-Leu, Met, D-Met |
| Phe | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa |
| Tyr | D-Tyr, Phe, D-Phe, L-Dopa, His, D-His |
| Cys | D-Cys, S--Me--Cys, Met, D-Met, Thr, D-Thr |
| Gln | D-Gln, Asn, D-Asn, Glu, D-Glu, Asp, D-Asp |
| Asn | D-Asn, Asp, D-Asp, Glu, D-Glu, Gln, D-Gln |
| Lys | D-Lys, Arg, D-Arg, homo-Arg, D-homo-Arg, Met, D-Met, Ile, D-Ile, Orn, D-Orn |
| Asp | D-Asp, D-Asn, Asn, Glu, D-Glu, Gln, D-Gln |
| Glu | D-Glu, D-Asp, Asp, Asn, D-Asn, Gln, D-Gln |
| Met | D-Met, S--Me--Cys, Ile, D-Ile, Leu, D-Leu, Val, D-Val |

EXAMPLES

Example 1

INSP141

The polypeptide sequence derived from combining SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22 is SEQ ID NO:24, which represents the translation of consecutive exons from INSP141. This polypeptide sequence was used as a query for a BLASTp of the NCBI non-redundant database. The top ten matches are shown in FIG. 1. As can be seen in FIG. 1, INSP141 shares homology to the anthrax toxin receptor precursor protein.

Example 2

INSP142

The polypeptide sequence derived from combining SEQ ID NO:26, SEQ ID NO:28, SEQ ID NO:30, SEQ ID NO:32, SEQ ID NO:34, SEQ ID NO:36; SEQ ID NO:38, SEQ ID NO:40, SEQ ID NO:42, SEQ ID NO:44, SEQ ID NO:46, SEQ ID NO:48, SEQ ID NO:50 is SEQ ID NO:52, which represents the translation of consecutive exons from INSP142. This polypeptide sequence was used as a query for a BLASTp of the NCBI non-redundant database. The top ten matches are shown in FIG. 2. As can be seen in FIG. 2, INSP141 shares homology to the anthrax toxin receptor precursor protein.

Example 3

INSP143

The polypeptide sequence derived from combining SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82; SEQ ID NO:84, SEQ ID NO:86, SEQ ID NO:88 is SEQ ID NO:90; which represents the translation of consecutive exons from INSP143. This polypeptide sequence was used as a query for a BLASTp of the NCBI non-redundant database. The top ten matches are shown in FIG. 3. As can be seen in FIG. 3, INSP143 shares homology to the anthrax toxin receptor precursor protein.

Example 4

INSP144

The polypeptide sequence derived from combining SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108 SEQ ID NO:110, SEQ ID NO:112, SEQ ID NO:114, SEQ ID NO:116, SEQ ID NO:118, SEQ ID NO:120, SEQ ID NO:122, SEQ ID NO:124 is SEQ ID NO:126, which represents the translation of consecutive exons from INSP143. This polypeptide sequence was used as a query for a BLASTp of the NCBI non-redundant database. The top ten matches are shown in FIG. 4. As can be seen in FIG. 4, INSP141 shares homology to the anthrax toxin receptor precursor protein.

Example 5

Signal Sequence

INSP141, INSP142, INSP143 and INSP144 are all predicted to possess a signal peptide at the start of the protein. The signal sequence, according to FIG. 6, spans from amino acid 1 to 27 (i.e. MGSHESLGPYFLVFLLLLLLPPPLFRA (SEQ ID NO: 152) of the INSP141, INSP142, INSP143 and INSP144 polypeptide sequence. The signal peptide cleavage site is between residues 27 and 28 of the INSP141, INSP142, INSP143 and INSP144 polypeptide sequence.

Example 6

Transmembrane Predictions

INSP141 and INSP142 are predicted to be secreted proteins, which do not contain transmembrane regions (FIGS. 6 and 7).

INSP143 and INSP144 are predicted to contain a transmembrane region (FIGS. 6 and 7). For both INSP143 and INSP144 the N-terminal is extracellular and the C-terminal intracellular.

INSP141 and INSP142, being soluble isoforms, could modulate the function of the integral isoforms INSP143 and INSP144.

Example 7

Summary of Cloning INSP141, INSP142 and INSP143-EC

INSP141, INSP142, INSP143, INSP144 are a family of splice variants of an anthrax receptor-like sequence prediction containing a vWF-I/A domain. All the sequences are full length and contain a predicted signal peptide.

INSP141 is a prediction for a 306 amino acid ORF (918 bp) encoded in 11 exons. INSP142 is a prediction for a 352 amino acid ORF (1056 bp) encoded in 13 exons. INSP143 is a prediction for a 608 amino acid ORF (1824 bp) encoded in 18 exons. INSP144 is a prediction for a 631 amino acid ORF (1893 bp) encoded in 17 exons. INSP141 and INSP142 are predicted to be secreted proteins. INSP143 and INSP144 are predicted to be type I transmembrane proteins. The extracellular domain cloned for INSP143 is identical to the extracellular domain of INSP144. A diagram of alignment of the exons of the different sequences is shown in FIG. 5. An alignment of the amino acid sequences of the ORFs and of the cloned sequences is shown in FIG. 6. An alignment of the nucleotide sequences of the predictions is shown in FIG. 7.

7.1 Preparation of Human cDNA Templates

First strand cDNA was prepared from a variety of normal human tissue total RNA samples (Clontech, Stratagene, Ambion, Biochain Institute and in-house preparations) using Superscript II RNase H⁻ Reverse Transcriptase (Invitrogen) according to the manufacturer's protocol. The following solution was prepared in a 1.5 ml Eppendorf tube:

Oligo $(dT)_{15}$ primer (1 µl at 500 µg/ml) (Promega),

2 µg human total RNA,

1 µl 10 mM dNTP mix (10 mM each of dATP, dGTP, dCTP and dTTP at neutral pH) and sterile distilled water to a final volume of 12 µl.

The solution was then, heated to 65° C. for 5 min and then chilled on ice. The contents were collected by brief centrifugation and 4 µl of 5× First-Strand Buffer, 2 µl 0.1 M DTT, and 1 µl RnaseOUT Recombinant Ribonuclease Inhibitor (40 units/µl, Invitrogen) were added. The contents of the tube were mixed gently and incubated at 42° C. for 2 min; then 1 µl (200 units) of SuperScript II enzyme was added and mixed gently by pipetting. The mixture was incubated at 42° C. for 50 min and then inactivated by heating at 70° C. for 15 min. To remove RNA complementary to the cDNA, 1 µl (2 units) of *E. Coli* RNase H (Invitrogen) was added and the reaction mixture incubated at 37° C. for 20 min. The final 21 µl reaction mix was diluted by adding 179 µl sterile water to give a total volume of 200 µl. The cDNA template used for the amplification of INSP141-INSP144 was derived from testis RNA.

7.2 cDNA Libraries

Human cDNA libraries (in bacteriophage lambda (λ) vectors) were purchased from Stratagene or Clontech or prepared at the Serono Pharmaceutical Research Institute in λ ZAP or λ GT10 vectors according to the manufacturer's protocol (Stratagene). Bacteriophage λ DNA was prepared from small scale cultures of infected *E. coli* host strain using the Wizard Lambda Preps DNA purification system according to the manufacturer's instructions (Promega, Corporation, Madison Wis.). cDNA library templates used for the amplification of INSP141-INSP144 were testis libraries and a mixed brain-lung-testis library.

7.3 Gene Specific Cloning Primers for PCR

A pairs of PCR primers having a length of between 18 and 25 bases was designed for amplifying the predicted coding sequence of the virtual cDNA using Primer Designer Software (Scientific & Educational Software, PO Box 72045, Durham, N.C. 27722-2045, USA). PCR primers were optimized to have a Tm close to 55±10° C. and a GC content of 40-60%. Primers were selected which had high selectivity for the target sequence (INSP141) with little or no none specific priming.

7.4 PCR Amplification of INSP141-INSP144 Family from Human cDNA Templates

Gene-specific cloning primers (INSP141-CP1 and INSP141-CP2, Table 3 and FIG. 7) were designed to amplify a cDNA fragment of 985 bp covering the entirety of the predicted INSP141 cds. The primer pair was used with the human testis cDNA samples and cDNA libraries as PCR templates. PCR was performed in a final volume of 50 µl containing:

1× PLATINUM Taq High Fidelity (HiFi) buffer,
2 mM MgSO$_4$,
200 µM dNTPs,
0.2 µM of each cloning primer,
1 unit of PLATINUM Taq DNA Polymerase High Fidelity (HiFi) (Invitrogen),
approximately 20 ng of template cDNA, and either 0× or 1× PCRx Enhancer solution (Invitrogen).

Cycling was performed using an MJ Research DNA Engine, programmed as follows: 94° C., 2 min; 40 cycles of 94° C., 30 sec, 57° C., 30 sec, and 68° C., 1 min 30 sec; followed by 1 cycle at 68° C. for 8 min and a holding cycle at 4° C.

30 µl of each amplification product was visualized on a 0.8% agarose gel in 1× TAE buffer (Invitrogen). Products of approximately the expected molecular weight were seen in the PCR products amplified from a testis cDNA library template. These products was purified from the gel using the Qiagen MinElute DNA Purification System (Qiagen), eluted in 10 µl of EB buffer (10 mM Tris.Cl, pH 8.5) and subcloned-directly.

7.5 Subcloning of PCR Products

The PCR products were subcloned into the topoisomerase I modified cloning vector (pCR4-TOPO) using the TA cloning kit purchased from the Invitrogen Corporation using the conditions specified by the manufacturer. Briefly, 4 µl of gel purified PCR product was incubated for 15 min at room temperature with 1 µl of TOPO vector and 1 µl salt solution. The reaction mixture was then transformed into *E. coli* strain TOP10 (Invitrogen) as follows: a 50 µl aliquot of One Shot TOP10 cells was thawed on ice and 2 µl of TOPO reaction was added. The mixture was incubated for 15 min on ice and then heat shocked by incubation at 42° C. for exactly 30 s. Samples were returned to ice and 250 µl of warm (room temperature) SOC media was added. Samples were incubated with shaking (220 rpm) for 1 h at 37° C. The transformation mixture was then plated on L-broth (LB) plates containing ampicillin (100 µg/ml) and incubated overnight at 37° C.

7.6 Plasmid DNA Preparation and Sequencing

A number of colonies were inoculated into 5 ml L-Broth (LB) containing ampicillin (100 µg/ml) and grown up overnight at 37° C. with shaking at 220 rpm. Miniprep plasmid DNA was prepared from the 5 ml culture using a Biorobot 8000 robotic system (Qiagen) or Wizard Plus SV Minipreps kit (Promega cat. no. 1460) according to the manufacturer's instructions. Plasmid DNA was eluted in 80 µl of sterile water. The DNA concentration was measured using a Spectramax 190 photometer (Molecular Devices). Plasmid DNA (200-500 ng) was subjected to DNA sequencing with the T3 primer using the BigDye Terminator system (Applied Biosystems cat. no. 4390246) according to the manufacturer's instructions. The primer sequence is shown in Table 3. Sequencing reactions were purified using Dye-Ex columns (Qiagen) or Montage SEQ 96 cleanup plates (Millipore cat. no. LSKS09624) then analyzed on an Applied Biosystems 3700 sequencer.

Sequence analysis identified a clone which matched the expected INSP142 sequence within the region amplified. An alignment of the nucleotide sequences of INSP141, INSP142 and INSP143 is shown in FIG. 7. The sequence contained the substitution P259A which was assumed to be a PCR-induced error. This sequence (1035 bp) is not the full length of the INSP142 cds due to the PCR primer positions. The sequence of the cloned cDNA fragment is deduced from FIG. 7. The plasmid of the cloned PCR product is pCR4-TOPO-INSP142 (truncated).

7.7 Creation of INSP141 cds and INSP143-ExtraCellular Domain (EC) by PCR

A pair of PCR amplification primers (INSP141-AP1 and INSP141-AP2, Table 3 and FIG. 7) was designed to re-amplify the portion of the INSP142 sequence cloned in plasmid pCR4-TOPO-INSP142 (truncated), which was common to the INSP141 and INSP142 cds and simultaneously add the 3'-most INSP141-specific 23 bp onto the 3' end of the product. An additional PCR primer (INSP143-AP1, Table 3 and FIG. 7) was also designed for use with INSP141-AP1 to re-amplify the portion of the INSP142 sequence cloned in plasmid pCR4-TOPO-INSP142 (truncated) which was common to the INSP143 and INSP142 cds and simultaneously add the 3'-most INSP143-specific 21 bp onto the 3' end of the product. The INSP141-AP1/INSP141-AP2 and INSP141-AP1/INSP143-AP1 primer pairs were used with plasmid pCR4-TOPO-INSP142 (truncated) as the PCR template in a final volume of 50 µl containing:

1× PLATINUM Taq High Fidelity (HiFi) buffer,
2 mM MgSO$_4$,
200 µM dNTPs,
0.2 µM of each amplification primer,
1 unit of PLATINUM Taq DNA Polymerase High Fidelity (HiFi) (Invitrogen),
approximately 300 ng of plasmid cDNA, and either 0×, 0.5×, 1×, or 2× PCRx Enhancer solution (Invitrogen).

Cycling was performed using an MJ Research DNA Engine, programmed as follows: 94° C., 2 min; 30 cycles of 94° C., 30 sec, 68° C., 1 min 30 sec; followed by 1 cycle at 68° C. for 7 min and a holding cycle at 4° C.

All 50 µl of each amplification product was visualized on a 0.8% agarose gel in 1× TAE buffer (Invitrogen). Products of approximately the expected molecular weight were purified from the gel using the Promega WIZARD PCR Preps DNA Purification System, eluted in 50 µl of water and subcloned directly.

TABLE 3

| INSP141, INSP142 and INSP143-EC domain cloning and sequencing primers | |
|---|---|
| Primer | Sequence (5'-3') |
| INSP141-CP1 | GTC ACA GGG ACA GCC AGA TA (SEQ ID NO: 153) |
| INSP141-CP2 | GCT GGT GAT GCT GAC ATT GC (SEQ ID NO: 154) |
| INSP141-AP1 | ATG GGG AGC CAT GAG TCC CTG GGG CCC TAC TTC CTG (SEQ ID NO: 155) |
| INSP141-AP2 | AGC TGA CTT CAA TAG AGT ACT CCC AAT GAT AGT GCT TTC ATT GAA GA (SEQ ID NO: 156) |
| INSP143-AP1 | GCG AAA AAT GCC ACA TGT GGT GCT GGT GAT GCT GAC ATT GCT CTT G (SEQ ID NO: 157) |

TABLE 3-continued

INSP141, INSP142 and INSP143-EC domain cloning and sequencing primers

| Primer | Sequence (5'-3') |
|---|---|
| 21M13 | TGT AAA ACG ACG GCC AGT (SEQ ID NO: 158) |
| M13REV | CAG GAA ACA GCT ATG ACC (SEQ ID NO: 159) |
| T7 | TAA TAC GAC TCA CTA TAG G (SEQ ID NO: 160) |
| T3 | ATT AAC CCT CAC TAA AGG (SEQ ID NO: 161) |

7.8 Subcloning of PCR Products

The PCR products were subcloned into the topoisomerase I modified cloning vector (pCR4-TOPO) using the TA cloning kit purchased from the Invitrogen Corporation using the conditions specified by the manufacturer. Briefly, 4 µl of gel purified PCR product was incubated for 15 min at room temperature with 1 µl of TOPO vector and 1 µl salt solution. The reaction mixture was then transformed into E. coli strain TOP10 (Invitrogen) as follows: a 50 µl aliquot of One Shot TOP10 cells was thawed on ice and 2 µl of TOPO reaction was added. The mixture was incubated for 15 min on ice and then heat shocked by incubation at 42° C. for exactly 30 s. Samples were returned to ice and 250 µl of warm (room temperature) SOC media was added. Samples were incubated with shaking (220 rpm) for 1 h at 37° C. The transformation mixture was then plated on L-broth (LB) plates containing ampicillin (100 µg/ml) and incubated overnight at 37° C.

7.9 Colony PCR

Colonies were inoculated into 50 µl sterile water using a sterile toothpick. A 10 µl aliquot of the inoculum was then subjected to PCR in a total reaction volume of 20 µl containing:
1× AMPLITAQ buffer,
200 µM dNTPs,
20 pmoles of T7 primer,
20 pmoles of T3 primer,
1 unit of AMPLITAQ (Applied Biosystems) using an MJ Research DNA Engine.

The cycling conditions were as follows: 94° C., 2 min; 30 cycles of 94° C., 30 sec, 48° C., 30 sec and 72° C. for 2 min. Samples were maintained at 4° C. (holding cycle) before further analysis.

PCR reaction products were analyzed on 1% agarose gels in 1× TAE buffer. Colonies which gave PCR products of approximately the expected molecular weight (918 bp for INSP141 or 1056 bp for INSP143+105 bp due to the multiple cloning site (MCS)) were grown) up overnight at 37° C. in 5 ml L-Broth (LB) containing ampicillin (100 µg/ml), with shaking at 220 rpm.

7.10 Plasmid DNA Preparation and Sequencing

Miniprep plasmid DNA was prepared from the 5 ml culture using a Biorobot 8000 robotic system (Qiagen) or Wizard Plus SV Minipreps kit (Promega cat. no. 1460) according to the manufacturer's instructions. Plasmid DNA was eluted in 80 µl of sterile water. The DNA concentration was measured using a Spectramax 190 photometer (Molecular Devices). Plasmid DNA (200-500 ng) was subjected to DNA sequencing with the T3 primers using the BigDye Terminator system (Applied Biosystems cat. no. 4390246) according to the manufacturer's instructions. The primer sequence is shown in Table 3. Sequencing reactions were purified using Dye-Ex columns (Qiagen) or Montage SEQ 96 cleanup plates (Millipore cat. no. LSKS09624) then analyzed on an Applied Biosystems 3700 sequencer.

Sequence analysis identified a clone which matched the expected INSP141 cds. The sequence contained the substitution P259A which had been present in the PCR template. The sequence of the cloned cDNA fragment is deduced from FIG. 7. The plasmid map of the cloned PCR product is pCR4-TOPO-INSP141. A second clone was identified which matched the expected INSP143-EC domain cds. The sequence also contained the substitution P259A which had been present in the PCR template. The sequence of the cloned cDNA fragment is deduced from FIG. 7. The plasmid map of the cloned PCR product is pCR4-TOPO-INSP143-EC.

Example 8

Expression and Purification of INSP141, INSP142, INSP143 and INSP144

Further experiments may now be performed to determine the tissue distribution and expression levels of the INSP141, INSP142; INSP143 and INSP144 polypeptides in vivo, on the basis of the nucleotide and amino acid sequence disclosed herein.

The presence of the transcripts for INSP141, INSP142, INSP143 and INSP144 may be investigated by PCR of cDNA from different human tissues. The INSP141, INSP142, INSP143 and INSP144 transcripts may be present at very low levels in the samples tested.

Therefore, extreme care is needed in the design of experiments to establish the presence of a transcript in various human tissues as a small amount of genomic contamination in the RNA preparation will provide a false positive result. Thus, all RNA should be treated with DNAse prior to use for reverse transcription. In addition, for each tissue a control reaction may be set up in which reverse transcription was not undertaken (a -ve RT control).

For example, 1 µg of total RNA from each tissue may be used to generate cDNA using Multiscript reverse transcriptase (ABI) and random hexamer primers. For each tissue, a control reaction is set up in which all the constituents are added except the reverse transcriptase (-ve RT control). PCR reactions are set up for each tissue on the reverse 4; transcribed RNA samples and the minus RT controls. INSP INSP141, INSP142, INSP143 and INSP144-specific primers may readily be designed on the basis of the sequence information provided herein. The presence of a product of the correct molecular weight in the reverse transcribed sample together with the absence of a product in the minus RT control may be taken as evidence for the presence of a transcript in that tissue. Any suitable cDNA libraries may be used to screen for the INSP141, INSP142, INSP143 and INSP144 transcripts, not only those generated as described above.

The tissue distribution pattern of the INSP141, INSP142, INSP143 and INSP144 polypeptides will provide further useful information in relation to the function of those polypeptides.

In addition, further experiments may now be performed using suitable expression vectors. For example, gateway expression clones pDEST12.2_INSP141-6HIS-V1 and pEAK12d_INSP141-6HIS-V1 were generated for INSP141. The last 23 bp of the Rev cloning primer added the 3' end of the INSP141 cds onto the previously amplified sequence (which was an alternative splice variant). ENTRY plasmid is pENTR_INSP141-6HIS-V1. Gateway expression clones pEAK12d_INSP143-EC-6HIS-V1 and pDEST12d_INSP143-EC-6HIS-V1 were generated for INSP143-EC. The last 21 bp of the Rev cloning primer added the 3' end of the INSP143 cds onto the previously amplified sequence (which was an alternative splice variant). INSP143 and INSP144 have in common the cloned extracellular region (INSP153-EC=INSP154-EC). Entry plasmid is pDONR-Zeo_INSP143-EC-6HIS-V1.

Transfection of mammalian cell lines with these vectors may enable the high level expression of the INSP141, INSP142, INSP143 and INSP144 proteins and thus enable the continued investigation of the functional characteristics of the INSP141, INSP142, INSP143 and INSP144 polypeptides. The following material and methods are an example of those suitable in such experiments:

Cell Culture

Human Embryonic Kidney 293 cells expressing the Epstein-Barr virus Nuclear Antigen (HEK293-EBNA, Invitrogen) are maintained in suspension in Ex-cell VPRO serum-free medium (seed stock, maintenance medium, JRH). Sixteen to 20 hours prior to transfection (Day-1), cells are seeded in 2× T225 flasks (50 ml per flask in DMEM/F12 (1:1) containing 2% FBS seeding medium (JRH) at a density of $2\times10^5$ cells/ml). The next day (transfection day 0) transfection takes place using the JetPEITM reagent (2 µl/µg of plasmid DNA, PolyPlus-transfection). For each flask, plasmid DNA is co-transfected with GFP (fluorescent reporter gene) DNA. The transfection mix is then added to the 2× T225 flasks and incubated at 37° C. (5% $CO_2$) for 6 days. Confirmation of positive transfection may be carried out by qualitative fluorescence examination at day 1 and day 6 (Axiovert 10 Zeiss).

On day 6 (harvest day), supernatants from the two flasks are pooled and centrifuged (e.g. 4° C., 400 g) and placed into a pot bearing a unique identifier. One aliquot (500 µl) is kept for QC of the 6His-tagged protein (internal bioprocessing QC).

Scale-up batches may be produced by following the protocol called "PEI transfection of suspension cells", referenced BP/PEI/HH/02/04, with Polyethyleneimine from Polysciences as transfection agent.

Purification Process

The culture medium sample containing the recombinant protein with a C-terminal 6His tag is diluted with cold buffer A (50 mM $NaH_2PO_4$; 600 mM NaCl; 8.7% (w/v) glycerol, pH 7.5). The sample is filtered then through a sterile filter (Millipore) and kept at 4° C. in a sterile square media bottle (Nalgene).

The purification is performed at 4° C. on the VISION workstation (Applied Biosystems) connected to an automatic sample loader (Labomatic). The purification procedure is composed of two sequential steps, metal affinity chromatography on a Poros 20 MC (Applied Biosystems) column charged with Ni ions (4.6×50 mm, 0.83 ml), followed by gel filtration on a Sephadex G-25 medium (Amersham Pharmacia) column (1.0×10 cm).

For the first chromatography step the metal affinity column is regenerated with 30 column volumes of EDTA solution (100 mM EDTA; 1M NaCl; pH 8.0), recharged with Ni ions through washing with 15 column volumes of a 1100 mM $NiSO_4$ solution, washed with 10 column volumes of buffer A, followed by 7 column volumes of buffer B (50 mM $NaH_2PO_4$; 600 mM NaCl; 8.7% (w/v) glycerol, 400 mM; imidazole, pH7.5), and finally equilibrated with 15 column volumes of buffer A containing 15 mM imidazole. The sample is transferred, by the Labomatic sample loader, into a 200 ml sample loop and subsequently charged onto the Ni metal affinity column at a flow rate of 10 ml/min. The column is washed with 12 column volumes of buffer A, followed by 28 column volumes of buffer A containing 20 mM imidazole. During the 20 mM imidazole wash loosely attached contaminating proteins are eluted from the column. The recombinant His-tagged protein is finally eluted with 10 column volumes of buffer B at a flow rate of 2 ml/min, ad the eluted protein is collected.

For the second chromatography step, the Sephadex G-25 gel-filtration column is regenerated with 2 ml of buffer D (1.137M NaCl; 2.7 mM KCl; 1.5 mM $KH_2PO_4$; 8 mM $Na_2HPO_4$; pH 7.2), and subsequently equilibrated with 4 column volumes of buffer C (137 mM NaCl; 2.7 mM KCl; 1.5 mM $KH_2PO_4$; 8 mM $Na_2HPO_4$; 20% (w/v) glycerol; pH 7.4). The peak fraction eluted from the Ni-column is automatically loaded onto the Sephadex G-25 column through the integrated sample loader on the VISION and the protein is eluted with buffer C at a flow rate of 2 ml/min. The fraction was filtered through a sterile centrifugation filter (Millipore), frozen and stored at −80° C. An aliquot of the sample is analyzed on SDS-PAGE (4-12% NuPAGE gel; Novex) Western blot with anti-His antibodies. The NuPAGE gel may be stained in a 0.1% Coomassie blue R250 staining solution (30% methanol, 10% acetic acid) at room temperature for 1 h and subsequently destained in 20% methanol, 7.5% acetic acid until the background is clear and the protein bands clearly visible.

Following the electrophoresis the proteins are electrotransferred from the gel to a nitrocellulose membrane. The membrane is blocked with 5% milk powder in buffer E (137 mM NaCl; 2.7 mM KCl; 1.5 mM $KH_2PO_4$; 8 mM $Na_2HPO_4$; 0.1% Tween 20, pH 7.4) for 1 h at room temperature, and subsequently incubated with a mixture of 2 rabbit polyclonal anti-His antibodies (G-18 and H-15, 0.2 µg/ml each; Santa Cruz) in 2.5% milk powder in buffer E overnight at 4° C. After a further 1 hour incubation at room temperature, the membrane is washed with buffer E (3×10 min), and then incubated with a secondary HRP-conjugated anti-rabbit antibody (DAKO, HRP 0399) diluted 1/3000 in buffer E containing 2.5% milk powder for 2 hours at room temperature. After washing with buffer E (3×10 minutes), the membrane is developed with the ECL kit (Amersham Pharmacia) for 1 min. The membrane is subsequently exposed to a Hyperfilm (Amersham Pharmacia), the film developed and the western blot image visually analysed.

For samples that showed detectable protein bands by Coomassie staining, the protein concentration may be determined using the BCA protein assay kit (Pierce) with bovine serum albumin as standard.

Furthermore, overexpression or knock-down of the expression of the polypeptides in cell lines may be used to determine the effect on transcriptional activation of the host cell genome. Dimerisation partners, co-activators and co-repressors of the INSP141, INSP142, INSP143 and INSP144 polypeptide may be identified by immunoprecipitation combined with Western blotting and immunoprecipitation combined with mass spectroscopy.

Example 9

Assays Targeting T Lymphocyte Responses

Fas-Ligand-Induced T Cell Death.

This assay will reveal new modulators of receptor mediated cell death.

In this assay, T cell apoptosis is induced by stimulating Jurkat cells (a human T cell line) with recombinant 6 Histidine-tagged Fas Ligand combined with a monoclonal anti 6-his antibody. Death is quantified by release of LDH, a cytoplasmic enzyme released in the culture medium when cells are dying. The read out is a calorimetric assay read at 490 nm. T cells have been shown to be pathogenic in many autoimmune diseases, being able to control antigen-specific T cell death is a therapeutic strategy (e.g. anti-TNF-α treatment in patient with Crohn's disease).

Human-MLR: Proliferation and Cytokine Secretion.

This cell-based assay measures the effects of novel proteins on lymphocyte proliferation and cytokine secretion or inhibition upon stimulation by PBMC from another donor (alloreactivity). These assay address antigen-specific T cell and antigen presenting cell functions, which are crucial cellular responses in any autoimmune diseases. Secreted cytokine (IL-2, 4, 5, 10, TNF-α and IFN-γ) are quantified by CBA.

Note: proliferation and cytokine secretion are independent responses.

Mouse-MLR: Proliferation.

This cell-based assay measures the effects of novel proteins on lymphocyte proliferation or inhibition of mouse spleen cells following stimulation by spleen cells from another donor (mouse strain). This cell-based assay measures the effect of novel proteins on. T lymphocyte and antigen presenting cell responses and will be used to confirm activity of positives and hits identify in the h-MLR assays. This assay will be use to select proteins that will be tested in murine model of human diseases.

Human PBMC Stimulated with the Superantigen, TSST.

Superantigens are strong modulators of the immune system affecting T cells. Superantigens influence immunologically mediated disorders such as IBD, inflammatory skin diseases like atopic dermatitis and psoriasis. In this cellular assay, we are specifically targeting T lymphocyte activation via the TCR but with different requirements than the r cell response to classical antigens, in particular in respect to co-stimulatory molecules.

Human PBMC Stimulated with Either ConA or PHA.

These cell-based assays measure the effects of novel proteins on cytokine secretion induced by two different stimuli acting on different cells as measured by a cytokine bead array (CBA) assay (IL-2, IFN-γ, TNF-α, IL-5, IL-4 and IL-10).

Most of cytokines can have dual actions, pro or anti-inflammatory, depending of the injury, milieu and cellular target. Any protein with the capability to modulate cytokine secretion may have a therapeutic potential (e.g. decreasing IFN-γ and TNF-α would be beneficial in Th1-mediated autoimmune disease in contrast decreasing IL-4, IL-5 may be beneficial in Th2-mediated-diseases, inducing IL-10 would interesting in MS and SLE).

Assays Targeting Monocyte/Macrophages and Granulocyte Responses

Human PBMC Stimulated with LPS.

This cell-based assay measures the effects of novel proteins on cytokine secretion (IFN-γ, TNF-α) induced by LPS acting on monocytes/macrophages and granulocytes.

Any protein with the capability to modulate IFN-γ and TNF-α secretion would be beneficial in Th1-mediated autoimmune diseases.

Assays Targeting Neutrophil Responses

Neutrophils are important in inflammation and autoimmune diseases such as Rheumatoid Arthritis. Leukocyte chemo-attractants such as IL-8 initiate a sequence of adhesive interactions between cells and the micro-vascular endothelium, resulting in activation, adhesion and finally migration of neutrophils. The tissue infiltration of neutrophils depends on a reorganisation of cytoskeleton elements associated with specific changes in cell morphology of these cells.

This cell-based assay measures the effect of novel proteins on cytoskeleton reorganization of human neutrophils.

Assays Targeting B Lymphocyte Responses

Autoantibodies as well as infiltrating B cells are thought to be important in the pathogenesis of various autoimmune diseases, such as systemic lupus erithematosus (SLE), rheumatoid arthritis (RA), Sjogren's syndrome and myasthenia gravis. Compelling evidence indicates that a disregulation in B cell homeostasis could affect immune tolerance leading to the inappropriate survival of autoreactive B cells producing pathogenic antibodies and sustained inflammation. The identification of new factors that play critical roles in the regulation of B cell proliferation, survival and differentiation following B cell receptor triggering are of high relevance in the development of novel therapies.

B Cell Proliferation.

This cell-based assay measures the effect of novel proteins on B cell survival.

B Cell Co-Stimulation.

This cell-based assay measures the effect of novel proteins on B cell co-stimulation.

Assays Targeting Monocytes and Microglial Responses

THP-1 Calcium Flux.

The $Ca^+$-flux in THP1-cell assay measures the effects of novel proteins on their ability to trigger an intracellular calcium release (a generic second messenger events) from the endoplasmic reticulum.

Microglia Cell Proliferation

During proliferation of microglial progenitors, a number of colony-stimulating factors, including some cytokines, are known to play key roles. Among them, M-CSF is crucial for the final step of maturation of macrophages/microglia and is not replaceable by any other factor. The evaluation of this biological response may represent a way to influence the microglial activity and therefore an opportunity to identify molecules with therapeutic potential from MS.

A cell-based assay was developed to measure the proliferative response of a microglia cell line to M-CSF. The feasibility and the robustness phases showed optimal results. This assay is in 96 well plates; non-radioactive substrate is required, easily automated.

Example 10

Analysis of INSP142 Gene Expression Levels by Real Time PCR (Taqman)

Total RNA from each sample was reverse transcribed using the Superscript III First-Strand Synthesis System for RT-PCR (Invitrogen, Cat. No. 18080-051) in a final reaction volume of 20 μl. 2 μg of total RNA was combined with 50 ng random hexamer primers, 10 mM each of dATP, dGTP, dCTP, and dTTP, and DEP C-treated water in a volume of 10 μl. The mixture was incubated at 65° C. for 5 min then chilled on ice for 1 min. The following 10 μl cDNA synthesis mix was prepared in a separate tube: 2 μl 10× RT buffer, 4 μl 25 mM $MgCl_2$, 2 μl 0.1M DTT, 1 μl RNASEOUT (40 units/μl), and 1 μl SUPERSCRIPT III RT enzyme (200 units/μl). The cDNA synthesis mix was added to the RNA/primer mixture, mixed gently and incubated at 25° C. for 10 min then at 50° C. for 50 min. The RT enzyme was then inactivated by incubating at 85° C. for 5 min. The mixture was chilled on ice and then 1 μl of E. coli Rnase H (2 units/μl) was added and the mixture incubated at 37° C. for 20 min. The mixture was chilled on ice and then diluted 1/250 with sterile water. Dilutions of the reverse transcriptase reaction were then subjected to real time PCR analysis on a TaqMan instrument (PE Biosystems 7700). PCR primers for human INSP142 and the housekeeping control gene glyceraldehyde 3-phosphate dehydrogenase (GAPDH) were designed using the Primer Express software (PE Biosystems). The forward primer was designed in exon 11. The reverse primer was designed spanning the exon 12-13 boundary. This primer should distinguish INSP142 from INSP141 but not from INSP143 or 144.

The sequences of the primers are shown in Table 4. The specificity and the optimal primer concentration to use for the TaqMan analysis were determined by testing the INSP142 primers on a series of dilutions of plasmid pEAK12d-INSP142-6HIS. Potential genomic DNA contamination of the cDNA was excluded by performing PCR reactions using primers specific for GAPDH intronic sequence. The absence of non-specific amplification was controlled by analyzing the PCR products on 4% agarose gels to ensure a single band of the expected molecular weight was produced.

SYBR Green Real-Time PCR reactions were carried out in a reaction volume of 50 μl containing 25 μl SYBR Green PCR master mix (PE Biosystems) (to which 0.5 units AmpErase Uracil N-Glycosylase (UNG, PE Biosystems) had previously been added), 300 nM of each amplification primer, and 5 μl of RT-PCR product. Cycling was performed using the ABI PRISM 7700 (TaqMan) Detection System programmed as follows: 1 cycle of 50° C. for 2 min; 1 cycle of 95° C. for 10 min; 40 cycles of 95° C. for 15 sec, 60° C. for 1 min. Each reaction was carried out in duplicate and the results averaged.

The primer-specific regions of the reverse-transcribed cDNA samples were thus amplified and their cycle threshold (Ct) values determined. The Ct value for each cDNA sample was normalized to that of the housekeeping gene GAPDH as follows. The difference in expression level between the GAPDH gene and the INSP142 gene in each cDNA sample was expressed as a difference in Ct value, i.e. Delta (δ) Ct=Ct (GAPDH)–Ct (INSP142). Results for each sample were then expressed as a fold difference in the number of cycles required for detectable INSP142 gene expression relative to that for GAPDH, according to the formula Fold Difference=$2^{(-\delta Ct)}$. Finally, the expression level of the INSP142 gene in each cDNA sample was shown relative to the GAPDH gene expression level, where GAPDH expression level=100%, by dividing 100 by the Fold Difference for INSP142.

Results

INSP142 primers were tested on a panel of approx. 100 normal and diseased human tissue samples, primary cells and cell lines in addition to 44 inflammatory bowel disease colon and ileum biopsies and 38 psoriasis biopsies from an IL18BP clinical trial. The primers used were able to distinguish INSP142 from the splice variant INSP141 but not from splice variants INSP143 or INSP144. Results are shown in tables 5-11 and represented graphically in FIGS. 10-16 below. The INSP142 was originally cloned from a testis cDNA. Taqman analysis of normal human tissues confirmed the expression of INSP142 in testis, however the expression level was very low (0.15 relative to GAPDH=100) (FIG. 10). INSP142 was also detected at similar levels in skin and lung and liver. In primary cells and cell lines INSP142 could be detected at similarly low levels in bone marrow and human dermal microvascular endothelial cells (FIG. 12), normal human dermal fibroblasts (FIG. 13), and in peripheral blood granulocytes as well as the eosinophil derived cell line EOL-3. Surprisingly, INSP142 expression could be detected in all colon and ileum IBD biopsy samples (FIG. 15) and psoriasis skin biopsies, possibly suggesting upregulation of the mRNA in inflammatory disease processes. Based on the expression data in primary cells and cell lines, multiple cell types in skin could be responsible for the expression of INSP142 in psoriasis.

CONCLUSION

Expression results show unexpected restricted expression of INSP42 in colon and ileum IBD biopsy samples and psoriasis skin biopsies.

This specific pattern of expression leads to the conclusion of the involvement of INSP142 in inflammatory bowel diseases, skin diseases or inflammation.

Preferably, the inflammatory disease is selected among Crohn's disease or ulcerative colitis.

Preferably, the skin disease is psoriasis, contact dermatitis or atopic eczema.

These surprising properties characterizing the polynucleotides or the corresponding polypeptides of the present invention make them particularly suitable for the preparation of a drug or pharmaceutical composition. The polynucleotides or the corresponding polypeptides of the present invention therefore display the unexpected finding of a restricted expression in specific tissues.

TABLE 4

TaqMan PCR primer sequences

| Primer | Sequence (5'-3') |
|---|---|
| INSP142-936F | CCCTGGGCCAAAACTAGAAAA (SEQ ID NO: 162) |
| INSP142-1044R | AAGAGAAGGACATGTGGTGCTG (SEQ ID NO: 163) |
| hGAPDH-F | CCACCCATGGCAAATTCC (SEQ ID NO: 164) |
| hGAPDH-R | GATGGGATTTCCATTGATGACA (SEQ ID NO: 165) |
| Intron-hGAPDH-F | CCTAGTCCCAGGGCTTTGATT (SEQ ID NO: 166) |
| Intron-hGAPDH-R | CTGTGCTCCCACTCCTGATTT (SEQ ID NO: 167) |

TABLE 5

Expression of INSP142 in major human tissues as measured by RT-PCR (TaqMan).

| major tissues collection | Ct hGAPDH | Ct hINSP142 | delta ct | Fold difference | Relative to GAPDH (=100) |
|---|---|---|---|---|---|
| S76 Brain | 20.56 | 34.02 | −13.46 | 11268.44 | 0.01 |
| S77 Heart | 21.36 | 34.10 | −12.74 | 6841.04 | 0.01 |
| S78 Kidney | 19.93 | 32.53 | −12.60 | 6186.90 | 0.02 |
| S79 liver | 22.79 | 33.77 | −10.98 | 2019.80 | 0.05 |
| S80 Lung | 22.92 | 33.00 | −10.09 | 1086.14 | 0.09 |
| S81 Placenta | 21.81 | 33.82 | −12.01 | 4124.49 | 0.02 |
| S82 skeletal Muscle | 17.74 | 33.86 | −16.12 | 71220.26 | 0.00 |
| S83 small intestine | 21.65 | 34.50 | −12.85 | 7383.04 | 0.01 |
| S84 Spleen | 21.71 | 34.74 | −13.04 | 8393.17 | 0.01 |
| S85 Thymus | 21.01 | 32.63 | −11.62 | 3147.52 | 0.03 |
| S86 Uterus | 21.56 | 32.58 | −11.03 | 2083.80 | 0.05 |
| S89 Spinal cord | 20.13 | 34.60 | −14.47 | 22693.63 | 0.00 |
| S 90 Cervix | 24.27 | 36.00 | −11.73 | 3396.74 | 0.03 |
| S91 colon | 21.50 | 33.64 | −12.14 | 4513.40 | 0.02 |
| S92 ovary | 23.24 | 33.83 | −10.59 | 1541.37 | 0.06 |
| S93 prostate | 20.88 | 33.33 | −12.45 | 5575.94 | 0.02 |
| S94 testis | 21.88 | 31.24 | −9.36 | 654.84 | 0.15 |
| S95 skin | 24.39 | 34.08 | −9.70 | 828.87 | 0.12 |

TABLE 5-continued

Expression of INSP142 in major human tissues as measured by RT-PCR (TaqMan).

| major tissues collection | Ct hGAPDH | Ct hINSP142 | delta ct | Fold difference | Relative to GAPDH (=100) |
|---|---|---|---|---|---|
| S113 pancreas | 23.26 | 33.45 | −10.19 | 1164.10 | 0.09 |
| S119 Breast | 21.52 | 35.58 | −14.06 | 17020.67 | 0.01 |
| S120 Stomach | 21.66 | 32.61 | −10.95 | 1978.24 | 0.05 |
| S122 Eye | 22.16 | 33.32 | −11.16 | 2280.29 | 0.04 |
| S147 Bladder | 21.46 | 34.08 | −12.62 | 6295.04 | 0.02 |

TABLE 6

Expression of INSP142 in comparative human tissues as measured by RT-PCR (TaqMan).

| Comparative tissues | Ct hGAPDH | Ct hINSP142 | delta ct | Fold difference | Relative to GAPDH (=100) |
|---|---|---|---|---|---|
| S76 Brain | 21.31 | 33.81 | −12.50 | 5789.68 | 0.02 |
| S140 fetal Brain | 19.73 | 32.72 | −12.98 | 8088.64 | 0.01 |
| S77 Heart | 22.60 | 35.60 | −13.00 | 8181.72 | 0.01 |
| S143 fetal Heart | 19.89 | 34.15 | −14.26 | 19580.66 | 0.01 |
| S78 Kidney | 20.94 | 33.37 | −12.43 | 5512.82 | 0.02 |
| S121 fetal Kidney | 20.41 | 34.04 | −13.63 | 12673.55 | 0.01 |
| S130 Lupus total RNA Kidney | 22.79 | 33.98 | −11.20 | 2347.74 | 0.04 |
| S135 Kidney tumor | 20.57 | 33.27 | −12.70 | 6667.30 | 0.01 |
| S79 liver | 23.85 | 32.73 | −8.88 | 470.18 | 0.21 |
| S142 fetal liver | 21.08 | 33.72 | −12.64 | 6374.85 | 0.02 |
| S127 Lupus total RNA liver | 24.39 | 34.07 | −9.67 | 816.10 | 0.12 |
| S131 Liver Cirrhosis | 22.99 | 35.29 | −12.30 | 5057.32 | 0.02 |
| S136 Liver Tumor | 19.24 | 34.12 | −14.88 | 30182.81 | 0.00 |
| S80 Lung | 23.65 | 33.42 | −9.76 | 868.58 | 0.12 |
| S144 Fetal Lung | 19.29 | 32.75 | −13.45 | 11203.00 | 0.01 |
| S128 Lupus total RNA Lung | 21.14 | 36.92 | −15.78 | 56206.04 | 0.00 |
| S132 Cirrhosis Lung | 18.13 | 33.36 | −15.23 | 38387.17 | 0.00 |
| S137 Lung Tumor | 22.72 | 34.21 | −11.50 | 2894.56 | 0.03 |
| S84 Spleen | 22.24 | 34.84 | −12.60 | 6229.86 | 0.02 |
| S141 Fetal Spleen | 22.06 | 32.99 | −10.93 | 1947.28 | 0.05 |
| S129 Lupus total RNA Spleen | 23.62 | 33.82 | −10.20 | 1174.15 | 0.09 |
| S133 Cirrhosis Spleen | 20.99 | 33.30 | −12.32 | 5104.76 | 0.03 |
| S117 Human Universal Reference | 17.56 | 33.41 | −15.85 | 59095.31 | 0.00 |

TABLE 7

Expression of INSP142 in secretory and immune tissues as measured by RT-PCR (TaqMan).

| Secretory and immunology samples | Ct hGAPDH | Ct hINSP142 | delta ct | Fold difference | Relative to GAPDH (=100) |
|---|---|---|---|---|---|
| S87 Bone Marrow | 23.63 | 33.33 | −9.70 | 831.14 | 0.12 |
| S88 Thyroid | 22.77 | 33.36 | −10.59 | 1536.53 | 0.07 |
| S115 Salivary Gland | 22.95 | 35.11 | −12.16 | 4585.12 | 0.02 |
| S116 Adrenal Gland | 21.94 | 34.62 | −12.68 | 6546.78 | 0.02 |
| S123 Mammary gland | 25.03 | 36.20 | −11.17 | 2302.46 | 0.04 |
| S125 Pituitary Gland | 23.48 | 34.11 | −10.62 | 1578.89 | 0.06 |
| S145 Lymph Node | 23.28 | 35.23 | −11.95 | 3965.59 | 0.03 |
| S146 Adipose | 20.35 | 35.40 | −15.05 | 33879.59 | 0.00 |
| S148 Appendix | 22.60 | 33.76 | −11.17 | 2296.39 | 0.04 |
| S149 Blood vessel Artery | 22.55 | 35.87 | −13.32 | 10218.47 | 0.01 |
| S150 Throat | 21.03 | 34.87 | −13.85 | 14750.27 | 0.01 |
| S75 Tonsil | 25.36 | 37.12 | −11.76 | 3466.37 | 0.03 |
| S54 Stroma | 22.17 | 34.02 | −11.86 | 3709.47 | 0.03 |
| S153 cells HDMEC | 24.32 | 34.27 | −9.96 | 993.65 | 0.10 |
| S157 cells HDMEC stimulated | 24.36 | 34.63 | −10.27 | 1237.64 | 0.08 |
| S155 cell HAoEC | 21.61 | 34.44 | −12.83 | 7302.87 | 0.01 |
| S158 cell HAoEC stimulated | 20.94 | 34.05 | −13.11 | 8861.15 | 0.01 |
| S11 RA2 | 22.78 | 34.43 | −11.65 | 3204.93 | 0.03 |
| S12 RA3 | 21.45 | 34.59 | −13.15 | 9058.87 | 0.01 |
| S13 OA1 | 26.13 | 39.39 | −13.26 | 9782.59 | 0.01 |
| S19 OA4 | 21.79 | 34.27 | −12.47 | 5686.33 | 0.02 |

TABLE 8

Expression of INSP142 in primary cells and cell lines as measured by RT-PCR (TaqMan).

| Primary cells and cell lines 1 | Ct hGAPDH | Ct hINSP142 | delta ct | Fold difference | Relative to GAPDH (=100) |
|---|---|---|---|---|---|
| S1 AG1518 fibroblast | 21.54 | 34.72 | −13.18 | 9258.32 | 0.01 |
| S2 Howard Ab | 21.23 | 33.97 | −12.74 | 6844.32 | 0.01 |
| S3 Clark N | 20.59 | 35.30 | −14.71 | 26795.20 | 0.00 |
| S4 NF1 | 20.69 | 34.13 | −13.44 | 11132.82 | 0.01 |
| S5 NF2 | 22.05 | 33.96 | −11.91 | 3843.39 | 0.03 |
| S6 SScN2 | 19.93 | 34.16 | −14.23 | 19207.12 | 0.01 |
| S7 SSCA2 | 19.11 | 33.27 | −14.16 | 18280.44 | 0.01 |
| S15 LN1 | 20.23 | 33.88 | −13.66 | 12923.86 | 0.01 |
| S16 Lab1 | 17.60 | 34.36 | −16.76 | 110689.17 | 0.00 |
| S17 LN14 | 20.96 | 34.26 | −13.29 | 10048.88 | 0.01 |
| S18 LA13 | 19.11 | 33.88 | −14.77 | 27965.97 | 0.00 |
| S9 NHDF2 | 23.84 | 34.10 | −10.26 | 1230.13 | 0.08 |
| S10 NHDF3 | 24.58 | 34.75 | −10.17 | 1148.35 | 0.09 |
| S55 JEHC | 20.53 | 34.16 | −13.63 | 12655.39 | 0.01 |
| S56 HT 1080 | 19.81 | 34.96 | −15.15 | 36287.57 | 0.00 |
| S57 MRC-5 | 20.31 | 35.68 | −15.37 | 42276.07 | 0.00 |
| S152 Cells Mob | 21.68 | 34.18 | −12.50 | 5775.85 | 0.02 |
| S155 Cells Mob stimulated | 20.44 | 34.57 | −14.13 | 17932.97 | 0.01 |
| S156 Cells Mob stimulated | 19.60 | 34.06 | −14.45 | 22429.61 | 0.00 |
| S20 K1 Keratinocytes Skin | 22.46 | 35.57 | −13.10 | 8800.61 | 0.01 |
| S21 K2 Keratinocytes Skin | 22.98 | 34.39 | −11.41 | 2728.24 | 0.04 |

TABLE 9

Expression of INSP 142 in primary cells and cell lines of immune or CNS origin as measured by RT-PCR (TaqMan)

| Primary cells and cell lines 2 | Ct hGAPDH | Ct hINSP142 | delta ct | Fold difference | Relative to GAPDH (=100) |
|---|---|---|---|---|---|
| S30 THP-1 mono/mac | 19.42 | 32.52 | −13.10 | 8772.67 | 0.01 |
| S35 KU812 basophil | 18.91 | 32.55 | −13.64 | 12735.76 | 0.01 |
| S37 KU812/PMA | 20.29 | 36.16 | −15.87 | 59778.10 | 0.00 |
| S43 Jurkat | 19.54 | 32.78 | −13.24 | 9648.25 | 0.01 |
| S58 PBMC1 | 21.68 | 33.98 | −12.30 | 5052.75 | 0.02 |
| S59 Granulocytes 1 | 23.97 | 33.84 | −9.88 | 940.48 | 0.11 |
| S61 PBMC2.2 | 22.12 | 33.56 | −11.44 | 2787.83 | 0.04 |
| S97 SK-N-AS | 19.94 | 33.72 | −13.78 | 14049.81 | 0.01 |
| S98 TE671 subclone 2 | 19.76 | 33.76 | −14.00 | 16356.00 | 0.01 |
| S99 KELLY | 18.07 | 32.83 | −14.76 | 27723.88 | 0.00 |
| S100 U-373 MG | 19.55 | 32.78 | −13.24 | 9648.51 | 0.01 |
| S101 U-87 MG | 20.86 | 33.50 | −12.64 | 6365.99 | 0.02 |
| S102 T98G | 18.61 | 33.69 | −15.08 | 34577.36 | 0.00 |
| S103 BE(2)-C | 19.21 | 33.21 | −14.00 | 16387.20 | 0.01 |
| S104 CCF-STGG1 | 20.19 | 32.81 | −12.62 | 6274.56 | 0.02 |
| S105 TE671 | 20.50 | 34.11 | −13.60 | 12448.79 | 0.01 |
| S106 A172 | 19.71 | 33.12 | −13.42 | 10928.99 | 0.01 |
| S107 132N1 | 19.15 | 33.29 | −14.14 | 18035.48 | 0.01 |
| S108 SK-PN-DW | 19.97 | 33.28 | −13.31 | 10145.36 | 0.01 |
| S38 MOLT-4 | 24.90 | 33.77 | −8.86 | 465.96 | 0.21 |
| S41 EOL-3 | 23.64 | 33.13 | −9.49 | 718.73 | 0.14 |
| S44 EOL-3 + IL2 | 24.08 | 34.34 | −10.27 | 1232.74 | 0.08 |

TABLE 10

Expression of INSP142 in diseased colon and ileum biopsies as measured by RT-PCR (TaqMan)

| IBD plate | Ct hGAPDH | Ct hINSP142 | delta ct | Fold difference | Relative to GAPDH (=100) |
|---|---|---|---|---|---|
| N1 | 24.43 | 33.67 | −9.25 | 607.54 | 0.16 |
| N2 | 22.86 | 32.88 | −10.03 | 1042.30 | 0.10 |
| N4 | 22.08 | 34.05 | −11.97 | 4001.87 | 0.02 |
| N5 | 23.15 | 32.65 | −9.50 | 723.01 | 0.14 |
| N9 | 22.73 | 32.10 | −9.37 | 662.65 | 0.15 |
| N10 | 23.38 | 32.67 | −9.29 | 626.27 | 0.16 |
| CD2 | 22.25 | 33.41 | −11.16 | 2295.06 | 0.04 |
| CD3 | 21.30 | 31.92 | −10.62 | 1575.62 | 0.06 |
| CD4 | 21.40 | 31.66 | −10.26 | 1222.40 | 0.08 |
| CD5 | 24.04 | 32.88 | −8.85 | 460.18 | 0.22 |
| CD6 | 23.46 | 32.31 | −8.85 | 460.46 | 0.22 |
| CD8 | 22.12 | 33.19 | −11.07 | 2148.23 | 0.05 |
| CD9 | 24.74 | 33.33 | −8.58 | 383.93 | 0.26 |
| CD10 | 23.18 | 34.11 | −10.93 | 1950.65 | 0.05 |
| CD13 | 24.11 | 32.82 | −8.72 | 420.26 | 0.24 |
| CD16 | 24.35 | 32.77 | −8.42 | 342.90 | 0.29 |
| CD17 | 25.58 | 33.02 | −7.44 | 174.20 | 0.57 |
| CD18 | 22.88 | 37.35 | −14.47 | 22720.95 | 0.00 |
| CD19 | 23.33 | 33.35 | −10.02 | 1038.70 | 0.10 |
| CD20 | 24.12 | 34.57 | −10.45 | 1399.73 | 0.07 |
| CD22 | 22.04 | 32.10 | −10.05 | 1061.10 | 0.09 |
| N11 | 23.60 | 33.78 | −10.18 | 1160.09 | 0.09 |
| N14 | 22.86 | 33.48 | −10.62 | 1577.89 | 0.06 |
| N26 | 23.48 | 35.52 | −12.04 | 4211.20 | 0.02 |
| N27 | 23.86 | 34.92 | −11.06 | 2133.33 | 0.05 |
| N29 | 24.61 | 35.11 | −10.50 | 1449.35 | 0.07 |
| N30 | 22.56 | 32.01 | −9.45 | 697.17 | 0.14 |
| CD4 bis | 22.91 | 31.80 | −8.89 | 475.04 | 0.21 |
| CD6 bis | 23.04 | 32.46 | −9.42 | 683.91 | 0.15 |
| CD23 | 25.11 | 32.42 | −7.31 | 158.27 | 0.63 |
| CD24 | 22.72 | 33.53 | −10.81 | 1792.74 | 0.06 |
| CD25 | 23.50 | 31.90 | −8.40 | 336.65 | 0.30 |
| CD26 | 23.18 | 32.30 | −9.12 | 557.15 | 0.18 |
| CD27 | 24.58 | 32.56 | −7.98 | 252.07 | 0.40 |
| CD28 | 23.15 | 32.50 | −9.35 | 654.35 | 0.15 |
| UC11 | 23.39 | 32.69 | −9.30 | 630.54 | 0.16 |
| UC12 | 22.61 | 33.70 | −11.09 | 2184.24 | 0.05 |
| UC13 | 22.96 | 32.15 | −9.19 | 584.33 | 0.17 |
| UC14 | 23.09 | 31.27 | −8.18 | 290.95 | 0.34 |
| UC16 | 23.10 | 32.85 | −9.75 | 861.54 | 0.12 |
| UC18 | 24.78 | 33.02 | −8.24 | 302.49 | 0.33 |
| UC19 | 22.74 | 32.58 | −9.84 | 918.60 | 0.11 |

TABLE 11

Expression of INSP142 in diseased skin biopsies from IL18BP clinical trial as measured by RT-PCR (TaqMan)

| Psoriasis | Ct hGAPDH | Ct hINSP142 | delta ct | Fold difference | Relative to GAPDH (=100) |
|---|---|---|---|---|---|
| #11 A2872102-2 | 21.03 | 32.84 | −11.81 | 3593.11 | 0.03 |
| #16 A2872103-1 | 24.86 | 33.95 | −9.09 | 544.94 | 0.18 |
| #28 A2872023-1 | 22.50 | 35.02 | −12.51 | 5842.32 | 0.02 |
| #36 A2872028-1 | 24.83 | 33.76 | −8.94 | 490.55 | 0.20 |
| #39 A2872025-1 | 24.43 | 32.88 | −8.44 | 347.88 | 0.29 |
| #59 E1328972-3 | 24.60 | 33.26 | −8.66 | 403.74 | 0.25 |
| #60 E1328972-2 | 22.21 | 32.91 | −10.70 | 1658.02 | 0.06 |
| #61 E1329004 | 24.60 | 33.37 | −8.77 | 435.59 | 0.23 |
| #63 E1328973-3 | 22.93 | 33.91 | −10.97 | 2011.18 | 0.05 |
| #64 E1329003-2 | 20.81 | 31.87 | −11.06 | 2135.78 | 0.05 |
| #66 E1328974-4 | 21.77 | 33.42 | −11.65 | 3224.67 | 0.03 |
| #68 E1328975-3 | 24.59 | 32.55 | −7.96 | 249.05 | 0.40 |
| #69 E1328975-4 | 23.59 | 33.57 | −9.97 | 1005.76 | 0.10 |
| #70 E1329004-2 | 22.27 | 33.00 | −10.73 | 1693.79 | 0.06 |
| #72 E1328976-4 | 23.54 | 32.71 | −9.16 | 573.83 | 0.17 |
| #73 E1329005-1 | 23.80 | 33.50 | −9.70 | 830.24 | 0.12 |
| #74 E1328977-2 | 24.17 | 32.97 | −8.79 | 443.66 | 0.23 |
| #75 E1328977-3 | 22.90 | 32.88 | −9.98 | 1010.36 | 0.10 |
| #77 E1348411-3 | 23.53 | 32.47 | −8.95 | 493.01 | 0.20 |
| #78 E1348411-2 | 21.64 | 34.12 | −12.48 | 5716.81 | 0.02 |
| #79 E1348411-1 | 21.83 | 31.29 | −9.45 | 701.55 | 0.14 |
| #80 E1348414-2 | 22.67 | 32.17 | −9.49 | 720.55 | 0.14 |
| #81 E1348414-1 | 22.12 | 32.54 | −10.42 | 1374.76 | 0.07 |
| #82 E1348446-1 | 23.42 | 31.65 | −8.23 | 299.96 | 0.33 |
| #83 E1348415-3 | 20.95 | 32.19 | −11.24 | 2412.57 | 0.04 |
| #84 E1348415-2 | 21.77 | 32.86 | −11.09 | 2181.65 | 0.05 |
| #85 E1348442-1 | 21.00 | 32.15 | −11.15 | 2265.41 | 0.04 |
| #86 E1348416-3 | 25.00 | 33.31 | −8.31 | 317.58 | 0.31 |
| #88 E1348445-1 | 23.70 | 33.27 | −9.57 | 760.60 | 0.13 |
| #91 E1317749-2 | 24.53 | 31.94 | −7.41 | 170.59 | 0.59 |
| #95 E1317719-2 | 24.94 | 32.12 | −7.18 | 145.45 | 0.69 |
| #96 E1317719-3 | 21.69 | 31.74 | −10.05 | 1059.76 | 0.09 |
| #97 E1317751-2 | 23.25 | 33.13 | −9.88 | 943.38 | 0.11 |
| #98 E1317723-2 | 24.09 | 35.40 | −11.32 | 2550.43 | 0.04 |
| #99 E1317723-3 | 22.10 | 32.31 | −10.21 | 1186.53 | 0.08 |
| #101 E1317718-2 | 20.26 | 32.63 | −12.38 | 5312.87 | 0.02 |
| #102 E1317718-3 | 22.52 | 33.42 | −10.89 | 1899.79 | 0.05 |
| #103 E1317750-2 | 23.82 | 32.43 | −8.61 | 390.29 | 0.26 |

We claim:

1. An isolated polypeptide that:
   (i) comprises the amino acid sequence as recited in SEQ ID NO:24 or SEQ ID NO:52;
   (ii) consists of the amino acid sequence as recited in SEQ ID NO:24 or SEQ ID NO:52;
   (iii) consists of the mature form of the polypeptide as recited in SEQ ID NO:24 or SEQ ID NO:52, in which the signal peptide consisting of amino acid residues 1-27 of SEQ NO:24 or SEQ ID NO:52 is cleaved; or
   (iv) is a functional equivalent having at least 95% sequence identity with a polypeptide according to (ii) or (iii) which functions as an Anthrax Toxin Receptor ("ATR")-like protein, contains a Metal Ion-Dependent Adhesion Site (MIDAS) motif and binds to an anthrax toxin.

2. The isolated polypeptide according to claim 1, said polypeptide comprising the amino acid sequence as recited in SEQ ID NO:24.

3. The isolated polypeptide according to claim 1, said polypeptide comprising the amino acid sequence as recited in SEQ ID NO:52.

4. The isolated polypeptide according to claim 1, said polypeptide consisting of the amino acid sequence as recited in SEQ ID NO:24.

5. The isolated polypeptide according to claim 1, said polypeptide consisting of the amino acid sequence as recited in SEQ ID NO:52.

6. The isolated polypeptide according to claim 1, said polypeptide consisting of the mature form of the polypeptide as recited in SEQ NO:24, in which the signal peptide consisting of amino acid residues 1-27 of SEQ NO:24 is cleaved.

7. The isolated polypeptide according to claim 1, wherein said polypeptide is a functional equivalent having at least 95% sequence identity with a polypeptide according to claim 1 ii) or iii) which functions as an ATR-like protein, contains a Metal Ion-Dependent Adhesion Site (MIDAS) motif and binds to an anthrax toxin.

8. The isolated polypeptide according to claim 1, said polypeptide consisting of the mature form of the polypeptide as recited in SEQ NO:52, in which the signal peptide consisting of amino acid residues 1-27 of SEQ ID NO:52 is cleaved.

* * * * *

UNITED STATES PATENT AND TRADEMARK OFFICE
CERTIFICATE OF CORRECTION

| | |
|---|---|
| PATENT NO. | : 8,222,371 B2 |
| APPLICATION NO. | : 11/718183 |
| DATED | : July 17, 2012 |
| INVENTOR(S) | : Mark Douglas Davies et al. |

It is certified that error appears in the above-identified patent and that said Letters Patent is hereby corrected as shown below:

Column 5,
Lines 3-6, "SEQ ID NO:24, SEQ ID NO:128, SEQ ID NO:130, SEQ ID NO:132, SEQ ID NO:134, SEQ ID NO:128, SEQ ID NO:130, SEQ ID NO:132, SEQ ID NO:134, SEQ ID NO:146" should read
--SEQ ID NO:24, SEQ ID NO:128, SEQ ID NO:130, SEQ ID NO:132, SEQ ID NO:134, SEQ ID NO:146--.

Column 6,
Line 29, "contain both" should read --containing both--.

Column 9,
Line 56, "SEQ ID NO:11)$_8$," should read --SEQ ID NO:108,--.

Column 10,
Lines 11-12, "in SEA ID NO:108" should read --in SEQ ID NO:108--.
Line 44, "exon g" should read --exon 8--.

Column 13,
 Line 42, "ANT_TG" should read --ANT_IG--.

Column 14,
Line 47, "May be used" should read --may be used--.

Column 15,
Line 37, "INSP42" should read --INSP142--.

Column 16,
Line 18, "in a patients" should read --in a patient,--.

Signed and Sealed this
Twenty-second Day of January, 2013

David J. Kappos
*Director of the United States Patent and Trademark Office*

Column 17,
Line 24, "ANT_TG" should read --ANT_IG--.
Line 58, "ANTACID" should read --ANT_IG--.

Column 22,
Lines 18-19, "an amino acids" should read --an amino acid--.
Line 49, "amino acids" should read --amino acid--.
Line 52, "include" should read --includes--.
Lines 66-67, "amino acids" should read --amino acid--.

Column 25,
Line 63, "SEQ ID NO:04," should read --SEQ ID NO:104,--.

Column 26,
Line 61, "SEQ ID NO:1100," should read --SEQ ID NO:104,--.

Column 29,
Line 1, "pith a biological sample wider" should read --with a biological sample under--.

Column 34,
Line 17, "or aprt$^+$" should read --or aprt±--.

Column 35,
Line 34, "peptizes" should read --peptides--.

Column 38,
Line 16, "calorimetric" should read --colorimetric--.

Column 43,
Line 36, "These be" should read --These producer cells may be--.

Column 44,
Line 35, "ligase chairs" should read --ligase chain--.

Column 46,
Line 44, "(r" should read --or--.

Column 47,
Line 16, "With a" should read --with a--.

Column 52,
Line 59, "A pairs of" should read --A pair of--.

Column 53,
Line 27, "products was" should read --products were--.

Column 55,
Line 54, "grown) up" should read --grown up--.

Column 56,
Line 45, "on the reverse 4;" should read --on the reverse--.

Column 57,
Line 59, "a 1100mM" should read --a 100mM--.

Column 58,
Line 6, "ad the" should read --and the--.

Column 59,
Line 2, "calorimetric" should read --colorimetric--.
Line 23, "on. T" should read --on T--.
Line 26, "will be use to" should read --will be used to--.
Line 34, "the r cell" should read --the T cell--.
Lines 48-49, "would interesting" should read --would be interesting--.

Column 62,
Line 4, "of INSP42" should read --of INSP142--.

Column 163,
Line 37, "and hinds" should read --and binds--.

UNITED STATES PATENT AND TRADEMARK OFFICE
CERTIFICATE OF CORRECTION

PATENT NO. : 8,222,371 B2
APPLICATION NO. : 11/718183
DATED : July 17, 2012
INVENTOR(S) : Mark Douglas Davies et al.

It is certified that error appears in the above-identified patent and that said Letters Patent is hereby corrected as shown below:

Column 5,
 Lines 3-6, "SEQ ID NO:24, SEQ ID NO:128, SEQ ID NO:130, SEQ ID NO:132, SEQ ID NO:134, SEQ ID NO:128, SEQ ID NO:130, SEQ ID NO:132, SEQ ID NO:134, SEQ ID NO:146"
  should read
  --SEQ ID NO:24, SEQ ID NO:128, SEQ ID NO:130, SEQ ID NO:132, SEQ ID NO:134, SEQ ID NO:146--.

Column 6,
Line 29, "contain both" should read --containing both--.

Column 9,
Line 56, "SEQ ID NO:11)$_8$," should read --SEQ ID NO:108,--.

Column 10,
Lines 11-12, "in SEA ID NO:108" should read --in SEQ ID NO:108--.
Line 44, "exon g" should read --exon 8--.

Column 13,
Line 42, "ANT_TG" should read --ANT_IG--.

Column 14,
Line 47, "May be used" should read --may be used--.

Column 15,
Line 37, "INSP42" should read --INSP142--.

This certificate supersedes the Certificate of Correction issued January 22, 2013.

Signed and Sealed this
Fifth Day of March, 2013

Teresa Stanek Rea
*Acting Director of the United States Patent and Trademark Office*

Column 16,
Line 18, "in a patients" should read --in a patient,--.

Column 17,
Line 24, "ANT_TG" should read --ANT_IG--.
Line 58, "ANTACID" should read --ANT_IG--.

Column 22,
Lines 18-19, "an amino acids" should read --an amino acid--.
Line 49, "amino acids" should read --amino acid--.
Line 52, "include" should read --includes--.
Lines 66-67, "amino acids" should read --amino acid--.

Column 25,
Line 63, "SEQ ID NO:04," should read --SEQ ID NO:104,--.

Column 26,
Line 61, "SEQ ID NO:1100," should read --SEQ ID NO:100,--.

Column 29,
Line 1, "pith a biological sample wider" should read --with a biological sample under--.

Column 34,
Line 17, "or aprt$^{+}$" should read --or aprt±--.

Column 35,
Line 34, "peptizes" should read --peptides--.

Column 38,
Line 16, "calorimetric" should read --colorimetric--.

Column 43,
Line 36, "These be" should read --These producer cells may be--.

Column 44,
Line 35, "ligase chairs" should read --ligase chain--.

Column 46,
Line 44, "(r" should read --or--.

Column 47,
Line 16, "With a" should read --with a--.

Column 52,
Line 59, "A pairs of" should read --A pair of--.

Column 53,
Line 27, "products was" should read --products were--.

Column 55,
Line 54, "grown) up" should read --grown up--.

Column 56,
Line 45, "on the reverse 4;" should read --on the reverse--.

Column 57,
Line 59, "a 1100mM" should read --a 100mM--.

Column 58,
Line 6, "ad the" should read --and the--.

Column 59,
Line 2, "calorimetric" should read --colorimetric--.
Line 23, "on. T" should read --on T--.
Line 26, "will be use to" should read --will be used to--.
Line 34, "the r cell" should read --the T cell--.
Lines 48-49, "would interesting" should read --would be interesting--.

Column 62,
Line 4, "of INSP42" should read --of INSP142--.

Column 163,
Line 37, "and hinds" should read --and binds--.